US008492333B2

(12) United States Patent
Yeaman et al.

(10) Patent No.: US 8,492,333 B2
(45) Date of Patent: Jul. 23, 2013

(54) PEPTIDES AND METHODS FOR INDUCING CELL DEATH

(75) Inventors: Michael R. Yeaman, Redondo Beach, CA (US); Nannette Y. Yount, San Juan Capistrano, CA (US); Eric P. Brass, Palos Verdes, CA (US)

(73) Assignee: Los Angeles Biomedical Research Institute at Harbor-UCLA Medical Center, Torrance, CA (US)

( * ) Notice: Subject to any disclaimer, the term of this patent is extended or adjusted under 35 U.S.C. 154(b) by 0 days.

(21) Appl. No.: 12/932,298

(22) Filed: Feb. 22, 2011

(65) Prior Publication Data

US 2011/0288006 A1 Nov. 24, 2011

Related U.S. Application Data

(60) Provisional application No. 61/338,747, filed on Feb. 22, 2010.

(51) Int. Cl.
*A61K 35/00* (2006.01)

(52) U.S. Cl.
USPC ......... 514/2.3; 514/18.9; 514/19.3; 514/21.4; 530/326

(58) Field of Classification Search
USPC .......................................................... 514/2.3
See application file for complete search history.

(56) References Cited

U.S. PATENT DOCUMENTS

| | | | |
|---|---|---|---|
| 6,576,239 | B1 | 6/2003 | Ruoslahti et al. |
| 6,743,769 | B1 | 6/2004 | Yeaman et al. |
| 7,067,621 | B2 | 6/2006 | Yeaman et al. |
| 2003/0175819 | A1 | 9/2003 | Reed et al. |
| 2006/0074016 | A1 | 4/2006 | Yeaman et al. |
| 2006/0135416 | A1 | 6/2006 | Yeaman et al. |
| 2007/0021597 | A1 | 1/2007 | Edwards et al. |

FOREIGN PATENT DOCUMENTS

| | | | |
|---|---|---|---|
| WO | WO/2005/108415 | * | 11/2005 |
| WO | WO/2009/042237 | * | 4/2009 |

OTHER PUBLICATIONS

Gregoret et al., Proteins: Structure, Function, and Genetics (2007) 9:99-107.*
Garcia Saez et al., Biophysical Journal (Jul. 2007) 93(1), 103-112.*
Akaike et al., "New paradigm of host defense against intracellular pathogens by nitric oxide," Nihon Hansenbyo Gakkai Zasshi., 78(1):41-47 (2009).
Altincicek et al., "Septic injury-inducible genes in medicinal maggots of the green blow fly *Lucilia sericata*," Insect Mol Biol., 18(1):119-125 (2009).
Arora et al., "Interactions of silver nanoparticles with primary mouse fibroblasts and liver cells," Toxicol Appl Pharmacol., 236(3):310-318 (2009).
Bai et al., "Identification of genes involved in immune response, microsatellite, and SNP markers from expressed sequence tags generated from hemocytes of freshwater pearl mussel (*Hyriopsis cumingii*)," Mar Biotechnol, 11(4):520-530 (2009).
Björstad et al., "The host defense peptide LL-37 selectively permeabilizes apoptotic leukocytes," antimicrob Agents Chemother, 53(3):1027-1038 (2009).
Bouzari N et al., "Defense of the skin with LL-37," J Invest Dermatol., 129(4):814-819 (2009).
Buonanno et al., "The protozoan toxin climacostol inhibits growth and induces apoptosis of human tumor cell lines," Chem Biol Interact., 176(2-3):151-164 (2008).
Chamorro et al., "The human antimicrobial peptide LL-37 suppresses apoptosis in keratinocytes," J Invest Dermatol, 129(4):937-944 (2009).
Chang et al., "Zebrafish peptidoglycan recognition protein SC (zfPGRP-SC) mediates multiple intracellular signaling pathways. Fish Shellfish," Immunol., 6(2):264-274 (2009).
Charroux et al., "Elimination of plasmatocytes by targeted apoptosis reveals their role in multiple aspects of the *Drosophila* immune response," Proc Natl Acad Sci U S A.,106(24):9797-9802 (2009).
Choi et al., "Sanguinarine, a benzophenanthridine alkaloid, induces apoptosis in MDA-MB-231 human breast carcinoma cells through a reactive oxygen species-mediated mitochondrial pathway," Chemotherapy, 54(4):279-287 (2008).
Cirioni et al., "Efficacy of LL-37 and granulocyte colony-stimulating factor in a neutropenic murine sepsis due to *Pseudomonas aeruginosa*," Shock, 30(4):443-448 (2008).
Feng et al., "Rise ML. Identification and analysis of differentially expressed genes in immune tissues of Atlantic cod stimulated with formalin-killed, atypical *Aeromonas salmonicida*," Physiol Genomics, 37(3):149-163 (2009).
Filler et al., "*Candida albicans* Stimulates Endothelial Cell Eicosanoid Production," J. Infect. Dis., 164:928-935 (1991).
Filler et al., "Mechanisms by Which *Candida albicans* Induces Endothelial Cell Prostagladin Syntheis," Infect. Immun, 62:1064-1069 (1994).
Filler et al., "Penetration and Damage of Endotheilial Cells by *Candida albicans*," Infect. Immun., 63:976-983 (1995).
Ghavami et al., "Brevinin-2R(1) semi-selectively kills cancer cells by a distinct mechanism, which involves the lysosomal-mitochondrial death pathway," J Cell Mol Med., 12(3):1005-1022 (2008).
Gillenwaters et al., "Sequence analysis and polymorphism discovery in 4 members of the bovine cathelicidin gene family," J Hered., 100(2):241-245 (2009).
Ginzburg et al., "Exogenous iron increases hemoglobin in beta-thalassemic mice," Exp Hematol., 37(2):172-183 (2009).
Goldman et al., "Targeted Gene Delivery to Kaposi's Sarcoma Cells cia the Fibroblast Growth Factor Receptor," Cancer Res., 15:1447-1451 (1997).

(Continued)

*Primary Examiner* — Karlheinz R Skowronek
*Assistant Examiner* — Catherine Mader
(74) *Attorney, Agent, or Firm* — Jones Day

(57) ABSTRACT

The invention provide isolated peptides, protides and conjugates having novel peptide sequences which are able to induce antimicrobial, anti-cancer, anti-inflammatory, anti-proliferative or programmed cell death activity. The invention also provides a method of inducing programmed cell death in a cell by contacting the cell with an isolated peptide, protide or conjugate described herein. In some aspects, the method can be used in the diagnosis, prevention, or treatment of a disease, such as an infection, cancer, autoimmune disease, or inflammatory disease.

23 Claims, 57 Drawing Sheets
(52 of 57 Drawing Sheet(s) Filed in Color)

OTHER PUBLICATIONS

Haines et al., "Killing of Trypanosomatid Parasites by a Modified Bovine Host Defense Peptide," BMAP-18. PLoS Negl Trop Dis., 3(2):e373 (2009).

Herrmann, "Converting bacteria to organelles: evolution of mitochondrial protein sorting," TRENDS Micro, 11(2):74-79 (2003).

Hsin et al., "The apoptotic effect of nanosilver is mediated by a ROS- and JNK-dependent mechanism involving the mitochondrial pathway in NIH3T3 cells," Toxicol Lett., 179(3):130-139 (2008).

Huang et al., "PD-1 expression by macrophages plays a pathologic role in altering microbial clearance and the innate inflammatory response to sepsis," Proc Natl Acad Sci U S A., 106(15):6303-6308 (2009).

Jiang et al., "Proteins induced by telomere dysfunction and DNA damage represent biomarkers of human aging and disease," Proc Natl Acad Sci U S A, 105(32):11299-11304 (2008).

Keilhoff et al., "Minocycline protects Schwann cells from ischemia-like injury and promotes axonal outgrowth in bioartificial nerve grafts lacking Wallerian degeneration," Exp Neurol., 212(1):189-200 (2008).

Kelley et al., "Protein structure prediction on the web: a case study using the Phyre server," Nature Protocols, 4:363-371 (2009).

Kilelee et al., Lysyl-Phosphatidylglycerol Attenuates Membrane Perturbation Rather than Surface Association of the Cationic Antimicrobial Peptide 6W-RP-1 in a Model Membrane System: Implications for Daptomycin Resistance, Antimicrobial Agents and Chemotherapy, 54(10):4476-4479 (2010).

Kitaichi et al., "Macrophage migration inhibitory factor ameliorates UV-induced photokeratitis in mice," Exp Eye Res., 86(6):929-935 (2008).

Kulkarni et al., "Antimicrobial peptide-induced apoptotic death of leishmania results from calcium-dependent, caspase-independent mitochondrial toxicity," J Biol Chem., 284(23):15496-15504 (2009).

Larkin et al., "Clustal W and Clustal X version 2.0," Bioinformatics, 23(21): 2947-2948 (2007).

Laskay et al., "Neutrophil granulocytes as host cells and transport vehicles for intracellular pathogens: apoptosis as infection-promoting factor," Immunobiology, 213(3-4):183-191 (2008).

Lin et al., "Epinecidin-1, an antimicrobial peptide from fish (*Epinephelus coioides*) which has an antitumor effect like lytic peptides in human fibrosarcoma cells," Peptides, 30(2):283-290 (2009).

Mader et al., "The human host defense peptide LL-37 induces apoptosis in a calpain- and apoptosis-inducing factor-dependent manner involving Bax activity," Mol Cancer Res., 7(5):689-702 (2009).

Medeiros et al., "Efferocytosis impairs pulmonary macrophage and lung antibacterial function via PGE2/EP2 signaling," J Exp Med., 206(1):61-68 (2009).

Mochon et al., "The antimicrobial peptide histatin-5 causes a spatially restricted disruption on the *Candida albicans* surface, allowing rapid entry of the peptide into the cytoplasm," PLoS Pathog., 4(10):e1000190 (2008).

Mook-Kanamori et al., "Daptomycin in experimental murine pneumococcal meningitis," BMC Infect Dis., 30:9:50 (2009).

O'Donoghue et al., "Recombinant bactericidal permeability increasing protein (rBPI21) inhibits surgery-induced tumour growth in a murine model of metastatic disease," Ir J Med Sci., 177(4):359-365 (2008).

Otte et al., "Human beta defensin 2 promotes intestinal wound healing in vitro," J Cell Biochem., 104(6):2286-2297 (2008).

Otte et al., "Effects of the cathelicidin LL-37 on intestinal epithelial barrier integrity," Regul Pept, 156(1-3):104-117 (2009).

Palm-Apergi et al., "The membrane repair response masks membrane disturbances caused by cell-penetrating peptide uptake," FASEB J., 23(1):214-223 (2009).

Polonelli et al., "Antibody complementarity-determining regions (CDRs) can display differential antimicrobial, antiviral and antitumor activities," PLoS One, 3(6):e2371 (2008).

Rahmoun et al., "Cytokine-induced CEACAM1 expression on keratinocytes is characteristic for psoriatic skin and contributes to a prolonged lifespan of neutrophils," J Invest Dermatol., 129(3):671-681(2009).

Remijsen et al , "Inhibition of spontaneous neutrophil apoptosis by parabutoporin acts independently of NADPH oxidase inhibition but by lipid raft-dependent stimulation of Akt," J Leukoc Biol., 85(3):497-507 (2009).

Reti et al, "Thymosin beta4 is cytoprotective in human gingival fibroblasts," Eur J Oral Sci., 116(5):424-30 (2008).

Rivero-Lezcano et al, "Detection of inhibition of antimicrobial activity by mycobacterial lysates in human monocytes infected with *Legionella pneumophilA*," J Immunol Methods, 336(1):16-21(2008).

Rodríguez-Martínez et al., "LL-37 regulates the overexpression of vascular endothelial growth factor (VEGF) and c-IAP-2 in human keratinocytes," Int J Dermatol., 47(5):457-462 (2008).

Savini et al. "*Origanum vulgare* induces apoptosis in human colon cancer caco2 cells," Nutr Cancer, 61(3):381-389 (2009).

Schulenburg et al., "Specificity of the innate immune system and diversity of C-type lectin domain (CTLD) proteins in the nematode *Caenorhabditis elegans*," Immunobiology, 213(3-4):237-250 (2008).

Shibusawa et al., "Antimicrobial cathelicidin peptide CAP11 suppresses HMGB1 release from lipopolysaccharide-stimulated mononuclear phagocytes via the prevention of necrotic cell death," Int J Mol Med., 23(3):341-346 (2009).

Shindyalov et al., "Protein structure alignment by incremental combinatorial extension (CE) of the optimal path," Protein Engineering, 11:739-747 (1998).

Singh et al., "cDNA microarray analysis reveals that antioxidant and immune genes are upregulated during involution of the bovine mammary gland,". J Dairy Sci., 91(6):2236-2246 (2008).

Smith et al., "Building Synthetic Antibodies as Adhesive Ligands for Integrins," J. Biol. Chem., 269: 32788-32795 (1995).

Von Heijne, "Mitochondrial targeting sequences may form amphiphilic helices," EMBO Journal, 5:1335-1342 (1986).

Wenghoefer et al., "Nuclear hBD-1 accumulation in malignant salivary gland tumours," BMC Cancer, 8:290 (2008).

Wong et al., "Autophagosome supports coxsackievirus B3 replication in host cells," J Virol., 82(18):9143-9153 (2008).

Xu et al., "Human alpha-defensin-1 inhibits growth of human lung adenocarcinoma xenograft in nude mice.," Mol Cancer Ther., 7(6):1588-1597 (2008).

Yang et al., "Effect of dimerization of a beta-turn antimicrobial peptide, PST13-RK, on antimicrobial activity and mammalian cell toxicity," Biotechnol Lett., 31(2):233-237 (2009).

Yeaman et al., "Synthetic Peptides That Exert Antimicrobial Activities in Whole Blood and Blood-Derived Matrices," Antimicrobial Agents and Chemotherapy, 46(12):3883-3891 (2002).

Yeaman et al., "Modular determinants of antimicrobial activity in platelet factor-4 family kinocidins," Bichimica et Biophysica Acta, 1768:609-619 (2007).

Yount et al., "Multidimensional signatures in antimicrobial peptides," PNAS, 1010:7363-7368 (2004).

Zasloff M., "Antimicrobial peptides and suppression of apoptosis in human skin," J Invest Dermatol., 129(4):824-826(2009).

Zhang et al, "Neutrophil secondary necrosis is induced by LL-37 derived from cathelicidin," J Leukoc Biol., 84(3):780-788 (2008).

Zhang et al., "Granulysin induces cathepsin B release from lysosomes of target tumor cells to attack mitochondria through processing of bid leading to Necroptosis," J Immunol., 182(11):6993-7000 (2009).

* cited by examiner

Human Holin-Like Proteins

Dnm-1 (dynamin-1 / pro-programmed cell death [apoptotic] holin-like protein)

```
  1  mgnrgmedli plvnrlqdaf saigqnadld lpqiavvggq sagkssvlen fvgrdflprg
 61  sgivtrrplv lqlvnattey aeflhckgkk ftdfeevrle ieaetdrvtg tnkgispvpi
121  nlrvysphvl nltlvdlpgm tkvpvgdqpp diefqirdml mqfvtkencl ilavspansd
181  lansdalkva kevdpqggrt igvitkldlm degtdardvl enkllplrrg yigvvnrsqk
241  didgkkdita alaaerkffl shpsyrhlad rmgtpylqkv lnqqltnhir dtlpglrnkl
301  qsqllsieke veeyknfrpd dparktkall qmvqqfavdf ekriegsgdq idtyelsgga
361  rinrifherf pfelvkmefd ekelrreisy aiknihgirt glftpdlafe atvkkqvqkl
421  kepsikcvdm vvseltatir kcseklqqyp rlreemeriv tthireregr tkeqvmllid
481  ielaymntnh edfigfanaq qrsnqmnkkk tsgnqdeilv irkgwltinn igimkggske
541  ywfvltaenl swykddeeke kkymlsvdnl klrdvekgfm sskhifalfn teqrnvykdy
601  rqlelacetq eevdswkasf lragvyperv gdkekasete engsdsfmhs mdpqlerqve
661  tirnlvdsym aivnktvrdl mpktimhlmi nntkefifse llanlyscgd qntlmeesae
721  qaqrrdemlr myhalkeals iigdinttv stpmpppvdd swlqvqsvpa grrsptsspt
```

Bax (pro-apoptotic holin-like molecule from humans / apoptosis pathway) 1F16

```
  1  mdgsgeqprg ggptsseqim ktgalllqgf iqdragrmgg eapelaldpv pqdastkkls
 61  eclkrigdel dsnmelqrmi aavdtdspre vffrvaadmf sdgnfnwgrv valfyfask
121  vlkalctkvp elirtimgwt ldflrerllg wiqdqggwdg llsyfgtptw qtvtifvagv
181  ltasltiwkk mg
```

Bcl-2 (anti-apoptotic holin-like protein from humans / apoptosis pathway) / 1G5M

```
  1  mahagrtgyd nreivmkyih yklsqrgyew dagddveenr teapegtese vvhlalrqag
 61  ddfsrryrgd faemssqlhl tpftargrfa tvveelfrdg vnwgrivaff efggvmcves
181  vnremsplvd nialwmteyl nrhlhtwiqd nggwdafvel ygpsmx
```

Figure 1

***S. aureus* Holin-Like Proteins**

CidA (pro-programmed cell death [apoptotic] holin-like protein)

```
  1   mhkvqliikl llqlgiiivi tyigteiqki fhlplagsiv glflfylllq fkivpltwve
 61   dganfllktm vfffipsvvg imdvaseitl nyilffavii igtcivalss gyiaekmsvk
121   hkqrkgiday e
```

LrgA (anti-programmed cell death [anti-apoptotic] protein)

```
  1   mvvkqqkdas kpahffhqvi vialvlfvsk iiesfmpipm pasviglvll fvllctgavk
 61   lgevekvgtt ltnnigllfv pagisvvnsl gvisqapfli igliivstil llictgyvtq iimkvtsrsk
121   gdkvtkkiki eeaqahd
```

Figure 2

>PERFORIN; PFN1_BOS
DTQRFLRPDGTCTLCRNALQKDVLQRLPLAITDWRAHGAGCKRRVVKLEGRSTE
DVAGEAANRIRNDWQVGLDVSPKPNANVRVTVAGSHSEDANFAAQKTHQDNY
RFSMDLVECRFYSFHLVHTPPVHPEFKRALKTLPPHFNTSTKPDYHRLISSYGTHF
IRSMELGGRISALTALRTCELALEGLTASEVEDCLAVEAEVSISDRASASPSFKAC
EEKKKNHKVGTSFHQAYRERHSNVDGGHHSTMHDLLFGSQAGPEQFSAWVASL
QDSPGLVDYTLEPLHMLVESQDPRREALRQAVSKYVTD

>BCL-2;BCL2_HUMAN
MAHAGRTGYDNREIVMKYIHYKLSQRGYEWDAGDVGAAPPGAAPAPGIFSSQP
GHTPHPAASRDPVARTSPLQTPAAPGAAAGPALSPVPPVVHLTLRQAGDDFSRR
YRRDFAEMSSQLHLTPFTARGRFATVVEELFRDGVNWGRIVAFFEFGGVMCVES
VNREMSPLVDNIALWMTEYLNRHLHTWIQDNGGWDAFVELYGPSMRPLFDFSW
LSLKTL LSLALVGACI TLGAYLGHK

>BCL-W;BCLW_HUMAN
MATPASAPDTRALVADFVGYKLRQKGYVCGAGPGEGPAADPLHQAMRAAGDE
FETRFRRTFSDLAAQLHVTPGSAQQRFTQVSDELFQGGPNWGRLVAFFVFGAAL
CAESVNKEMEPLVGQVQEWMVAYLETRLADWIHSSGGWAEFTALYGDGALEE
ARRLREGNWASVRTVLTGAVALGALVTVGAFFASK

Figure 3

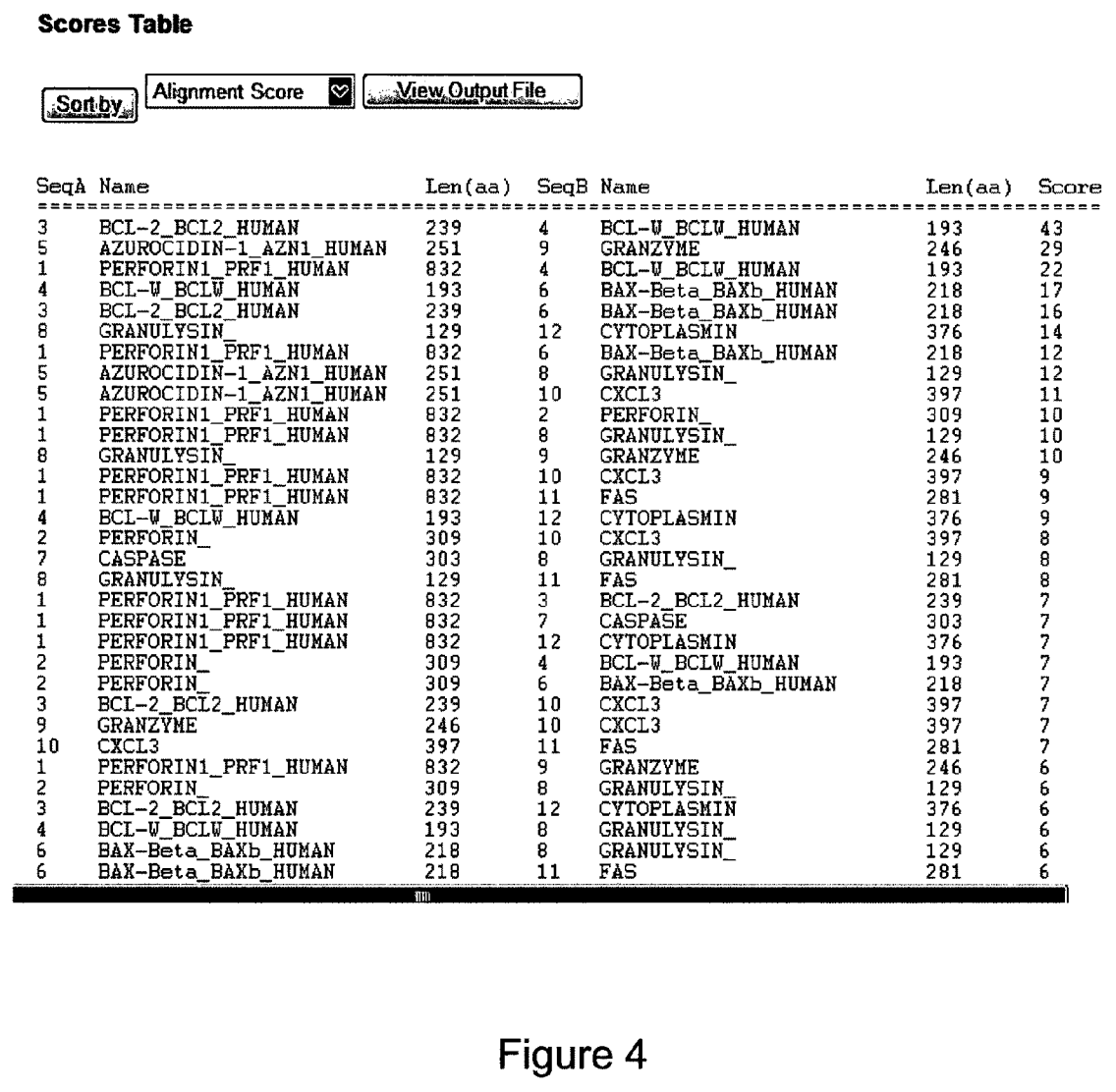

Scores Table

Sort by | Alignment Score | View Output File

| SeqA | Name | Len(aa) | SeqB | Name | Len(aa) | Score |
|---|---|---|---|---|---|---|
| 3 | BCL-2_BCL2_HUMAN | 239 | 4 | BCL-W_BCLW_HUMAN | 193 | 43 |
| 5 | AZUROCIDIN-1_AZN1_HUMAN | 251 | 9 | GRANZYME | 246 | 29 |
| 1 | PERFORIN1_PRF1_HUMAN | 832 | 4 | BCL-W_BCLW_HUMAN | 193 | 22 |
| 4 | BCL-W_BCLW_HUMAN | 193 | 6 | BAX-Beta_BAXb_HUMAN | 218 | 17 |
| 3 | BCL-2_BCL2_HUMAN | 239 | 6 | BAX-Beta_BAXb_HUMAN | 218 | 16 |
| 8 | GRANULYSIN_ | 129 | 12 | CYTOPLASMIN | 376 | 14 |
| 1 | PERFORIN1_PRF1_HUMAN | 832 | 6 | BAX-Beta_BAXb_HUMAN | 218 | 12 |
| 5 | AZUROCIDIN-1_AZN1_HUMAN | 251 | 8 | GRANULYSIN_ | 129 | 12 |
| 5 | AZUROCIDIN-1_AZN1_HUMAN | 251 | 10 | CXCL3 | 397 | 11 |
| 1 | PERFORIN1_PRF1_HUMAN | 832 | 2 | PERFORIN_ | 309 | 10 |
| 1 | PERFORIN1_PRF1_HUMAN | 832 | 8 | GRANULYSIN_ | 129 | 10 |
| 8 | GRANULYSIN_ | 129 | 9 | GRANZYME | 246 | 10 |
| 1 | PERFORIN1_PRF1_HUMAN | 832 | 10 | CXCL3 | 397 | 9 |
| 1 | PERFORIN1_PRF1_HUMAN | 832 | 11 | FAS | 281 | 9 |
| 4 | BCL-W_BCLW_HUMAN | 193 | 12 | CYTOPLASMIN | 376 | 9 |
| 2 | PERFORIN_ | 309 | 10 | CXCL3 | 397 | 8 |
| 7 | CASPASE | 303 | 8 | GRANULYSIN_ | 129 | 8 |
| 8 | GRANULYSIN_ | 129 | 11 | FAS | 281 | 8 |
| 1 | PERFORIN1_PRF1_HUMAN | 832 | 3 | BCL-2_BCL2_HUMAN | 239 | 7 |
| 1 | PERFORIN1_PRF1_HUMAN | 832 | 7 | CASPASE | 303 | 7 |
| 1 | PERFORIN1_PRF1_HUMAN | 832 | 12 | CYTOPLASMIN | 376 | 7 |
| 2 | PERFORIN_ | 309 | 4 | BCL-W_BCLW_HUMAN | 193 | 7 |
| 2 | PERFORIN_ | 309 | 6 | BAX-Beta_BAXb_HUMAN | 218 | 7 |
| 3 | BCL-2_BCL2_HUMAN | 239 | 10 | CXCL3 | 397 | 7 |
| 9 | GRANZYME | 246 | 10 | CXCL3 | 397 | 7 |
| 10 | CXCL3 | 397 | 11 | FAS | 281 | 7 |
| 1 | PERFORIN1_PRF1_HUMAN | 832 | 9 | GRANZYME | 246 | 6 |
| 2 | PERFORIN_ | 309 | 8 | GRANULYSIN_ | 129 | 6 |
| 3 | BCL-2_BCL2_HUMAN | 239 | 12 | CYTOPLASMIN | 376 | 6 |
| 4 | BCL-W_BCLW_HUMAN | 193 | 8 | GRANULYSIN_ | 129 | 6 |
| 6 | BAX-Beta_BAXb_HUMAN | 218 | 8 | GRANULYSIN_ | 129 | 6 |
| 6 | BAX-Beta_BAXb_HUMAN | 218 | 11 | FAS | 281 | 6 |

Figure 4

```
BCL-2_BCL2_HUMAN              ------------------------FTARGRFATVVEELFRDG-------- 141
BCL-W_BCLW_HUMAN              ------------------------GSAQQRFTQVSDELFQGG-------- 90
BAX-Beta_BAXb_HUMAN           -------------------------SPREVFFRVAADMFSDGN------- 104
PERFORIN1_PRF1_HUMAN          EEVYKRPLFLQPTYRYHRLPLPEQGSPLEAQLDAFVSVLRETPSLLQLRD 300
GRANULYSIN_                   ------------------------EGPQGDLLTKTQELGRDYR------- 51
CYTOPLASMIN                   -----------------EVRAQLLELPYARKELSLLVLLPDDG------- 236
PERFORIN_                     -----------------------LISSYGTHFIRSMELGGRIS------- 173
AZUROCIDIN-1_AZN1_HUMAN       -----------------------LQNATVEAGTRCQVAGWGSQ------- 157
GRANZYME                      -----------------------SSKAQVKPGQLCSVAGWGYV------- 150
CXCL3                         ------------------------SAPHQPGPSLWAEAKTSEAP------ 219
CASPASE                       ------------------------KDGVTPIKDLTAHFRGDRCKT----- 173
FAS                           ------------------------PPPEKKELRKVAHLTGKSN------- 154

BCL-2_BCL2_HUMAN              ----------------------VNWGRIVAFFEFGGVMCVESVNREMSPL 169
BCL-W_BCLW_HUMAN              ----------------------PNWGRLVAFFVFGAALCAESVNKEMEPL 118
BAX-Beta_BAXb_HUMAN           ----------------------FNWGRVVALFYFASKLVLKALCTKVPEL 132
PERFORIN1_PRF1_HUMAN          AHGPPPALVFSCQMGVGRTNLGMVLGTLILLHRSGTTSQPEAAPTQAKPL 350
GRANULYSIN_                   ----------------------TCLTIVQKLKKMVDKPTQRSVSNAATRV 79
CYTOPLASMIN                   -------------------VELSTVEKSLTFEKLTAWTKPDCMKSTEVEV 267
PERFORIN_                     -------------------ALTALRTCELALEGLTASEVEDCLAVEAEVS 204
AZUROCIDIN-1_AZN1_HUMAN       ----------------------RSGGRLSRFPRFVNVTVTPEDQCRPNNV 185
GRANZYME                      -------------------------SMSTLATTLQEVLLTVQKDCQCERL 175
CXCL3                         ----------------------STQDPSTQASTASSPAPEENAPSEGQRV 247
CASPASE                       ---------------------LLEKPKLFFIQACRGTELDDGIQADSGPI 202
FAS                           -----------------------SRSMPLEWEDTYGIVLLSGVKYKKGGL 181

BCL-2_BCL2_HUMAN              VDNIALWMTEYLNRH----------------------------------- 184
BCL-W_BCLW_HUMAN              VGQVQEWMVAYLETR----------------------------------- 133
BAX-Beta_BAXb_HUMAN           IRTIMGWTLDFLRER----------------------------------- 147
PERFORIN1_PRF1_HUMAN          PMEQFQVIQSFLRMVPQGRRMVEEVDRAITACAELHDLKEVVLENQKKLE 400
GRANULYSIN_                   CRTGRSRWRDVCRNF----------------------------------- 94
CYTOPLASMIN                   LLPKFKLQEDYDMESVLRHLG----------------------------- 288
PERFORIN_                     ISDRASASPSFKACEEKKKNHKVG-------------------------- 228
AZUROCIDIN-1_AZN1_HUMAN       CTGVLTRRGGICNGD----------------------------------- 200
GRANZYME                      FHGNYSRATEICVGDPKKTQTGFK-------------------------- 199
CXCL3                         WGQGQSPRPENSLEREEMGPVPAHT------------------------- 272
CASPASE                       NDTDANPRYKIPVEADFLFAYS---------------------------- 224
FAS                           VINETGLYFVVSKVVYFRGQSCNNLP------------------------ 206
```

Figure 5

Helix 1 of Human Bcl-2, Isoform 1 or 2: NREIVMKYIHYKLS mahagrtgydnreivmkyihyklsqrgyewdagdvgaaprtsapgrespvvhltlrqagddfsrryrrdfaemss Helix 2 of Human Bcl-2, Isoform 1 or 2: HLALRQAGDDFSRRYR g d d v e e n r t e a p e g t e s e v v h l a l r q a g d d f s r r y r g d f a e m s s q l h l t p f t a r g r f a t v v e e l f r d g v n w g r i v a Helix 2 of Human Bcl-X1: SQSNRELVVDFLSYKLSQK Helix 2 of Human Bcl-W: TRALVADFVGYKLRQK g p l g s m a t p a s a p d t r a l v a d f v g y k l r q k g y v c g a g p g e g p a a d p l h q a m r a a g d e f e t r f r r t f s d l a a q l h v t p Helix 4 of Human Bax: RVVALFYFASKLVLKALCTK prvffrvaadmfsdgnfnwgrvvalfyfasklvlkalctkvpelirtimgwtldflrerllgwiqdqggwdgl Helix 1 of Human CTL Granulysin: RDYRTCLTIVQKLKKM g r d y r t c l t i v q k l k k m v d k p t q r s v s n a a t r v c r t g r s r w r d v c r n f m r r y q s r v i q g l v a g e t a q q i c e d l r Helix 1-2 Span of Human CTL Granulysin: QKLKKMVDKPTQRSVSN g r d y r t c l t i v q k l k k m v d k p t q r s v s n a a t r v c r t g r s r w r d v c r n f m r r y q s r v i q g l v a g e t a q q i c e d l r Bax (1F16)
Helix 1: 104-129 Grey Bax Helix-1:104-129
positive dark grey (A)

Bax Helix-1: 104-129
KD most hydrophilic dark grey ; most hydrophobic med. grey (B)

Bax (1F16)
Helix 2: 168-190 grey

Bax helix 168-190 vs. IL-8 helix 54-72

Bax helix 168-190 vs. Magainin 1-24

SEQUENCE LISTING

```
<160> NUMBER OF SEQ ID NOS: 428

<210> SEQ ID NO 1
<211> LENGTH: 26
<212> TYPE: PRT
<213> ORGANISM: Artificial Sequence
<220> FEATURE:
<223> OTHER INFORMATION: Engineered peptides based on Bax protein

<400> SEQUENCE: 1

Asn Phe Asn Trp Gly Arg Val Val Ala Leu Phe Tyr Phe Ala Ser Lys
 1              5                   10                  15

Leu Val Leu Lys Ala Leu Cys Thr Lys Val
            20                  25


<210> SEQ ID NO 2
<211> LENGTH: 22
<212> TYPE: PRT
<213> ORGANISM: Artificial Sequence
<220> FEATURE:
<223> OTHER INFORMATION: Engineered peptides based on Bax protein

<400> SEQUENCE: 2

Thr Trp Gln Thr Val Thr Ile Phe Val Ala Gly Val Leu Thr Ala Ser
 1              5                   10                  15

Leu Thr Ile Trp Lys Lys
            20


<210> SEQ ID NO 3
<211> LENGTH: 26
<212> TYPE: PRT
<213> ORGANISM: Artificial Sequence
<220> FEATURE:
<223> OTHER INFORMATION: Engineered peptides based on Bax protein
<220> FEATURE:
```

```
<221> NAME/KEY: VARIANT
<222> LOCATION: 23
<223> OTHER INFORMATION: Xaa = Ser, Thr, Tyr and other
      natural/non-natural H-bond donor/acceptor residue

<400> SEQUENCE: 3

Asn Phe Asn Trp Gly Arg Val Val Ala Leu Phe Tyr Phe Ala Ser Lys
 1               5                  10                  15

Leu Val Leu Lys Ala Leu Xaa Thr Lys Val
            20                  25


<210> SEQ ID NO 4
<211> LENGTH: 26
<212> TYPE: PRT
<213> ORGANISM: Artificial Sequence
<220> FEATURE:
<223> OTHER INFORMATION: Engineered peptides based on Bax protein
<220> FEATURE:
<221> NAME/KEY: VARIANT
<222> LOCATION: 23
<223> OTHER INFORMATION: Xaa = Lys, Arg, Asn, Gln and
      other natural/non-natural basic residue
<220> FEATURE:
<221> NAME/KEY: VARIANT
<222> LOCATION: 25
<223> OTHER INFORMATION: Xaa = cysteine or other natural/non-natural
      thiol residue

<400> SEQUENCE: 4

Asn Phe Asn Trp Gly Arg Val Val Ala Leu Phe Tyr Phe Ala Ser Lys
 1               5                  10                  15

Leu Val Leu Lys Ala Leu Xaa Thr Xaa Val
            20                  25


<210> SEQ ID NO 5
<211> LENGTH: 23
<212> TYPE: PRT
<213> ORGANISM: Artificial Sequence
<220> FEATURE:
<223> OTHER INFORMATION: Engineered peptides based on Bax protein

<400> SEQUENCE: 5

Trp Gly Arg Val Val Ala Leu Phe Tyr Phe Ala Ser Lys Leu Val Leu
 1               5                  10                  15

Lys Ala Leu Cys Thr Lys Val
            20


<210> SEQ ID NO 6
<211> LENGTH: 23
<212> TYPE: PRT
<213> ORGANISM: Artificial Sequence
<220> FEATURE:
<223> OTHER INFORMATION: Engineered peptides based on Bax protein
<220> FEATURE:
<221> NAME/KEY: VARIANT
<222> LOCATION: 20
<223> OTHER INFORMATION: Xaa = Ser, Thr, Tyr and other
      natural/non-natural H-bond donor/acceptor residue

<400> SEQUENCE: 6

Trp Gly Arg Val Val Ala Leu Phe Tyr Phe Ala Ser Lys Leu Val Leu
 1               5                  10                  15

Lys Ala Leu Xaa Thr Lys Val
            20


<210> SEQ ID NO 7
<211> LENGTH: 21
<212> TYPE: PRT
```

<213> ORGANISM: Artificial Sequence
<220> FEATURE:
<223> OTHER INFORMATION: Engineered peptides based on Bax protein

<400> SEQUENCE: 7

```
Arg Val Val Ala Leu Phe Tyr Phe Ala Ser Lys Leu Val Leu Lys Ala
 1               5                  10                  15

Leu Cys Thr Lys Val
            20
```

<210> SEQ ID NO 8
<211> LENGTH: 21
<212> TYPE: PRT
<213> ORGANISM: Artificial Sequence
<220> FEATURE:
<223> OTHER INFORMATION: Engineered peptides based on Bax protein
<220> FEATURE:
<221> NAME/KEY: VARIANT
<222> LOCATION: 18
<223> OTHER INFORMATION: Xaa = Ser, Thr, Tyr and other natural/non-natural H-bond donor/acceptor residue

<400> SEQUENCE: 8

```
Arg Val Val Ala Leu Phe Tyr Phe Ala Ser Lys Leu Val Leu Lys Ala
 1               5                  10                  15

Leu Xaa Thr Lys Val
            20
```

<210> SEQ ID NO 9
<211> LENGTH: 18
<212> TYPE: PRT
<213> ORGANISM: Artificial Sequence
<220> FEATURE:
<223> OTHER INFORMATION: Engineered peptides based on Bax protein

<400> SEQUENCE: 9

```
Ala Leu Phe Tyr Phe Ala Ser Lys Leu Val Leu Lys Ala Leu Cys Thr
 1               5                  10                  15

Lys Val
```

<210> SEQ ID NO 10
<211> LENGTH: 18
<212> TYPE: PRT
<213> ORGANISM: Artificial Sequence
<220> FEATURE:
<223> OTHER INFORMATION: Engineered peptides based on Bax protein
<220> FEATURE:
<221> NAME/KEY: VARIANT
<222> LOCATION: 15
<223> OTHER INFORMATION: Xaa = Ser, Thr, Tyr and other natural/non-natural H-bond donor/acceptor residue

<400> SEQUENCE: 10

```
Ala Leu Phe Tyr Phe Ala Ser Lys Leu Val Leu Lys Ala Leu Xaa Thr
 1               5                  10                  15

Lys Val
```

<210> SEQ ID NO 11
<211> LENGTH: 22
<212> TYPE: PRT
<213> ORGANISM: Artificial Sequence
<220> FEATURE:
<223> OTHER INFORMATION: Engineered peptides based on Bax protein
<220> FEATURE:
<221> NAME/KEY: VARIANT
<222> LOCATION: 11
<223> OTHER INFORMATION: Xaa = Lys, Arg, Asn, Gln and other natural/non-natural basic residue

<400> SEQUENCE: 11

Thr Trp Gln Thr Val Thr Ile Phe Val Ala Xaa Val Leu Thr Ala Ser
 1               5                   10                  15

Leu Thr Ile Trp Lys Lys
            20

<210> SEQ ID NO 12
<211> LENGTH: 19
<212> TYPE: PRT
<213> ORGANISM: Artificial Sequence
<220> FEATURE:
<223> OTHER INFORMATION: Engineered peptides based on Bax protein

<400> SEQUENCE: 12

Thr Val Thr Ile Phe Val Ala Gly Val Leu Thr Ala Ser Leu Thr Ile
 1               5                   10                  15

Trp Lys Lys

<210> SEQ ID NO 13
<211> LENGTH: 19
<212> TYPE: PRT
<213> ORGANISM: Artificial Sequence
<220> FEATURE:
<223> OTHER INFORMATION: Engineered peptides based on Bax protein
<220> FEATURE:
<221> NAME/KEY: VARIANT
<222> LOCATION: 8
<223> OTHER INFORMATION: Xaa = Lys, Arg, Asn, Gln and
      other natural/non-natural basic residue

<400> SEQUENCE: 13

Thr Val Thr Ile Phe Val Ala Xaa Val Leu Thr Ala Ser Leu Thr Ile
 1               5                   10                  15

Trp Lys Lys

<210> SEQ ID NO 14
<211> LENGTH: 19
<212> TYPE: PRT
<213> ORGANISM: Artificial Sequence
<220> FEATURE:
<223> OTHER INFORMATION: Engineered peptides based on Bcl-W protein

<400> SEQUENCE: 14

Thr Arg Ala Leu Val Ala Asp Phe Val Gly Tyr Lys Leu Arg Gln Lys
 1               5                   10                  15

Gly Tyr Val

<210> SEQ ID NO 15
<211> LENGTH: 17
<212> TYPE: PRT
<213> ORGANISM: Artificial Sequence
<220> FEATURE:
<223> OTHER INFORMATION: Engineered peptides based on Bcl-W protein

<400> SEQUENCE: 15

Thr Arg Phe Arg Arg Thr Phe Ser Asp Leu Ala Ala Gln Leu His Val
 1               5                   10                  15

Thr

<210> SEQ ID NO 16
<211> LENGTH: 35
<212> TYPE: PRT
<213> ORGANISM: Artificial Sequence
<220> FEATURE:

<223> OTHER INFORMATION: Engineered peptides based on Bcl-W protein

<400> SEQUENCE: 16

Ala Arg Arg Leu Arg Glu Gly Asn Trp Ala Ser Val Arg Thr Val Leu
 1               5                   10                  15

Thr Gly Ala Val Ala Leu Gly Ala Leu Val Thr Val Gly Ala Phe Phe
            20                  25                  30

Ala Ser Lys
        35

<210> SEQ ID NO 17
<211> LENGTH: 19
<212> TYPE: PRT
<213> ORGANISM: Artificial Sequence
<220> FEATURE:
<223> OTHER INFORMATION: Engineered peptides based on Bcl-W protein
<220> FEATURE:
<221> NAME/KEY: VARIANT
<222> LOCATION: 7
<223> OTHER INFORMATION: Xaa = Lys, Arg, Asn, Gln and
      other natural/non-natural basic residue

<400> SEQUENCE: 17

Thr Arg Ala Leu Val Ala Xaa Phe Val Gly Tyr Lys Leu Arg Gln Lys
 1               5                   10                  15

Gly Tyr Val

<210> SEQ ID NO 18
<211> LENGTH: 17
<212> TYPE: PRT
<213> ORGANISM: Artificial Sequence
<220> FEATURE:
<223> OTHER INFORMATION: Engineered peptides based on Bcl-W protein
<220> FEATURE:
<221> NAME/KEY: VARIANT
<222> LOCATION: 5
<223> OTHER INFORMATION: Xaa = Lys, Arg, Asn, Gln and
      other natural/non-natural basic residue

<400> SEQUENCE: 18

Thr Arg Phe Arg Xaa Thr Phe Ser Asp Leu Ala Ala Gln Leu His Val
 1               5                   10                  15

Thr

<210> SEQ ID NO 19
<211> LENGTH: 17
<212> TYPE: PRT
<213> ORGANISM: Artificial Sequence
<220> FEATURE:
<223> OTHER INFORMATION: Engineered peptides based on Bcl-W protein
<220> FEATURE:
<221> NAME/KEY: VARIANT
<222> LOCATION: 9
<223> OTHER INFORMATION: Xaa = Lys, Arg, Asn, Gln and
      other natural/non-natural basic residue

<400> SEQUENCE: 19

Thr Arg Phe Arg Arg Thr Phe Ser Xaa Leu Ala Ala Gln Leu His Val
 1               5                   10                  15

Thr

<210> SEQ ID NO 20
<211> LENGTH: 34
<212> TYPE: PRT
<213> ORGANISM: Artificial Sequence
<220> FEATURE:
<223> OTHER INFORMATION: Engineered peptides based on Bcl-W protein

<400> SEQUENCE: 20

```
Arg Arg Leu Arg Glu Gly Asn Trp Ala Ser Val Arg Thr Val Leu Thr
 1               5                  10                  15

Gly Ala Val Ala Leu Gly Ala Leu Val Thr Val Gly Ala Phe Phe Ala
            20                  25                  30

Ser Lys
```

<210> SEQ ID NO 21
<211> LENGTH: 34
<212> TYPE: PRT
<213> ORGANISM: Artificial Sequence
<220> FEATURE:
<223> OTHER INFORMATION: Engineered peptides based on Bcl-W protein
<220> FEATURE:
<221> NAME/KEY: VARIANT
<222> LOCATION: 5
<223> OTHER INFORMATION: Xaa = Lys, Arg, Asn, Gln and other natural/non-natural basic residue

<400> SEQUENCE: 21

```
Arg Arg Leu Arg Xaa Gly Asn Trp Ala Ser Val Arg Thr Val Leu Thr
 1               5                  10                  15

Gly Ala Val Ala Leu Gly Ala Leu Val Thr Val Gly Ala Phe Phe Ala
            20                  25                  30

Ser Lys
```

<210> SEQ ID NO 22
<211> LENGTH: 34
<212> TYPE: PRT
<213> ORGANISM: Artificial Sequence
<220> FEATURE:
<223> OTHER INFORMATION: Engineered peptides based on Bcl-W protein
<220> FEATURE:
<221> NAME/KEY: VARIANT
<222> LOCATION: 17
<223> OTHER INFORMATION: Xaa = Lys, Arg, Asn, Gln and other natural/non-natural basic residue

<400> SEQUENCE: 22

```
Arg Arg Leu Arg Glu Gly Asn Trp Ala Ser Val Arg Thr Val Leu Thr
 1               5                  10                  15

Xaa Ala Val Ala Leu Gly Ala Leu Val Thr Val Gly Ala Phe Phe Ala
            20                  25                  30

Ser Lys
```

<210> SEQ ID NO 23
<211> LENGTH: 34
<212> TYPE: PRT
<213> ORGANISM: Artificial Sequence
<220> FEATURE:
<223> OTHER INFORMATION: Engineered peptides based on Bcl-W protein
<220> FEATURE:
<221> NAME/KEY: VARIANT
<222> LOCATION: 22
<223> OTHER INFORMATION: Xaa = Lys, Arg, Asn, Gln and other natural/non-natural basic residue

<400> SEQUENCE: 23

```
Arg Arg Leu Arg Glu Gly Asn Trp Ala Ser Val Arg Thr Val Leu Thr
 1               5                  10                  15

Gly Ala Val Ala Leu Xaa Ala Leu Val Thr Val Gly Ala Phe Phe Ala
            20                  25                  30

Ser Lys
```

<210> SEQ ID NO 24
<211> LENGTH: 34
<212> TYPE: PRT
<213> ORGANISM: Artificial Sequence
<220> FEATURE:
<223> OTHER INFORMATION: Engineered peptides based on Bcl-W protein
<220> FEATURE:
<221> NAME/KEY: VARIANT
<222> LOCATION: 28
<223> OTHER INFORMATION: Xaa = Lys, Arg, Asn, Gln and
other natural/non-natural basic residue

<400> SEQUENCE: 24

```
Arg Arg Leu Arg Glu Gly Asn Trp Ala Ser Val Arg Thr Val Leu Thr
 1               5                  10                  15

Gly Ala Val Ala Leu Gly Ala Leu Val Thr Val Xaa Ala Phe Phe Ala
            20                  25                  30

Ser Lys
```

<210> SEQ ID NO 25
<211> LENGTH: 34
<212> TYPE: PRT
<213> ORGANISM: Artificial Sequence
<220> FEATURE:
<223> OTHER INFORMATION: Engineered peptides based on Bcl-W protein
<220> FEATURE:
<221> NAME/KEY: VARIANT
<222> LOCATION: 5, 17, 22, 28
<223> OTHER INFORMATION: Xaa = Lys, Arg, Asn, Gln and
other natural/non-natural basic residue

<400> SEQUENCE: 25

```
Arg Arg Leu Arg Xaa Gly Asn Trp Ala Ser Val Arg Thr Val Leu Thr
 1               5                  10                  15

Xaa Ala Val Ala Leu Xaa Ala Leu Val Thr Val Xaa Ala Phe Phe Ala
            20                  25                  30

Ser Lys
```

<210> SEQ ID NO 26
<211> LENGTH: 17
<212> TYPE: PRT
<213> ORGANISM: Artificial Sequence
<220> FEATURE:
<223> OTHER INFORMATION: Engineered peptides based on Bcl-xBetta protein

<400> SEQUENCE: 26

```
Phe Leu Ser Tyr Lys Leu Ser Gln Lys Gly Tyr Ser Trp Ser Gln Phe
 1               5                  10                  15

Ser
```

<210> SEQ ID NO 27
<211> LENGTH: 25
<212> TYPE: PRT
<213> ORGANISM: Artificial Sequence
<220> FEATURE:
<223> OTHER INFORMATION: Engineered peptides based on Bcl-xBetta protein

<400> SEQUENCE: 27

```
Leu Arg Tyr Arg Arg Ala Phe Ser Asp Leu Thr Ser Gln Leu His Ile
 1               5                  10                  15

Thr Pro Gly Thr Ala Tyr Gln Ser Phe
            20                  25
```

<210> SEQ ID NO 28
<211> LENGTH: 20

<212> TYPE: PRT
<213> ORGANISM: Artificial Sequence
<220> FEATURE:
<223> OTHER INFORMATION: Engineered peptides based on Bcl-xBetta protein

<400> SEQUENCE: 28

```
Gly Trp Val Arg Thr Lys Pro Leu Val Cys Pro Phe Ser Leu Ala Ser
 1               5                  10                  15

Gly Gln Arg Ser
            20
```

<210> SEQ ID NO 29
<211> LENGTH: 21
<212> TYPE: PRT
<213> ORGANISM: Artificial Sequence
<220> FEATURE:
<223> OTHER INFORMATION: Engineered peptides based on Bcl-xBetta protein

<400> SEQUENCE: 29

```
Gly Gln Arg Ser Pro Thr Ala Leu Leu Leu Tyr Leu Phe Leu Leu Cys
 1               5                  10                  15

Trp Val Ile Val Gly
            20
```

<210> SEQ ID NO 30
<211> LENGTH: 25
<212> TYPE: PRT
<213> ORGANISM: Artificial Sequence
<220> FEATURE:
<223> OTHER INFORMATION: Engineered peptides based on Bcl-xBetta protein
<220> FEATURE:
<221> NAME/KEY: VARIANT
<222> LOCATION: 9
<223> OTHER INFORMATION: Xaa = Lys, Arg, Asn, Gln and
other natural/non-natural basic residue

<400> SEQUENCE: 30

```
Leu Arg Tyr Arg Arg Ala Phe Ser Xaa Leu Thr Ser Gln Leu His Ile
 1               5                  10                  15

Thr Pro Gly Thr Ala Tyr Gln Ser Phe
            20                  25
```

<210> SEQ ID NO 31
<211> LENGTH: 20
<212> TYPE: PRT
<213> ORGANISM: Artificial Sequence
<220> FEATURE:
<223> OTHER INFORMATION: Engineered peptides based on Bcl-xBetta protein
<220> FEATURE:
<221> NAME/KEY: VARIANT
<222> LOCATION: 10
<223> OTHER INFORMATION: Xaa = Ser, Thr, Tyr and other
natural/non-natural H-bond donor/acceptor residue

<400> SEQUENCE: 31

```
Gly Trp Val Arg Thr Lys Pro Leu Val Xaa Pro Phe Ser Leu Ala Ser
 1               5                  10                  15

Gly Gln Arg Ser
            20
```

<210> SEQ ID NO 32
<211> LENGTH: 20
<212> TYPE: PRT
<213> ORGANISM: Artificial Sequence
<220> FEATURE:
<223> OTHER INFORMATION: Engineered peptides based on Bcl-xBetta protein
<220> FEATURE:
<221> NAME/KEY: VARIANT -continued

```
<222> LOCATION: 10
<223> OTHER INFORMATION: Xaa = Ser, Thr, Tyr and other
      natural/non-natural H-bond donor/acceptor residue
<220> FEATURE:
<221> NAME/KEY: VARIANT
<222> LOCATION: 17
<223> OTHER INFORMATION: Xaa = Lys, Arg, Asn, Gln and other
      natural/non-natural basic residue

<400> SEQUENCE: 32

Gly Trp Val Arg Thr Lys Pro Leu Val Xaa Pro Phe Ser Leu Ala Ser
 1               5                  10                  15

Xaa Gln Arg Ser
            20


<210> SEQ ID NO 33
<211> LENGTH: 21
<212> TYPE: PRT
<213> ORGANISM: Artificial Sequence
<220> FEATURE:
<223> OTHER INFORMATION: Engineered peptides based on Bcl-xBetta protein
<220> FEATURE:
<221> NAME/KEY: VARIANT
<222> LOCATION: 9
<223> OTHER INFORMATION: Xaa = Ser, Thr, Tyr and other
      natural/non-natural H-bond donor/acceptor residue

<400> SEQUENCE: 33

Gly Gln Arg Ser Pro Thr Ala Leu Xaa Leu Tyr Leu Phe Leu Leu Cys
 1               5                  10                  15

Trp Val Ile Val Gly
            20


<210> SEQ ID NO 34
<211> LENGTH: 21
<212> TYPE: PRT
<213> ORGANISM: Artificial Sequence
<220> FEATURE:
<223> OTHER INFORMATION: Engineered peptides based on Bcl-xBetta protein
<220> FEATURE:
<221> NAME/KEY: VARIANT
<222> LOCATION: 16
<223> OTHER INFORMATION: Xaa = Ser, Thr, Tyr and other
      natural/non-natural H-bond donor/acceptor residue

<400> SEQUENCE: 34

Gly Gln Arg Ser Pro Thr Ala Leu Leu Leu Tyr Leu Phe Leu Leu Xaa
 1               5                  10                  15

Trp Val Ile Val Gly
            20


<210> SEQ ID NO 35
<211> LENGTH: 21
<212> TYPE: PRT
<213> ORGANISM: Artificial Sequence
<220> FEATURE:
<223> OTHER INFORMATION: Engineered peptides based on Bcl-xBetta protein
<220> FEATURE:
<221> NAME/KEY: VARIANT
<222> LOCATION: 21
<223> OTHER INFORMATION: Xaa = Lys, Arg, Asn, Gln and
      other natural/non-natural basic residue

<400> SEQUENCE: 35

Gly Gln Arg Ser Pro Thr Ala Leu Leu Leu Tyr Leu Phe Leu Leu Cys
 1               5                  10                  15

Trp Val Ile Val Xaa
            20
```

<210> SEQ ID NO 36
<211> LENGTH: 21
<212> TYPE: PRT
<213> ORGANISM: Artificial Sequence
<220> FEATURE:
<223> OTHER INFORMATION: Engineered peptides based on Bcl-xBetta protein
<220> FEATURE:
<221> NAME/KEY: VARIANT
<222> LOCATION: 9, 16
<223> OTHER INFORMATION: Xaa = Ser, Thr, Tyr and other natural/non-natural H-bond donor/acceptor residue
<220> FEATURE:
<221> NAME/KEY: VARIANT
<222> LOCATION: 21
<223> OTHER INFORMATION: Xaa = Lys, Arg, Asn, Gln and other natural/non-natural basic residue

<400> SEQUENCE: 36

```
Gly Gln Arg Ser Pro Thr Ala Leu Xaa Leu Tyr Leu Phe Leu Leu Xaa
 1               5                  10                  15

Trp Val Ile Val Xaa
            20
```

<210> SEQ ID NO 37
<211> LENGTH: 18
<212> TYPE: PRT
<213> ORGANISM: Artificial Sequence
<220> FEATURE:
<223> OTHER INFORMATION: Engineered peptides based on Bak protein

<400> SEQUENCE: 37

```
Arg Val Val Ala Leu Leu Gly Phe Gly Tyr Arg Leu Ala Leu His Val
 1               5                  10                  15

Tyr Gln
```

<210> SEQ ID NO 38
<211> LENGTH: 24
<212> TYPE: PRT
<213> ORGANISM: Artificial Sequence
<220> FEATURE:
<223> OTHER INFORMATION: Engineered peptides based on Bak protein

<400> SEQUENCE: 38

```
Ile Leu Asn Val Leu Val Val Leu Gly Val Val Leu Leu Gly Gln Phe
 1               5                  10                  15

Val Val Arg Arg Phe Phe Lys Ser
            20
```

<210> SEQ ID NO 39
<211> LENGTH: 18
<212> TYPE: PRT
<213> ORGANISM: Artificial Sequence
<220> FEATURE:
<223> OTHER INFORMATION: Engineered peptides based on Bak protein
<220> FEATURE:
<221> NAME/KEY: VARIANT
<222> LOCATION: 7
<223> OTHER INFORMATION: Xaa = Lys, Arg, Asn, Gln and other natural/non-natural basic residue

<400> SEQUENCE: 39

```
Arg Val Val Ala Leu Leu Xaa Phe Gly Tyr Arg Leu Ala Leu His Val
 1               5                  10                  15

Tyr Gln
```

<210> SEQ ID NO 40
<211> LENGTH: 18

```
<212> TYPE: PRT
<213> ORGANISM: Artificial Sequence
<220> FEATURE:
<223> OTHER INFORMATION: Engineered peptides based on Bak protein
<220> FEATURE:
<221> NAME/KEY: VARIANT
<222> LOCATION: 9
<223> OTHER INFORMATION: Xaa = Lys, Arg, Asn, Gln and
      other natural/non-natural basic residue

<400> SEQUENCE: 40

Arg Val Val Ala Leu Leu Gly Phe Xaa Tyr Arg Leu Ala Leu His Val
 1               5                  10                  15

Tyr Gln


<210> SEQ ID NO 41
<211> LENGTH: 18
<212> TYPE: PRT
<213> ORGANISM: Artificial Sequence
<220> FEATURE:
<223> OTHER INFORMATION: Engineered peptides based on Bak protein
<220> FEATURE:
<221> NAME/KEY: VARIANT
<222> LOCATION: 7, 9
<223> OTHER INFORMATION: Xaa = Lys, Arg, Asn, Gln and
      other natural/non-natural basic residue

<400> SEQUENCE: 41

Arg Val Val Ala Leu Leu Xaa Phe Xaa Tyr Arg Leu Ala Leu His Val
 1               5                  10                  15

Tyr Gln


<210> SEQ ID NO 42
<211> LENGTH: 18
<212> TYPE: PRT
<213> ORGANISM: Artificial Sequence
<220> FEATURE:
<223> OTHER INFORMATION: Engineered peptides based on Bak protein

<400> SEQUENCE: 42

Arg Val Val Ala Leu Tyr Gly Phe Gly Tyr Arg Leu Ala Leu His Val
 1               5                  10                  15

Tyr Gln


<210> SEQ ID NO 43
<211> LENGTH: 18
<212> TYPE: PRT
<213> ORGANISM: Artificial Sequence
<220> FEATURE:
<223> OTHER INFORMATION: Engineered peptides based on Bak protein

<400> SEQUENCE: 43

Arg Val Val Ala Leu Trp Gly Phe Gly Tyr Arg Leu Ala Leu His Val
 1               5                  10                  15

Tyr Gln


<210> SEQ ID NO 44
<211> LENGTH: 18
<212> TYPE: PRT
<213> ORGANISM: Artificial Sequence
<220> FEATURE:
<223> OTHER INFORMATION: Engineered peptides based on Bak protein
<220> FEATURE:
<221> NAME/KEY: VARIANT
<222> LOCATION: 7, 9
<223> OTHER INFORMATION: Xaa = Lys, Arg, Asn, Gln and
      other natural/non-natural basic residue
```

<400> SEQUENCE: 44

Arg Val Val Ala Leu Tyr Xaa Phe Xaa Tyr Arg Leu Ala Leu His Val
1 5 10 15

Tyr Gln

<210> SEQ ID NO 45
<211> LENGTH: 18
<212> TYPE: PRT
<213> ORGANISM: Artificial Sequence
<220> FEATURE:
<223> OTHER INFORMATION: Engineered peptides based on Bak protein
<220> FEATURE:
<221> NAME/KEY: VARIANT
<222> LOCATION: 7, 9
<223> OTHER INFORMATION: Xaa = Lys, Arg, Asn, Gln and
other natural/non-natural basic residue

<400> SEQUENCE: 45

Arg Val Val Ala Leu Trp Xaa Phe Xaa Tyr Arg Leu Ala Leu His Val
1 5 10 15

Tyr Gln

<210> SEQ ID NO 46
<211> LENGTH: 24
<212> TYPE: PRT
<213> ORGANISM: Artificial Sequence
<220> FEATURE:
<223> OTHER INFORMATION: Engineered peptides based on Bak protein
<220> FEATURE:
<221> NAME/KEY: VARIANT
<222> LOCATION: 7
<223> OTHER INFORMATION: Xaa = Ser, Thr, Tyr and other
natural/non-natural H-bond donor/acceptor residue

<400> SEQUENCE: 46

Ile Leu Asn Val Leu Val Xaa Leu Gly Val Val Leu Leu Gly Gln Phe
1 5 10 15

Val Val Arg Arg Phe Phe Lys Ser
20

<210> SEQ ID NO 47
<211> LENGTH: 18
<212> TYPE: PRT
<213> ORGANISM: Artificial Sequence
<220> FEATURE:
<223> OTHER INFORMATION: Engineered peptides based on Bak protein
<220> FEATURE:
<221> NAME/KEY: VARIANT
<222> LOCATION: 7
<223> OTHER INFORMATION: Xaa = Lys, Arg, Asn, Gln and
other natural/non-natural basic residue

<400> SEQUENCE: 47

Ile Leu Asn Val Leu Val Xaa Leu Val Leu Gly Gln Phe Val Arg Phe
1 5 10 15

Lys Ser

<210> SEQ ID NO 48
<211> LENGTH: 18
<212> TYPE: PRT
<213> ORGANISM: Artificial Sequence
<220> FEATURE:
<223> OTHER INFORMATION: Engineered peptides based on Bcl-2 protein

<400> SEQUENCE: 48

Asn Arg Glu Ile Val Met Lys Tyr Ile His Tyr Lys Leu Ser Gln Arg
1 5 10 15

Gly Tyr

<210> SEQ ID NO 49
<211> LENGTH: 18
<212> TYPE: PRT
<213> ORGANISM: Artificial Sequence
<220> FEATURE:
<223> OTHER INFORMATION: Engineered peptides based on Bcl-2 protein
<220> FEATURE:
<221> NAME/KEY: VARIANT
<222> LOCATION: 3
<223> OTHER INFORMATION: Xaa = Lys, Arg, Asn, Gln and
other natural/non-natural basic residue

<400> SEQUENCE: 49

Asn Arg Xaa Ile Val Met Lys Tyr Ile His Tyr Lys Leu Ser Gln Arg
1 5 10 15

Gly Tyr

<210> SEQ ID NO 50
<211> LENGTH: 18
<212> TYPE: PRT
<213> ORGANISM: Artificial Sequence
<220> FEATURE:
<223> OTHER INFORMATION: Engineered peptides based on Bcl-2 protein
<220> FEATURE:
<221> NAME/KEY: VARIANT
<222> LOCATION: 6
<223> OTHER INFORMATION: Xaa = Ser, Thr, Tyr and other
natural/non-natural H-bond donor/acceptor residue

<400> SEQUENCE: 50

Asn Arg Glu Ile Val Xaa Lys Tyr Ile His Tyr Lys Leu Ser Gln Arg
1 5 10 15

Gly Tyr

<210> SEQ ID NO 51
<211> LENGTH: 18
<212> TYPE: PRT
<213> ORGANISM: Artificial Sequence
<220> FEATURE:
<223> OTHER INFORMATION: Engineered peptides based on Bcl-2 protein
<220> FEATURE:
<221> NAME/KEY: VARIANT
<222> LOCATION: 10
<223> OTHER INFORMATION: Xaa = Lys, Arg, Asn, Gln and
other natural/non-natural basic residue

<400> SEQUENCE: 51

Asn Arg Glu Ile Val Met Lys Tyr Ile Xaa Tyr Lys Leu Ser Gln Arg
1 5 10 15

Gly Tyr

<210> SEQ ID NO 52
<211> LENGTH: 18
<212> TYPE: PRT
<213> ORGANISM: Artificial Sequence
<220> FEATURE:
<223> OTHER INFORMATION: Engineered peptides based on Bcl-2 protein
<220> FEATURE:
<221> NAME/KEY: VARIANT
<222> LOCATION: 3, 10
<223> OTHER INFORMATION: Xaa = Lys, Arg, Asn, Gln and
other natural/non-natural basic residue
<220> FEATURE:
<221> NAME/KEY: VARIANT
<222> LOCATION: 6
<223> OTHER INFORMATION: Xaa = Ser, Thr, Tyr and other
natural/non-natural H-bond donor/acceptor residue

<400> SEQUENCE: 52

Asn Arg Xaa Ile Val Xaa Lys Tyr Ile Xaa Tyr Lys Leu Ser Gln Arg
1 5 10 15

Gly Tyr

<210> SEQ ID NO 53
<211> LENGTH: 16
<212> TYPE: PRT
<213> ORGANISM: Artificial Sequence
<220> FEATURE:
<223> OTHER INFORMATION: Engineered peptides based on Bcl-2 isoform 1 protein

<400> SEQUENCE: 53

Leu Ala Leu Arg Gln Ala Gly Asp Asp Phe Ser Arg Arg Tyr Arg Gly
1 5 10 15

<210> SEQ ID NO 54
<211> LENGTH: 16
<212> TYPE: PRT
<213> ORGANISM: Artificial Sequence
<220> FEATURE:
<223> OTHER INFORMATION: Engineered peptides based on Bcl-2 isoform 1 protein
<220> FEATURE:
<221> NAME/KEY: VARIANT
<222> LOCATION: 8
<223> OTHER INFORMATION: Xaa = Lys, Arg, Asn, Gln and other natural/non-natural basic residue

<400> SEQUENCE: 54

Leu Ala Leu Arg Gln Ala Gly Xaa Asp Phe Ser Arg Arg Tyr Arg Gly
1 5 10 15

<210> SEQ ID NO 55
<211> LENGTH: 16
<212> TYPE: PRT
<213> ORGANISM: Artificial Sequence
<220> FEATURE:
<223> OTHER INFORMATION: Engineered peptides based on Bcl-2 isoform 1 protein
<220> FEATURE:
<221> NAME/KEY: VARIANT
<222> LOCATION: 9
<223> OTHER INFORMATION: Xaa = Lys, Arg, Asn, Gln and other natural/non-natural basic residue

<400> SEQUENCE: 55

Leu Ala Leu Arg Gln Ala Gly Asp Xaa Phe Ser Arg Arg Tyr Arg Gly
1 5 10 15

<210> SEQ ID NO 56
<211> LENGTH: 16
<212> TYPE: PRT
<213> ORGANISM: Artificial Sequence
<220> FEATURE:
<223> OTHER INFORMATION: Engineered peptides based on Bcl-2 isoform 1 protein
<220> FEATURE:
<221> NAME/KEY: VARIANT
<222> LOCATION: 8
<223> OTHER INFORMATION: Xaa = Lys, Arg, Asn, Gln and other natural/non-natural basic residue
<220> FEATURE:
<221> NAME/KEY: VARIANT
<222> LOCATION: 9
<223> OTHER INFORMATION: Xaa = Ser, Thr, Tyr and other natural/non-natural H-bond donor/acceptor residue

<400> SEQUENCE: 56

-continued

```
Leu Ala Leu Arg Gln Ala Gly Xaa Xaa Phe Ser Arg Arg Tyr Arg Gly
 1               5                  10                  15


<210> SEQ ID NO 57
<211> LENGTH: 16
<212> TYPE: PRT
<213> ORGANISM: Artificial Sequence
<220> FEATURE:
<223> OTHER INFORMATION: Engineered peptides based on Bcl-2 isoform 1
      protein
<220> FEATURE:
<221> NAME/KEY: VARIANT
<222> LOCATION: 7
<223> OTHER INFORMATION: Xaa = anthrylalanine or other non-natural amino
      acid
<220> FEATURE:
<221> NAME/KEY: VARIANT
<222> LOCATION: 8
<223> OTHER INFORMATION: Xaa = Lys, Arg, Asn, Gln and
      other natural/non-natural basic residue
<220> FEATURE:
<221> NAME/KEY: VARIANT
<222> LOCATION: 9
<223> OTHER INFORMATION: Xaa = Ser, Thr, Tyr and other
      natural/non-natural H-bond donor/acceptor residue

<400> SEQUENCE: 57

Leu Ala Leu Arg Gln Ala Xaa Xaa Xaa Phe Ser Arg Arg Tyr Arg Gly
 1               5                  10                  15


<210> SEQ ID NO 58
<211> LENGTH: 35
<212> TYPE: PRT
<213> ORGANISM: Artificial Sequence
<220> FEATURE:
<223> OTHER INFORMATION: Engineered peptides based on Mfn-1 protein

<400> SEQUENCE: 58

Lys Glu Ile Asp Gln Leu Glu Lys Ile Gln Asn Asn Ser Lys Leu Leu
 1               5                  10                  15

Arg Asn Lys Ala Val Gln Leu Glu Asn Glu Leu Glu Asn Phe Thr Lys
            20                  25                  30

Gln Phe Leu
        35


<210> SEQ ID NO 59
<211> LENGTH: 35
<212> TYPE: PRT
<213> ORGANISM: Artificial Sequence
<220> FEATURE:
<223> OTHER INFORMATION: Engineered peptides based on Mfn-1 protein
<220> FEATURE:
<221> NAME/KEY: VARIANT
<222> LOCATION: 4
<223> OTHER INFORMATION: Xaa = Lys, Arg, Asn, Gln and
      other natural/non-natural basic residue

<400> SEQUENCE: 59

Lys Glu Ile Xaa Gln Leu Glu Lys Ile Gln Asn Asn Ser Lys Leu Leu
 1               5                  10                  15

Arg Asn Lys Ala Val Gln Leu Glu Asn Glu Leu Glu Asn Phe Thr Lys
            20                  25                  30

Gln Phe Leu
        35


<210> SEQ ID NO 60
<211> LENGTH: 35
<212> TYPE: PRT
```

```
<213> ORGANISM: Artificial Sequence
<220> FEATURE:
<223> OTHER INFORMATION: Engineered peptides based on Mfn-1 protein
<220> FEATURE:
<221> NAME/KEY: VARIANT
<222> LOCATION: 4, 7, 24
<223> OTHER INFORMATION: Xaa = Lys, Arg, Asn, Gln and
      other natural/non-natural basic residue

<400> SEQUENCE: 60

Lys Glu Ile Xaa Gln Leu Xaa Lys Ile Gln Asn Asn Ser Lys Leu Leu
 1               5                  10                  15

Arg Asn Lys Ala Val Gln Leu Xaa Asn Glu Leu Glu Asn Phe Thr Lys
            20                  25                  30

Gln Phe Leu
        35


<210> SEQ ID NO 61
<211> LENGTH: 35
<212> TYPE: PRT
<213> ORGANISM: Artificial Sequence
<220> FEATURE:
<223> OTHER INFORMATION: Engineered peptides based on Mfn-1 protein
<220> FEATURE:
<221> NAME/KEY: VARIANT
<222> LOCATION: 4, 7, 24
<223> OTHER INFORMATION: Xaa = Lys, Arg, Asn, Gln and
      other natural/non-natural basic residue

<400> SEQUENCE: 61

Lys Glu Ile Xaa Gln Leu Xaa Lys Ile Gln Asn Asn Ser Lys Leu Leu
 1               5                  10                  15

Arg Asn Lys Ala Val Gln Leu Xaa Asn Glu Leu Glu Asn Phe Thr Lys
            20                  25                  30

Gln Phe Leu
        35


<210> SEQ ID NO 62
<211> LENGTH: 35
<212> TYPE: PRT
<213> ORGANISM: Artificial Sequence
<220> FEATURE:
<223> OTHER INFORMATION: Engineered peptides based on Mfn-1 protein
<220> FEATURE:
<221> NAME/KEY: VARIANT
<222> LOCATION: 4, 7, 24, 26
<223> OTHER INFORMATION: Xaa = Lys, Arg, Asn, Gln and
      other natural/non-natural basic residue

<400> SEQUENCE: 62

Lys Glu Ile Xaa Gln Leu Xaa Lys Ile Gln Asn Asn Ser Lys Leu Leu
 1               5                  10                  15

Arg Asn Lys Ala Val Gln Leu Xaa Asn Xaa Leu Glu Asn Phe Thr Lys
            20                  25                  30

Gln Phe Leu
        35


<210> SEQ ID NO 63
<211> LENGTH: 35
<212> TYPE: PRT
<213> ORGANISM: Artificial Sequence
<220> FEATURE:
<223> OTHER INFORMATION: Engineered peptides based on Mfn-1 protein
<220> FEATURE:
<221> NAME/KEY: VARIANT
<222> LOCATION: 4, 7, 24, 26, 28
<223> OTHER INFORMATION: Xaa = Lys, Arg, Asn, Gln and
      other natural/non-natural basic residue
```

<400> SEQUENCE: 63

Lys Glu Ile Xaa Gln Leu Xaa Lys Ile Gln Asn Asn Ser Lys Leu Leu
1 5 10 15

Arg Asn Lys Ala Val Gln Leu Xaa Asn Xaa Leu Xaa Asn Phe Thr Lys
20 25 30

Gln Phe Leu
35

<210> SEQ ID NO 64
<211> LENGTH: 16
<212> TYPE: PRT
<213> ORGANISM: Artificial Sequence
<220> FEATURE:
<223> OTHER INFORMATION: Engineered peptides based on Mfn-1 protein

<400> SEQUENCE: 64

Lys Ile Gln Asn Asn Ser Lys Leu Leu Arg Asn Lys Ala Val Gln Leu
1 5 10 15

<210> SEQ ID NO 65
<211> LENGTH: 40
<212> TYPE: PRT
<213> ORGANISM: Artificial Sequence
<220> FEATURE:
<223> OTHER INFORMATION: Engineered peptides based on Mfn-2 protein

<400> SEQUENCE: 65

Asn Lys Lys Ile Glu Val Leu Asp Ser Leu Gln Ser Lys Ala Lys Leu
1 5 10 15

Leu Arg Asn Lys Ala Gly Trp Leu Asp Ser Glu Leu Asn Met Phe Thr
20 25 30

His Gln Tyr Leu Gln Pro Ser Arg
35 40

<210> SEQ ID NO 66
<211> LENGTH: 40
<212> TYPE: PRT
<213> ORGANISM: Artificial Sequence
<220> FEATURE:
<223> OTHER INFORMATION: Engineered peptides based on Mfn-2 protein
<220> FEATURE:
<221> NAME/KEY: VARIANT
<222> LOCATION: 5
<223> OTHER INFORMATION: Xaa = Lys, Arg, Asn, Gln and
other natural/non-natural basic residue

<400> SEQUENCE: 66

Asn Lys Lys Ile Xaa Val Leu Asp Ser Leu Gln Ser Lys Ala Lys Leu
1 5 10 15

Leu Arg Asn Lys Ala Gly Trp Leu Asp Ser Glu Leu Asn Met Phe Thr
20 25 30

His Gln Tyr Leu Gln Pro Ser Arg
35 40

<210> SEQ ID NO 67
<211> LENGTH: 40
<212> TYPE: PRT
<213> ORGANISM: Artificial Sequence
<220> FEATURE:
<223> OTHER INFORMATION: Engineered peptides based on Mfn-2 protein
<220> FEATURE:
<221> NAME/KEY: VARIANT
<222> LOCATION: 8
<223> OTHER INFORMATION: Xaa = Lys, Arg, Asn, Gln and
other natural/non-natural basic residue

<400> SEQUENCE: 67

```
Asn Lys Lys Ile Glu Val Leu Xaa Ser Leu Gln Ser Lys Ala Lys Leu
 1               5                  10                  15

Leu Arg Asn Lys Ala Gly Trp Leu Asp Ser Glu Leu Asn Met Phe Thr
            20                  25                  30

His Gln Tyr Leu Gln Pro Ser Arg
        35                  40
```

<210> SEQ ID NO 68
<211> LENGTH: 40
<212> TYPE: PRT
<213> ORGANISM: Artificial Sequence
<220> FEATURE:
<223> OTHER INFORMATION: Engineered peptides based on Mfn-2 protein
<220> FEATURE:
<221> NAME/KEY: VARIANT
<222> LOCATION: 25
<223> OTHER INFORMATION: Xaa = Lys, Arg, Asn, Gln and other natural/non-natural basic residue

<400> SEQUENCE: 68

```
Asn Lys Lys Ile Glu Val Leu Asp Ser Leu Gln Ser Lys Ala Lys Leu
 1               5                  10                  15

Leu Arg Asn Lys Ala Gly Trp Leu Xaa Ser Glu Leu Asn Met Phe Thr
            20                  25                  30

His Gln Tyr Leu Gln Pro Ser Arg
        35                  40
```

<210> SEQ ID NO 69
<211> LENGTH: 40
<212> TYPE: PRT
<213> ORGANISM: Artificial Sequence
<220> FEATURE:
<223> OTHER INFORMATION: Engineered peptides based on Mfn-2 protein
<220> FEATURE:
<221> NAME/KEY: VARIANT
<222> LOCATION: 27
<223> OTHER INFORMATION: Xaa = Lys, Arg, Asn, Gln and other natural/non-natural basic residue

<400> SEQUENCE: 69

```
Asn Lys Lys Ile Glu Val Leu Asp Ser Leu Gln Ser Lys Ala Lys Leu
 1               5                  10                  15

Leu Arg Asn Lys Ala Gly Trp Leu Asp Ser Xaa Leu Asn Met Phe Thr
            20                  25                  30

His Gln Tyr Leu Gln Pro Ser Arg
        35                  40
```

<210> SEQ ID NO 70
<211> LENGTH: 40
<212> TYPE: PRT
<213> ORGANISM: Artificial Sequence
<220> FEATURE:
<223> OTHER INFORMATION: Engineered peptides based on Mfn-2 protein
<220> FEATURE:
<221> NAME/KEY: VARIANT
<222> LOCATION: 30
<223> OTHER INFORMATION: Xaa = Ser, Thr, Tyr and other natural/non-natural H-bond donor/acceptor residue

<400> SEQUENCE: 70

```
Asn Lys Lys Ile Glu Val Leu Asp Ser Leu Gln Ser Lys Ala Lys Leu
 1               5                  10                  15

Leu Arg Asn Lys Ala Gly Trp Leu Asp Ser Glu Leu Asn Xaa Phe Thr
            20                  25                  30
```

```
His Gln Tyr Leu Gln Pro Ser Arg
        35                  40


<210> SEQ ID NO 71
<211> LENGTH: 40
<212> TYPE: PRT
<213> ORGANISM: Artificial Sequence
<220> FEATURE:
<223> OTHER INFORMATION: Engineered peptides based on Mfn-2 protein
<220> FEATURE:
<221> NAME/KEY: VARIANT
<222> LOCATION: 5, 8, 25, 27, 30
<223> OTHER INFORMATION: Xaa = Lys, Arg, Asn, Gln and
      other natural/non-natural basic residue
<220> FEATURE:
<221> NAME/KEY: VARIANT
<222> LOCATION: 30
<223> OTHER INFORMATION: Xaa = Ser, Thr, Tyr and other
      natural/non-natural H-bond donor/acceptor residue

<400> SEQUENCE: 71

Asn Lys Lys Ile Xaa Val Leu Xaa Ser Leu Gln Ser Lys Ala Lys Leu
 1               5                  10                  15

Leu Arg Asn Lys Ala Gly Trp Leu Xaa Ser Xaa Leu Asn Xaa Phe Thr
            20                  25                  30

His Gln Tyr Leu Gln Pro Ser Arg
        35                  40


<210> SEQ ID NO 72
<211> LENGTH: 23
<212> TYPE: PRT
<213> ORGANISM: Artificial Sequence
<220> FEATURE:
<223> OTHER INFORMATION: Engineered peptides based on Mfn-2 protein

<400> SEQUENCE: 72

Lys Lys Ile Glu Val Leu Asp Ser Leu Gln Ser Lys Ala Lys Leu Leu
 1               5                  10                  15

Arg Asn Lys Ala Gly Trp Leu
            20


<210> SEQ ID NO 73
<211> LENGTH: 23
<212> TYPE: PRT
<213> ORGANISM: Artificial Sequence
<220> FEATURE:
<223> OTHER INFORMATION: Engineered peptides based on Mfn-2 protein
<220> FEATURE:
<221> NAME/KEY: VARIANT
<222> LOCATION: 4
<223> OTHER INFORMATION: Xaa = Lys, Arg, Asn, Gln and
      other natural/non-natural basic residue

<400> SEQUENCE: 73

Lys Lys Ile Xaa Val Leu Asp Ser Leu Gln Ser Lys Ala Lys Leu Leu
 1               5                  10                  15

Arg Asn Lys Ala Gly Trp Leu
            20


<210> SEQ ID NO 74
<211> LENGTH: 23
<212> TYPE: PRT
<213> ORGANISM: Artificial Sequence
<220> FEATURE:
<223> OTHER INFORMATION: Engineered peptides based on Mfn-2 protein
<220> FEATURE:
<221> NAME/KEY: VARIANT
<222> LOCATION: 7
```

<223> OTHER INFORMATION: Xaa = Lys, Arg, Asn, Gln and
other natural/non-natural basic residue

<400> SEQUENCE: 74

Lys Lys Ile Glu Val Leu Xaa Ser Leu Gln Ser Lys Ala Lys Leu Leu
1 5 10 15

Arg Asn Lys Ala Gly Trp Leu
20

<210> SEQ ID NO 75
<211> LENGTH: 23
<212> TYPE: PRT
<213> ORGANISM: Artificial Sequence
<220> FEATURE:
<223> OTHER INFORMATION: Engineered peptides based on Mfn-2 protein
<220> FEATURE:
<221> NAME/KEY: VARIANT
<222> LOCATION: 4, 7
<223> OTHER INFORMATION: Xaa = Lys, Arg, Asn, Gln and
other natural/non-natural basic residue

<400> SEQUENCE: 75

Lys Lys Ile Xaa Val Leu Xaa Ser Leu Gln Ser Lys Ala Lys Leu Leu
1 5 10 15

Arg Asn Lys Ala Gly Trp Leu
20

<210> SEQ ID NO 76
<211> LENGTH: 18
<212> TYPE: PRT
<213> ORGANISM: Artificial Sequence
<220> FEATURE:
<223> OTHER INFORMATION: Engineered peptides based on Dnm-1 protein

<400> SEQUENCE: 76

Lys Leu Leu Pro Leu Arg Arg Gly Tyr Ile Gly Val Val Asn Arg Ser
1 5 10 15

Gln Lys

<210> SEQ ID NO 77
<211> LENGTH: 14
<212> TYPE: PRT
<213> ORGANISM: Artificial Sequence
<220> FEATURE:
<223> OTHER INFORMATION: Engineered peptides based on Dnm-1 protein

<400> SEQUENCE: 77

Arg Lys Phe Phe Leu Ser His Pro Ser Tyr Arg His Leu Ala
1 5 10

<210> SEQ ID NO 78
<211> LENGTH: 15
<212> TYPE: PRT
<213> ORGANISM: Artificial Sequence
<220> FEATURE:
<223> OTHER INFORMATION: Engineered peptides based on Dnm-1 protein

<400> SEQUENCE: 78

Gly Leu Arg Asn Lys Leu Gln Ser Gln Leu Leu Ser Ile Glu Lys
1 5 10 15

<210> SEQ ID NO 79
<211> LENGTH: 18
<212> TYPE: PRT
<213> ORGANISM: Artificial Sequence
<220> FEATURE:
<223> OTHER INFORMATION: Engineered peptides based on Dnm-1 protein -continued

<400> SEQUENCE: 79

Ala Arg Lys Thr Lys Ala Leu Leu Gln Met Val Gln Gln Phe Ala Val
1 5 10 15

Asp Phe

<210> SEQ ID NO 80
<211> LENGTH: 11
<212> TYPE: PRT
<213> ORGANISM: Artificial Sequence
<220> FEATURE:
<223> OTHER INFORMATION: Engineered peptides based on Dnm-1 protein

<400> SEQUENCE: 80

Ala Thr Val Lys Lys Gln Val Gln Lys Leu Lys
1 5 10

<210> SEQ ID NO 81
<211> LENGTH: 20
<212> TYPE: PRT
<213> ORGANISM: Artificial Sequence
<220> FEATURE:
<223> OTHER INFORMATION: Engineered peptides based on Dnm-1 protein

<400> SEQUENCE: 81

Val Ile Arg Lys Gly Trp Leu Thr Ile Asn Asn Ile Gly Ile Met Lys
1 5 10 15

Gly Gly Ser Lys
20

<210> SEQ ID NO 82
<211> LENGTH: 30
<212> TYPE: PRT
<213> ORGANISM: Artificial Sequence
<220> FEATURE:
<223> OTHER INFORMATION: Engineered peptides based on Dnm-1 protein

<400> SEQUENCE: 82

Asn Leu Lys Leu Arg Asp Val Glu Lys Gly Phe Met Ser Ser Lys His
1 5 10 15

Ile Phe Ala Leu Phe Asn Thr Glu Gln Arg Asn Val Tyr Lys
20 25 30

<210> SEQ ID NO 83
<211> LENGTH: 17
<212> TYPE: PRT
<213> ORGANISM: Artificial Sequence
<220> FEATURE:
<223> OTHER INFORMATION: Engineered peptides based on Dnm-1 protein

<400> SEQUENCE: 83

Lys Ala Ser Phe Leu Arg Ala Gly Val Tyr Pro Glu Arg Val Gly Asp
1 5 10 15

Lys

<210> SEQ ID NO 84
<211> LENGTH: 15
<212> TYPE: PRT
<213> ORGANISM: Artificial Sequence
<220> FEATURE:
<223> OTHER INFORMATION: Engineered peptides based on Dnm-1 protein
<220> FEATURE:
<221> NAME/KEY: VARIANT
<222> LOCATION: 14
<223> OTHER INFORMATION: Xaa = Lys, Arg, Asn, Gln and other
natural/non-natural basic residue

<400> SEQUENCE: 84

Gly Leu Arg Asn Lys Leu Gln Ser Gln Leu Leu Ser Ile Xaa Lys
1 5 10 15

<210> SEQ ID NO 85
<211> LENGTH: 18
<212> TYPE: PRT
<213> ORGANISM: Artificial Sequence
<220> FEATURE:
<223> OTHER INFORMATION: Engineered peptides based on Dnm-1 protein
<220> FEATURE:
<221> NAME/KEY: VARIANT
<222> LOCATION: 17
<223> OTHER INFORMATION: Xaa = Lys, Arg, Asn, Gln and other natural/non-natural basic residue

<400> SEQUENCE: 85

Ala Arg Lys Thr Lys Ala Leu Leu Gln Met Val Gln Gln Phe Ala Val
1 5 10 15

Xaa Phe

<210> SEQ ID NO 86
<211> LENGTH: 30
<212> TYPE: PRT
<213> ORGANISM: Artificial Sequence
<220> FEATURE:
<223> OTHER INFORMATION: Engineered peptides based on Dnm-1 protein
<220> FEATURE:
<221> NAME/KEY: VARIANT
<222> LOCATION: 6
<223> OTHER INFORMATION: Xaa = Lys, Arg, Asn, Gln and other natural/non-natural basic residue

<400> SEQUENCE: 86

Asn Leu Lys Leu Arg Xaa Val Glu Lys Gly Phe Met Ser Ser Lys His
1 5 10 15

Ile Phe Ala Leu Phe Asn Thr Glu Gln Arg Asn Val Tyr Lys
20 25 30

<210> SEQ ID NO 87
<211> LENGTH: 30
<212> TYPE: PRT
<213> ORGANISM: Artificial Sequence
<220> FEATURE:
<223> OTHER INFORMATION: Engineered peptides based on Dnm-1 protein
<220> FEATURE:
<221> NAME/KEY: VARIANT
<222> LOCATION: 8
<223> OTHER INFORMATION: Xaa = Lys, Arg, Asn, Gln and other natural/non-natural basic residue

<400> SEQUENCE: 87

Asn Leu Lys Leu Arg Asp Val Xaa Lys Gly Phe Met Ser Ser Lys His
1 5 10 15

Ile Phe Ala Leu Phe Asn Thr Glu Gln Arg Asn Val Tyr Lys
20 25 30

<210> SEQ ID NO 88
<211> LENGTH: 30
<212> TYPE: PRT
<213> ORGANISM: Artificial Sequence
<220> FEATURE:
<223> OTHER INFORMATION: Engineered peptides based on Dnm-1 protein
<220> FEATURE:
<221> NAME/KEY: VARIANT
<222> LOCATION: 24
<223> OTHER INFORMATION: Xaa = Lys, Arg, Asn, Gln and other natural/non-natural basic residue

<400> SEQUENCE: 88

Asn Leu Lys Leu Arg Asp Val Glu Lys Gly Phe Met Ser Ser Lys His
1 5 10 15

Ile Phe Ala Leu Phe Asn Thr Xaa Gln Arg Asn Val Tyr Lys
20 25 30

<210> SEQ ID NO 89
<211> LENGTH: 30
<212> TYPE: PRT
<213> ORGANISM: Artificial Sequence
<220> FEATURE:
<223> OTHER INFORMATION: Engineered peptides based on Dnm-1 protein
<220> FEATURE:
<221> NAME/KEY: VARIANT
<222> LOCATION: 6, 8
<223> OTHER INFORMATION: Xaa = Lys, Arg, Asn, Gln and
other natural/non-natural basic residue

<400> SEQUENCE: 89

Asn Leu Lys Leu Arg Xaa Val Xaa Lys Gly Phe Met Ser Ser Lys His
1 5 10 15

Ile Phe Ala Leu Phe Asn Thr Glu Gln Arg Asn Val Tyr Lys
20 25 30

<210> SEQ ID NO 90
<211> LENGTH: 30
<212> TYPE: PRT
<213> ORGANISM: Artificial Sequence
<220> FEATURE:
<223> OTHER INFORMATION: Engineered peptides based on Dnm-1 protein
<220> FEATURE:
<221> NAME/KEY: VARIANT
<222> LOCATION: 6, 8, 24
<223> OTHER INFORMATION: Xaa = Lys, Arg, Asn, Gln and
other natural/non-natural basic residue

<400> SEQUENCE: 90

Asn Leu Lys Leu Arg Xaa Val Xaa Lys Gly Phe Met Ser Ser Lys His
1 5 10 15

Ile Phe Ala Leu Phe Asn Thr Xaa Gln Arg Asn Val Tyr Lys
20 25 30

<210> SEQ ID NO 91
<211> LENGTH: 17
<212> TYPE: PRT
<213> ORGANISM: Artificial Sequence
<220> FEATURE:
<223> OTHER INFORMATION: Engineered peptides based on Dnm-1 protein
<220> FEATURE:
<221> NAME/KEY: VARIANT
<222> LOCATION: 12
<223> OTHER INFORMATION: Xaa = Lys, Arg, Asn, Gln and
other natural/non-natural basic residue

<400> SEQUENCE: 91

Lys Ala Ser Phe Leu Arg Ala Gly Val Tyr Pro Xaa Arg Val Gly Asp
1 5 10 15

Lys

<210> SEQ ID NO 92
<211> LENGTH: 17
<212> TYPE: PRT
<213> ORGANISM: Artificial Sequence
<220> FEATURE:
<223> OTHER INFORMATION: Engineered peptides based on Dnm-1 protein
<220> FEATURE:
<221> NAME/KEY: VARIANT
<222> LOCATION: 16
<223> OTHER INFORMATION: Xaa = Lys, Arg, Asn, Gln and
other natural/non-natural basic residue

<400> SEQUENCE: 92

Lys Ala Ser Phe Leu Arg Ala Gly Val Tyr Pro Glu Arg Val Gly Xaa
1 5 10 15

Lys

<210> SEQ ID NO 93
<211> LENGTH: 17
<212> TYPE: PRT
<213> ORGANISM: Artificial Sequence
<220> FEATURE:
<223> OTHER INFORMATION: Engineered peptides based on Dnm-1 protein
<220> FEATURE:
<221> NAME/KEY: VARIANT
<222> LOCATION: 12, 16
<223> OTHER INFORMATION: Xaa = Lys, Arg, Asn, Gln and
other natural/non-natural basic residue

<400> SEQUENCE: 93

Lys Ala Ser Phe Leu Arg Ala Gly Val Tyr Pro Xaa Arg Val Gly Xaa
1 5 10 15

Lys

<210> SEQ ID NO 94
<211> LENGTH: 20
<212> TYPE: PRT
<213> ORGANISM: Artificial Sequence
<220> FEATURE:
<223> OTHER INFORMATION: Engineered peptides based on Dnm-2 protein

<400> SEQUENCE: 94

Lys Leu Ala Lys Glu Val Asp Pro Gln Gly Leu Arg Thr Ile Gly Val
1 5 10 15

Ile Thr Lys Leu
20

<210> SEQ ID NO 95
<211> LENGTH: 15
<212> TYPE: PRT
<213> ORGANISM: Artificial Sequence
<220> FEATURE:
<223> OTHER INFORMATION: Engineered peptides based on Dnm-2 protein

<400> SEQUENCE: 95

Ala Leu Arg Ser Lys Leu Gln Ser Gln Leu Leu Ser Leu Glu Lys
1 5 10 15

<210> SEQ ID NO 96
<211> LENGTH: 16
<212> TYPE: PRT
<213> ORGANISM: Artificial Sequence
<220> FEATURE:
<223> OTHER INFORMATION: Engineered peptides based on Dnm-2 protein

<400> SEQUENCE: 96

Thr Arg Lys Thr Lys Ala Leu Leu Gln Met Val Gln Gln Phe Gly Val
1 5 10 15

<210> SEQ ID NO 97
<211> LENGTH: 11
<212> TYPE: PRT
<213> ORGANISM: Artificial Sequence
<220> FEATURE:
<223> OTHER INFORMATION: Engineered peptides based on Dnm-2 protein

<400> SEQUENCE: 97

Ala Ile Val Lys Lys Gln Val Val Lys Leu Lys
 1               5                   10

<210> SEQ ID NO 98
<211> LENGTH: 18
<212> TYPE: PRT
<213> ORGANISM: Artificial Sequence
<220> FEATURE:
<223> OTHER INFORMATION: Engineered peptides based on Dnm-2 protein

<400> SEQUENCE: 98

Ala Gln Gln Arg Ser Thr Gln Leu Asn Lys Lys Arg Ala Ile Pro Asn
 1               5                   10                  15

Gln Gly

<210> SEQ ID NO 99
<211> LENGTH: 40
<212> TYPE: PRT
<213> ORGANISM: Artificial Sequence
<220> FEATURE:
<223> OTHER INFORMATION: Engineered peptides based on Dnm-2 protein

<400> SEQUENCE: 99

Lys Glu Lys Lys Tyr Met Leu Pro Leu Asp Asn Leu Lys Ile Arg Asp
 1               5                   10                  15

Val Glu Lys Gly Phe Met Ser Asn Lys His Val Phe Ala Ile Phe Asn
            20                  25                  30

Thr Glu Gln Arg Asn Val Tyr Lys
        35                  40

<210> SEQ ID NO 100
<211> LENGTH: 30
<212> TYPE: PRT
<213> ORGANISM: Artificial Sequence
<220> FEATURE:
<223> OTHER INFORMATION: Engineered peptides based on Dnm-2 protein

<400> SEQUENCE: 100

Asn Leu Lys Ile Arg Asp Val Glu Lys Gly Phe Met Ser Asn Lys His
 1               5                   10                  15

Val Phe Ala Ile Phe Asn Thr Glu Gln Arg Asn Val Tyr Lys
            20                  25                  30

<210> SEQ ID NO 101
<211> LENGTH: 18
<212> TYPE: PRT
<213> ORGANISM: Artificial Sequence
<220> FEATURE:
<223> OTHER INFORMATION: Engineered peptides based on Dnm-2 protein

<400> SEQUENCE: 101

Ser Trp Lys Ala Ser Phe Leu Arg Ala Gly Val Tyr Pro Glu Lys Asp
 1               5                   10                  15

Gln Ala

<210> SEQ ID NO 102
<211> LENGTH: 20
<212> TYPE: PRT
<213> ORGANISM: Artificial Sequence
<220> FEATURE:
<223> OTHER INFORMATION: Engineered peptides based on Dnm-2 protein
<220> FEATURE:
<221> NAME/KEY: VARIANT
<222> LOCATION: 5
<223> OTHER INFORMATION: Xaa = Lys, Arg, Asn, Gln and
      other natural/non-natural basic residue

<400> SEQUENCE: 102

```
Lys Leu Ala Lys Xaa Val Asp Pro Gln Gly Leu Arg Thr Ile Gly Val
 1               5                  10                  15

Ile Thr Lys Leu
            20
```

<210> SEQ ID NO 103
<211> LENGTH: 20
<212> TYPE: PRT
<213> ORGANISM: Artificial Sequence
<220> FEATURE:
<223> OTHER INFORMATION: Engineered peptides based on Dnm-2 protein
<220> FEATURE:
<221> NAME/KEY: VARIANT
<222> LOCATION: 7
<223> OTHER INFORMATION: Xaa = Lys, Arg, Asn, Gln and
      other natural/non-natural basic residue

<400> SEQUENCE: 103

```
Lys Leu Ala Lys Glu Val Xaa Pro Gln Gly Leu Arg Thr Ile Gly Val
 1               5                  10                  15

Ile Thr Lys Leu
            20
```

<210> SEQ ID NO 104
<211> LENGTH: 20
<212> TYPE: PRT
<213> ORGANISM: Artificial Sequence
<220> FEATURE:
<223> OTHER INFORMATION: Engineered peptides based on Dnm-2 protein
<220> FEATURE:
<221> NAME/KEY: VARIANT
<222> LOCATION: 5, 7
<223> OTHER INFORMATION: Xaa = Lys, Arg, Asn, Gln and
      other natural/non-natural basic residue

<400> SEQUENCE: 104

```
Lys Leu Ala Lys Xaa Val Xaa Pro Gln Gly Leu Arg Thr Ile Gly Val
 1               5                  10                  15

Ile Thr Lys Leu
            20
```

<210> SEQ ID NO 105
<211> LENGTH: 15
<212> TYPE: PRT
<213> ORGANISM: Artificial Sequence
<220> FEATURE:
<223> OTHER INFORMATION: Engineered peptides based on Dnm-2 protein
<220> FEATURE:
<221> NAME/KEY: VARIANT
<222> LOCATION: 14
<223> OTHER INFORMATION: Xaa = Lys, Arg, Asn, Gln and
      other natural/non-natural basic residue

<400> SEQUENCE: 105

```
Ala Leu Arg Ser Lys Leu Gln Ser Gln Leu Leu Ser Leu Xaa Lys
 1               5                  10                  15
```

<210> SEQ ID NO 106
<211> LENGTH: 11
<212> TYPE: PRT
<213> ORGANISM: Artificial Sequence
<220> FEATURE:
<223> OTHER INFORMATION: Engineered peptides based on Dnm-2 protein
<220> FEATURE:

<221> NAME/KEY: VARIANT
<222> LOCATION: 1
<223> OTHER INFORMATION: Xaa = anthrylalanine or other non-natural amino acid

<400> SEQUENCE: 106

Xaa Ile Val Lys Lys Gln Val Val Lys Leu Lys
1 5 10

<210> SEQ ID NO 107
<211> LENGTH: 15
<212> TYPE: PRT
<213> ORGANISM: Artificial Sequence
<220> FEATURE:
<223> OTHER INFORMATION: Engineered peptides based on Dnm-2 protein

<400> SEQUENCE: 107

Lys Glu Lys Lys Tyr Met Leu Pro Leu Asp Asn Leu Lys Ile Arg
1 5 10 15

<210> SEQ ID NO 108
<211> LENGTH: 15
<212> TYPE: PRT
<213> ORGANISM: Artificial Sequence
<220> FEATURE:
<223> OTHER INFORMATION: Engineered peptides based on Dnm-2 protein
<220> FEATURE:
<221> NAME/KEY: VARIANT
<222> LOCATION: 2
<223> OTHER INFORMATION: Xaa = Ser, Thr, Tyr and other natural/non-natural H-bond donor/acceptor residue

<400> SEQUENCE: 108

Lys Xaa Lys Lys Tyr Met Leu Pro Leu Asp Asn Leu Lys Ile Arg
1 5 10 15

<210> SEQ ID NO 109
<211> LENGTH: 15
<212> TYPE: PRT
<213> ORGANISM: Artificial Sequence
<220> FEATURE:
<223> OTHER INFORMATION: Engineered peptides based on Dnm-2 protein
<220> FEATURE:
<221> NAME/KEY: VARIANT
<222> LOCATION: 6
<223> OTHER INFORMATION: Xaa = Ser, Thr, Tyr and other natural/non-natural H-bond donor/acceptor residue

<400> SEQUENCE: 109

Lys Glu Lys Lys Tyr Xaa Leu Pro Leu Asp Asn Leu Lys Ile Arg
1 5 10 15

<210> SEQ ID NO 110
<211> LENGTH: 15
<212> TYPE: PRT
<213> ORGANISM: Artificial Sequence
<220> FEATURE:
<223> OTHER INFORMATION: Engineered peptides based on Dnm-2 protein
<220> FEATURE:
<221> NAME/KEY: VARIANT
<222> LOCATION: 10
<223> OTHER INFORMATION: Xaa = Lys, Arg, Asn, Gln and other natural/non-natural basic residue

<400> SEQUENCE: 110

Lys Glu Lys Lys Tyr Met Leu Pro Leu Xaa Asn Leu Lys Ile Arg
1 5 10 15

<210> SEQ ID NO 111
<211> LENGTH: 15

<212> TYPE: PRT
<213> ORGANISM: Artificial Sequence
<220> FEATURE:
<223> OTHER INFORMATION: Engineered peptides based on Dnm-2 protein
<220> FEATURE:
<221> NAME/KEY: VARIANT
<222> LOCATION: 10
<223> OTHER INFORMATION: Xaa = Ser, Thr, Tyr and other natural/non-natural H-bond donor/acceptor residue

<400> SEQUENCE: 111

```
Lys Glu Lys Lys Tyr Met Leu Pro Leu Xaa Asn Leu Lys Ile Arg
 1               5                  10                  15
```

<210> SEQ ID NO 112
<211> LENGTH: 15
<212> TYPE: PRT
<213> ORGANISM: Artificial Sequence
<220> FEATURE:
<223> OTHER INFORMATION: Engineered peptides based on Dnm-2 protein
<220> FEATURE:
<221> NAME/KEY: VARIANT
<222> LOCATION: 2
<223> OTHER INFORMATION: Xaa = Ser, Thr, Tyr and other natural/non-natural H-bond donor/acceptor residue
<220> FEATURE:
<221> NAME/KEY: VARIANT
<222> LOCATION: 10
<223> OTHER INFORMATION: Xaa = Lys, Arg, Asn, Gln and other natural/non-natural basic residue

<400> SEQUENCE: 112

```
Lys Xaa Lys Lys Tyr Met Leu Pro Leu Xaa Asn Leu Lys Ile Arg
 1               5                  10                  15
```

<210> SEQ ID NO 113
<211> LENGTH: 15
<212> TYPE: PRT
<213> ORGANISM: Artificial Sequence
<220> FEATURE:
<223> OTHER INFORMATION: Engineered peptides based on Dnm-2 protein
<220> FEATURE:
<221> NAME/KEY: VARIANT
<222> LOCATION: 2, 6
<223> OTHER INFORMATION: Xaa = Ser, Thr, Tyr and other natural/non-natural H-bond donor/acceptor residue
<220> FEATURE:
<221> NAME/KEY: VARIANT
<222> LOCATION: 10
<223> OTHER INFORMATION: Xaa = Lys, Arg, Asn, Gln and other natural/non-natural basic residue

<400> SEQUENCE: 113

```
Lys Xaa Lys Lys Tyr Xaa Leu Pro Leu Xaa Asn Leu Lys Ile Arg
 1               5                  10                  15
```

<210> SEQ ID NO 114
<211> LENGTH: 22
<212> TYPE: PRT
<213> ORGANISM: Artificial Sequence
<220> FEATURE:
<223> OTHER INFORMATION: Engineered peptides based on Dnm-2 protein

<400> SEQUENCE: 114

```
Lys Gly Phe Met Ser Asn Lys His Val Phe Ala Ile Phe Asn Thr Glu
 1               5                  10                  15

Gln Arg Asn Val Tyr Lys
            20
```

<210> SEQ ID NO 115
<211> LENGTH: 40

<212> TYPE: PRT
<213> ORGANISM: Artificial Sequence
<220> FEATURE:
<223> OTHER INFORMATION: Engineered peptides based on Dnm-2 protein
<220> FEATURE:
<221> NAME/KEY: VARIANT
<222> LOCATION: 2
<223> OTHER INFORMATION: Xaa = Ser, Thr, Tyr and other natural/non-natural H-bond donor/acceptor residue

<400> SEQUENCE: 115

```
Lys Xaa Lys Lys Tyr Met Leu Pro Leu Asp Asn Leu Lys Ile Arg Asp
 1               5                  10                  15

Val Glu Lys Gly Phe Met Ser Asn Lys His Val Phe Ala Ile Phe Asn
            20                  25                  30

Thr Glu Gln Arg Asn Val Tyr Lys
        35                  40
```

<210> SEQ ID NO 116
<211> LENGTH: 40
<212> TYPE: PRT
<213> ORGANISM: Artificial Sequence
<220> FEATURE:
<223> OTHER INFORMATION: Engineered peptides based on Dnm-2 protein
<220> FEATURE:
<221> NAME/KEY: VARIANT
<222> LOCATION: 6
<223> OTHER INFORMATION: Xaa = Ser, Thr, Tyr and other natural/non-natural H-bond donor/acceptor residue

<400> SEQUENCE: 116

```
Lys Glu Lys Lys Tyr Xaa Leu Pro Leu Asp Asn Leu Lys Ile Arg Asp
 1               5                  10                  15

Val Glu Lys Gly Phe Met Ser Asn Lys His Val Phe Ala Ile Phe Asn
            20                  25                  30

Thr Glu Gln Arg Asn Val Tyr Lys
        35                  40
```

<210> SEQ ID NO 117
<211> LENGTH: 40
<212> TYPE: PRT
<213> ORGANISM: Artificial Sequence
<220> FEATURE:
<223> OTHER INFORMATION: Engineered peptides based on Dnm-2 protein
<220> FEATURE:
<221> NAME/KEY: VARIANT
<222> LOCATION: 22
<223> OTHER INFORMATION: Xaa = Ser, Thr, Tyr and other natural/non-natural H-bond donor/acceptor residue

<400> SEQUENCE: 117

```
Lys Glu Lys Lys Tyr Met Leu Pro Leu Asp Asn Leu Lys Ile Arg Asp
 1               5                  10                  15

Val Glu Lys Gly Phe Xaa Ser Asn Lys His Val Phe Ala Ile Phe Asn
            20                  25                  30

Thr Glu Gln Arg Asn Val Tyr Lys
        35                  40
```

<210> SEQ ID NO 118
<211> LENGTH: 30
<212> TYPE: PRT
<213> ORGANISM: Artificial Sequence
<220> FEATURE:
<223> OTHER INFORMATION: Engineered peptides based on Dnm-2 protein
<220> FEATURE:
<221> NAME/KEY: VARIANT
<222> LOCATION: 6
<223> OTHER INFORMATION: Xaa = Lys, Arg, Asn, Gln and other natural/non-natural basic residue

<400> SEQUENCE: 118

Asn Leu Lys Ile Arg Xaa Val Glu Lys Gly Phe Met Ser Asn Lys His
1 5 10 15

Val Phe Ala Ile Phe Asn Thr Glu Gln Arg Asn Val Tyr Lys
20 25 30

<210> SEQ ID NO 119
<211> LENGTH: 30
<212> TYPE: PRT
<213> ORGANISM: Artificial Sequence
<220> FEATURE:
<223> OTHER INFORMATION: Engineered peptides based on Dnm-2 protein
<220> FEATURE:
<221> NAME/KEY: VARIANT
<222> LOCATION: 8
<223> OTHER INFORMATION: Xaa = Lys, Arg, Asn, Gln and
other natural/non-natural basic residue

<400> SEQUENCE: 119

Asn Leu Lys Ile Arg Asp Val Xaa Lys Gly Phe Met Ser Asn Lys His
1 5 10 15

Val Phe Ala Ile Phe Asn Thr Glu Gln Arg Asn Val Tyr Lys
20 25 30

<210> SEQ ID NO 120
<211> LENGTH: 30
<212> TYPE: PRT
<213> ORGANISM: Artificial Sequence
<220> FEATURE:
<223> OTHER INFORMATION: Engineered peptides based on Dnm-2 protein
<220> FEATURE:
<221> NAME/KEY: VARIANT
<222> LOCATION: 6, 8, 24
<223> OTHER INFORMATION: Xaa = Lys, Arg, Asn, Gln and
other natural/non-natural basic residue

<400> SEQUENCE: 120

Asn Leu Lys Ile Arg Xaa Val Xaa Lys Gly Phe Met Ser Asn Lys His
1 5 10 15

Val Phe Ala Ile Phe Asn Thr Xaa Gln Arg Asn Val Tyr Lys
20 25 30

<210> SEQ ID NO 121
<211> LENGTH: 18
<212> TYPE: PRT
<213> ORGANISM: Artificial Sequence
<220> FEATURE:
<223> OTHER INFORMATION: Engineered peptides based on Dnm-2 protein
<220> FEATURE:
<221> NAME/KEY: VARIANT
<222> LOCATION: 14
<223> OTHER INFORMATION: Xaa = Lys, Arg, Asn, Gln and
other natural/non-natural basic residue

<400> SEQUENCE: 121

Ser Trp Lys Ala Ser Phe Leu Arg Ala Gly Val Tyr Pro Xaa Lys Asp
1 5 10 15

Gln Ala

<210> SEQ ID NO 122
<211> LENGTH: 18
<212> TYPE: PRT
<213> ORGANISM: Artificial Sequence
<220> FEATURE:
<223> OTHER INFORMATION: Engineered peptides based on Ncl protein

<400> SEQUENCE: 122

Gln Lys Lys Gly Lys Lys Ala Ala Ala Thr Ser Ala Lys Lys Val Val
1 5 10 15

Val Ser

<210> SEQ ID NO 123
<211> LENGTH: 16
<212> TYPE: PRT
<213> ORGANISM: Artificial Sequence
<220> FEATURE:
<223> OTHER INFORMATION: Engineered peptides based on Ncl protein

<400> SEQUENCE: 123

Thr Lys Lys Val Ala Val Ala Thr Pro Ala Lys Lys Ala Ala Val Thr
1 5 10 15

<210> SEQ ID NO 124
<211> LENGTH: 19
<212> TYPE: PRT
<213> ORGANISM: Artificial Sequence
<220> FEATURE:
<223> OTHER INFORMATION: Engineered peptides based on Ncl protein

<400> SEQUENCE: 124

Lys Lys Gly Ala Ala Ile Pro Ala Lys Gly Ala Lys Asn Gly Lys Asn
1 5 10 15

Ala Lys Lys

<210> SEQ ID NO 125
<211> LENGTH: 18
<212> TYPE: PRT
<213> ORGANISM: Artificial Sequence
<220> FEATURE:
<223> OTHER INFORMATION: Engineered peptides based on Ncl protein

<400> SEQUENCE: 125

Ala Lys Gly Lys Lys Ala Ala Lys Val Val Pro Val Lys Ala Lys Asn
1 5 10 15

Val Ala

<210> SEQ ID NO 126
<211> LENGTH: 18
<212> TYPE: PRT
<213> ORGANISM: Artificial Sequence
<220> FEATURE:
<223> OTHER INFORMATION: Engineered peptides based on Ncl protein

<400> SEQUENCE: 126

Val Lys Glu Ala Pro Gly Lys Arg Lys Lys Glu Met Ala Lys Gln Lys
1 5 10 15

Ala Ala

<210> SEQ ID NO 127
<211> LENGTH: 19
<212> TYPE: PRT
<213> ORGANISM: Artificial Sequence
<220> FEATURE:
<223> OTHER INFORMATION: Engineered peptides based on Ncl protein

<400> SEQUENCE: 127

Lys Ala Leu Glu Leu Thr Gly Leu Lys Val Phe Gly Asn Glu Ile Lys
1 5 10 15

Leu Glu Lys

-continued

<210> SEQ ID NO 128
<211> LENGTH: 25
<212> TYPE: PRT
<213> ORGANISM: Artificial Sequence
<220> FEATURE:
<223> OTHER INFORMATION: Engineered peptides based on Ncl protein

<400> SEQUENCE: 128

```
Lys Gly Lys Asp Ser Lys Lys Glu Arg Asp Ala Arg Thr Leu Leu Ala
 1               5                  10                  15

Lys Asn Leu Pro Tyr Lys Val Thr Gln
            20                  25
```

<210> SEQ ID NO 129
<211> LENGTH: 16
<212> TYPE: PRT
<213> ORGANISM: Artificial Sequence
<220> FEATURE:
<223> OTHER INFORMATION: Engineered peptides based on Ncl protein

<400> SEQUENCE: 129

```
Ile Arg Leu Val Ser Lys Asp Gly Lys Ser Lys Gly Ile Ala Tyr Ile
 1               5                  10                  15
```

<210> SEQ ID NO 130
<211> LENGTH: 32
<212> TYPE: PRT
<213> ORGANISM: Artificial Sequence
<220> FEATURE:
<223> OTHER INFORMATION: Engineered peptides based on Ncl protein

<400> SEQUENCE: 130

```
Lys Gly Gln Asn Gln Asp Tyr Arg Gly Gly Lys Asn Ser Thr Trp Ser
 1               5                  10                  15

Gly Glu Ser Lys Thr Leu Val Leu Ser Asn Leu Ser Tyr Ser Ala Thr
            20                  25                  30
```

<210> SEQ ID NO 131
<211> LENGTH: 21
<212> TYPE: PRT
<213> ORGANISM: Artificial Sequence
<220> FEATURE:
<223> OTHER INFORMATION: Engineered peptides based on Ncl protein

<400> SEQUENCE: 131

```
Lys Ala Thr Phe Ile Lys Val Pro Gln Asn Gln Asn Gly Lys Ser Lys
 1               5                  10                  15

Gly Tyr Ala Phe Ile
            20
```

<210> SEQ ID NO 132
<211> LENGTH: 18
<212> TYPE: PRT
<213> ORGANISM: Artificial Sequence
<220> FEATURE:
<223> OTHER INFORMATION: Engineered peptides based on Ncl protein
<220> FEATURE:
<221> NAME/KEY: VARIANT
<222> LOCATION: 8
<223> OTHER INFORMATION: Xaa = Ser, Thr, Tyr and other
      natural/non-natural H-bond donor/acceptor residue

<400> SEQUENCE: 132

```
Gln Lys Lys Gly Lys Lys Ala Xaa Ala Thr Ser Ala Lys Lys Val Tyr
 1               5                  10                  15

Val Ser
```

<210> SEQ ID NO 133
<211> LENGTH: 18
<212> TYPE: PRT
<213> ORGANISM: Artificial Sequence
<220> FEATURE:
<223> OTHER INFORMATION: Engineered peptides based on Ncl protein

<400> SEQUENCE: 133

Gln Lys Lys Gly Lys Lys Ala Ala Ala Thr Ser Ala Lys Lys Val Tyr
1 5 10 15

Val Ser

<210> SEQ ID NO 134
<211> LENGTH: 18
<212> TYPE: PRT
<213> ORGANISM: Artificial Sequence
<220> FEATURE:
<223> OTHER INFORMATION: Engineered peptides based on Ncl protein

<400> SEQUENCE: 134

Gln Lys Lys Gly Lys Lys Ala Ala Ala Thr Ser Ala Lys Lys Val Trp
1 5 10 15

Val Ser

<210> SEQ ID NO 135
<211> LENGTH: 18
<212> TYPE: PRT
<213> ORGANISM: Artificial Sequence
<220> FEATURE:
<223> OTHER INFORMATION: Engineered peptides based on Ncl protein
<220> FEATURE:
<221> NAME/KEY: VARIANT
<222> LOCATION: 8
<223> OTHER INFORMATION: Xaa = Ser, Thr, Tyr and other natural/non-natural H-bond donor/acceptor residue

<400> SEQUENCE: 135

Gln Lys Lys Gly Lys Lys Ala Xaa Ala Thr Ser Ala Lys Lys Val Tyr
1 5 10 15

Val Ser

<210> SEQ ID NO 136
<211> LENGTH: 18
<212> TYPE: PRT
<213> ORGANISM: Artificial Sequence
<220> FEATURE:
<223> OTHER INFORMATION: Engineered peptides based on Ncl protein
<220> FEATURE:
<221> NAME/KEY: VARIANT
<222> LOCATION: 8
<223> OTHER INFORMATION: Xaa = Ser, Thr, Tyr and other natural/non-natural H-bond donor/acceptor residue

<400> SEQUENCE: 136

Gln Lys Lys Gly Lys Lys Ala Xaa Ala Thr Ser Ala Lys Lys Val Trp
1 5 10 15

Val Ser

<210> SEQ ID NO 137
<211> LENGTH: 19
<212> TYPE: PRT
<213> ORGANISM: Artificial Sequence
<220> FEATURE:
<223> OTHER INFORMATION: Engineered peptides based on Ncl protein
<220> FEATURE:
<221> NAME/KEY: VARIANT
<222> LOCATION: 5
<223> OTHER INFORMATION: Xaa = Ser, Thr, Tyr and other
      natural/non-natural H-bond donor/acceptor residue

<400> SEQUENCE: 137

Lys Lys Gly Ala Xaa Ile Pro Ala Lys Gly Ala Lys Asn Gly Lys Asn
1               5                   10                  15

Ala Lys Lys

<210> SEQ ID NO 138
<211> LENGTH: 18
<212> TYPE: PRT
<213> ORGANISM: Artificial Sequence
<220> FEATURE:
<223> OTHER INFORMATION: Engineered peptides based on Ncl protein
<220> FEATURE:
<221> NAME/KEY: VARIANT
<222> LOCATION: 11
<223> OTHER INFORMATION: Xaa = Ser, Thr, Tyr and other
      natural/non-natural H-bond donor/acceptor residue

<400> SEQUENCE: 138

Ala Lys Gly Lys Lys Ala Ala Lys Val Val Xaa Val Lys Ala Lys Asn
1               5                   10                  15

Val Ala

<210> SEQ ID NO 139
<211> LENGTH: 18
<212> TYPE: PRT
<213> ORGANISM: Artificial Sequence
<220> FEATURE:
<223> OTHER INFORMATION: Engineered peptides based on Ncl protein
<220> FEATURE:
<221> NAME/KEY: VARIANT
<222> LOCATION: 3
<223> OTHER INFORMATION: Xaa = Lys, Arg, Asn, Gln and
      other natural/non-natural basic residue

<400> SEQUENCE: 139

Val Lys Xaa Ala Pro Gly Lys Arg Lys Lys Glu Met Ala Lys Gln Lys
1               5                   10                  15

Ala Ala

<210> SEQ ID NO 140
<211> LENGTH: 18
<212> TYPE: PRT
<213> ORGANISM: Artificial Sequence
<220> FEATURE:
<223> OTHER INFORMATION: Engineered peptides based on Ncl protein
<220> FEATURE:
<221> NAME/KEY: VARIANT
<222> LOCATION: 11
<223> OTHER INFORMATION: Xaa = Lys, Arg, Asn, Gln and
      other natural/non-natural basic residue

<400> SEQUENCE: 140

Val Lys Glu Ala Pro Gly Lys Arg Lys Lys Xaa Met Ala Lys Gln Lys
1               5                   10                  15

Ala Ala

<210> SEQ ID NO 141
<211> LENGTH: 18
<212> TYPE: PRT
<213> ORGANISM: Artificial Sequence
<220> FEATURE:
<223> OTHER INFORMATION: Engineered peptides based on Ncl protein
<220> FEATURE:
<221> NAME/KEY: VARIANT
<222> LOCATION: 12
<223> OTHER INFORMATION: Xaa = Ser, Thr, Tyr and other
      natural/non-natural H-bond donor/acceptor residue

<400> SEQUENCE: 141

Val Lys Glu Ala Pro Gly Lys Arg Lys Lys Glu Xaa Ala Lys Gln Lys
 1               5                  10                  15

Ala Ala

<210> SEQ ID NO 142
<211> LENGTH: 18
<212> TYPE: PRT
<213> ORGANISM: Artificial Sequence
<220> FEATURE:
<223> OTHER INFORMATION: Engineered peptides based on Ncl protein
<220> FEATURE:
<221> NAME/KEY: VARIANT
<222> LOCATION: 3, 11
<223> OTHER INFORMATION: Xaa = Lys, Arg, Asn, Gln and
      other natural/non-natural basic residue
<220> FEATURE:
<221> NAME/KEY: VARIANT
<222> LOCATION: 12
<223> OTHER INFORMATION: Xaa = Ser, Thr, Tyr and other
      natural/non-natural H-bond donor/acceptor residue

<400> SEQUENCE: 142

Val Lys Xaa Ala Pro Gly Lys Arg Lys Lys Xaa Xaa Ala Lys Gln Lys
 1               5                  10                  15

Ala Ala

<210> SEQ ID NO 143
<211> LENGTH: 19
<212> TYPE: PRT
<213> ORGANISM: Artificial Sequence
<220> FEATURE:
<223> OTHER INFORMATION: Engineered peptides based on Ncl protein
<220> FEATURE:
<221> NAME/KEY: VARIANT
<222> LOCATION: 4
<223> OTHER INFORMATION: Xaa = Lys, Arg, Asn, Gln and
      other natural/non-natural basic residue

<400> SEQUENCE: 143

Lys Ala Leu Xaa Leu Thr Gly Leu Lys Val Phe Gly Asn Glu Ile Lys
 1               5                  10                  15

Leu Glu Lys

<210> SEQ ID NO 144
<211> LENGTH: 19
<212> TYPE: PRT
<213> ORGANISM: Artificial Sequence
<220> FEATURE:
<223> OTHER INFORMATION: Engineered peptides based on Ncl protein
<220> FEATURE:
<221> NAME/KEY: VARIANT
<222> LOCATION: 14
<223> OTHER INFORMATION: Xaa = Lys, Arg, Asn, Gln and
      other natural/non-natural basic residue

<400> SEQUENCE: 144

Lys Ala Leu Glu Leu Thr Gly Leu Lys Val Phe Gly Asn Xaa Ile Lys
 1               5                  10                  15

Leu Glu Lys

<210> SEQ ID NO 145
<211> LENGTH: 19
<212> TYPE: PRT

<213> ORGANISM: Artificial Sequence
<220> FEATURE:
<223> OTHER INFORMATION: Engineered peptides based on Ncl protein
<220> FEATURE:
<221> NAME/KEY: VARIANT
<222> LOCATION: 18
<223> OTHER INFORMATION: Xaa = Lys, Arg, Asn, Gln and
other natural/non-natural basic residue

<400> SEQUENCE: 145

Lys Ala Leu Glu Leu Thr Gly Leu Lys Val Phe Gly Asn Glu Ile Lys
1 5 10 15

Leu Xaa Lys

<210> SEQ ID NO 146
<211> LENGTH: 19
<212> TYPE: PRT
<213> ORGANISM: Artificial Sequence
<220> FEATURE:
<223> OTHER INFORMATION: Engineered peptides based on Ncl protein
<220> FEATURE:
<221> NAME/KEY: VARIANT
<222> LOCATION: 4, 14, 18
<223> OTHER INFORMATION: Xaa = Lys, Arg, Asn, Gln and
other natural/non-natural basic residue

<400> SEQUENCE: 146

Lys Ala Leu Xaa Leu Thr Gly Leu Lys Val Phe Gly Asn Xaa Ile Lys
1 5 10 15

Leu Xaa Lys

<210> SEQ ID NO 147
<211> LENGTH: 25
<212> TYPE: PRT
<213> ORGANISM: Artificial Sequence
<220> FEATURE:
<223> OTHER INFORMATION: Engineered peptides based on Ncl protein
<220> FEATURE:
<221> NAME/KEY: VARIANT
<222> LOCATION: 4
<223> OTHER INFORMATION: Xaa = Ser, Thr, Tyr and other
natural/non-natural H-bond donor/acceptor residue

<400> SEQUENCE: 147

Lys Gly Lys Xaa Ser Lys Lys Glu Arg Asp Ala Arg Thr Leu Leu Ala
1 5 10 15

Lys Asn Leu Pro Tyr Lys Val Thr Gln
20 25

<210> SEQ ID NO 148
<211> LENGTH: 25
<212> TYPE: PRT
<213> ORGANISM: Artificial Sequence
<220> FEATURE:
<223> OTHER INFORMATION: Engineered peptides based on Ncl protein
<220> FEATURE:
<221> NAME/KEY: VARIANT
<222> LOCATION: 8
<223> OTHER INFORMATION: Xaa = Ser, Thr, Tyr and other
natural/non-natural H-bond donor/acceptor residue

<400> SEQUENCE: 148

Lys Gly Lys Asp Ser Lys Lys Xaa Arg Asp Ala Arg Thr Leu Leu Ala
1 5 10 15

Lys Asn Leu Pro Tyr Lys Val Thr Gln
20 25

<210> SEQ ID NO 149

-continued

```
<211> LENGTH: 25
<212> TYPE: PRT
<213> ORGANISM: Artificial Sequence
<220> FEATURE:
<223> OTHER INFORMATION: Engineered peptides based on Ncl protein
<220> FEATURE:
<221> NAME/KEY: VARIANT
<222> LOCATION: 10
<223> OTHER INFORMATION: Xaa = Lys, Arg, Asn, Gln and
      other natural/non-natural basic residue

<400> SEQUENCE: 149

Lys Gly Lys Asp Ser Lys Lys Glu Arg Xaa Ala Arg Thr Leu Leu Ala
 1               5                  10                  15

Lys Asn Leu Pro Tyr Lys Val Thr Gln
            20                  25


<210> SEQ ID NO 150
<211> LENGTH: 25
<212> TYPE: PRT
<213> ORGANISM: Artificial Sequence
<220> FEATURE:
<223> OTHER INFORMATION: Engineered peptides based on Ncl protein
<220> FEATURE:
<221> NAME/KEY: VARIANT
<222> LOCATION: 4
<223> OTHER INFORMATION: Xaa = Ser, Thr, Tyr and other
      natural/non-natural H-bond donor/acceptor residue
<220> FEATURE:
<221> NAME/KEY: VARIANT
<222> LOCATION: 8, 10
<223> OTHER INFORMATION: Xaa = Lys, Arg, Asn, Gln and
      other natural/non-natural basic residue

<400> SEQUENCE: 150

Lys Gly Lys Xaa Ser Lys Lys Xaa Arg Xaa Ala Arg Thr Leu Leu Ala
 1               5                  10                  15

Lys Asn Leu Pro Tyr Lys Val Thr Gln
            20                  25


<210> SEQ ID NO 151
<211> LENGTH: 16
<212> TYPE: PRT
<213> ORGANISM: Artificial Sequence
<220> FEATURE:
<223> OTHER INFORMATION: Engineered peptides based on Ncl protein

<400> SEQUENCE: 151

Ile Arg Leu Val Ser Lys Phe Gly Lys Ser Lys Gly Ile Ala Tyr Ile
 1               5                  10                  15


<210> SEQ ID NO 152
<211> LENGTH: 16
<212> TYPE: PRT
<213> ORGANISM: Artificial Sequence
<220> FEATURE:
<223> OTHER INFORMATION: Engineered peptides based on Ncl protein

<400> SEQUENCE: 152

Ile Arg Leu Val Ser Lys Tyr Gly Lys Ser Lys Gly Ile Ala Tyr Ile
 1               5                  10                  15


<210> SEQ ID NO 153
<211> LENGTH: 16
<212> TYPE: PRT
<213> ORGANISM: Artificial Sequence
<220> FEATURE:
<223> OTHER INFORMATION: Engineered peptides based on Ncl protein

<400> SEQUENCE: 153
```

Ile Arg Leu Val Ser Lys Trp Gly Lys Ser Lys Gly Ile Ala Tyr Ile
1 5 10 15

<210> SEQ ID NO 154
<211> LENGTH: 17
<212> TYPE: PRT
<213> ORGANISM: Artificial Sequence
<220> FEATURE:
<223> OTHER INFORMATION: Engineered peptides based on Ncl protein

<400> SEQUENCE: 154

Ile Arg Leu Val Ser Lys Leu Trp Gly Lys Ser Lys Gly Ile Ala Tyr
1 5 10 15

Ile

<210> SEQ ID NO 155
<211> LENGTH: 12
<212> TYPE: PRT
<213> ORGANISM: Artificial Sequence
<220> FEATURE:
<223> OTHER INFORMATION: Engineered peptides based on Ncl protein

<400> SEQUENCE: 155

Ile Arg Leu Val Ser Lys Asp Gly Lys Ser Lys Gly
1 5 10

<210> SEQ ID NO 156
<211> LENGTH: 13
<212> TYPE: PRT
<213> ORGANISM: Artificial Sequence
<220> FEATURE:
<223> OTHER INFORMATION: Engineered peptides based on Ncl protein

<400> SEQUENCE: 156

Ile Arg Leu Val Ser Lys Phe Gly Lys Ser Lys Gly Ile
1 5 10

<210> SEQ ID NO 157
<211> LENGTH: 12
<212> TYPE: PRT
<213> ORGANISM: Artificial Sequence
<220> FEATURE:
<223> OTHER INFORMATION: Engineered peptides based on Ncl protein

<400> SEQUENCE: 157

Ile Arg Leu Val Ser Lys Tyr Gly Lys Ser Lys Gly
1 5 10

<210> SEQ ID NO 158
<211> LENGTH: 12
<212> TYPE: PRT
<213> ORGANISM: Artificial Sequence
<220> FEATURE:
<223> OTHER INFORMATION: Engineered peptides based on Ncl protein

<400> SEQUENCE: 158

Ile Arg Leu Val Ser Lys Trp Gly Lys Ser Lys Gly
1 5 10

<210> SEQ ID NO 159
<211> LENGTH: 13
<212> TYPE: PRT
<213> ORGANISM: Artificial Sequence
<220> FEATURE:
<223> OTHER INFORMATION: Engineered peptides based on Ncl protein

<400> SEQUENCE: 159

```
Ile Arg Leu Val Ser Lys Leu Trp Gly Lys Ser Lys Gly
 1               5                   10


<210> SEQ ID NO 160
<211> LENGTH: 32
<212> TYPE: PRT
<213> ORGANISM: Artificial Sequence
<220> FEATURE:
<223> OTHER INFORMATION: Engineered peptides based on Ncl protein
<220> FEATURE:
<221> NAME/KEY: VARIANT
<222> LOCATION: 6
<223> OTHER INFORMATION: Xaa = Lys, Arg, Asn, Gln and
      other natural/non-natural basic residue

<400> SEQUENCE: 160

Lys Gly Gln Asn Gln Xaa Tyr Arg Gly Gly Lys Asn Ser Thr Trp Ser
 1               5                   10                  15

Gly Glu Ser Lys Thr Leu Val Leu Ser Asn Leu Ser Tyr Ser Ala Thr
            20                  25                  30


<210> SEQ ID NO 161
<211> LENGTH: 32
<212> TYPE: PRT
<213> ORGANISM: Artificial Sequence
<220> FEATURE:
<223> OTHER INFORMATION: Engineered peptides based on Ncl protein
<220> FEATURE:
<221> NAME/KEY: VARIANT
<222> LOCATION: 18
<223> OTHER INFORMATION: Xaa = Lys, Arg, Asn, Gln and
      other natural/non-natural basic residue

<400> SEQUENCE: 161

Lys Gly Gln Asn Gln Asp Tyr Arg Gly Gly Lys Asn Ser Thr Trp Ser
 1               5                   10                  15

Gly Xaa Ser Lys Thr Leu Val Leu Ser Asn Leu Ser Tyr Ser Ala Thr
            20                  25                  30


<210> SEQ ID NO 162
<211> LENGTH: 32
<212> TYPE: PRT
<213> ORGANISM: Artificial Sequence
<220> FEATURE:
<223> OTHER INFORMATION: Engineered peptides based on Ncl protein
<220> FEATURE:
<221> NAME/KEY: VARIANT
<222> LOCATION: 6, 18
<223> OTHER INFORMATION: Xaa = Lys, Arg, Asn, Gln and
      other natural/non-natural basic residue

<400> SEQUENCE: 162

Lys Gly Gln Asn Gln Xaa Tyr Arg Gly Gly Lys Asn Ser Thr Trp Ser
 1               5                   10                  15

Gly Xaa Ser Lys Thr Leu Val Leu Ser Asn Leu Ser Tyr Ser Ala Thr
            20                  25                  30


<210> SEQ ID NO 163
<211> LENGTH: 32
<212> TYPE: PRT
<213> ORGANISM: Artificial Sequence
<220> FEATURE:
<223> OTHER INFORMATION: Engineered peptides based on Ncl protein
<220> FEATURE:
<221> NAME/KEY: VARIANT
<222> LOCATION: 3, 18
<223> OTHER INFORMATION: Xaa = Lys, Arg, Asn, Gln and
      other natural/non-natural basic residue
```

<400> SEQUENCE: 163

```
Lys Gly Xaa Asn Gln Asp Tyr Arg Leu Gly Lys Asn Ser Thr Trp Ser
 1               5                  10                  15

Gly Xaa Ser Lys Thr Leu Val Leu Ser Asn Leu Ser Tyr Ser Ala Thr
            20                  25                  30
```

<210> SEQ ID NO 164
<211> LENGTH: 21
<212> TYPE: PRT
<213> ORGANISM: Artificial Sequence
<220> FEATURE:
<223> OTHER INFORMATION: Engineered peptides based on Ncl protein
<220> FEATURE:
<221> NAME/KEY: VARIANT
<222> LOCATION: 3, 18
<223> OTHER INFORMATION: Xaa = Lys, Arg, Asn, Gln and other natural/non-natural basic residue

<400> SEQUENCE: 164

```
Lys Gly Xaa Asn Gln Asp Tyr Arg Leu Gly Lys Asn Ser Thr Trp Ser
 1               5                  10                  15

Gly Xaa Ser Lys Thr
            20
```

<210> SEQ ID NO 165
<211> LENGTH: 21
<212> TYPE: PRT
<213> ORGANISM: Artificial Sequence
<220> FEATURE:
<223> OTHER INFORMATION: Engineered peptides based on Ncl protein
<220> FEATURE:
<221> NAME/KEY: VARIANT
<222> LOCATION: 13
<223> OTHER INFORMATION: Xaa = Ser, Thr, Tyr and other natural/non-natural H-bond donor/acceptor residue

<400> SEQUENCE: 165

```
Lys Ala Thr Phe Ile Lys Val Pro Gln Asn Gln Asn Xaa Lys Ser Lys
 1               5                  10                  15

Gly Tyr Ala Phe Ile
            20
```

<210> SEQ ID NO 166
<211> LENGTH: 21
<212> TYPE: PRT
<213> ORGANISM: Artificial Sequence
<220> FEATURE:
<223> OTHER INFORMATION: Engineered peptides based on Ncl protein

<400> SEQUENCE: 166

```
Lys Ala Thr Phe Ile Lys Val Pro Gln Asn Gln Asn Leu Lys Ser Lys
 1               5                  10                  15

Gly Tyr Ala Phe Ile
            20
```

<210> SEQ ID NO 167
<211> LENGTH: 21
<212> TYPE: PRT
<213> ORGANISM: Artificial Sequence
<220> FEATURE:
<223> OTHER INFORMATION: Engineered peptides based on Ncl protein

<400> SEQUENCE: 167

```
Lys Ala Thr Phe Ile Lys Val Pro Gln Asn Gln Asn Tyr Lys Ser Lys
 1               5                  10                  15

Gly Tyr Ala Phe Ile
```

20

<210> SEQ ID NO 168
<211> LENGTH: 21
<212> TYPE: PRT
<213> ORGANISM: Artificial Sequence
<220> FEATURE:
<223> OTHER INFORMATION: Engineered peptides based on Ncl protein

<400> SEQUENCE: 168

Lys Ala Thr Phe Ile Lys Val Pro Gln Asn Gln Asn Phe Lys Ser Lys
1 5 10 15

Gly Tyr Ala Phe Ile
20

<210> SEQ ID NO 169
<211> LENGTH: 21
<212> TYPE: PRT
<213> ORGANISM: Artificial Sequence
<220> FEATURE:
<223> OTHER INFORMATION: Engineered peptides based on Ncl protein

<400> SEQUENCE: 169

Lys Ala Thr Phe Ile Lys Val Pro Gln Asn Gln Asn Trp Lys Ser Lys
1 5 10 15

Gly Tyr Ala Phe Ile
20

<210> SEQ ID NO 170
<211> LENGTH: 18
<212> TYPE: PRT
<213> ORGANISM: Artificial Sequence
<220> FEATURE:
<223> OTHER INFORMATION: Engineered peptides based on Ncl protein

<400> SEQUENCE: 170

Lys Ala Thr Phe Ile Lys Val Pro Gln Asn Gln Asn Gly Lys Ser Lys
1 5 10 15

Gly Tyr

<210> SEQ ID NO 171
<211> LENGTH: 18
<212> TYPE: PRT
<213> ORGANISM: Artificial Sequence
<220> FEATURE:
<223> OTHER INFORMATION: Engineered peptides based on Ncl protein
<220> FEATURE:
<221> NAME/KEY: VARIANT
<222> LOCATION: 13
<223> OTHER INFORMATION: Xaa = Ser, Thr, Tyr and other
natural/non-natural H-bond donor/acceptor residue

<400> SEQUENCE: 171

Lys Ala Thr Phe Ile Lys Val Pro Gln Asn Gln Asn Xaa Lys Ser Lys
1 5 10 15

Gly Tyr

<210> SEQ ID NO 172
<211> LENGTH: 18
<212> TYPE: PRT
<213> ORGANISM: Artificial Sequence
<220> FEATURE:
<223> OTHER INFORMATION: Engineered peptides based on Ncl protein

<400> SEQUENCE: 172

Lys Ala Thr Phe Ile Lys Val Pro Gln Asn Gln Asn Leu Lys Ser Lys

-continued 1 5 10 15

Gly Tyr

<210> SEQ ID NO 173
<211> LENGTH: 18
<212> TYPE: PRT
<213> ORGANISM: Artificial Sequence
<220> FEATURE:
<223> OTHER INFORMATION: Engineered peptides based on Ncl protein

<400> SEQUENCE: 173

Lys Ala Thr Phe Ile Lys Val Pro Gln Asn Gln Asn Tyr Lys Ser Lys
1 5 10 15

Gly Tyr

<210> SEQ ID NO 174
<211> LENGTH: 18
<212> TYPE: PRT
<213> ORGANISM: Artificial Sequence
<220> FEATURE:
<223> OTHER INFORMATION: Engineered peptides based on Ncl protein

<400> SEQUENCE: 174

Lys Ala Thr Phe Ile Lys Val Pro Gln Asn Gln Asn Phe Lys Ser Lys
1 5 10 15

Gly Tyr

<210> SEQ ID NO 175
<211> LENGTH: 18
<212> TYPE: PRT
<213> ORGANISM: Artificial Sequence
<220> FEATURE:
<223> OTHER INFORMATION: Engineered peptides based on Ncl protein

<400> SEQUENCE: 175

Lys Ala Thr Phe Ile Lys Val Pro Gln Asn Gln Asn Trp Lys Ser Lys
1 5 10 15

Gly Tyr

<210> SEQ ID NO 176
<211> LENGTH: 15
<212> TYPE: PRT
<213> ORGANISM: Artificial Sequence
<220> FEATURE:
<223> OTHER INFORMATION: Engineered peptides based on Csp3 protein

<400> SEQUENCE: 176

Ser Lys Ser Ile Lys Asn Leu Glu Pro Lys Ile Ile His Gly Ser
1 5 10 15

<210> SEQ ID NO 177
<211> LENGTH: 31
<212> TYPE: PRT
<213> ORGANISM: Artificial Sequence
<220> FEATURE:
<223> OTHER INFORMATION: Engineered peptides based on Csp3 protein

<400> SEQUENCE: 177

Leu Lys Lys Ile Thr Asn Phe Phe Arg Gly Asp Arg Cys Arg Ser Leu
1 5 10 15

Thr Gly Lys Pro Lys Leu Phe Ile Ile Gln Ala Cys Arg Gly Thr
20 25 30

<210> SEQ ID NO 178

<211> LENGTH: 31
<212> TYPE: PRT
<213> ORGANISM: Artificial Sequence
<220> FEATURE:
<223> OTHER INFORMATION: Engineered peptides based on Csp3 protein

<400> SEQUENCE: 178

```
Phe Ile Gln Ser Leu Cys Ala Met Leu Lys Gln Tyr Ala Asp Lys Leu
 1               5                  10                  15

Glu Phe Met His Ile Leu Thr Arg Val Asn Arg Lys Val Ala Thr
            20                  25                  30
```

<210> SEQ ID NO 179
<211> LENGTH: 15
<212> TYPE: PRT
<213> ORGANISM: Artificial Sequence
<220> FEATURE:
<223> OTHER INFORMATION: Engineered peptides based on Csp3 protein
<220> FEATURE:
<221> NAME/KEY: VARIANT
<222> LOCATION: 8
<223> OTHER INFORMATION: Xaa = Lys, Arg, Asn, Gln and other natural/non-natural basic residue

<400> SEQUENCE: 179

```
Ser Lys Ser Ile Lys Asn Leu Xaa Pro Lys Ile Ile His Gly Ser
 1               5                  10                  15
```

<210> SEQ ID NO 180
<211> LENGTH: 15
<212> TYPE: PRT
<213> ORGANISM: Artificial Sequence
<220> FEATURE:
<223> OTHER INFORMATION: Engineered peptides based on Csp3 protein

<400> SEQUENCE: 180

```
Ser Lys Ser Ile Lys Asn Leu Glu Pro Lys Ile Ile Tyr Gly Ser
 1               5                  10                  15
```

<210> SEQ ID NO 181
<211> LENGTH: 15
<212> TYPE: PRT
<213> ORGANISM: Artificial Sequence
<220> FEATURE:
<223> OTHER INFORMATION: Engineered peptides based on Csp3 protein
<220> FEATURE:
<221> NAME/KEY: VARIANT
<222> LOCATION: 14
<223> OTHER INFORMATION: Xaa = Lys, Arg, Asn, Gln and other natural/non-natural basic residue

<400> SEQUENCE: 181

```
Ser Lys Ser Ile Lys Asn Leu Glu Pro Lys Ile Ile Tyr Xaa Ser
 1               5                  10                  15
```

<210> SEQ ID NO 182
<211> LENGTH: 15
<212> TYPE: PRT
<213> ORGANISM: Artificial Sequence
<220> FEATURE:
<223> OTHER INFORMATION: Engineered peptides based on Csp3 protein
<220> FEATURE:
<221> NAME/KEY: VARIANT
<222> LOCATION: 8, 14
<223> OTHER INFORMATION: Xaa = Lys, Arg, Asn, Gln and other natural/non-natural basic residue

<400> SEQUENCE: 182

```
Ser Lys Ser Ile Lys Asn Leu Xaa Pro Lys Ile Ile Tyr Xaa Ser
 1               5                  10                  15
```

<210> SEQ ID NO 183
<211> LENGTH: 31
<212> TYPE: PRT
<213> ORGANISM: Artificial Sequence
<220> FEATURE:
<223> OTHER INFORMATION: Engineered peptides based on Csp3 protein
<220> FEATURE:
<221> NAME/KEY: VARIANT
<222> LOCATION: 11
<223> OTHER INFORMATION: Xaa = Lys, Arg, Asn, Gln and other natural/non-natural basic residue

<400> SEQUENCE: 183

```
Leu Lys Lys Ile Thr Asn Phe Phe Arg Gly Xaa Arg Cys Arg Ser Leu
 1               5                   10                  15

Thr Gly Lys Pro Lys Leu Phe Ile Ile Gln Ala Cys Arg Gly Thr
            20                  25                  30
```

<210> SEQ ID NO 184
<211> LENGTH: 31
<212> TYPE: PRT
<213> ORGANISM: Artificial Sequence
<220> FEATURE:
<223> OTHER INFORMATION: Engineered peptides based on Csp3 protein
<220> FEATURE:
<221> NAME/KEY: VARIANT
<222> LOCATION: 13
<223> OTHER INFORMATION: Xaa = Ser, Thr, Tyr and other natural/non-natural H-bond donor/acceptor residue

<400> SEQUENCE: 184

```
Leu Lys Lys Ile Thr Asn Phe Phe Arg Gly Asp Arg Xaa Arg Ser Leu
 1               5                   10                  15

Thr Gly Lys Pro Lys Leu Phe Ile Ile Gln Ala Cys Arg Gly Thr
            20                  25                  30
```

<210> SEQ ID NO 185
<211> LENGTH: 31
<212> TYPE: PRT
<213> ORGANISM: Artificial Sequence
<220> FEATURE:
<223> OTHER INFORMATION: Engineered peptides based on Csp3 protein
<220> FEATURE:
<221> NAME/KEY: VARIANT
<222> LOCATION: 28
<223> OTHER INFORMATION: Xaa = Ser, Thr, Tyr and other natural/non-natural H-bond donor/acceptor residue

<400> SEQUENCE: 185

```
Leu Lys Lys Ile Thr Asn Phe Phe Arg Gly Asp Arg Cys Arg Ser Leu
 1               5                   10                  15

Thr Gly Lys Pro Lys Leu Phe Ile Ile Gln Ala Xaa Arg Gly Thr
            20                  25                  30
```

<210> SEQ ID NO 186
<211> LENGTH: 30
<212> TYPE: PRT
<213> ORGANISM: Artificial Sequence
<220> FEATURE:
<223> OTHER INFORMATION: Engineered peptides based on Csp3 protein
<220> FEATURE:
<221> NAME/KEY: VARIANT
<222> LOCATION: 10
<223> OTHER INFORMATION: Xaa = Lys, Arg, Asn, Gln and other natural/non-natural basic residue
<220> FEATURE:
<221> NAME/KEY: VARIANT
<222> LOCATION: 12, 27
<223> OTHER INFORMATION: Xaa = Ser, Thr, Tyr and other natural/non-natural H-bond donor/acceptor residue

<400> SEQUENCE: 186

```
Leu Lys Lys Ile Thr Asn Phe Arg Gly Xaa Arg Xaa Arg Ser Leu Thr
 1               5                  10                  15

Gly Lys Pro Lys Leu Phe Ile Ile Gln Ala Xaa Arg Gly Thr
            20                  25                  30
```

<210> SEQ ID NO 187
<211> LENGTH: 18
<212> TYPE: PRT
<213> ORGANISM: Artificial Sequence
<220> FEATURE:
<223> OTHER INFORMATION: Engineered peptides based on Csp3 protein
<220> FEATURE:
<221> NAME/KEY: VARIANT
<222> LOCATION: 10
<223> OTHER INFORMATION: Xaa = Lys, Arg, Asn, Gln and other natural/non-natural basic residue
<220> FEATURE:
<221> NAME/KEY: VARIANT
<222> LOCATION: 12
<223> OTHER INFORMATION: Xaa = Ser, Thr, Tyr and other natural/non-natural H-bond donor/acceptor residue

<400> SEQUENCE: 187

```
Leu Lys Lys Ile Thr Asn Phe Arg Gly Xaa Arg Xaa Arg Ser Leu Thr
 1               5                  10                  15

Gly Lys
```

<210> SEQ ID NO 188
<211> LENGTH: 24
<212> TYPE: PRT
<213> ORGANISM: Artificial Sequence
<220> FEATURE:
<223> OTHER INFORMATION: Engineered peptides based on Bad protein

<400> SEQUENCE: 188

```
Phe Arg Gly Arg Ser Arg Ser Ala Pro Pro Asn Leu Trp Ala Ala Gln
 1               5                  10                  15

Arg Tyr Gly Arg Glu Leu Arg Arg
            20
```

<210> SEQ ID NO 189
<211> LENGTH: 26
<212> TYPE: PRT
<213> ORGANISM: Artificial Sequence
<220> FEATURE:
<223> OTHER INFORMATION: Engineered peptides based on Bad protein

<400> SEQUENCE: 189

```
Arg Arg Met Ser Asp Glu Phe Val Asp Ser Phe Lys Lys Gly Leu Pro
 1               5                  10                  15

Arg Pro Lys Ser Ala Gly Thr Ala Thr Gln
            20                  25
```

<210> SEQ ID NO 190
<211> LENGTH: 20
<212> TYPE: PRT
<213> ORGANISM: Artificial Sequence
<220> FEATURE:
<223> OTHER INFORMATION: Engineered peptides based on Bad protein

<400> SEQUENCE: 190

```
Phe Val Asp Ser Phe Lys Lys Gly Leu Pro Arg Pro Lys Ser Ala Gly
 1               5                  10                  15
```

Thr Ala Thr Gln
20

<210> SEQ ID NO 191
<211> LENGTH: 24
<212> TYPE: PRT
<213> ORGANISM: Artificial Sequence
<220> FEATURE:
<223> OTHER INFORMATION: Engineered peptides based on Bad protein
<220> FEATURE:
<221> NAME/KEY: VARIANT
<222> LOCATION: 21
<223> OTHER INFORMATION: Xaa = Lys, Arg, Asn, Gln and other natural/non-natural basic residue

<400> SEQUENCE: 191

Phe Arg Gly Arg Ser Arg Ser Ala Pro Pro Asn Leu Trp Ala Ala Gln
1 5 10 15

Arg Tyr Gly Arg Xaa Leu Arg Arg
20

<210> SEQ ID NO 192
<211> LENGTH: 26
<212> TYPE: PRT
<213> ORGANISM: Artificial Sequence
<220> FEATURE:
<223> OTHER INFORMATION: Engineered peptides based on Bad protein
<220> FEATURE:
<221> NAME/KEY: VARIANT
<222> LOCATION: 5
<223> OTHER INFORMATION: Xaa = Lys, Arg, Asn, Gln and other natural/non-natural basic residue

<400> SEQUENCE: 192

Arg Arg Met Ser Xaa Glu Phe Val Asp Ser Phe Lys Lys Gly Leu Pro
1 5 10 15

Arg Pro Lys Ser Ala Gly Thr Ala Thr Gln
20 25

<210> SEQ ID NO 193
<211> LENGTH: 26
<212> TYPE: PRT
<213> ORGANISM: Artificial Sequence
<220> FEATURE:
<223> OTHER INFORMATION: Engineered peptides based on Bad protein
<220> FEATURE:
<221> NAME/KEY: VARIANT
<222> LOCATION: 6
<223> OTHER INFORMATION: Xaa = Lys, Arg, Asn, Gln and other natural/non-natural basic residue

<400> SEQUENCE: 193

Arg Arg Met Ser Asp Xaa Phe Val Asp Ser Phe Lys Lys Gly Leu Pro
1 5 10 15

Arg Pro Lys Ser Ala Gly Thr Ala Thr Gln
20 25

<210> SEQ ID NO 194
<211> LENGTH: 26
<212> TYPE: PRT
<213> ORGANISM: Artificial Sequence
<220> FEATURE:
<223> OTHER INFORMATION: Engineered peptides based on Bad protein
<220> FEATURE:
<221> NAME/KEY: VARIANT
<222> LOCATION: 9
<223> OTHER INFORMATION: Xaa = Lys, Arg, Asn, Gln and other natural/non-natural basic residue

<400> SEQUENCE: 194

Arg Arg Met Ser Asp Glu Phe Val Xaa Ser Phe Lys Lys Gly Leu Pro
1 5 10 15

Arg Pro Lys Ser Ala Gly Thr Ala Thr Gln
20 25

<210> SEQ ID NO 195
<211> LENGTH: 26
<212> TYPE: PRT
<213> ORGANISM: Artificial Sequence
<220> FEATURE:
<223> OTHER INFORMATION: Engineered peptides based on Bad protein
<220> FEATURE:
<221> NAME/KEY: VARIANT
<222> LOCATION: 5, 6, 9
<223> OTHER INFORMATION: Xaa = Lys, Arg, Asn, Gln and other natural/non-natural basic residue

<400> SEQUENCE: 195

Arg Arg Met Ser Xaa Xaa Phe Val Xaa Ser Phe Lys Lys Gly Leu Pro
1 5 10 15

Arg Pro Lys Ser Ala Gly Thr Ala Thr Gln
20 25

<210> SEQ ID NO 196
<211> LENGTH: 26
<212> TYPE: PRT
<213> ORGANISM: Artificial Sequence
<220> FEATURE:
<223> OTHER INFORMATION: Engineered peptides based on Bad protein
<220> FEATURE:
<221> NAME/KEY: VARIANT
<222> LOCATION: 3
<223> OTHER INFORMATION: Xaa = Ser, Thr, Tyr and other natural/non-natural H-bond donor/acceptor residue
<220> FEATURE:
<221> NAME/KEY: VARIANT
<222> LOCATION: 5, 6, 9
<223> OTHER INFORMATION: Xaa = Lys, Arg, Asn, Gln and other natural/non-natural basic residue

<400> SEQUENCE: 196

Arg Arg Xaa Ser Xaa Xaa Phe Val Xaa Ser Phe Lys Lys Gly Leu Pro
1 5 10 15

Arg Pro Lys Ser Ala Gly Thr Ala Thr Gln
20 25

<210> SEQ ID NO 197
<211> LENGTH: 20
<212> TYPE: PRT
<213> ORGANISM: Artificial Sequence
<220> FEATURE:
<223> OTHER INFORMATION: Engineered peptides based on Bad protein
<220> FEATURE:
<221> NAME/KEY: VARIANT
<222> LOCATION: 3
<223> OTHER INFORMATION: Xaa = Lys, Arg, Asn, Gln and other natural/non-natural basic residue

<400> SEQUENCE: 197

Phe Val Xaa Ser Phe Lys Lys Gly Leu Pro Arg Pro Lys Ser Ala Gly
1 5 10 15

Thr Ala Thr Gln
20

<210> SEQ ID NO 198
<211> LENGTH: 16
<212> TYPE: PRT
<213> ORGANISM: Artificial Sequence
<220> FEATURE:
<223> OTHER INFORMATION: Engineered peptides based on Bad protein
<220> FEATURE:
<221> NAME/KEY: VARIANT
<222> LOCATION: 3
<223> OTHER INFORMATION: Xaa = Lys, Arg, Asn, Gln and other natural/non-natural basic residue
<220> FEATURE:
<221> NAME/KEY: VARIANT
<222> LOCATION: 10
<223> OTHER INFORMATION: Xaa = Ser, Thr, Tyr and other natural/non-natural H-bond donor/acceptor residue

<400> SEQUENCE: 198

Phe Val Xaa Ser Phe Lys Lys Gly Leu Xaa Arg Pro Lys Ser Ala Gly
1 5 10 15

<210> SEQ ID NO 199
<211> LENGTH: 16
<212> TYPE: PRT
<213> ORGANISM: Artificial Sequence
<220> FEATURE:
<223> OTHER INFORMATION: Engineered peptides based on Bad protein
<220> FEATURE:
<221> NAME/KEY: VARIANT
<222> LOCATION: 3
<223> OTHER INFORMATION: Xaa = Lys, Arg, Asn, Gln and other natural/non-natural basic residue

<400> SEQUENCE: 199

Phe Val Xaa Ser Phe Lys Lys Gly Leu Tyr Arg Pro Lys Ser Ala Gly
1 5 10 15

<210> SEQ ID NO 200
<211> LENGTH: 14
<212> TYPE: PRT
<213> ORGANISM: Artificial Sequence
<220> FEATURE:
<223> OTHER INFORMATION: Engineered peptides based on Prf-1 protein

<400> SEQUENCE: 200

Lys Arg Ser His Lys Phe Val Pro Gly Ala Trp Leu Ala Gly
1 5 10

<210> SEQ ID NO 201
<211> LENGTH: 19
<212> TYPE: PRT
<213> ORGANISM: Artificial Sequence
<220> FEATURE:
<223> OTHER INFORMATION: Engineered peptides based on Prf-1 protein

<400> SEQUENCE: 201

Val Thr Ser Leu Arg Arg Ser Gly Ser Phe Pro Val Asp Thr Gln Arg
1 5 10 15

Phe Leu Arg

<210> SEQ ID NO 202
<211> LENGTH: 16
<212> TYPE: PRT
<213> ORGANISM: Artificial Sequence
<220> FEATURE:
<223> OTHER INFORMATION: Engineered peptides based on Prf-1 protein

<400> SEQUENCE: 202

Arg Ser Ile Arg Asn Asp Trp Lys Val Gly Leu Asp Val Thr Pro Lys
1 5 10 15

<210> SEQ ID NO 203
<211> LENGTH: 20

<212> TYPE: PRT
<213> ORGANISM: Artificial Sequence
<220> FEATURE:
<223> OTHER INFORMATION: Engineered peptides based on Prf-1 protein

<400> SEQUENCE: 203

Arg Arg Glu Ala Leu Arg Arg Ala Leu Ser Gln Tyr Leu Thr Asp Arg
1 5 10 15

Ala Arg Trp Arg
20

<210> SEQ ID NO 204
<211> LENGTH: 14
<212> TYPE: PRT
<213> ORGANISM: Artificial Sequence
<220> FEATURE:
<223> OTHER INFORMATION: Engineered peptides based on Prf-1 protein

<400> SEQUENCE: 204

Asn Leu Asn His Gly His Leu Lys Phe Arg Tyr His Ala Arg
1 5 10

<210> SEQ ID NO 205
<211> LENGTH: 14
<212> TYPE: PRT
<213> ORGANISM: Artificial Sequence
<220> FEATURE:
<223> OTHER INFORMATION: Engineered peptides based on Prf-1 protein
<220> FEATURE:
<221> NAME/KEY: VARIANT
<222> LOCATION: 8
<223> OTHER INFORMATION: Xaa = Ser, Thr, Tyr and other natural/non-natural H-bond donor/acceptor residue

<400> SEQUENCE: 205

Lys Arg Ser His Lys Phe Val Xaa Gly Ala Trp Leu Ala Gly
1 5 10

<210> SEQ ID NO 206
<211> LENGTH: 19
<212> TYPE: PRT
<213> ORGANISM: Artificial Sequence
<220> FEATURE:
<223> OTHER INFORMATION: Engineered peptides based on Prf-1 protein
<220> FEATURE:
<221> NAME/KEY: VARIANT
<222> LOCATION: 11
<223> OTHER INFORMATION: Xaa = Ser, Thr, Tyr and other natural/non-natural H-bond donor/acceptor residue

<400> SEQUENCE: 206

Val Thr Ser Leu Arg Arg Ser Gly Ser Phe Xaa Val Asp Thr Gln Arg
1 5 10 15

Phe Leu Arg

<210> SEQ ID NO 207
<211> LENGTH: 19
<212> TYPE: PRT
<213> ORGANISM: Artificial Sequence
<220> FEATURE:
<223> OTHER INFORMATION: Engineered peptides based on Prf-1 protein
<220> FEATURE:
<221> NAME/KEY: VARIANT
<222> LOCATION: 13
<223> OTHER INFORMATION: Xaa = Lys, Arg, Asn, Gln and other natural/non-natural basic residue

<400> SEQUENCE: 207

Val Thr Ser Leu Arg Arg Ser Gly Ser Phe Pro Val Xaa Thr Gln Arg 1 5 10 15

Phe Leu Arg

<210> SEQ ID NO 208
<211> LENGTH: 19
<212> TYPE: PRT
<213> ORGANISM: Artificial Sequence
<220> FEATURE:
<223> OTHER INFORMATION: Engineered peptides based on Prf-1 protein
<220> FEATURE:
<221> NAME/KEY: VARIANT
<222> LOCATION: 11
<223> OTHER INFORMATION: Xaa = Ser, Thr, Tyr and other natural/non-natural H-bond donor/acceptor residue
<220> FEATURE:
<221> NAME/KEY: VARIANT
<222> LOCATION: 13
<223> OTHER INFORMATION: Xaa = Lys, Arg, Asn, Gln and other natural/non-natural basic residue

<400> SEQUENCE: 208

Val Thr Ser Leu Arg Arg Ser Gly Ser Phe Xaa Val Xaa Thr Gln Arg
1 5 10 15

Phe Leu Arg

<210> SEQ ID NO 209
<211> LENGTH: 16
<212> TYPE: PRT
<213> ORGANISM: Artificial Sequence
<220> FEATURE:
<223> OTHER INFORMATION: Engineered peptides based on Prf-1 protein
<220> FEATURE:
<221> NAME/KEY: VARIANT
<222> LOCATION: 6
<223> OTHER INFORMATION: Xaa = Lys, Arg, Asn, Gln and other natural/non-natural basic residue

<400> SEQUENCE: 209

Arg Ser Ile Arg Asn Xaa Trp Lys Val Gly Leu Asp Val Thr Pro Lys
1 5 10 15

<210> SEQ ID NO 210
<211> LENGTH: 14
<212> TYPE: PRT
<213> ORGANISM: Artificial Sequence
<220> FEATURE:
<223> OTHER INFORMATION: Engineered peptides based on Prf-1 protein

<400> SEQUENCE: 210

Arg Ser Ile Arg Asn Asp Trp Lys Val Gly Leu Asp Val Thr
1 5 10

<210> SEQ ID NO 211
<211> LENGTH: 14
<212> TYPE: PRT
<213> ORGANISM: Artificial Sequence
<220> FEATURE:
<223> OTHER INFORMATION: Engineered peptides based on Prf-1 protein
<220> FEATURE:
<221> NAME/KEY: VARIANT
<222> LOCATION: 6
<223> OTHER INFORMATION: Xaa = Lys, Arg, Asn, Gln and other natural/non-natural basic residue

<400> SEQUENCE: 211

Arg Ser Ile Arg Asn Xaa Trp Lys Val Gly Leu Asp Val Thr
1 5 10

<210> SEQ ID NO 212

<211> LENGTH: 20
<212> TYPE: PRT
<213> ORGANISM: Artificial Sequence
<220> FEATURE:
<223> OTHER INFORMATION: Engineered peptides based on Prf-1 protein
<220> FEATURE:
<221> NAME/KEY: VARIANT
<222> LOCATION: 3
<223> OTHER INFORMATION: Xaa = Lys, Arg, Asn, Gln and
other natural/non-natural basic residue

<400> SEQUENCE: 212

```
Arg Arg Xaa Ala Leu Arg Arg Ala Leu Ser Gln Tyr Leu Thr Asp Arg
 1               5                  10                  15

Ala Arg Trp Arg
            20
```

<210> SEQ ID NO 213
<211> LENGTH: 20
<212> TYPE: PRT
<213> ORGANISM: Artificial Sequence
<220> FEATURE:
<223> OTHER INFORMATION: Engineered peptides based on Prf-1 protein
<220> FEATURE:
<221> NAME/KEY: VARIANT
<222> LOCATION: 15
<223> OTHER INFORMATION: Xaa = Lys, Arg, Asn, Gln and
other natural/non-natural basic residue

<400> SEQUENCE: 213

```
Arg Arg Glu Ala Leu Arg Arg Ala Leu Ser Gln Tyr Leu Thr Xaa Arg
 1               5                  10                  15

Ala Arg Trp Arg
            20
```

<210> SEQ ID NO 214
<211> LENGTH: 20
<212> TYPE: PRT
<213> ORGANISM: Artificial Sequence
<220> FEATURE:
<223> OTHER INFORMATION: Engineered peptides based on Prf-1 protein
<220> FEATURE:
<221> NAME/KEY: VARIANT
<222> LOCATION: 3, 15
<223> OTHER INFORMATION: Xaa = Lys, Arg, Asn, Gln and
other natural/non-natural basic residue

<400> SEQUENCE: 214

```
Arg Arg Xaa Ala Leu Arg Arg Ala Leu Ser Gln Tyr Leu Thr Xaa Arg
 1               5                  10                  15

Ala Arg Trp Arg
            20
```

<210> SEQ ID NO 215
<211> LENGTH: 20
<212> TYPE: PRT
<213> ORGANISM: Artificial Sequence
<220> FEATURE:
<223> OTHER INFORMATION: Engineered peptides based on Prf-1 protein
<220> FEATURE:
<221> NAME/KEY: VARIANT
<222> LOCATION: 2
<223> OTHER INFORMATION: Xaa = Ser, Thr, Tyr and other
natural/non-natural H-bond donor/acceptor residue
<220> FEATURE:
<221> NAME/KEY: VARIANT
<222> LOCATION: 3, 15
<223> OTHER INFORMATION: Xaa = Lys, Arg, Asn, Gln and
other natural/non-natural basic residue

<400> SEQUENCE: 215

-continued

Arg Xaa Xaa Ala Leu Arg Arg Ala Leu Ser Gln Tyr Leu Thr Xaa Arg
 1               5                   10                  15

Ala Arg Trp Arg
            20

<210> SEQ ID NO 216
<211> LENGTH: 14
<212> TYPE: PRT
<213> ORGANISM: Artificial Sequence
<220> FEATURE:
<223> OTHER INFORMATION: Engineered peptides based on Prf-1 protein
<220> FEATURE:
<221> NAME/KEY: VARIANT
<222> LOCATION: 4
<223> OTHER INFORMATION: Xaa = Lys, Arg, Asn, Gln and
      other natural/non-natural basic residue

<400> SEQUENCE: 216

Asn Leu Asn Xaa Gly His Leu Lys Phe Arg Tyr His Ala Arg
 1               5                   10

<210> SEQ ID NO 217
<211> LENGTH: 14
<212> TYPE: PRT
<213> ORGANISM: Artificial Sequence
<220> FEATURE:
<223> OTHER INFORMATION: Engineered peptides based on Prf-1 protein
<220> FEATURE:
<221> NAME/KEY: VARIANT
<222> LOCATION: 4, 6
<223> OTHER INFORMATION: Xaa = Lys, Arg, Asn, Gln and
      other natural/non-natural basic residue

<400> SEQUENCE: 217

Asn Leu Asn Xaa Gly Xaa Leu Lys Phe Arg Tyr His Ala Arg
 1               5                   10

<210> SEQ ID NO 218
<211> LENGTH: 14
<212> TYPE: PRT
<213> ORGANISM: Artificial Sequence
<220> FEATURE:
<223> OTHER INFORMATION: Engineered peptides based on Prf-1 protein
<220> FEATURE:
<221> NAME/KEY: VARIANT
<222> LOCATION: 4, 6, 12
<223> OTHER INFORMATION: Xaa = Lys, Arg, Asn, Gln and
      other natural/non-natural basic residue

<400> SEQUENCE: 218

Asn Leu Asn Xaa Gly Xaa Leu Lys Phe Arg Tyr Xaa Ala Arg
 1               5                   10

<210> SEQ ID NO 219
<211> LENGTH: 14
<212> TYPE: PRT
<213> ORGANISM: Artificial Sequence
<220> FEATURE:
<223> OTHER INFORMATION: Engineered peptides based on Prf-1 protein
<220> FEATURE:
<221> NAME/KEY: VARIANT
<222> LOCATION: 4
<223> OTHER INFORMATION: Xaa = Ser, Thr, Tyr and other
      natural/non-natural H-bond donor/acceptor residue

<400> SEQUENCE: 219

Asn Leu Asn Xaa Gly His Leu Lys Phe Arg Tyr His Ala Arg
 1               5                   10

<210> SEQ ID NO 220
<211> LENGTH: 14
<212> TYPE: PRT
<213> ORGANISM: Artificial Sequence
<220> FEATURE:
<223> OTHER INFORMATION: Engineered peptides based on Prf-1 protein
<220> FEATURE:
<221> NAME/KEY: VARIANT
<222> LOCATION: 4
<223> OTHER INFORMATION: Xaa = Lys, Arg, Asn, Gln and
other natural/non-natural basic residue
<220> FEATURE:
<221> NAME/KEY: VARIANT
<222> LOCATION: 6
<223> OTHER INFORMATION: Xaa = Ser, Thr, Tyr and other
natural/non-natural H-bond donor/acceptor residue

<400> SEQUENCE: 220

Asn Leu Asn Xaa Gly Xaa Leu Lys Phe Arg Tyr His Ala Arg
1 5 10

<210> SEQ ID NO 221
<211> LENGTH: 14
<212> TYPE: PRT
<213> ORGANISM: Artificial Sequence
<220> FEATURE:
<223> OTHER INFORMATION: Engineered peptides based on Prf-1 protein
<220> FEATURE:
<221> NAME/KEY: VARIANT
<222> LOCATION: 4, 6
<223> OTHER INFORMATION: Xaa = Lys, Arg, Asn, Gln and
other natural/non-natural basic residue
<220> FEATURE:
<221> NAME/KEY: VARIANT
<222> LOCATION: 12
<223> OTHER INFORMATION: Xaa = Ser, Thr, Tyr and other
natural/non-natural H-bond donor/acceptor residue

<400> SEQUENCE: 221

Asn Leu Asn Xaa Gly Xaa Leu Lys Phe Arg Tyr Xaa Ala Arg
1 5 10

<210> SEQ ID NO 222
<211> LENGTH: 14
<212> TYPE: PRT
<213> ORGANISM: Artificial Sequence
<220> FEATURE:
<223> OTHER INFORMATION: Engineered peptides based on Prf-1 protein
<220> FEATURE:
<221> NAME/KEY: VARIANT
<222> LOCATION: 1
<223> OTHER INFORMATION: Xaa = anthrylalanine or other non-natural amino
acid
<220> FEATURE:
<221> NAME/KEY: VARIANT
<222> LOCATION: 4, 6, 12
<223> OTHER INFORMATION: Xaa = Lys, Arg, Asn, Gln and
other natural/non-natural basic residue

<400> SEQUENCE: 222

Xaa Leu Asn Xaa Gly Xaa Leu Lys Phe Arg Tyr Xaa Ala Arg
1 5 10

<210> SEQ ID NO 223
<211> LENGTH: 14
<212> TYPE: PRT
<213> ORGANISM: Artificial Sequence
<220> FEATURE:
<223> OTHER INFORMATION: Engineered peptides based on Prf-1 protein
<220> FEATURE:
<221> NAME/KEY: VARIANT
<222> LOCATION: 1
<223> OTHER INFORMATION: Xaa = anthrylalanine or other non-natural amino
acid

```
<220> FEATURE:
<221> NAME/KEY: VARIANT
<222> LOCATION: 4, 6
<223> OTHER INFORMATION: Xaa = Lys, Arg, Asn, Gln and
      other natural/non-natural basic residue
<220> FEATURE:
<221> NAME/KEY: VARIANT
<222> LOCATION: 12
<223> OTHER INFORMATION: Xaa = Ser, Thr, Tyr and other
      natural/non-natural H-bond donor/acceptor residue

<400> SEQUENCE: 223

Xaa Leu Asn Xaa Gly Xaa Leu Lys Phe Arg Tyr Xaa Ala Arg
 1               5                  10


<210> SEQ ID NO 224
<211> LENGTH: 17
<212> TYPE: PRT
<213> ORGANISM: Artificial Sequence
<220> FEATURE:
<223> OTHER INFORMATION: Engineered peptides based on Granulysin protein

<400> SEQUENCE: 224

Leu Gly Arg Asp Tyr Arg Thr Cys Leu Thr Ile Val Gln Lys Leu Lys
 1               5                  10                  15

Lys


<210> SEQ ID NO 225
<211> LENGTH: 23
<212> TYPE: PRT
<213> ORGANISM: Artificial Sequence
<220> FEATURE:
<223> OTHER INFORMATION: Engineered peptides based on Granulysin protein

<400> SEQUENCE: 225

Lys Pro Thr Gln Arg Ser Val Ser Asn Ala Ala Thr Arg Val Cys Arg
 1               5                  10                  15

Thr Gly Arg Ser Arg Trp Arg
            20


<210> SEQ ID NO 226
<211> LENGTH: 18
<212> TYPE: PRT
<213> ORGANISM: Artificial Sequence
<220> FEATURE:
<223> OTHER INFORMATION: Engineered peptides based on Granulysin protein

<400> SEQUENCE: 226

Ser Arg Trp Arg Arg Arg Tyr Gln Ser Arg Val Thr Gln Gly Leu Val
 1               5                  10                  15

Ala Gly


<210> SEQ ID NO 227
<211> LENGTH: 17
<212> TYPE: PRT
<213> ORGANISM: Artificial Sequence
<220> FEATURE:
<223> OTHER INFORMATION: Engineered peptides based on Granulysin protein
<220> FEATURE:
<221> NAME/KEY: VARIANT
<222> LOCATION: 4
<223> OTHER INFORMATION: Xaa = Lys, Arg, Asn, Gln and
      other natural/non-natural basic residue

<400> SEQUENCE: 227

Leu Gly Arg Xaa Tyr Arg Thr Cys Leu Thr Ile Val Gln Lys Leu Lys
 1               5                  10                  15
```

Lys

<210> SEQ ID NO 228
<211> LENGTH: 17
<212> TYPE: PRT
<213> ORGANISM: Artificial Sequence
<220> FEATURE:
<223> OTHER INFORMATION: Engineered peptides based on Granulysin protein
<220> FEATURE:
<221> NAME/KEY: VARIANT
<222> LOCATION: 8
<223> OTHER INFORMATION: Xaa = Ser, Thr, Tyr and other
natural/non-natural H-bond donor/acceptor residue

<400> SEQUENCE: 228

Leu Gly Arg Asp Tyr Arg Thr Xaa Leu Thr Ile Val Gln Lys Leu Lys
1 5 10 15

Lys

<210> SEQ ID NO 229
<211> LENGTH: 17
<212> TYPE: PRT
<213> ORGANISM: Artificial Sequence
<220> FEATURE:
<223> OTHER INFORMATION: Engineered peptides based on Granulysin protein
<220> FEATURE:
<221> NAME/KEY: VARIANT
<222> LOCATION: 4
<223> OTHER INFORMATION: Xaa = Lys, Arg, Asn, Gln and
other natural/non-natural basic residue
<220> FEATURE:
<221> NAME/KEY: VARIANT
<222> LOCATION: 8
<223> OTHER INFORMATION: Xaa = Ser, Thr, Tyr and other
natural/non-natural H-bond donor/acceptor residue

<400> SEQUENCE: 229

Leu Gly Arg Xaa Tyr Arg Thr Xaa Leu Thr Ile Val Gln Lys Leu Lys
1 5 10 15

Lys

<210> SEQ ID NO 230
<211> LENGTH: 23
<212> TYPE: PRT
<213> ORGANISM: Artificial Sequence
<220> FEATURE:
<223> OTHER INFORMATION: Engineered peptides based on Granulysin protein
<220> FEATURE:
<221> NAME/KEY: VARIANT
<222> LOCATION: 15
<223> OTHER INFORMATION: Xaa = Ser, Thr, Tyr and other
natural/non-natural H-bond donor/acceptor residue

<400> SEQUENCE: 230

Lys Pro Thr Gln Arg Ser Val Ser Asn Ala Ala Thr Arg Val Xaa Arg
1 5 10 15

Thr Gly Arg Ser Arg Trp Arg
20

<210> SEQ ID NO 231
<211> LENGTH: 18
<212> TYPE: PRT
<213> ORGANISM: Artificial Sequence
<220> FEATURE:
<223> OTHER INFORMATION: Engineered peptides based on Granulysin protein
<220> FEATURE:
<221> NAME/KEY: VARIANT
<222> LOCATION: 15
<223> OTHER INFORMATION: Xaa = Ser, Thr, Tyr and other
natural/non-natural H-bond donor/acceptor residue

<400> SEQUENCE: 231

Lys Pro Thr Gln Arg Ser Val Ser Asn Ala Ala Thr Arg Val Xaa Arg
1 5 10 15

Thr Gly

<210> SEQ ID NO 232
<211> LENGTH: 18
<212> TYPE: PRT
<213> ORGANISM: Artificial Sequence
<220> FEATURE:
<223> OTHER INFORMATION: Engineered peptides based on Granulysin protein
<220> FEATURE:
<221> NAME/KEY: VARIANT
<222> LOCATION: 15
<223> OTHER INFORMATION: Xaa = Ser, Thr, Tyr and other natural/non-natural H-bond donor/acceptor residue

<400> SEQUENCE: 232

Lys Pro Thr Gln Arg Ser Val Ser Asn Tyr Ala Thr Arg Val Xaa Arg
1 5 10 15

Thr Gly

<210> SEQ ID NO 233
<211> LENGTH: 18
<212> TYPE: PRT
<213> ORGANISM: Artificial Sequence
<220> FEATURE:
<223> OTHER INFORMATION: Engineered peptides based on Granulysin protein
<220> FEATURE:
<221> NAME/KEY: VARIANT
<222> LOCATION: 15
<223> OTHER INFORMATION: Xaa = Ser, Thr, Tyr and other natural/non-natural H-bond donor/acceptor residue

<400> SEQUENCE: 233

Lys Pro Thr Gln Arg Ser Val Ser Asn Phe Ala Thr Arg Val Xaa Arg
1 5 10 15

Thr Gly

<210> SEQ ID NO 234
<211> LENGTH: 17
<212> TYPE: PRT
<213> ORGANISM: Artificial Sequence
<220> FEATURE:
<223> OTHER INFORMATION: Engineered peptides based on Granulysin protein

<400> SEQUENCE: 234

Ser Arg Trp Arg Arg Tyr Gln Ser Arg Val Thr Gln Tyr Leu Val Ala
1 5 10 15

Gly

<210> SEQ ID NO 235
<211> LENGTH: 17
<212> TYPE: PRT
<213> ORGANISM: Artificial Sequence
<220> FEATURE:
<223> OTHER INFORMATION: Engineered peptides based on Granulysin protein
<220> FEATURE:
<221> NAME/KEY: VARIANT
<222> LOCATION: 1
<223> OTHER INFORMATION: Xaa = anthrylalanine or other non-natural amino acid

<400> SEQUENCE: 235

Xaa Arg Trp Arg Arg Tyr Gln Ser Arg Val Thr Gln Tyr Leu Val Ala
1 5 10 15

Gly

<210> SEQ ID NO 236
<211> LENGTH: 27
<212> TYPE: PRT
<213> ORGANISM: Artificial Sequence
<220> FEATURE:
<223> OTHER INFORMATION: Engineered peptides based on CidA protein

<400> SEQUENCE: 236

```
Gln Lys Ile Phe His Leu Pro Leu Ala Gly Ser Ile Val Gly Leu Phe
 1               5                  10                  15

Leu Phe Tyr Leu Leu Leu Gln Phe Lys Ile Val
            20                  25
```

<210> SEQ ID NO 237
<211> LENGTH: 41
<212> TYPE: PRT
<213> ORGANISM: Artificial Sequence
<220> FEATURE:
<223> OTHER INFORMATION: Engineered peptides based on CidA protein

<400> SEQUENCE: 237

```
Glu Ile Thr Leu Asn Tyr Ile Leu Phe Phe Ala Val Ile Ile Ile Gly
 1               5                  10                  15

Thr Cys Ile Val Ala Leu Ser Ser Gly Tyr Ile Ala Glu Lys Met Ser
            20                  25                  30

Val Lys His Lys Gln Arg Lys Gly Ile
        35                  40
```

<210> SEQ ID NO 238
<211> LENGTH: 27
<212> TYPE: PRT
<213> ORGANISM: Artificial Sequence
<220> FEATURE:
<223> OTHER INFORMATION: Engineered peptides based on CidA protein
<220> FEATURE:
<221> NAME/KEY: VARIANT
<222> LOCATION: 10
<223> OTHER INFORMATION: Xaa = Lys, Arg, Asn, Gln and
      other natural/non-natural basic residue

<400> SEQUENCE: 238

```
Gln Lys Ile Phe His Leu Pro Leu Ala Xaa Ser Ile Val Gly Leu Phe
 1               5                  10                  15

Leu Phe Tyr Leu Leu Leu Gln Phe Lys Ile Val
            20                  25
```

<210> SEQ ID NO 239
<211> LENGTH: 27
<212> TYPE: PRT
<213> ORGANISM: Artificial Sequence
<220> FEATURE:
<223> OTHER INFORMATION: Engineered peptides based on CidA protein

<400> SEQUENCE: 239

```
Gln Lys Ile Phe His Leu Pro Leu Ala Gly Ser Ile Val Gly Leu Phe
 1               5                  10                  15

Leu Phe Tyr Leu Gly Leu Gln Phe Lys Ile Val
            20                  25
```

<210> SEQ ID NO 240
<211> LENGTH: 27
<212> TYPE: PRT
<213> ORGANISM: Artificial Sequence

```
<220> FEATURE:
<223> OTHER INFORMATION: Engineered peptides based on CidA protein
<220> FEATURE:
<221> NAME/KEY: VARIANT
<222> LOCATION: 10
<223> OTHER INFORMATION: Xaa = Lys, Arg, Asn, Gln and
      other natural/non-natural basic residue

<400> SEQUENCE: 240

Gln Lys Ile Phe His Leu Pro Leu Ala Xaa Ser Ile Val Gly Leu Phe
 1               5                  10                  15

Leu Phe Tyr Leu Gly Leu Gln Phe Lys Ile Val
            20                  25


<210> SEQ ID NO 241
<211> LENGTH: 20
<212> TYPE: PRT
<213> ORGANISM: Artificial Sequence
<220> FEATURE:
<223> OTHER INFORMATION: Engineered peptides based on CidA protein
<220> FEATURE:
<221> NAME/KEY: VARIANT
<222> LOCATION: 3
<223> OTHER INFORMATION: Xaa = Lys, Arg, Asn, Gln and
      other natural/non-natural basic residue

<400> SEQUENCE: 241

Leu Ala Xaa Ser Ile Val Gly Leu Phe Leu Phe Tyr Leu Gly Leu Gln
 1               5                  10                  15

Phe Lys Ile Val
            20


<210> SEQ ID NO 242
<211> LENGTH: 20
<212> TYPE: PRT
<213> ORGANISM: Artificial Sequence
<220> FEATURE:
<223> OTHER INFORMATION: Engineered peptides based on CidA protein
<220> FEATURE:
<221> NAME/KEY: VARIANT
<222> LOCATION: 3, 7
<223> OTHER INFORMATION: Xaa = Lys, Arg, Asn, Gln and
      other natural/non-natural basic residue

<400> SEQUENCE: 242

Leu Ala Xaa Ser Ile Val Xaa Leu Phe Leu Phe Tyr Leu Gly Leu Gln
 1               5                  10                  15

Phe Lys Ile Val
            20


<210> SEQ ID NO 243
<211> LENGTH: 41
<212> TYPE: PRT
<213> ORGANISM: Artificial Sequence
<220> FEATURE:
<223> OTHER INFORMATION: Engineered peptides based on CidA protein
<220> FEATURE:
<221> NAME/KEY: VARIANT
<222> LOCATION: 18, 31
<223> OTHER INFORMATION: Xaa = Ser, Thr, Tyr and other
      natural/non-natural H-bond donor/acceptor residue

<400> SEQUENCE: 243

Glu Ile Thr Leu Asn Tyr Ile Leu Phe Phe Ala Val Ile Ile Ile Gly
 1               5                  10                  15

Thr Xaa Ile Val Ala Leu Ser Ser Gly Tyr Ile Ala Glu Lys Xaa Ser
            20                  25                  30

Val Lys His Lys Gln Arg Lys Gly Ile
```

35 40

<210> SEQ ID NO 244
<211> LENGTH: 14
<212> TYPE: PRT
<213> ORGANISM: Artificial Sequence
<220> FEATURE:
<223> OTHER INFORMATION: Engineered peptides based on CidA protein

<400> SEQUENCE: 244

Ala Glu Lys Met Ser Val Lys His Lys Gln Arg Lys Gly Ile
1 5 10

<210> SEQ ID NO 245
<211> LENGTH: 14
<212> TYPE: PRT
<213> ORGANISM: Artificial Sequence
<220> FEATURE:
<223> OTHER INFORMATION: Engineered peptides based on CidA protein
<220> FEATURE:
<221> NAME/KEY: VARIANT
<222> LOCATION: 2
<223> OTHER INFORMATION: Xaa = Lys, Arg, Asn, Gln and other natural/non-natural basic residue

<400> SEQUENCE: 245

Ala Xaa Lys Met Ser Val Lys His Lys Gln Arg Lys Gly Ile
1 5 10

<210> SEQ ID NO 246
<211> LENGTH: 14
<212> TYPE: PRT
<213> ORGANISM: Artificial Sequence
<220> FEATURE:
<223> OTHER INFORMATION: Engineered peptides based on CidA protein

<400> SEQUENCE: 246

Ala Leu Lys Met Ser Val Lys His Lys Gln Arg Lys Gly Ile
1 5 10

<210> SEQ ID NO 247
<211> LENGTH: 14
<212> TYPE: PRT
<213> ORGANISM: Artificial Sequence
<220> FEATURE:
<223> OTHER INFORMATION: Engineered peptides based on CidA protein
<220> FEATURE:
<221> NAME/KEY: VARIANT
<222> LOCATION: 4
<223> OTHER INFORMATION: Xaa = Ser, Thr, Tyr and other natural/non-natural H-bond donor/acceptor residue

<400> SEQUENCE: 247

Ala Leu Lys Xaa Ser Val Lys His Lys Gln Arg Lys Gly Ile
1 5 10

<210> SEQ ID NO 248
<211> LENGTH: 17
<212> TYPE: PRT
<213> ORGANISM: Artificial Sequence
<220> FEATURE:
<223> OTHER INFORMATION: Engineered peptides based on LrgA protein

<400> SEQUENCE: 248

Lys Val Thr Ser Arg Ser Lys Gly Asp Lys Val Thr Lys Lys Ile Lys
1 5 10 15

Ile

<210> SEQ ID NO 249
<211> LENGTH: 17
<212> TYPE: PRT
<213> ORGANISM: Artificial Sequence
<220> FEATURE:
<223> OTHER INFORMATION: Engineered peptides based on LrgA protein

<400> SEQUENCE: 249

Lys Val Thr Ser Arg Ser Lys Gly Asp Lys Val Thr Lys Trp Ile Lys
 1               5                  10                  15

Ile

<210> SEQ ID NO 250
<211> LENGTH: 17
<212> TYPE: PRT
<213> ORGANISM: Artificial Sequence
<220> FEATURE:
<223> OTHER INFORMATION: Engineered peptides based on LrgA protein
<220> FEATURE:
<221> NAME/KEY: VARIANT
<222> LOCATION: 14
<223> OTHER INFORMATION: Xaa = Asp, Glu or other anionic residue

<400> SEQUENCE: 250

Lys Val Thr Ser Arg Ser Lys Gly Asp Lys Val Thr Lys Xaa Ile Lys
 1               5                  10                  15

Ile

<210> SEQ ID NO 251
<211> LENGTH: 17
<212> TYPE: PRT
<213> ORGANISM: Artificial Sequence
<220> FEATURE:
<223> OTHER INFORMATION: Engineered peptides based on LrgA protein
<220> FEATURE:
<221> NAME/KEY: VARIANT
<222> LOCATION: 14
<223> OTHER INFORMATION: Xaa = Ser, Thr, Tyr and other
natural/non-natural H-bond donor/acceptor residue

<400> SEQUENCE: 251

Lys Val Thr Ser Arg Ser Lys Gly Asp Lys Val Thr Lys Xaa Ile Lys
 1               5                  10                  15

Ile

<210> SEQ ID NO 252
<211> LENGTH: 28
<212> TYPE: PRT
<213> ORGANISM: Artificial Sequence
<220> FEATURE:
<223> OTHER INFORMATION: Engineered peptides based on Lambda S21 protein

<400> SEQUENCE: 252

Ser Leu Val Leu Gly Phe Leu Thr Tyr Leu Thr Asn Leu Tyr Phe Lys
 1               5                  10                  15

Ile Arg Glu Asp Arg Arg Lys Ala Ala Arg Gly Glu
            20                  25

<210> SEQ ID NO 253
<211> LENGTH: 28
<212> TYPE: PRT
<213> ORGANISM: Artificial Sequence
<220> FEATURE:
<223> OTHER INFORMATION: Engineered peptides based on Lambda S21 protein
<220> FEATURE:
<221> NAME/KEY: VARIANT
<222> LOCATION: 19
<223> OTHER INFORMATION: Xaa = Lys, Arg, Asn, Gln or other natural/non-natural basic residue

<400> SEQUENCE: 253

Ser Leu Val Leu Gly Phe Leu Thr Tyr Leu Thr Asn Leu Tyr Phe Lys
1 5 10 15

Ile Arg Xaa Asp Arg Arg Lys Ala Ala Arg Gly Glu
20 25

<210> SEQ ID NO 254
<211> LENGTH: 28
<212> TYPE: PRT
<213> ORGANISM: Artificial Sequence
<220> FEATURE:
<223> OTHER INFORMATION: Engineered peptides based on Lambda S21 protein
<220> FEATURE:
<221> NAME/KEY: VARIANT
<222> LOCATION: 20
<223> OTHER INFORMATION: Xaa = Lys, Arg, Asn, Gln or other natural/non-natural basic residue

<400> SEQUENCE: 254

Ser Leu Val Leu Gly Phe Leu Thr Tyr Leu Thr Asn Leu Tyr Phe Lys
1 5 10 15

Ile Arg Glu Xaa Arg Arg Lys Ala Ala Arg Gly Glu
20 25

<210> SEQ ID NO 255
<211> LENGTH: 28
<212> TYPE: PRT
<213> ORGANISM: Artificial Sequence
<220> FEATURE:
<223> OTHER INFORMATION: Engineered peptides based on Lambda S21 protein
<220> FEATURE:
<221> NAME/KEY: VARIANT
<222> LOCATION: 19, 20
<223> OTHER INFORMATION: Xaa = Ser, Thr, Tyr or other natural/non-natural H-bond donor/acceptor residue

<400> SEQUENCE: 255

Ser Leu Val Leu Gly Phe Leu Thr Tyr Leu Thr Asn Leu Tyr Phe Lys
1 5 10 15

Ile Arg Xaa Xaa Arg Arg Lys Ala Ala Arg Gly Glu
20 25

<210> SEQ ID NO 256
<211> LENGTH: 15
<212> TYPE: PRT
<213> ORGANISM: Artificial Sequence
<220> FEATURE:
<223> OTHER INFORMATION: Engineered peptides based on Lambda S21 protein
<220> FEATURE:
<221> NAME/KEY: VARIANT
<222> LOCATION: 7, 8
<223> OTHER INFORMATION: Xaa = Ser, Thr, Tyr or other natural/non-natural H-bond donor/acceptor residue

<400> SEQUENCE: 256

Leu Tyr Phe Lys Ile Arg Xaa Xaa Arg Arg Lys Ala Ala Arg Gly
1 5 10 15

<210> SEQ ID NO 257
<211> LENGTH: 17
<212> TYPE: PRT
<213> ORGANISM: Artificial Sequence
<220> FEATURE:
<223> OTHER INFORMATION: Engineered peptides based on Holin protein

<400> SEQUENCE: 257

Ala Tyr Leu Arg Gly Arg Tyr Asn Gly Gly Ala Phe Thr Lys Thr Val
1 5 10 15

Ile

<210> SEQ ID NO 258
<211> LENGTH: 22
<212> TYPE: PRT
<213> ORGANISM: Artificial Sequence
<220> FEATURE:
<223> OTHER INFORMATION: Engineered peptides based on Holin protein

<400> SEQUENCE: 258

Ser Ile Gly Ser Leu Ile Lys Arg Phe Ala Ala Lys Lys Ala Gly Val
1 5 10 15

Glu Asp Gly Arg Asn Gln
20

<210> SEQ ID NO 259
<211> LENGTH: 16
<212> TYPE: PRT
<213> ORGANISM: Artificial Sequence
<220> FEATURE:
<223> OTHER INFORMATION: Engineered peptides based on Holin protein

<400> SEQUENCE: 259

Ser Ile Gly Ser Leu Ile Lys Arg Phe Ala Ala Lys Lys Ala Gly Val
1 5 10 15

<210> SEQ ID NO 260
<211> LENGTH: 17
<212> TYPE: PRT
<213> ORGANISM: Artificial Sequence
<220> FEATURE:
<223> OTHER INFORMATION: Engineered peptides based on Holin protein
<220> FEATURE:
<221> NAME/KEY: VARIANT
<222> LOCATION: 1
<223> OTHER INFORMATION: Xaa = anthrylalanine or other non-natural amino acid

<400> SEQUENCE: 260

Xaa Tyr Leu Arg Gly Arg Tyr Asn Gly Gly Ala Phe Thr Lys Thr Val
1 5 10 15

Ile

<210> SEQ ID NO 261
<211> LENGTH: 22
<212> TYPE: PRT
<213> ORGANISM: Artificial Sequence
<220> FEATURE:
<223> OTHER INFORMATION: Engineered peptides based on Holin protein
<220> FEATURE:
<221> NAME/KEY: VARIANT
<222> LOCATION: 17
<223> OTHER INFORMATION: Xaa = Lys, Arg, Asn, Gln or other natural/non-natural basic residue

<400> SEQUENCE: 261

Ser Ile Gly Ser Leu Ile Lys Arg Phe Ala Ala Lys Lys Ala Gly Val
1 5 10 15

Xaa Asp Gly Arg Asn Gln
20

<210> SEQ ID NO 262
<211> LENGTH: 22
<212> TYPE: PRT
<213> ORGANISM: Artificial Sequence -continued

```
<220> FEATURE:
<223> OTHER INFORMATION: Engineered peptides based on Holin protein
<220> FEATURE:
<221> NAME/KEY: VARIANT
<222> LOCATION: 18
<223> OTHER INFORMATION: Xaa = Lys, Arg, Asn, Gln or
      other natural/non-natural basic residue

<400> SEQUENCE: 262

Ser Ile Gly Ser Leu Ile Lys Arg Phe Ala Ala Lys Lys Ala Gly Val
 1              5                   10                  15

Glu Xaa Gly Arg Asn Gln
            20


<210> SEQ ID NO 263
<211> LENGTH: 16
<212> TYPE: PRT
<213> ORGANISM: Artificial Sequence
<220> FEATURE:
<223> OTHER INFORMATION: Engineered peptides based on Holin protein
<220> FEATURE:
<221> NAME/KEY: VARIANT
<222> LOCATION: 11
<223> OTHER INFORMATION: Xaa = Ser, Thr, Tyr or other
      natural/non-natural H-bond donor/acceptor residue

<400> SEQUENCE: 263

Ser Ile Gly Ser Leu Ile Lys Arg Phe Ala Xaa Lys Lys Ala Gly Val
 1              5                   10                  15


<210> SEQ ID NO 264
<211> LENGTH: 18
<212> TYPE: PRT
<213> ORGANISM: Artificial Sequence
<220> FEATURE:
<223> OTHER INFORMATION: Novel therapeutic peptide designs based on
      programmed cell death effector domains

<400> SEQUENCE: 264

Ala Leu Phe Tyr Phe Ala Ser Lys Leu Val Leu Lys Ala Leu Tyr Thr
 1              5                   10                  15

Lys Val


<210> SEQ ID NO 265
<211> LENGTH: 14
<212> TYPE: PRT
<213> ORGANISM: Artificial Sequence
<220> FEATURE:
<223> OTHER INFORMATION: Novel therapeutic peptide designs based on
      programmed cell death effector domains

<400> SEQUENCE: 265

Ala Leu Lys Tyr Ser Val Lys His Lys Gln Arg Lys Gly Ile
 1              5                   10


<210> SEQ ID NO 266
<211> LENGTH: 18
<212> TYPE: PRT
<213> ORGANISM: Artificial Sequence
<220> FEATURE:
<223> OTHER INFORMATION: Novel therapeutic peptide designs based on
      programmed cell death effector domains

<400> SEQUENCE: 266

Leu Lys Lys Ile Thr Asn Phe Arg Gly Lys Arg Tyr Arg Ser Leu Thr
 1              5                   10                  15

Gly Lys
```

<210> SEQ ID NO 267
<211> LENGTH: 15
<212> TYPE: PRT
<213> ORGANISM: Artificial Sequence
<220> FEATURE:
<223> OTHER INFORMATION: Novel therapeutic peptide designs based on
programmed cell death effector domains

<400> SEQUENCE: 267

```
Ala Leu Arg Ser Lys Leu Gln Ser Gln Leu Leu Ser Leu Arg Lys
 1               5                  10                  15
```

<210> SEQ ID NO 268
<211> LENGTH: 16
<212> TYPE: PRT
<213> ORGANISM: Artificial Sequence
<220> FEATURE:
<223> OTHER INFORMATION: Novel therapeutic peptide designs based on
programmed cell death effector domains

<400> SEQUENCE: 268

```
Ser Ile Gly Ser Leu Ile Lys Arg Phe Ala Tyr Lys Lys Ala Gly Val
 1               5                  10                  15
```

<210> SEQ ID NO 269
<211> LENGTH: 19
<212> TYPE: PRT
<213> ORGANISM: Artificial Sequence
<220> FEATURE:
<223> OTHER INFORMATION: Novel therapeutic peptide designs based on
programmed cell death effector domains

<400> SEQUENCE: 269

```
Thr Arg Ala Leu Val Ala Lys Phe Val Gly Tyr Lys Leu Arg Gln Lys
 1               5                  10                  15

Gly Tyr Val
```

<210> SEQ ID NO 270
<211> LENGTH: 26
<212> TYPE: PRT
<213> ORGANISM: Artificial Sequence
<220> FEATURE:
<223> OTHER INFORMATION: Novel therapeutic peptide designs based on
programmed cell death effector domains

<400> SEQUENCE: 270

```
Asn Phe Asn Trp Gly Arg Val Val Ala Leu Phe Tyr Phe Ala Ser Lys
 1               5                  10                  15

Leu Val Leu Lys Ala Leu Tyr Thr Lys Val
            20                  25
```

<210> SEQ ID NO 271
<211> LENGTH: 19
<212> TYPE: PRT
<213> ORGANISM: Artificial Sequence
<220> FEATURE:
<223> OTHER INFORMATION: Novel therapeutic peptide designs based on
programmed cell death effector domains

<400> SEQUENCE: 271

```
Thr Val Thr Ile Phe Val Ala Lys Val Leu Thr Ala Ser Leu Thr Ile
 1               5                  10                  15

Trp Lys Lys
```

<210> SEQ ID NO 272
<211> LENGTH: 17

<212> TYPE: PRT
<213> ORGANISM: Artificial Sequence
<220> FEATURE:
<223> OTHER INFORMATION: Novel therapeutic peptide designs based on programmed cell death effector domains

<400> SEQUENCE: 272

Thr Arg Phe Arg Arg Thr Phe Ser Lys Leu Ala Ala Gln Leu His Val
1 5 10 15

Thr

<210> SEQ ID NO 273
<211> LENGTH: 21
<212> TYPE: PRT
<213> ORGANISM: Artificial Sequence
<220> FEATURE:
<223> OTHER INFORMATION: Novel therapeutic peptide designs based on programmed cell death effector domains

<400> SEQUENCE: 273

Gly Gln Arg Ser Pro Thr Ala Leu Ser Leu Tyr Leu Phe Leu Leu Tyr
1 5 10 15

Trp Val Ile Val Lys
20

<210> SEQ ID NO 274
<211> LENGTH: 23
<212> TYPE: PRT
<213> ORGANISM: Artificial Sequence
<220> FEATURE:
<223> OTHER INFORMATION: Novel therapeutic peptide designs based on programmed cell death effector domains

<400> SEQUENCE: 274

Lys Lys Ile Glu Val Leu Lys Ser Leu Gln Ser Lys Ala Lys Leu Leu
1 5 10 15

Arg Asn Lys Ala Gly Trp Leu
20

<210> SEQ ID NO 275
<211> LENGTH: 15
<212> TYPE: PRT
<213> ORGANISM: Artificial Sequence
<220> FEATURE:
<223> OTHER INFORMATION: Novel therapeutic peptide designs based on programmed cell death effector domains

<400> SEQUENCE: 275

Gly Leu Arg Asn Lys Leu Gln Ser Gln Leu Leu Ser Ile Lys Lys
1 5 10 15

<210> SEQ ID NO 276
<211> LENGTH: 20
<212> TYPE: PRT
<213> ORGANISM: Artificial Sequence
<220> FEATURE:
<223> OTHER INFORMATION: Novel therapeutic peptide designs based on programmed cell death effector domains

<400> SEQUENCE: 276

Lys Leu Ala Lys Lys Val Asp Pro Gln Gly Leu Arg Thr Ile Gly Val
1 5 10 15

Ile Thr Lys Leu
20

<210> SEQ ID NO 277

<211> LENGTH: 15
<212> TYPE: PRT
<213> ORGANISM: Artificial Sequence
<220> FEATURE:
<223> OTHER INFORMATION: Novel therapeutic peptide designs based on programmed cell death effector domains

<400> SEQUENCE: 277

Lys Ser Lys Lys Tyr Thr Leu Pro Leu Lys Asn Leu Lys Ile Arg
1 5 10 15

<210> SEQ ID NO 278
<211> LENGTH: 15
<212> TYPE: PRT
<213> ORGANISM: Artificial Sequence
<220> FEATURE:
<223> OTHER INFORMATION: Novel therapeutic peptide designs based on programmed cell death effector domains

<400> SEQUENCE: 278

Ser Lys Ser Ile Lys Asn Leu Lys Pro Lys Ile Ile Tyr Lys Ser
1 5 10 15

<210> SEQ ID NO 279
<211> LENGTH: 20
<212> TYPE: PRT
<213> ORGANISM: Artificial Sequence
<220> FEATURE:
<223> OTHER INFORMATION: Novel therapeutic peptide designs based on programmed cell death effector domains

<400> SEQUENCE: 279

Leu Ala Lys Ser Ile Val Arg Leu Phe Leu Phe Tyr Leu Gly Leu Gln
1 5 10 15

Phe Lys Ile Val
20

<210> SEQ ID NO 280
<211> LENGTH: 780
<212> TYPE: PRT
<213> ORGANISM: Homo sapiens
<220> FEATURE:
<223> OTHER INFORMATION: programmed cell death / holin-like proteins - Dnm1 (Fig. 1)

<400> SEQUENCE: 280

Met Gly Asn Arg Gly Met Glu Asp Leu Ile Pro Leu Val Asn Arg Leu
1 5 10 15

Gln Asp Ala Phe Ser Ala Ile Gly Gln Asn Ala Asp Leu Asp Leu Pro
20 25 30

Gln Ile Ala Val Val Gly Gly Gln Ser Ala Gly Lys Ser Ser Val Leu
35 40 45

Glu Asn Phe Val Gly Arg Asp Phe Leu Pro Arg Gly Ser Gly Ile Val
50 55 60

Thr Arg Arg Pro Leu Val Leu Gln Leu Val Asn Ala Thr Thr Glu Tyr
65 70 75 80

Ala Glu Phe Leu His Cys Lys Gly Lys Lys Phe Thr Asp Phe Glu Glu
85 90 95

Val Arg Leu Glu Ile Glu Ala Glu Thr Asp Arg Val Thr Gly Thr Asn
100 105 110

Lys Gly Ile Ser Pro Val Pro Ile Asn Leu Arg Val Tyr Ser Pro His
115 120 125

Val Leu Asn Leu Thr Leu Val Asp Leu Pro Gly Met Thr Lys Val Pro
130 135 140

-continued

Val Gly Asp Gln Pro Pro Asp Ile Glu Phe Gln Ile Arg Asp Met Leu
145 150 155 160

Met Gln Phe Val Thr Lys Glu Asn Cys Leu Ile Leu Ala Val Ser Pro
165 170 175

Ala Asn Ser Asp Leu Ala Asn Ser Asp Ala Leu Lys Val Ala Lys Glu
180 185 190

Val Asp Pro Gln Gly Gln Arg Thr Ile Gly Val Ile Thr Lys Leu Asp
195 200 205

Leu Met Asp Glu Gly Thr Asp Ala Arg Asp Val Leu Glu Asn Lys Leu
210 215 220

Leu Pro Leu Arg Arg Gly Tyr Ile Gly Val Val Asn Arg Ser Gln Lys
225 230 235 240

Asp Ile Asp Gly Lys Lys Asp Ile Thr Ala Ala Leu Ala Ala Glu Arg
245 250 255

Lys Phe Phe Leu Ser His Pro Ser Tyr Arg His Leu Ala Asp Arg Met
260 265 270

Gly Thr Pro Tyr Leu Gln Lys Val Leu Asn Gln Gln Leu Thr Asn His
275 280 285

Ile Arg Asp Thr Leu Pro Gly Leu Arg Asn Lys Leu Gln Ser Gln Leu
290 295 300

Leu Ser Ile Glu Lys Glu Val Glu Glu Tyr Lys Asn Phe Arg Pro Asp
305 310 315 320

Asp Pro Ala Arg Lys Thr Lys Ala Leu Leu Gln Met Val Gln Gln Phe
325 330 335

Ala Val Asp Phe Glu Lys Arg Ile Glu Gly Ser Gly Asp Gln Ile Asp
340 345 350

Thr Tyr Glu Leu Ser Gly Gly Ala Arg Ile Asn Arg Ile Phe His Glu
355 360 365

Arg Phe Pro Phe Glu Leu Val Lys Met Glu Phe Asp Glu Lys Glu Leu
370 375 380

Arg Arg Glu Ile Ser Tyr Ala Ile Lys Asn Ile His Gly Ile Arg Thr
385 390 395 400

Gly Leu Phe Thr Pro Asp Leu Ala Phe Glu Ala Thr Val Lys Lys Gln
405 410 415

Val Gln Lys Leu Lys Glu Pro Ser Ile Lys Cys Val Asp Met Val Val
420 425 430

Ser Glu Leu Thr Ala Thr Ile Arg Lys Cys Ser Glu Lys Leu Gln Gln
435 440 445

Tyr Pro Arg Leu Arg Glu Glu Met Glu Arg Ile Val Thr Thr His Ile
450 455 460

Arg Glu Arg Glu Gly Arg Thr Lys Glu Gln Val Met Leu Leu Ile Asp
465 470 475 480

Ile Glu Leu Ala Tyr Met Asn Thr Asn His Glu Asp Phe Ile Gly Phe
485 490 495

Ala Asn Ala Gln Gln Arg Ser Asn Gln Met Asn Lys Lys Lys Thr Ser
500 505 510

Gly Asn Gln Asp Glu Ile Leu Val Ile Arg Lys Gly Trp Leu Thr Ile
515 520 525

Asn Asn Ile Gly Ile Met Lys Gly Gly Ser Lys Glu Tyr Trp Phe Val
530 535 540

Leu Thr Ala Glu Asn Leu Ser Trp Tyr Lys Asp Asp Glu Glu Lys Glu
545 550 555 560

Lys Lys Tyr Met Leu Ser Val Asp Asn Leu Lys Leu Arg Asp Val Glu

```
                565                 570                 575

Lys Gly Phe Met Ser Ser Lys His Ile Phe Ala Leu Phe Asn Thr Glu
            580                 585                 590

Gln Arg Asn Val Tyr Lys Asp Tyr Arg Gln Leu Glu Leu Ala Cys Glu
        595                 600                 605

Thr Gln Glu Glu Val Asp Ser Trp Lys Ala Ser Phe Leu Arg Ala Gly
    610                 615                 620

Val Tyr Pro Glu Arg Val Gly Asp Lys Glu Lys Ala Ser Glu Thr Glu
625                 630                 635                 640

Glu Asn Gly Ser Asp Ser Phe Met His Ser Met Asp Pro Gln Leu Glu
                645                 650                 655

Arg Gln Val Glu Thr Ile Arg Asn Leu Val Asp Ser Tyr Met Ala Ile
            660                 665                 670

Val Asn Lys Thr Val Arg Asp Leu Met Pro Lys Thr Ile Met His Leu
        675                 680                 685

Met Ile Asn Asn Thr Lys Glu Phe Ile Phe Ser Glu Leu Leu Ala Asn
    690                 695                 700

Leu Tyr Ser Cys Gly Asp Gln Asn Thr Leu Met Glu Glu Ser Ala Glu
705                 710                 715                 720

Gln Ala Gln Arg Arg Asp Glu Met Leu Arg Met Tyr His Ala Leu Lys
                725                 730                 735

Glu Ala Leu Ser Ile Ile Gly Asp Ile Asn Thr Thr Thr Val Ser Thr
            740                 745                 750

Pro Met Pro Pro Pro Val Asp Asp Ser Trp Leu Gln Val Gln Ser Val
        755                 760                 765

Pro Ala Gly Arg Arg Ser Pro Thr Ser Ser Pro Thr
    770                 775                 780


<210> SEQ ID NO 281
<211> LENGTH: 191
<212> TYPE: PRT
<213> ORGANISM: Homo sapiens
<220> FEATURE:
<223> OTHER INFORMATION: programmed cell death / holin-like proteins -
      Bax (Fig. 1)

<400> SEQUENCE: 281

Met Asp Gly Ser Gly Glu Gln Pro Arg Gly Gly Gly Pro Thr Ser Ser
 1               5                  10                  15

Glu Gln Ile Met Lys Thr Gly Ala Leu Leu Leu Gln Gly Phe Ile Gln
            20                  25                  30

Asp Arg Ala Gly Arg Met Gly Gly Glu Ala Pro Glu Leu Ala Leu Asp
        35                  40                  45

Pro Val Pro Gln Asp Ala Ser Thr Lys Lys Leu Ser Glu Cys Leu Lys
    50                  55                  60

Arg Ile Gly Asp Glu Leu Asp Ser Asn Met Glu Leu Gln Arg Met Ile
65                  70                  75                  80

Ala Ala Val Asp Thr Asp Ser Pro Arg Glu Val Phe Phe Arg Val Ala
                85                  90                  95

Ala Asp Met Phe Ser Asp Gly Asn Phe Asn Trp Gly Arg Val Val Ala
            100                 105                 110

Leu Phe Tyr Phe Ala Ser Lys Val Leu Lys Ala Leu Cys Thr Lys Val
        115                 120                 125

Pro Glu Leu Ile Arg Thr Ile Met Gly Trp Thr Leu Asp Phe Leu Arg
    130                 135                 140

Glu Arg Leu Leu Gly Trp Ile Gln Asp Gln Gly Gly Trp Asp Gly Leu
```

-continued 145 150 155 160

Leu Ser Tyr Phe Gly Thr Pro Thr Trp Gln Thr Val Thr Ile Phe Val
165 170 175

Ala Gly Val Leu Thr Ala Ser Leu Thr Ile Trp Lys Lys Met Gly
180 185 190

<210> SEQ ID NO 282
<211> LENGTH: 166
<212> TYPE: PRT
<213> ORGANISM: Homo sapiens
<220> FEATURE:
<223> OTHER INFORMATION: programmed cell death / holin-like proteins - Bcl-2 (Fig. 1)
<220> FEATURE:
<221> NAME/KEY: VARIANT
<222> LOCATION: 166
<223> OTHER INFORMATION: Xaa = Any Amino Acid

<400> SEQUENCE: 282

Met Ala His Ala Gly Arg Thr Gly Tyr Asp Asn Arg Glu Ile Val Met
1 5 10 15

Lys Tyr Ile His Tyr Lys Leu Ser Gln Arg Gly Tyr Glu Trp Asp Ala
20 25 30

Gly Asp Asp Val Glu Glu Asn Arg Thr Glu Ala Pro Glu Gly Thr Glu
35 40 45

Ser Glu Val Val His Leu Ala Leu Arg Gln Ala Gly Asp Asp Phe Ser
50 55 60

Arg Arg Tyr Arg Gly Asp Phe Ala Glu Met Ser Ser Gln Leu His Leu
65 70 75 80

Thr Pro Phe Thr Ala Arg Gly Arg Phe Ala Thr Val Val Glu Glu Leu
85 90 95

Phe Arg Asp Gly Val Asn Trp Gly Arg Ile Val Ala Phe Phe Glu Phe
100 105 110

Gly Gly Val Met Cys Val Glu Ser Val Asn Arg Glu Met Ser Pro Leu
115 120 125

Val Asp Asn Ile Ala Leu Trp Met Thr Glu Tyr Leu Asn Arg His Leu
130 135 140

His Thr Trp Ile Gln Asp Asn Gly Gly Trp Asp Ala Phe Val Glu Leu
145 150 155 160

Tyr Gly Pro Ser Met Xaa
165

<210> SEQ ID NO 283
<211> LENGTH: 131
<212> TYPE: PRT
<213> ORGANISM: Staphylococcus aureus
<220> FEATURE:
<223> OTHER INFORMATION: programmed cell death / holin-like proteins - CidA (Fig. 2)

<400> SEQUENCE: 283

Met His Lys Val Gln Leu Ile Ile Lys Leu Leu Leu Gln Leu Gly Ile
1 5 10 15

Ile Ile Val Ile Thr Tyr Ile Gly Thr Glu Ile Gln Lys Ile Phe His
20 25 30

Leu Pro Leu Ala Gly Ser Ile Val Gly Leu Phe Leu Phe Tyr Leu Leu
35 40 45

Leu Gln Phe Lys Ile Val Pro Leu Thr Trp Val Glu Asp Gly Ala Asn
50 55 60

Phe Leu Leu Lys Thr Met Val Phe Phe Phe Ile Pro Ser Val Val Gly

```
65                  70                  75                  80

Ile Met Asp Val Ala Ser Glu Ile Thr Leu Asn Tyr Ile Leu Phe Phe
                85                  90                  95

Ala Val Ile Ile Ile Gly Thr Cys Ile Val Ala Leu Ser Ser Gly Tyr
            100                 105                 110

Ile Ala Glu Lys Met Ser Val Lys His Lys Gln Arg Lys Gly Ile Asp
        115                 120                 125

Ala Tyr Glu
    130


<210> SEQ ID NO 284
<211> LENGTH: 147
<212> TYPE: PRT
<213> ORGANISM: Staphylococcus aureus
<220> FEATURE:
<223> OTHER INFORMATION: programmed cell death  proteins - LrgA (Fig. 2)

<400> SEQUENCE: 284

Met Val Val Lys Gln Gln Lys Asp Ala Ser Lys Pro Ala His Phe Phe
 1               5                  10                  15

His Gln Val Ile Val Ile Ala Leu Val Leu Phe Val Ser Lys Ile Ile
            20                  25                  30

Glu Ser Phe Met Pro Ile Pro Met Pro Ala Ser Val Ile Gly Leu Val
        35                  40                  45

Leu Leu Phe Val Leu Leu Cys Thr Gly Ala Val Lys Leu Gly Glu Val
    50                  55                  60

Glu Lys Val Gly Thr Thr Leu Thr Asn Asn Ile Gly Leu Leu Phe Val
65                  70                  75                  80

Pro Ala Gly Ile Ser Val Val Asn Ser Leu Gly Val Ile Ser Gln Ala
                85                  90                  95

Pro Phe Leu Ile Ile Gly Leu Ile Ile Val Ser Thr Ile Leu Leu Leu
            100                 105                 110

Ile Cys Thr Gly Tyr Val Thr Gln Ile Ile Met Lys Val Thr Ser Arg
        115                 120                 125

Ser Lys Gly Asp Lys Val Thr Lys Lys Ile Lys Ile Glu Glu Ala Gln
    130                 135                 140

Ala His Asp
145


<210> SEQ ID NO 285
<211> LENGTH: 309
<212> TYPE: PRT
<213> ORGANISM: Bos taurus
<220> FEATURE:
<223> OTHER INFORMATION: Perforin 1 protein (Fig. 3)

<400> SEQUENCE: 285

Asp Thr Gln Arg Phe Leu Arg Pro Asp Gly Thr Cys Thr Leu Cys Arg
 1               5                  10                  15

Asn Ala Leu Gln Lys Asp Val Leu Gln Arg Leu Pro Leu Ala Ile Thr
            20                  25                  30

Asp Trp Arg Ala His Gly Ala Gly Cys Lys Arg Arg Val Val Lys Leu
        35                  40                  45

Glu Gly Arg Ser Thr Glu Asp Val Ala Gly Glu Ala Ala Asn Arg Ile
    50                  55                  60

Arg Asn Asp Trp Gln Val Gly Leu Asp Val Ser Pro Lys Pro Asn Ala
65                  70                  75                  80

Asn Val Arg Val Thr Val Ala Gly Ser His Ser Glu Asp Ala Asn Phe
```

```
                85                  90                  95

Ala Ala Gln Lys Thr His Gln Asp Asn Tyr Arg Phe Ser Met Asp Leu
            100                 105                 110

Val Glu Cys Arg Phe Tyr Ser Phe His Leu Val His Thr Pro Pro Val
        115                 120                 125

His Pro Glu Phe Lys Arg Ala Leu Lys Thr Leu Pro Pro His Phe Asn
    130                 135                 140

Thr Ser Thr Lys Pro Asp Tyr His Arg Leu Ile Ser Ser Tyr Gly Thr
145                 150                 155                 160

His Phe Ile Arg Ser Met Glu Leu Gly Gly Arg Ile Ser Ala Leu Thr
                165                 170                 175

Ala Leu Arg Thr Cys Glu Leu Ala Leu Glu Gly Leu Thr Ala Ser Glu
            180                 185                 190

Val Glu Asp Cys Leu Ala Val Glu Ala Glu Val Ser Ile Ser Asp Arg
        195                 200                 205

Ala Ser Ala Ser Pro Ser Phe Lys Ala Cys Glu Glu Lys Lys Lys Asn
    210                 215                 220

His Lys Val Gly Thr Ser Phe His Gln Ala Tyr Arg Glu Arg His Ser
225                 230                 235                 240

Asn Val Asp Gly Gly His His Ser Thr Met His Asp Leu Leu Phe Gly
                245                 250                 255

Ser Gln Ala Gly Pro Glu Gln Phe Ser Ala Trp Val Ala Ser Leu Gln
            260                 265                 270

Asp Ser Pro Gly Leu Val Asp Tyr Thr Leu Glu Pro Leu His Met Leu
        275                 280                 285

Val Glu Ser Gln Asp Pro Arg Arg Glu Ala Leu Arg Gln Ala Val Ser
    290                 295                 300

Lys Tyr Val Thr Asp
305


<210> SEQ ID NO 286
<211> LENGTH: 239
<212> TYPE: PRT
<213> ORGANISM: Homo sapiens
<220> FEATURE:
<223> OTHER INFORMATION: Bcl-2 protein (Fig. 3)

<400> SEQUENCE: 286

Met Ala His Ala Gly Arg Thr Gly Tyr Asp Asn Arg Glu Ile Val Met
 1               5                  10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140
```

```
Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Gly His Lys
225                 230                 235


<210> SEQ ID NO 287
<211> LENGTH: 193
<212> TYPE: PRT
<213> ORGANISM: Homo sapiens
<220> FEATURE:
<223> OTHER INFORMATION: BCL-W protein (Fig. 3)

<400> SEQUENCE: 287

Met Ala Thr Pro Ala Ser Ala Pro Asp Thr Arg Ala Leu Val Ala Asp
 1               5                  10                  15

Phe Val Gly Tyr Lys Leu Arg Gln Lys Gly Tyr Val Cys Gly Ala Gly
            20                  25                  30

Pro Gly Glu Gly Pro Ala Ala Asp Pro Leu His Gln Ala Met Arg Ala
        35                  40                  45

Ala Gly Asp Glu Phe Glu Thr Arg Phe Arg Arg Thr Phe Ser Asp Leu
    50                  55                  60

Ala Ala Gln Leu His Val Thr Pro Gly Ser Ala Gln Gln Arg Phe Thr
65                  70                  75                  80

Gln Val Ser Asp Glu Leu Phe Gln Gly Gly Pro Asn Trp Gly Arg Leu
                85                  90                  95

Val Ala Phe Phe Val Phe Gly Ala Ala Leu Cys Ala Glu Ser Val Asn
            100                 105                 110

Lys Glu Met Glu Pro Leu Val Gly Gln Val Gln Glu Trp Met Val Ala
        115                 120                 125

Tyr Leu Glu Thr Arg Leu Ala Asp Trp Ile His Ser Ser Gly Gly Trp
    130                 135                 140

Ala Glu Phe Thr Ala Leu Tyr Gly Asp Gly Ala Leu Glu Glu Ala Arg
145                 150                 155                 160

Arg Leu Arg Glu Gly Asn Trp Ala Ser Val Arg Thr Val Leu Thr Gly
                165                 170                 175

Ala Val Ala Leu Gly Ala Leu Val Thr Val Gly Ala Phe Phe Ala Ser
            180                 185                 190

Lys


<210> SEQ ID NO 288
<211> LENGTH: 19
<212> TYPE: PRT
<213> ORGANISM: Artificial Sequence
<220> FEATURE:
<223> OTHER INFORMATION: engineered peptide based on programmed cell
      death effector proteins

<400> SEQUENCE: 288

Ser Gln Ser Asn Arg Glu Leu Val Val Asp Phe Leu Ser Tyr Lys Leu
 1               5                  10                  15
```

Ser Gln Lys

<210> SEQ ID NO 289
<211> LENGTH: 17
<212> TYPE: PRT
<213> ORGANISM: Artificial Sequence
<220> FEATURE:
<223> OTHER INFORMATION: engineered peptide based on programmed cell death effector proteins

<400> SEQUENCE: 289

```
Gln Lys Leu Lys Lys Met Val Asp Lys Pro Thr Gln Arg Ser Val Ser
 1               5                  10                  15

Asn
```

<210> SEQ ID NO 290
<211> LENGTH: 76
<212> TYPE: PRT
<213> ORGANISM: Homo sapiens
<220> FEATURE:
<223> OTHER INFORMATION: Helix 1 of human Bcl-2

<400> SEQUENCE: 290

```
Met Ala His Ala Gly Arg Thr Gly Tyr Asp Asn Arg Glu Ile Val Met
 1               5                  10                  15

Lys Tyr Ile His Tyr Lys Leu Ser Gln Arg Gly Tyr Glu Trp Asp Ala
            20                  25                  30

Gly Asp Asp Val Glu Glu Asn Arg Thr Glu Ala Pro Glu Gly Thr Glu
        35                  40                  45

Ser Glu Val Val His Leu Thr Leu Arg Gln Ala Gly Asp Asp Phe Ser
    50                  55                  60

Arg Arg Tyr Arg Arg Asp Phe Ala Glu Met Ser Ser
65                  70                  75
```

<210> SEQ ID NO 291
<211> LENGTH: 76
<212> TYPE: PRT
<213> ORGANISM: Homo sapiens
<220> FEATURE:
<223> OTHER INFORMATION: Helix 2 of human Bcl-2

<400> SEQUENCE: 291

```
Gly Asp Asp Val Glu Glu Asn Arg Thr Glu Ala Pro Glu Gly Thr Glu
 1               5                  10                  15

Ser Glu Val Val His Leu Ala Leu Arg Gln Ala Gly Asp Asp Phe Ser
            20                  25                  30

Arg Arg Tyr Arg Gly Asp Phe Ala Glu Met Ser Ser Gln Leu His Leu
        35                  40                  45

Thr Pro Phe Thr Ala Arg Gly Arg Phe Ala Thr Val Val Glu Glu Leu
    50                  55                  60

Phe Arg Asp Gly Val Asn Trp Gly Arg Ile Val Ala
65                  70                  75
```

<210> SEQ ID NO 292
<211> LENGTH: 77
<212> TYPE: PRT
<213> ORGANISM: Homo sapiens
<220> FEATURE:
<223> OTHER INFORMATION: Helix 1 of human Bcl-X1

<400> SEQUENCE: 292

```
Met Ser Gln Ser Asn Arg Glu Leu Val Val Asp Phe Leu Ser Tyr Lys
```

-continued

```
 1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Met Glu Thr Pro
        35                  40                  45

Ser Ala Ile Asn Gly Asn Pro Ser Trp His Lys Leu Ala Asp Ser Pro
    50                  55                  60

Ala Val Asn Gly Ala Thr Gly His Ser Ser Ser Leu Asp
65                  70                  75


<210> SEQ ID NO 293
<211> LENGTH: 77
<212> TYPE: PRT
<213> ORGANISM: Homo sapiens
<220> FEATURE:
<223> OTHER INFORMATION: Helix 2 of human Bcl-W

<400> SEQUENCE: 293

Gly Pro Leu Gly Ser Met Ala Thr Pro Ala Ser Ala Pro Asp Thr Arg
 1               5                   10                  15

Ala Leu Val Ala Asp Phe Val Gly Tyr Lys Leu Arg Gln Lys Gly Tyr
            20                  25                  30

Val Cys Gly Ala Gly Pro Gly Glu Gly Pro Ala Ala Asp Pro Leu His
        35                  40                  45

Gln Ala Met Arg Ala Ala Gly Asp Glu Phe Glu Thr Arg Phe Arg Arg
    50                  55                  60

Thr Phe Ser Asp Leu Ala Ala Gln Leu His Val Thr Pro
65                  70                  75


<210> SEQ ID NO 294
<211> LENGTH: 74
<212> TYPE: PRT
<213> ORGANISM: Homo sapiens
<220> FEATURE:
<223> OTHER INFORMATION: Helix 4 of human Bax

<400> SEQUENCE: 294

Pro Arg Glu Val Phe Phe Arg Val Ala Ala Asp Met Phe Ser Asp Gly
 1               5                   10                  15

Asn Phe Asn Trp Gly Arg Val Val Ala Leu Phe Tyr Phe Ala Ser Lys
            20                  25                  30

Leu Val Leu Lys Ala Leu Cys Thr Lys Val Pro Glu Leu Ile Arg Thr
        35                  40                  45

Ile Met Gly Trp Thr Leu Asp Phe Leu Arg Glu Arg Leu Leu Gly Trp
    50                  55                  60

Ile Gln Asp Gln Gly Gly Trp Asp Gly Leu
65                  70


<210> SEQ ID NO 295
<211> LENGTH: 74
<212> TYPE: PRT
<213> ORGANISM: Homo sapiens
<220> FEATURE:
<223> OTHER INFORMATION: Helix 1 of human CTL Granulysin

<400> SEQUENCE: 295

Gly Arg Asp Tyr Arg Thr Cys Leu Thr Ile Val Gln Lys Leu Lys Lys
 1               5                   10                  15

Met Val Asp Lys Pro Thr Gln Arg Ser Val Ser Asn Ala Ala Thr Arg
            20                  25                  30
```

```
Val Cys Arg Thr Gly Arg Ser Arg Trp Arg Asp Val Cys Arg Asn Phe
        35                  40                  45

Met Arg Arg Tyr Gln Ser Arg Val Ile Gln Gly Leu Val Ala Gly Glu
    50                  55                  60

Thr Ala Gln Gln Ile Cys Glu Asp Leu Arg
65                  70


<210> SEQ ID NO 296
<211> LENGTH: 74
<212> TYPE: PRT
<213> ORGANISM: Homo sapiens
<220> FEATURE:
<223> OTHER INFORMATION: Helix 1-2 span of human CTL Granulysin

<400> SEQUENCE: 296

Gly Arg Asp Tyr Arg Thr Cys Leu Thr Ile Val Gln Lys Leu Lys Lys
 1               5                  10                  15

Met Val Asp Lys Pro Thr Gln Arg Ser Val Ser Asn Ala Ala Thr Arg
            20                  25                  30

Val Cys Arg Thr Gly Arg Ser Arg Trp Arg Asp Val Cys Arg Asn Phe
        35                  40                  45

Met Arg Arg Tyr Gln Ser Arg Val Ile Gln Gly Leu Val Ala Gly Glu
    50                  55                  60

Thr Ala Gln Gln Ile Cys Glu Asp Leu Arg
65                  70


<210> SEQ ID NO 297
<211> LENGTH: 18
<212> TYPE: PRT
<213> ORGANISM: Homo sapiens

<400> SEQUENCE: 297

Phe Thr Ala Arg Gly Arg Phe Ala Thr Val Val Glu Glu Leu Phe Arg
 1               5                  10                  15

Asp Gly


<210> SEQ ID NO 298
<211> LENGTH: 18
<212> TYPE: PRT
<213> ORGANISM: Homo sapiens

<400> SEQUENCE: 298

Gly Ser Ala Gln Gln Arg Phe Thr Gln Val Ser Asp Glu Leu Phe Gln
 1               5                  10                  15

Gly Gly


<210> SEQ ID NO 299
<211> LENGTH: 18
<212> TYPE: PRT
<213> ORGANISM: Homo sapiens

<400> SEQUENCE: 299

Ser Pro Arg Glu Val Phe Phe Arg Val Ala Ala Asp Met Phe Ser Asp
 1               5                  10                  15

Gly Asn


<210> SEQ ID NO 300
<211> LENGTH: 50
<212> TYPE: PRT
<213> ORGANISM: Homo sapiens

<400> SEQUENCE: 300
```

Glu Glu Val Tyr Lys Arg Pro Leu Phe Leu Gln Pro Thr Tyr Arg Tyr
1 5 10 15

His Arg Leu Pro Leu Pro Glu Gln Gly Ser Pro Leu Glu Ala Gln Leu
20 25 30

Asp Ala Phe Val Ser Val Leu Arg Glu Thr Pro Ser Leu Leu Gln Leu
35 40 45

Arg Asp
50

<210> SEQ ID NO 301
<211> LENGTH: 19
<212> TYPE: PRT
<213> ORGANISM: Homo sapiens

<400> SEQUENCE: 301

Glu Gly Pro Gln Gly Asp Leu Leu Thr Lys Thr Gln Glu Leu Gly Arg
1 5 10 15

Asp Tyr Arg

<210> SEQ ID NO 302
<211> LENGTH: 26
<212> TYPE: PRT
<213> ORGANISM: Homo sapiens

<400> SEQUENCE: 302

Glu Val Arg Ala Gln Leu Leu Glu Leu Pro Tyr Ala Arg Lys Glu Leu
1 5 10 15

Ser Leu Leu Val Leu Leu Pro Asp Asp Gly
20 25

<210> SEQ ID NO 303
<211> LENGTH: 20
<212> TYPE: PRT
<213> ORGANISM: Homo sapiens

<400> SEQUENCE: 303

Leu Ile Ser Ser Tyr Gly Thr His Phe Ile Arg Ser Met Glu Leu Gly
1 5 10 15

Gly Arg Ile Ser
20

<210> SEQ ID NO 304
<211> LENGTH: 20
<212> TYPE: PRT
<213> ORGANISM: Homo sapiens

<400> SEQUENCE: 304

Leu Gln Asn Ala Thr Val Glu Ala Gly Thr Arg Cys Gln Val Ala Gly
1 5 10 15

Trp Gly Ser Gln
20

<210> SEQ ID NO 305
<211> LENGTH: 20
<212> TYPE: PRT
<213> ORGANISM: Homo sapiens

<400> SEQUENCE: 305

Ser Ser Lys Ala Gln Val Lys Pro Gly Gln Leu Cys Ser Val Ala Gly
1 5 10 15

Trp Gly Tyr Val

20

<210> SEQ ID NO 306
<211> LENGTH: 20
<212> TYPE: PRT
<213> ORGANISM: Homo sapiens

<400> SEQUENCE: 306

Ser Ala Pro His Gln Pro Gly Pro Ser Leu Trp Ala Glu Ala Lys Thr
1 5 10 15

Ser Glu Ala Pro
20

<210> SEQ ID NO 307
<211> LENGTH: 21
<212> TYPE: PRT
<213> ORGANISM: Homo sapiens

<400> SEQUENCE: 307

Lys Asp Gly Val Thr Pro Ile Lys Asp Leu Thr Ala His Phe Arg Gly
1 5 10 15

Asp Arg Cys Lys Thr
20

<210> SEQ ID NO 308
<211> LENGTH: 19
<212> TYPE: PRT
<213> ORGANISM: Homo sapiens

<400> SEQUENCE: 308

Pro Pro Pro Glu Lys Lys Glu Leu Arg Lys Val Ala His Leu Thr Gly
1 5 10 15

Lys Ser Asn

<210> SEQ ID NO 309
<211> LENGTH: 28
<212> TYPE: PRT
<213> ORGANISM: Homo sapiens

<400> SEQUENCE: 309

Val Asn Trp Gly Arg Ile Val Ala Phe Phe Glu Phe Gly Gly Val Met
1 5 10 15

Cys Val Glu Ser Val Asn Arg Glu Met Ser Pro Leu
20 25

<210> SEQ ID NO 310
<211> LENGTH: 28
<212> TYPE: PRT
<213> ORGANISM: Homo sapiens

<400> SEQUENCE: 310

Pro Asn Trp Gly Arg Leu Val Ala Phe Phe Val Phe Gly Ala Ala Leu
1 5 10 15

Cys Ala Glu Ser Val Asn Lys Glu Met Glu Pro Leu
20 25

<210> SEQ ID NO 311
<211> LENGTH: 28
<212> TYPE: PRT
<213> ORGANISM: Homo sapiens

<400> SEQUENCE: 311

Phe Asn Trp Gly Arg Val Val Ala Leu Phe Tyr Phe Ala Ser Lys Leu 1 5 10 15

Val Leu Lys Ala Leu Cys Thr Lys Val Pro Glu Leu
20 25

<210> SEQ ID NO 312
<211> LENGTH: 50
<212> TYPE: PRT
<213> ORGANISM: Homo sapiens

<400> SEQUENCE: 312

Ala His Gly Pro Pro Pro Ala Leu Val Phe Ser Cys Gln Met Gly Val
1 5 10 15

Gly Arg Thr Asn Leu Gly Met Val Leu Gly Thr Leu Ile Leu Leu His
20 25 30

Arg Ser Gly Thr Thr Ser Gln Pro Glu Ala Ala Pro Thr Gln Ala Lys
35 40 45

Pro Leu
50

<210> SEQ ID NO 313
<211> LENGTH: 28
<212> TYPE: PRT
<213> ORGANISM: Homo sapiens

<400> SEQUENCE: 313

Thr Cys Leu Thr Ile Val Gln Lys Leu Lys Lys Met Val Asp Lys Pro
1 5 10 15

Thr Gln Arg Ser Val Ser Asn Ala Ala Thr Arg Val
20 25

<210> SEQ ID NO 314
<211> LENGTH: 31
<212> TYPE: PRT
<213> ORGANISM: Homo sapiens

<400> SEQUENCE: 314

Val Glu Leu Ser Thr Val Glu Lys Ser Leu Thr Phe Glu Lys Leu Thr
1 5 10 15

Ala Trp Thr Lys Pro Asp Cys Met Lys Ser Thr Glu Val Glu Val
20 25 30

<210> SEQ ID NO 315
<211> LENGTH: 31
<212> TYPE: PRT
<213> ORGANISM: Homo sapiens

<400> SEQUENCE: 315

Ala Leu Thr Ala Leu Arg Thr Cys Glu Leu Ala Leu Glu Gly Leu Thr
1 5 10 15

Ala Ser Glu Val Glu Asp Cys Leu Ala Val Glu Ala Glu Val Ser
20 25 30

<210> SEQ ID NO 316
<211> LENGTH: 28
<212> TYPE: PRT
<213> ORGANISM: Homo sapiens

<400> SEQUENCE: 316

Arg Ser Gly Gly Arg Leu Ser Arg Phe Pro Arg Phe Val Asn Val Thr
1 5 10 15

Val Thr Pro Glu Asp Gln Cys Arg Pro Asn Asn Val
20 25

<210> SEQ ID NO 317
<211> LENGTH: 25
<212> TYPE: PRT
<213> ORGANISM: Homo sapiens

<400> SEQUENCE: 317

Ser Met Ser Thr Leu Ala Thr Thr Leu Gln Glu Val Leu Leu Thr Val
 1               5                  10                  15

Gln Lys Asp Cys Gln Cys Glu Arg Leu
            20                  25

<210> SEQ ID NO 318
<211> LENGTH: 28
<212> TYPE: PRT
<213> ORGANISM: Homo sapiens

<400> SEQUENCE: 318

Ser Thr Gln Asp Pro Ser Thr Gln Ala Ser Thr Ala Ser Ser Pro Ala
 1               5                  10                  15

Pro Glu Glu Asn Ala Pro Ser Glu Gly Gln Arg Val
            20                  25

<210> SEQ ID NO 319
<211> LENGTH: 29
<212> TYPE: PRT
<213> ORGANISM: Homo sapiens

<400> SEQUENCE: 319

Leu Leu Glu Lys Pro Lys Leu Phe Phe Ile Gln Ala Cys Arg Gly Thr
 1               5                  10                  15

Glu Leu Asp Asp Gly Ile Gln Ala Asp Ser Gly Pro Ile
            20                  25

<210> SEQ ID NO 320
<211> LENGTH: 27
<212> TYPE: PRT
<213> ORGANISM: Homo sapiens

<400> SEQUENCE: 320

Ser Arg Ser Met Pro Leu Glu Trp Glu Asp Thr Tyr Gly Ile Val Leu
 1               5                  10                  15

Leu Ser Gly Val Lys Tyr Lys Lys Gly Gly Leu
            20                  25

<210> SEQ ID NO 321
<211> LENGTH: 15
<212> TYPE: PRT
<213> ORGANISM: Homo sapiens

<400> SEQUENCE: 321

Val Asp Asn Ile Ala Leu Trp Met Thr Glu Tyr Leu Asn Arg His
 1               5                  10                  15

<210> SEQ ID NO 322
<211> LENGTH: 15
<212> TYPE: PRT
<213> ORGANISM: Homo sapiens

<400> SEQUENCE: 322

Val Gly Gln Val Gln Glu Trp Met Val Ala Tyr Leu Glu Thr Arg
 1               5                  10                  15

-continued

<210> SEQ ID NO 323
<211> LENGTH: 15
<212> TYPE: PRT
<213> ORGANISM: Homo sapiens

<400> SEQUENCE: 323

Ile Arg Thr Ile Met Gly Trp Thr Leu Asp Phe Leu Arg Glu Arg
1 5 10 15

<210> SEQ ID NO 324
<211> LENGTH: 50
<212> TYPE: PRT
<213> ORGANISM: Homo sapiens

<400> SEQUENCE: 324

Pro Met Glu Gln Phe Gln Val Ile Gln Ser Phe Leu Arg Met Val Pro
1 5 10 15

Gln Gly Arg Arg Met Val Glu Glu Val Asp Arg Ala Ile Thr Ala Cys
20 25 30

Ala Glu Leu His Asp Leu Lys Glu Val Val Leu Glu Asn Gln Lys Lys
35 40 45

Leu Glu
50

<210> SEQ ID NO 325
<211> LENGTH: 15
<212> TYPE: PRT
<213> ORGANISM: Homo sapiens

<400> SEQUENCE: 325

Cys Arg Thr Gly Arg Ser Arg Trp Arg Asp Val Cys Arg Asn Phe
1 5 10 15

<210> SEQ ID NO 326
<211> LENGTH: 21
<212> TYPE: PRT
<213> ORGANISM: Homo sapiens

<400> SEQUENCE: 326

Leu Leu Pro Lys Phe Lys Leu Gln Glu Asp Tyr Asp Met Glu Ser Val
1 5 10 15

Leu Arg His Leu Gly
20

<210> SEQ ID NO 327
<211> LENGTH: 24
<212> TYPE: PRT
<213> ORGANISM: Homo sapiens

<400> SEQUENCE: 327

Ile Ser Asp Arg Ala Ser Ala Ser Pro Ser Phe Lys Ala Cys Glu Glu
1 5 10 15

Lys Lys Lys Asn His Lys Val Gly
20

<210> SEQ ID NO 328
<211> LENGTH: 15
<212> TYPE: PRT
<213> ORGANISM: Homo sapiens

<400> SEQUENCE: 328

Cys Thr Gly Val Leu Thr Arg Arg Gly Gly Ile Cys Asn Gly Asp
1 5 10 15

<210> SEQ ID NO 329
<211> LENGTH: 24
<212> TYPE: PRT
<213> ORGANISM: Homo sapiens

<400> SEQUENCE: 329

```
Phe His Gly Asn Tyr Ser Arg Ala Thr Glu Ile Cys Val Gly Asp Pro
 1               5                  10                  15

Lys Lys Thr Gln Thr Gly Phe Lys
            20
```

<210> SEQ ID NO 330
<211> LENGTH: 25
<212> TYPE: PRT
<213> ORGANISM: Homo sapiens

<400> SEQUENCE: 330

```
Trp Gly Gln Gly Gln Ser Pro Arg Pro Glu Asn Ser Leu Glu Arg Glu
 1               5                  10                  15

Glu Met Gly Pro Val Pro Ala His Thr
            20                  25
```

<210> SEQ ID NO 331
<211> LENGTH: 22
<212> TYPE: PRT
<213> ORGANISM: Homo sapiens

<400> SEQUENCE: 331

```
Asn Asp Thr Asp Ala Asn Pro Arg Tyr Lys Ile Pro Val Glu Ala Asp
 1               5                  10                  15

Phe Leu Phe Ala Tyr Ser
            20
```

<210> SEQ ID NO 332
<211> LENGTH: 25
<212> TYPE: PRT
<213> ORGANISM: Homo sapiens

<400> SEQUENCE: 332

```
Val Ile Asn Glu Thr Gly Leu Tyr Phe Val Tyr Ser Lys Val Tyr Phe
 1               5                  10                  15

Arg Gly Gln Ser Cys Asn Asn Leu Pro
            20                  25
```

<210> SEQ ID NO 333
<211> LENGTH: 53
<212> TYPE: PRT
<213> ORGANISM: Homo sapiens

<400> SEQUENCE: 333

```
Pro Leu Gln Thr Pro Ala Ala Pro Gly Ala Ala Ala Gly Pro Ala Leu
 1               5                  10                  15

Ser Pro Val Pro Pro Val Val His Leu Thr Leu Arg Gln Ala Gly Asp
            20                  25                  30

Asp Phe Ser Arg Arg Tyr Arg Arg Asp Phe Ala Glu Met Ser Ser Gln
        35                  40                  45

Leu His Leu Thr Pro
    50
```

<210> SEQ ID NO 334
<211> LENGTH: 34
<212> TYPE: PRT

<213> ORGANISM: Homo sapiens

<400> SEQUENCE: 334

Ala Asp Pro Leu His Gln Ala Met Arg Ala Ala Gly Asp Glu Phe Glu
1 5 10 15

Thr Arg Phe Arg Arg Thr Phe Ser Asp Leu Ala Ala Gln Leu His Val
20 25 30

Thr Pro

<210> SEQ ID NO 335
<211> LENGTH: 38
<212> TYPE: PRT
<213> ORGANISM: Homo sapiens

<400> SEQUENCE: 335

Pro Val Pro Gln Asp Ala Ser Thr Lys Lys Leu Ser Glu Cys Leu Lys
1 5 10 15

Arg Ile Gly Asp Glu Leu Asp Ser Asn Met Glu Leu Gln Arg Met Ile
20 25 30

Ala Ala Val Asp Thr Asp
35

<210> SEQ ID NO 336
<211> LENGTH: 82
<212> TYPE: PRT
<213> ORGANISM: Homo sapiens

<400> SEQUENCE: 336

Glu Pro Val Leu Phe Leu Arg Ala Asp Glu Asp Phe Val Ser Tyr Thr
1 5 10 15

Pro Arg Asp Lys Gln Asn Leu His Glu Asn Leu Gln Gly Leu Gly Pro
20 25 30

Gly Val Arg Val Glu Ser Leu Glu Leu Ala Ile Arg Lys Glu Ile His
35 40 45

Asp Phe Ala Gln Leu Ser Glu Asn Thr Tyr His Val Tyr His Asn Thr
50 55 60

Glu Asp Leu Trp Gly Glu Pro His Ala Val Ala Ile His Gly Glu Asp
65 70 75 80

Asp Leu

<210> SEQ ID NO 337
<211> LENGTH: 29
<212> TYPE: PRT
<213> ORGANISM: Homo sapiens

<400> SEQUENCE: 337

Leu Val Phe Ser Arg Leu Ser Pro Glu Tyr Tyr Asp Pro Ala Arg Ala
1 5 10 15

His Leu Arg Asp Gly Glu Lys Ser Cys Pro Cys Gly Gln
20 25

<210> SEQ ID NO 338
<211> LENGTH: 61
<212> TYPE: PRT
<213> ORGANISM: Homo sapiens

<400> SEQUENCE: 338

Gly His Glu Ala Phe Leu Leu Thr Glu Gly Ser Glu Glu Lys Arg Ser
1 5 10 15

Ala Lys Thr Val Asn Gln Leu Ala His Ala Leu His Gln Asp Lys Gln

```
            20                  25                  30

Leu His Ala Gly Ser Leu Val Ser Val Met Trp Pro Asn Ser Lys Cys
        35                  40                  45

Pro Leu Leu Lys Asp Asp Leu Val Leu Met Asp Ser Pro
    50                  55                  60


<210> SEQ ID NO 339
<211> LENGTH: 47
<212> TYPE: PRT
<213> ORGANISM: Homo sapiens

<400> SEQUENCE: 339

Pro Val Ser Ile Ser Ser Ala Leu Ala Met Val Leu Leu Gly Ala Lys
 1               5                  10                  15

Gly Asn Thr Ala Thr Gln Met Ala Gln Ala Leu Ser Leu Asn Thr Glu
            20                  25                  30

Glu Asp Ile His Arg Ala Phe Gln Ser Leu Leu Thr Glu Val Asn
        35                  40                  45


<210> SEQ ID NO 340
<211> LENGTH: 77
<212> TYPE: PRT
<213> ORGANISM: Homo sapiens

<400> SEQUENCE: 340

Ile Leu Ala Val Ser Pro Ala Asn Ser Asp Leu Ala Asn Ser Asp Ala
 1               5                  10                  15

Leu Lys Val Ala Lys Glu Val Asp Pro Gln Gly Gln Arg Thr Ile Gly
            20                  25                  30

Val Ile Thr Lys Leu Asp Leu Met Asp Glu Gly Thr Asp Ala Arg Asp
        35                  40                  45

Val Leu Glu Asn Lys Leu Leu Pro Leu Arg Arg Gly Tyr Ile Gly Val
    50                  55                  60

Val Asn Arg Ser Gln Lys Asp Ile Asp Gly Lys Lys Asp
65                  70                  75


<210> SEQ ID NO 341
<211> LENGTH: 85
<212> TYPE: PRT
<213> ORGANISM: Homo sapiens

<400> SEQUENCE: 341

Pro Ser Leu Pro Ser Gln Ala Val Trp Ser Gln Gly Pro Pro Pro Pro
 1               5                  10                  15

Pro Pro Tyr Gly Arg Leu Leu Ala Asn Ser Asn Ala His Pro Gly Pro
            20                  25                  30

Phe Pro Pro Ser Thr Gly Ala Gln Ser Thr Ala His Pro Pro Val Ser
        35                  40                  45

Thr His His His His His Gln Gln Gln Gln Gln Gln Gln Gln Gln Gln
    50                  55                  60

Gln Gln Gln Gln Gln Gln Gln Gln Gln His His Gly Asn Ser Gly Pro
65                  70                  75                  80

Pro Pro Pro Gly Ala
                85


<210> SEQ ID NO 342
<211> LENGTH: 52
<212> TYPE: PRT
<213> ORGANISM: Homo sapiens
```

<400> SEQUENCE: 342

Leu Cys Leu Leu Val Met Phe Phe Met Val Leu Val Ala Leu Val Gly
1 5 10 15

Leu Gly Leu Gly Met Phe Gln Leu Phe His Leu Gln Lys Glu Leu Ala
20 25 30

Glu Leu Arg Glu Ser Thr Ser Gln Met His Thr Ala Ser Ser Leu Glu
35 40 45

Lys Gln Ile Gly
50

<210> SEQ ID NO 343
<211> LENGTH: 58
<212> TYPE: PRT
<213> ORGANISM: Homo sapiens

<400> SEQUENCE: 343

Phe Ala Ala Gln Lys Thr His Gln Asp Asn Tyr Arg Phe Ser Met Asp
1 5 10 15

Leu Val Glu Cys Arg Phe Tyr Ser Phe His Leu Val His Thr Pro Pro
20 25 30

Val His Pro Glu Phe Lys Arg Ala Leu Lys Thr Leu Pro Pro His Phe
35 40 45

Asn Thr Ser Thr Lys Pro Asp Tyr His Arg
50 55

<210> SEQ ID NO 344
<211> LENGTH: 58
<212> TYPE: PRT
<213> ORGANISM: Homo sapiens

<400> SEQUENCE: 344

Met Asp Glu Ser Val Val Leu Glu Pro Glu Ala Thr Gly Glu Ser Ser
1 5 10 15

Ser Leu Glu Pro Thr Pro Ser Ser Gln Glu Ala Gln Arg Ala Leu Gly
20 25 30

Thr Ser Pro Glu Leu Pro Thr Gly Val Thr Gly Ser Ser Gly Thr Arg
35 40 45

Leu Pro Pro Thr Pro Lys Ala Gln Asp Gly
50 55

<210> SEQ ID NO 345
<211> LENGTH: 44
<212> TYPE: PRT
<213> ORGANISM: Homo sapiens

<400> SEQUENCE: 345

Ala Tyr Asp Leu Arg Arg Arg Glu Arg Gln Ser Arg Gln Thr Phe Ser
1 5 10 15

Ile Ser Ser Met Ser Glu Asn Gly Tyr Asp Pro Gln Gln Asn Leu Asn
20 25 30

Asp Leu Met Leu Leu Gln Leu Asp Arg Glu Ala Asn
35 40

<210> SEQ ID NO 346
<211> LENGTH: 44
<212> TYPE: PRT
<213> ORGANISM: Homo sapiens

<400> SEQUENCE: 346

Ala His Asn Ile Lys Glu Gln Glu Arg Thr Gln Gln Phe Ile Pro Val

```
 1               5                   10                  15

Lys Arg Pro Ile Pro His Pro Ala Tyr Asn Pro Lys Asn Phe Ser Asn
            20                  25                  30

Asp Ile Met Leu Leu Gln Leu Glu Arg Lys Ala Lys
        35                  40


<210> SEQ ID NO 347
<211> LENGTH: 63
<212> TYPE: PRT
<213> ORGANISM: Homo sapiens

<400> SEQUENCE: 347

Glu Asp Asp Glu Glu Glu Asp Glu Phe Glu Pro Pro Ile Val Lys Gly
 1               5                   10                  15

Val Lys Pro Ala Lys Ala Ala Pro Ala Ala Pro Ala Ser Glu Asp Glu
            20                  25                  30

Glu Asp Asp Glu Asp Glu Asp Asp Glu Glu Asp Asp Asp Glu Glu Glu
        35                  40                  45

Glu Asp Asp Ser Glu Glu Glu Val Met Glu Ile Thr Thr Ala Lys
    50                  55                  60


<210> SEQ ID NO 348
<211> LENGTH: 47
<212> TYPE: PRT
<213> ORGANISM: Homo sapiens

<400> SEQUENCE: 348

Phe Asp Val Ile Val Tyr Asn Asp Cys Ser Cys Ala Lys Met Gln Asp
 1               5                   10                  15

Leu Leu Lys Lys Ala Ser Glu Glu Asp His Thr Asn Ala Ala Cys Phe
            20                  25                  30

Ala Cys Ile Leu Leu Ser His Gly Glu Glu Asn Val Ile Tyr Gly
        35                  40                  45


<210> SEQ ID NO 349
<211> LENGTH: 18
<212> TYPE: PRT
<213> ORGANISM: Homo sapiens

<400> SEQUENCE: 349

Phe Thr Ala Arg Gly Arg Phe Ala Thr Val Val Glu Glu Leu Phe Arg
 1               5                   10                  15

Asp Gly


<210> SEQ ID NO 350
<211> LENGTH: 18
<212> TYPE: PRT
<213> ORGANISM: Homo sapiens

<400> SEQUENCE: 350

Gly Ser Ala Gln Gln Arg Phe Thr Gln Val Ser Asp Glu Leu Phe Gln
 1               5                   10                  15

Gly Gly


<210> SEQ ID NO 351
<211> LENGTH: 18
<212> TYPE: PRT
<213> ORGANISM: Homo sapiens

<400> SEQUENCE: 351

Ser Pro Arg Glu Val Phe Phe Arg Val Ala Ala Asp Met Phe Ser Asp
```

```
1               5                   10                  15

Gly Asn


<210> SEQ ID NO 352
<211> LENGTH: 70
<212> TYPE: PRT
<213> ORGANISM: Homo sapiens

<400> SEQUENCE: 352

Val Ala Ile His Gly Glu Asp Asp Leu His Val Thr Glu Glu Val Tyr
1               5                   10                  15

Lys Arg Pro Leu Phe Leu Gln Pro Thr Tyr Arg Tyr His Arg Leu Pro
            20                  25                  30

Leu Pro Glu Gln Gly Ser Pro Leu Glu Ala Gln Leu Asp Ala Phe Val
        35                  40                  45

Ser Val Leu Arg Glu Thr Pro Ser Leu Leu Gln Leu Arg Asp Ala His
    50                  55                  60

Gly Pro Pro Pro Ala Leu
65                  70


<210> SEQ ID NO 353
<211> LENGTH: 19
<212> TYPE: PRT
<213> ORGANISM: Homo sapiens

<400> SEQUENCE: 353

Glu Gly Pro Gln Gly Asp Leu Leu Thr Lys Thr Gln Glu Leu Gly Arg
1               5                   10                  15

Asp Tyr Arg


<210> SEQ ID NO 354
<211> LENGTH: 44
<212> TYPE: PRT
<213> ORGANISM: Homo sapiens

<400> SEQUENCE: 354

Gly Ile Asp Val Thr Thr Glu Leu Asp Ser Trp Ile Asp Lys Phe Cys
1               5                   10                  15

Leu Asp Ala Asp Val Phe Val Leu Val Ala Asn Ser Glu Ser Thr Leu
            20                  25                  30

Met Gln Thr Glu Lys His Phe Phe His Lys Val Ser
        35                  40


<210> SEQ ID NO 355
<211> LENGTH: 19
<212> TYPE: PRT
<213> ORGANISM: Homo sapiens

<400> SEQUENCE: 355

Lys Ala Gly Thr Gln Tyr Leu Leu Arg Thr Ala Asn Arg Leu Phe Gly
1               5                   10                  15

Glu Lys Thr


<210> SEQ ID NO 356
<211> LENGTH: 57
<212> TYPE: PRT
<213> ORGANISM: Homo sapiens

<400> SEQUENCE: 356

Gln Lys Asp Ile Asp Gly Lys Lys Asp Ile Thr Ala Ala Leu Ala Ala
1               5                   10                  15
```

Glu Arg Lys Phe Phe Leu Ser His Pro Ser Tyr Arg His Leu Ala Asp
20 25 30

Arg Met Gly Thr Pro Tyr Leu Gln Lys Val Leu Asn Gln Gln Leu Thr
35 40 45

Asn His Ile Arg Asp Thr Leu Pro Gly
50 55

<210> SEQ ID NO 357
<211> LENGTH: 70
<212> TYPE: PRT
<213> ORGANISM: Homo sapiens

<400> SEQUENCE: 357

Asn Ser Gly Pro Pro Pro Pro Gly Ala Phe Pro His Pro Leu Glu Gly
1 5 10 15

Gly Ser Ser His His Ala His Pro Tyr Ala Met Ser Pro Ser Leu Gly
20 25 30

Ser Leu Arg Pro Tyr Pro Pro Gly Pro Ala His Leu Pro Pro Pro His
35 40 45

Ser Gln Val Ser Tyr Ser Gln Ala Gly Pro Asn Gly Pro Pro Val Ser
50 55 60

Ser Ser Ser Asn Ser Ser
65 70

<210> SEQ ID NO 358
<211> LENGTH: 22
<212> TYPE: PRT
<213> ORGANISM: Homo sapiens

<400> SEQUENCE: 358

His Pro Ser Pro Pro Pro Glu Lys Lys Glu Leu Arg Lys Val Ala His
1 5 10 15

Leu Thr Gly Lys Ser Asn
20

<210> SEQ ID NO 359
<211> LENGTH: 20
<212> TYPE: PRT
<213> ORGANISM: Homo sapiens

<400> SEQUENCE: 359

Leu Ile Ser Ser Tyr Gly Thr His Phe Ile Arg Ser Met Glu Leu Gly
1 5 10 15

Gly Arg Ile Ser
20

<210> SEQ ID NO 360
<211> LENGTH: 18
<212> TYPE: PRT
<213> ORGANISM: Homo sapiens

<400> SEQUENCE: 360

Gly Pro Val Gly Thr Glu Leu Phe Arg Val Pro Pro Val Ser Thr Ala
1 5 10 15

Ala Thr

<210> SEQ ID NO 361
<211> LENGTH: 20
<212> TYPE: PRT
<213> ORGANISM: Homo sapiens

<400> SEQUENCE: 361

Leu Thr Ser Ser Val Thr Ile Leu Pro Leu Pro Leu Gln Asn Ala Thr
1 5 10 15

Val Glu Ala Gly
20

<210> SEQ ID NO 362
<211> LENGTH: 22
<212> TYPE: PRT
<213> ORGANISM: Homo sapiens

<400> SEQUENCE: 362

Leu Glu Arg Lys Ala Lys Trp Thr Thr Ala Val Arg Pro Leu Arg Leu
1 5 10 15

Pro Ser Ser Lys Ala Gln
20

<210> SEQ ID NO 363
<211> LENGTH: 23
<212> TYPE: PRT
<213> ORGANISM: Homo sapiens

<400> SEQUENCE: 363

Gly Lys Lys Thr Pro Ala Lys Val Val Pro Met Lys Ala Lys Ser Val
1 5 10 15

Ala Glu Glu Glu Asp Asp Glu
20

<210> SEQ ID NO 364
<211> LENGTH: 21
<212> TYPE: PRT
<213> ORGANISM: Homo sapiens

<400> SEQUENCE: 364

Lys Asp Gly Val Thr Pro Ile Lys Asp Leu Thr Ala His Phe Arg Gly
1 5 10 15

Asp Arg Cys Lys Thr
20

<210> SEQ ID NO 365
<211> LENGTH: 43
<212> TYPE: PRT
<213> ORGANISM: Homo sapiens

<400> SEQUENCE: 365

Val Asn Trp Gly Arg Ile Val Ala Phe Phe Glu Phe Gly Gly Val Met
1 5 10 15

Cys Val Glu Ser Val Asn Arg Glu Met Ser Pro Leu Val Asp Asn Ile
20 25 30

Ala Leu Trp Met Thr Glu Tyr Leu Asn Arg His
35 40

<210> SEQ ID NO 366
<211> LENGTH: 43
<212> TYPE: PRT
<213> ORGANISM: Homo sapiens

<400> SEQUENCE: 366

Pro Asn Trp Gly Arg Leu Val Ala Phe Phe Val Phe Gly Ala Ala Leu
1 5 10 15

Cys Ala Glu Ser Val Asn Lys Glu Met Glu Pro Leu Val Gly Gln Val
20 25 30

Gln Glu Trp Met Val Ala Tyr Leu Glu Thr Arg
35 40

<210> SEQ ID NO 367
<211> LENGTH: 43
<212> TYPE: PRT
<213> ORGANISM: Homo sapiens

<400> SEQUENCE: 367

Phe Asn Trp Gly Arg Val Val Ala Leu Phe Tyr Phe Ala Ser Lys Leu
1 5 10 15

Val Leu Lys Ala Leu Cys Thr Lys Val Pro Glu Leu Ile Arg Thr Ile
20 25 30

Met Gly Trp Thr Leu Asp Phe Leu Arg Glu Arg
35 40

<210> SEQ ID NO 368
<211> LENGTH: 88
<212> TYPE: PRT
<213> ORGANISM: Homo sapiens

<400> SEQUENCE: 368

Leu Arg Asp Ala His Gly Pro Pro Pro Ala Leu Val Phe Ser Cys Gln
1 5 10 15

Met Gly Val Gly Arg Thr Asn Leu Gly Met Val Leu Gly Thr Leu Ile
20 25 30

Leu Leu His Arg Ser Gly Thr Thr Ser Gln Pro Glu Ala Ala Pro Thr
35 40 45

Gln Ala Lys Pro Leu Pro Met Glu Gln Phe Gln Val Ile Gln Ser Phe
50 55 60

Leu Arg Met Val Pro Gln Gly Arg Arg Met Val Glu Glu Val Asp Arg
65 70 75 80

Ala Ile Thr Ala Cys Ala Glu Leu
85

<210> SEQ ID NO 369
<211> LENGTH: 43
<212> TYPE: PRT
<213> ORGANISM: Homo sapiens

<400> SEQUENCE: 369

Thr Cys Leu Thr Ile Val Gln Lys Leu Lys Lys Met Val Asp Lys Pro
1 5 10 15

Thr Gln Arg Ser Val Ser Asn Ala Ala Thr Arg Val Cys Arg Thr Gly
20 25 30

Arg Ser Arg Trp Arg Asp Val Cys Arg Asn Phe
35 40

<210> SEQ ID NO 370
<211> LENGTH: 49
<212> TYPE: PRT
<213> ORGANISM: Homo sapiens

<400> SEQUENCE: 370

Glu Arg Leu Ser Arg Pro Asn Ile Phe Ile Leu Asn Asn Arg Trp Asp
1 5 10 15

Ala Ser Ala Ser Glu Pro Glu Tyr Met Glu Glu Val Arg Arg Gln His
20 25 30

Met Glu Arg Cys Thr Ser Phe Leu Val Asp Glu Leu Gly Val Val Asp
35 40 45

Arg

<210> SEQ ID NO 371
<211> LENGTH: 46
<212> TYPE: PRT
<213> ORGANISM: Homo sapiens

<400> SEQUENCE: 371

Cys Gln Phe Leu Ser Thr Phe Lys Glu Ser Cys Leu Gln Phe Tyr His
1 5 10 15

Ala Glu Leu Lys Glu Leu Ser Phe Ile Arg Ala Ala Glu Glu Ser Arg
20 25 30

Lys His Ile Asn Thr Trp Val Ser Lys Lys Thr Glu Gly Lys
35 40 45

<210> SEQ ID NO 372
<211> LENGTH: 51
<212> TYPE: PRT
<213> ORGANISM: Homo sapiens

<400> SEQUENCE: 372

Leu Arg Asn Lys Leu Gln Ser Gln Leu Leu Ser Ile Glu Lys Glu Val
1 5 10 15

Glu Glu Tyr Lys Asn Phe Arg Pro Asp Asp Pro Ala Arg Lys Thr Lys
20 25 30

Ala Leu Leu Gln Met Val Gln Gln Phe Ala Val Asp Phe Glu Lys Arg
35 40 45

Ile Glu Gly
50

<210> SEQ ID NO 373
<211> LENGTH: 89
<212> TYPE: PRT
<213> ORGANISM: Homo sapiens

<400> SEQUENCE: 373

Gly Pro Pro Val Ser Ser Ser Ser Asn Ser Ser Ser Ser Thr Ser Gln
1 5 10 15

Gly Ser Tyr Pro Cys Ser His Pro Ser Pro Ser Gln Gly Pro Gln Gly
20 25 30

Ala Pro Tyr Pro Phe Pro Pro Val Pro Thr Val Thr Thr Ser Ser Ala
35 40 45

Thr Leu Ser Thr Val Ile Ala Thr Val Ala Ser Ser Pro Ala Gly Tyr
50 55 60

Lys Thr Ala Ser Pro Pro Gly Pro Pro Pro Tyr Gly Lys Arg Ala Pro
65 70 75 80

Ser Pro Gly Ala Tyr Lys Thr Ala Ile
85

<210> SEQ ID NO 374
<211> LENGTH: 44
<212> TYPE: PRT
<213> ORGANISM: Homo sapiens

<400> SEQUENCE: 374

Ser Arg Ser Met Pro Leu Glu Trp Glu Asp Thr Tyr Gly Ile Val Leu
1 5 10 15

Leu Ser Gly Val Lys Tyr Lys Lys Gly Gly Leu Val Ile Asn Glu Thr
20 25 30

```
Gly Leu Tyr Phe Val Tyr Ser Lys Val Tyr Phe Arg
        35                  40


<210> SEQ ID NO 375
<211> LENGTH: 46
<212> TYPE: PRT
<213> ORGANISM: Homo sapiens

<400> SEQUENCE: 375

Ala Leu Thr Ala Leu Arg Thr Cys Glu Leu Ala Leu Glu Gly Leu Thr
 1               5                  10                  15

Ala Ser Glu Val Glu Asp Cys Leu Ala Val Glu Ala Glu Val Ser Ile
            20                  25                  30

Ser Asp Arg Ala Ser Ala Ser Pro Ser Phe Lys Ala Cys Glu
        35                  40                  45


<210> SEQ ID NO 376
<211> LENGTH: 46
<212> TYPE: PRT
<213> ORGANISM: Homo sapiens

<400> SEQUENCE: 376

Trp Gln Ser Ser Ala Pro His Gln Pro Gly Pro Ser Leu Trp Ala Glu
 1               5                  10                  15

Ala Lys Thr Ser Glu Ala Pro Ser Thr Gln Asp Pro Ser Thr Gln Ala
            20                  25                  30

Ser Thr Ala Ser Ser Pro Ala Pro Glu Glu Asn Ala Pro Ser
        35                  40                  45


<210> SEQ ID NO 377
<211> LENGTH: 42
<212> TYPE: PRT
<213> ORGANISM: Homo sapiens

<400> SEQUENCE: 377

Thr Arg Cys Gln Val Ala Gly Trp Gly Ser Gln Arg Ser Gly Gly Arg
 1               5                  10                  15

Leu Ser Arg Phe Pro Arg Phe Val Asn Val Thr Val Thr Pro Glu Asp
            20                  25                  30

Gln Cys Arg Pro Asn Asn Val Cys Thr Gly
        35                  40


<210> SEQ ID NO 378
<211> LENGTH: 58
<212> TYPE: PRT
<213> ORGANISM: Homo sapiens

<400> SEQUENCE: 378

Arg Pro Leu Arg Leu Pro Ser Ser Lys Ala Gln Val Lys Pro Gly Gln
 1               5                  10                  15

Leu Cys Ser Val Ala Gly Trp Gly Tyr Val Ser Met Ser Thr Leu Ala
            20                  25                  30

Thr Thr Leu Gln Glu Val Leu Leu Thr Val Gln Lys Asp Cys Gln Cys
        35                  40                  45

Glu Arg Leu Phe His Gly Asn Tyr Ser Arg
    50                  55


<210> SEQ ID NO 379
<211> LENGTH: 47
<212> TYPE: PRT
<213> ORGANISM: Homo sapiens
```

<400> SEQUENCE: 379

Glu Glu Asp Glu Asp Asp Glu Asp Glu Asp Asp Glu Glu Glu Asp Asp
1 5 10 15

Glu Asp Asp Asp Glu Glu Glu Glu Glu Glu Glu Pro Val Lys Ala Ala
20 25 30

Pro Gly Lys Arg Lys Lys Glu Met Thr Lys Gln Lys Glu Ala Pro
35 40 45

<210> SEQ ID NO 380
<211> LENGTH: 45
<212> TYPE: PRT
<213> ORGANISM: Homo sapiens

<400> SEQUENCE: 380

Leu Leu Glu Lys Pro Lys Leu Phe Phe Ile Gln Ala Cys Arg Gly Thr
1 5 10 15

Glu Leu Asp Asp Gly Ile Gln Ala Asp Ser Gly Pro Ile Asn Asp Thr
20 25 30

Asp Ala Asn Pro Arg Tyr Lys Ile Pro Val Glu Ala Asp
35 40 45

<210> SEQ ID NO 381
<211> LENGTH: 41
<212> TYPE: PRT
<213> ORGANISM: Homo sapiens

<400> SEQUENCE: 381

Gly Pro Ala Leu Ser Pro Val Pro Pro Val Val His Leu Thr Leu Arg
1 5 10 15

Gln Ala Gly Asp Asp Phe Ser Arg Arg Tyr Arg Arg Asp Phe Ala Glu
20 25 30

Met Ser Ser Gln Leu His Leu Thr Pro
35 40

<210> SEQ ID NO 382
<211> LENGTH: 31
<212> TYPE: PRT
<213> ORGANISM: Homo sapiens

<400> SEQUENCE: 382

Leu His Gln Ala Met Arg Ala Ala Gly Asp Glu Phe Glu Thr Arg Phe
1 5 10 15

Arg Arg Thr Phe Ser Asp Leu Ala Ala Gln Leu His Val Thr Pro
20 25 30

<210> SEQ ID NO 383
<211> LENGTH: 31
<212> TYPE: PRT
<213> ORGANISM: Homo sapiens

<400> SEQUENCE: 383

Thr Lys Lys Leu Ser Glu Cys Leu Lys Arg Ile Gly Asp Glu Leu Asp
1 5 10 15

Ser Asn Met Glu Leu Gln Arg Met Ile Ala Ala Val Asp Thr Asp
20 25 30

<210> SEQ ID NO 384
<211> LENGTH: 58
<212> TYPE: PRT
<213> ORGANISM: Homo sapiens

<400> SEQUENCE: 384

Val Ser Tyr Thr Pro Arg Asp Lys Gln Asn Leu His Glu Asn Leu Gln
1 5 10 15

Gly Leu Gly Pro Gly Val Arg Val Glu Ser Leu Glu Leu Ala Ile Arg
20 25 30

Lys Glu Ile His Asp Phe Ala Gln Leu Ser Glu Asn Thr Tyr His Val
35 40 45

Tyr His Asn Thr Glu Asp Leu Trp Gly Glu
50 55

<210> SEQ ID NO 385
<211> LENGTH: 29
<212> TYPE: PRT
<213> ORGANISM: Homo sapiens

<400> SEQUENCE: 385

Leu Val Phe Ser Arg Leu Ser Pro Glu Tyr Tyr Asp Pro Ala Arg Ala
1 5 10 15

His Leu Arg Asp Gly Glu Lys Ser Cys Pro Cys Gly Gln
20 25

<210> SEQ ID NO 386
<211> LENGTH: 44
<212> TYPE: PRT
<213> ORGANISM: Homo sapiens

<400> SEQUENCE: 386

Phe Lys Gly Lys Trp Asn Glu Pro Phe Asp Glu Thr Tyr Thr Arg Glu
1 5 10 15

Met Pro Phe Lys Ile Asn Gln Glu Glu Gln Arg Pro Val Gln Met Met
20 25 30

Tyr Gln Glu Ala Thr Phe Lys Leu Ala His Val Gly
35 40

<210> SEQ ID NO 387
<211> LENGTH: 48
<212> TYPE: PRT
<213> ORGANISM: Homo sapiens

<400> SEQUENCE: 387

Tyr Arg Phe Ser Met Asp Leu Val Glu Cys Arg Phe Tyr Ser Phe His
1 5 10 15

Leu Val His Thr Pro Pro Val His Pro Glu Phe Lys Arg Ala Leu Lys
20 25 30

Thr Leu Pro Pro His Phe Asn Thr Ser Thr Lys Pro Asp Tyr His Arg
35 40 45

<210> SEQ ID NO 388
<211> LENGTH: 39
<212> TYPE: PRT
<213> ORGANISM: Homo sapiens

<400> SEQUENCE: 388

Ile Ser Ser Met Ser Glu Asn Gly Tyr Asp Pro Gln Gln Asn Leu Asn
1 5 10 15

Asp Leu Met Leu Leu Gln Leu Asp Arg Glu Ala Asn Leu Thr Ser Ser
20 25 30

Val Thr Ile Leu Pro Leu Pro
35

<210> SEQ ID NO 389

<211> LENGTH: 40
<212> TYPE: PRT
<213> ORGANISM: Homo sapiens

<400> SEQUENCE: 389

Val Lys Arg Pro Ile Pro His Pro Ala Tyr Asn Pro Lys Asn Phe Ser
 1               5                  10                  15

Asn Asp Ile Met Leu Leu Gln Leu Glu Arg Lys Ala Lys Trp Thr Thr
            20                  25                  30

Ala Val Arg Pro Leu Arg Leu Pro
        35                  40

<210> SEQ ID NO 390
<211> LENGTH: 48
<212> TYPE: PRT
<213> ORGANISM: Homo sapiens

<400> SEQUENCE: 390

Gly Thr Ser Pro Glu Leu Pro Thr Gly Val Thr Gly Ser Ser Gly Thr
 1               5                  10                  15

Arg Leu Pro Pro Thr Pro Lys Ala Gln Asp Gly Gly Pro Val Gly Thr
            20                  25                  30

Glu Leu Phe Arg Val Pro Pro Val Ser Thr Ala Ala Thr Trp Gln Ser
        35                  40                  45

<210> SEQ ID NO 391
<211> LENGTH: 40
<212> TYPE: PRT
<213> ORGANISM: Homo sapiens

<400> SEQUENCE: 391

Asp Cys Ser Cys Ala Lys Met Gln Asp Leu Leu Lys Lys Ala Ser Glu
 1               5                  10                  15

Glu Asp His Thr Asn Ala Ala Cys Phe Ala Cys Ile Leu Leu Ser His
            20                  25                  30

Gly Glu Glu Asn Val Ile Tyr Gly
        35                  40

<210> SEQ ID NO 392
<211> LENGTH: 37
<212> TYPE: PRT
<213> ORGANISM: Homo sapiens

<400> SEQUENCE: 392

Leu Gly Met Phe Gln Leu Phe His Leu Gln Lys Glu Leu Ala Glu Leu
 1               5                  10                  15

Arg Glu Ser Thr Ser Gln Met His Thr Ala Ser Ser Leu Glu Lys Gln
            20                  25                  30

Ile Gly His Pro Ser
        35

<210> SEQ ID NO 393
<211> LENGTH: 18
<212> TYPE: PRT
<213> ORGANISM: Homo sapiens

<400> SEQUENCE: 393

Phe Thr Ala Arg Gly Arg Phe Ala Thr Val Val Glu Glu Leu Phe Arg
 1               5                  10                  15

Asp Gly

<210> SEQ ID NO 394
<211> LENGTH: 18
<212> TYPE: PRT
<213> ORGANISM: Homo sapiens

<400> SEQUENCE: 394

Gly Ser Ala Gln Gln Arg Phe Thr Gln Val Ser Asp Glu Leu Phe Gln
1 5 10 15

Gly Gly

<210> SEQ ID NO 395
<211> LENGTH: 18
<212> TYPE: PRT
<213> ORGANISM: Homo sapiens

<400> SEQUENCE: 395

Ser Pro Arg Glu Val Phe Phe Arg Val Ala Ala Asp Met Phe Ser Asp
1 5 10 15

Gly Asn

<210> SEQ ID NO 396
<211> LENGTH: 55
<212> TYPE: PRT
<213> ORGANISM: Homo sapiens

<400> SEQUENCE: 396

Phe Leu Gln Pro Thr Tyr Arg Tyr His Arg Leu Pro Leu Pro Glu Gln
1 5 10 15

Gly Ser Pro Leu Glu Ala Gln Leu Asp Ala Phe Val Ser Val Leu Arg
20 25 30

Glu Thr Pro Ser Leu Leu Gln Leu Arg Asp Ala His Gly Pro Pro Pro
35 40 45

Ala Leu Val Phe Ser Cys Gln
50 55

<210> SEQ ID NO 397
<211> LENGTH: 19
<212> TYPE: PRT
<213> ORGANISM: Homo sapiens

<400> SEQUENCE: 397

Glu Gly Pro Gln Gly Asp Leu Leu Thr Lys Thr Gln Glu Leu Gly Arg
1 5 10 15

Asp Tyr Arg

<210> SEQ ID NO 398
<211> LENGTH: 26
<212> TYPE: PRT
<213> ORGANISM: Homo sapiens

<400> SEQUENCE: 398

Glu Val Arg Ala Gln Leu Leu Glu Leu Pro Tyr Ala Arg Lys Glu Leu
1 5 10 15

Ser Leu Leu Val Leu Leu Pro Asp Asp Gly
20 25

<210> SEQ ID NO 399
<211> LENGTH: 20
<212> TYPE: PRT
<213> ORGANISM: Homo sapiens

<400> SEQUENCE: 399

Leu Ile Ser Ser Tyr Gly Thr His Phe Ile Arg Ser Met Glu Leu Gly
1 5 10 15

Gly Arg Ile Ser
20

<210> SEQ ID NO 400
<211> LENGTH: 20
<212> TYPE: PRT
<213> ORGANISM: Homo sapiens

<400> SEQUENCE: 400

Leu Gln Asn Ala Thr Val Glu Ala Gly Thr Arg Cys Gln Val Ala Gly
1 5 10 15

Trp Gly Ser Gln
20

<210> SEQ ID NO 401
<211> LENGTH: 20
<212> TYPE: PRT
<213> ORGANISM: Homo sapiens

<400> SEQUENCE: 401

Ser Ser Lys Ala Gln Val Lys Pro Gly Gln Leu Cys Ser Val Ala Gly
1 5 10 15

Trp Gly Tyr Val
20

<210> SEQ ID NO 402
<211> LENGTH: 20
<212> TYPE: PRT
<213> ORGANISM: Homo sapiens

<400> SEQUENCE: 402

Ser Ala Pro His Gln Pro Gly Pro Ser Leu Trp Ala Glu Ala Lys Thr
1 5 10 15

Ser Glu Ala Pro
20

<210> SEQ ID NO 403
<211> LENGTH: 21
<212> TYPE: PRT
<213> ORGANISM: Homo sapiens

<400> SEQUENCE: 403

Lys Asp Gly Val Thr Pro Ile Lys Asp Leu Thr Ala His Phe Arg Gly
1 5 10 15

Asp Arg Cys Lys Thr
20

<210> SEQ ID NO 404
<211> LENGTH: 19
<212> TYPE: PRT
<213> ORGANISM: Homo sapiens

<400> SEQUENCE: 404

Pro Pro Pro Glu Lys Lys Glu Leu Arg Lys Val Ala His Leu Thr Gly
1 5 10 15

Lys Ser Asn

<210> SEQ ID NO 405
<211> LENGTH: 42
<212> TYPE: PRT
<213> ORGANISM: Homo sapiens

<400> SEQUENCE: 405

```
Val Asn Trp Gly Arg Ile Val Ala Phe Phe Glu Phe Gly Gly Val Met
 1              5                   10                  15

Cys Val Glu Ser Val Asn Arg Glu Met Ser Pro Leu Val Asp Asn Ile
            20                  25                  30

Ala Leu Trp Met Thr Glu Tyr Leu Asn Arg
        35                  40
```

<210> SEQ ID NO 406
<211> LENGTH: 43
<212> TYPE: PRT
<213> ORGANISM: Homo sapiens

<400> SEQUENCE: 406

```
Pro Asn Trp Gly Arg Leu Val Ala Phe Phe Val Phe Gly Ala Ala Leu
 1              5                   10                  15

Cys Ala Glu Ser Val Asn Lys Glu Met Glu Pro Leu Val Gly Gln Val
            20                  25                  30

Gln Glu Trp Met Val Ala Tyr Leu Glu Thr Arg
        35                  40
```

<210> SEQ ID NO 407
<211> LENGTH: 43
<212> TYPE: PRT
<213> ORGANISM: Homo sapiens

<400> SEQUENCE: 407

```
Phe Asn Trp Gly Arg Val Val Ala Leu Phe Tyr Phe Ala Ser Lys Leu
 1              5                   10                  15

Val Leu Lys Ala Leu Cys Thr Lys Val Pro Glu Leu Ile Arg Thr Ile
            20                  25                  30

Met Gly Trp Thr Leu Asp Phe Leu Arg Glu Arg
        35                  40
```

<210> SEQ ID NO 408
<211> LENGTH: 72
<212> TYPE: PRT
<213> ORGANISM: Homo sapiens

<400> SEQUENCE: 408

```
Ala Leu Val Phe Ser Cys Gln Met Gly Val Gly Arg Thr Asn Leu Gly
 1              5                   10                  15

Met Val Leu Gly Thr Leu Ile Leu Leu His Arg Ser Gly Thr Thr Ser
            20                  25                  30

Gln Pro Glu Ala Ala Pro Thr Gln Ala Lys Pro Leu Pro Met Glu Gln
        35                  40                  45

Phe Gln Val Ile Gln Ser Phe Leu Arg Met Val Pro Gln Gly Arg Arg
    50                  55                  60

Met Val Glu Glu Val Asp Arg Ala
65                  70
```

<210> SEQ ID NO 409
<211> LENGTH: 43
<212> TYPE: PRT
<213> ORGANISM: Homo sapiens

<400> SEQUENCE: 409

```
Thr Cys Leu Thr Ile Val Gln Lys Leu Lys Lys Met Val Asp Lys Pro
 1              5                   10                  15
```

Thr Gln Arg Ser Val Ser Asn Ala Ala Thr Arg Val Cys Arg Thr Gly
20 25 30

Arg Ser Arg Trp Arg Asp Val Cys Arg Asn Phe
35 40

<210> SEQ ID NO 410
<211> LENGTH: 53
<212> TYPE: PRT
<213> ORGANISM: Homo sapiens

<400> SEQUENCE: 410

Val Glu Leu Ser Thr Val Glu Lys Ser Leu Thr Phe Glu Lys Leu Thr
1 5 10 15

Ala Trp Thr Lys Pro Asp Cys Met Lys Ser Thr Glu Val Glu Leu Val
20 25 30

Leu Leu Pro Lys Phe Lys Leu Gln Glu Asp Tyr Asp Met Glu Ser Val
35 40 45

Leu Arg His Leu Gly
50

<210> SEQ ID NO 411
<211> LENGTH: 55
<212> TYPE: PRT
<213> ORGANISM: Homo sapiens

<400> SEQUENCE: 411

Ala Leu Thr Ala Leu Arg Thr Cys Glu Leu Ala Leu Glu Gly Leu Thr
1 5 10 15

Ala Ser Glu Val Glu Asp Cys Leu Ala Val Glu Ala Glu Val Ser Ile
20 25 30

Ser Asp Arg Ala Ser Ala Ser Pro Ser Phe Lys Ala Cys Glu Glu Lys
35 40 45

Lys Lys Asn His Lys Val Gly
50 55

<210> SEQ ID NO 412
<211> LENGTH: 43
<212> TYPE: PRT
<213> ORGANISM: Homo sapiens

<400> SEQUENCE: 412

Arg Ser Gly Gly Arg Leu Ser Arg Phe Pro Arg Phe Val Asn Val Thr
1 5 10 15

Val Thr Pro Glu Asp Gln Cys Arg Pro Asn Asn Val Cys Thr Gly Val
20 25 30

Leu Thr Arg Arg Gly Gly Ile Cys Asn Gly Asp
35 40

<210> SEQ ID NO 413
<211> LENGTH: 49
<212> TYPE: PRT
<213> ORGANISM: Homo sapiens

<400> SEQUENCE: 413

Ser Met Ser Thr Leu Ala Thr Thr Leu Gln Glu Val Leu Leu Thr Val
1 5 10 15

Gln Lys Asp Cys Gln Cys Glu Arg Leu Phe His Gly Asn Tyr Ser Arg
20 25 30

Ala Thr Glu Ile Cys Val Gly Asp Pro Lys Lys Thr Gln Thr Gly Phe
35 40 45

Lys

<210> SEQ ID NO 414
<211> LENGTH: 52
<212> TYPE: PRT
<213> ORGANISM: Homo sapiens

<400> SEQUENCE: 414

Ser Thr Gln Asp Pro Ser Thr Gln Ala Ser Thr Ala Ser Ser Pro Ala
1 5 10 15

Pro Glu Glu Asn Ala Pro Ser Glu Gly Gln Arg Val Trp Gly Gln Gly
20 25 30

Gln Ser Pro Arg Glu Asn Ser Leu Glu Arg Glu Glu Met Gly Pro Val
35 40 45

Pro Ala His Thr
50

<210> SEQ ID NO 415
<211> LENGTH: 51
<212> TYPE: PRT
<213> ORGANISM: Homo sapiens

<400> SEQUENCE: 415

Leu Leu Glu Lys Pro Lys Leu Phe Phe Ile Gln Ala Cys Arg Gly Thr
1 5 10 15

Glu Leu Asp Asp Gly Ile Gln Ala Asp Ser Gly Pro Ile Asn Asp Thr
20 25 30

Asp Ala Asn Pro Arg Tyr Lys Ile Pro Val Glu Ala Asp Phe Leu Phe
35 40 45

Ala Tyr Ser
50

<210> SEQ ID NO 416
<211> LENGTH: 52
<212> TYPE: PRT
<213> ORGANISM: Homo sapiens

<400> SEQUENCE: 416

Ser Arg Ser Met Pro Leu Glu Trp Glu Asp Thr Tyr Gly Ile Val Leu
1 5 10 15

Leu Ser Gly Val Lys Tyr Lys Lys Gly Gly Leu Val Ile Asn Glu Thr
20 25 30

Gly Leu Tyr Phe Val Tyr Ser Lys Val Tyr Phe Arg Gly Gln Ser Cys
35 40 45

Asn Asn Leu Pro
50

<210> SEQ ID NO 417
<211> LENGTH: 47
<212> TYPE: PRT
<213> ORGANISM: Homo sapiens

<400> SEQUENCE: 417

Gly Gly Trp Asp Ala Phe Val Glu Leu Tyr Gly Pro Ser Met Arg Pro
1 5 10 15

Leu Phe Asp Phe Ser Trp Leu Ser Leu Lys Thr Leu Leu Ser Leu Ala
20 25 30

Leu Val Gly Ala Cys Ile Thr Leu Gly Ala Tyr Leu Gly His Lys
35 40 45

<210> SEQ ID NO 418
<211> LENGTH: 52
<212> TYPE: PRT
<213> ORGANISM: Homo sapiens

<400> SEQUENCE: 418

```
Gly Gly Trp Ala Glu Phe Thr Ala Leu Tyr Gly Asp Gly Ala Leu Glu
 1               5                  10                  15

Glu Ala Arg Arg Leu Arg Glu Gly Asn Trp Ala Ser Val Arg Thr Val
            20                  25                  30

Leu Thr Gly Ala Val Ala Leu Gly Ala Leu Val Thr Val Gly Ala Phe
        35                  40                  45

Phe Ala Ser Lys
    50
```

<210> SEQ ID NO 419
<211> LENGTH: 63
<212> TYPE: PRT
<213> ORGANISM: Homo sapiens

<400> SEQUENCE: 419

```
Gly Gly Trp Val Arg Leu Leu Lys Pro Pro His Pro His His Arg Ala
 1               5                  10                  15

Leu Thr Thr Ala Pro Ala Pro Pro Ser Leu Pro Pro Ala Thr Pro Leu
            20                  25                  30

Gly Pro Trp Ala Phe Trp Ser Arg Ser Gln Trp Cys Pro Leu Pro Ile
        35                  40                  45

Phe Arg Ser Ser Asp Val Val Tyr Asn Ala Phe Ser Leu Arg Val
    50                  55                  60
```

<210> SEQ ID NO 420
<211> LENGTH: 70
<212> TYPE: PRT
<213> ORGANISM: Homo sapiens

<400> SEQUENCE: 420

```
Ala Gly Pro Val Ala Pro Arg Asp Leu Ile Ala Arg Gly Ser Leu Arg
 1               5                  10                  15

Glu Asp Asp Leu Val Ser Pro Asp Ala Leu Ser Thr Val Arg Glu Met
            20                  25                  30

Asp Val Ala Asn Phe Arg Arg Val Pro Arg Met Pro Ile Tyr Gly Thr
        35                  40                  45

Ala Gln Pro Ser Ala Lys Ala Leu Gly Ser Ile Leu Ala Tyr Leu Thr
    50                  55                  60

Asp Ala Lys Arg Arg Ile
65                  70
```

<210> SEQ ID NO 421
<211> LENGTH: 35
<212> TYPE: PRT
<213> ORGANISM: Homo sapiens

<400> SEQUENCE: 421

```
Met Arg Arg Tyr Gln Ser Arg Val Ile Gln Gly Leu Val Ala Gly Glu
 1               5                  10                  15

Thr Ala Gln Gln Ile Cys Glu Asp Leu Arg Leu Cys Ile Pro Ser Thr
            20                  25                  30

Gly Pro Leu
        35
```

<210> SEQ ID NO 422
<211> LENGTH: 54
<212> TYPE: PRT
<213> ORGANISM: Homo sapiens

<400> SEQUENCE: 422

Ala Asp Leu Ser Ala Met Ser Ala Glu Arg Asp Leu Cys Leu Ser Lys
1 5 10 15

Phe Val His Lys Ser Phe Val Glu Val Asn Glu Glu Gly Thr Glu Ala
20 25 30

Ala Ala Ala Ser Ser Cys Phe Val Val Ala Glu Cys Cys Met Glu Ser
35 40 45

Gly Pro Arg Phe Cys Ala
50

<210> SEQ ID NO 423
<211> LENGTH: 54
<212> TYPE: PRT
<213> ORGANISM: Homo sapiens

<400> SEQUENCE: 423

Glu Arg His Ser Asn Val Asp Gly Gly His His Ser Thr Met His Asp
1 5 10 15

Leu Leu Phe Gly Ser Gln Ala Gly Pro Glu Gln Phe Ser Ala Trp Val
20 25 30

Ala Ser Leu Gln Asp Ser Pro Gly Leu Val Asp Tyr Thr Leu Glu Pro
35 40 45

Leu His Met Leu Val Glu
50

<210> SEQ ID NO 424
<211> LENGTH: 51
<212> TYPE: PRT
<213> ORGANISM: Homo sapiens

<400> SEQUENCE: 424

Gly Gly Thr Pro Leu Val Cys Glu Gly Leu Ala His Gly Val Ala Ser
1 5 10 15

Phe Ser Leu Gly Pro Cys Gly Arg Gly Pro Asp Phe Phe Thr Arg Val
20 25 30

Ala Leu Phe Arg Asp Trp Ile Asp Gly Val Leu Asn Asn Pro Gly Pro
35 40 45

Gly Pro Ala
50

<210> SEQ ID NO 425
<211> LENGTH: 47
<212> TYPE: PRT
<213> ORGANISM: Homo sapiens

<400> SEQUENCE: 425

Gly Asp Ser Gly Gly Pro Leu Val Cys Lys Asp Val Ala Gln Gly Ile
1 5 10 15

Leu Ser Tyr Gly Asn Lys Lys Gly Thr Pro Pro Gly Val Tyr Ile Lys
20 25 30

Val Ser His Phe Leu Pro Trp Ile Lys Arg Thr Met Lys Arg Leu
35 40 45

<210> SEQ ID NO 426
<211> LENGTH: 57
<212> TYPE: PRT

-continued

```
<213> ORGANISM: Homo sapiens

<400> SEQUENCE: 426

Met Ala His Val Ser Val Val Pro Val Ser Ser Glu Gly Thr Pro Ser
 1              5                   10                  15

Arg Glu Pro Val Ala Ser Gly Ser Trp Thr Pro Lys Ala Glu Glu Pro
            20                  25                  30

Ile His Ala Thr Met Asp Pro Gln Arg Leu Gly Val Leu Ile Thr Pro
        35                  40                  45

Val Pro Asp Ala Gln Ala Ala Thr Arg
    50                  55


<210> SEQ ID NO 427
<211> LENGTH: 54
<212> TYPE: PRT
<213> ORGANISM: Homo sapiens

<400> SEQUENCE: 427

Thr Val Pro Gly Tyr Tyr Ser Trp Arg Ser Pro Gly Arg Gly Ser Trp
 1              5                   10                  15

Phe Val Gln Ala Leu Cys Ser Ile Leu Glu Glu His Gly Lys Asp Leu
            20                  25                  30

Glu Ile Met Gln Ile Leu Thr Arg Val Asn Asp Arg Val Ala Arg His
        35                  40                  45

Phe Glu Ser Gln Ser Asp
    50


<210> SEQ ID NO 428
<211> LENGTH: 53
<212> TYPE: PRT
<213> ORGANISM: Homo sapiens

<400> SEQUENCE: 428

Leu Ser His Lys Val Tyr Met Arg Asn Ser Lys Tyr Pro Gln Asp Leu
 1              5                   10                  15

Val Met Met Glu Gly Lys Met Met Ser Tyr Cys Thr Thr Gly Met Trp
            20                  25                  30

Ala Arg Ser Ser Tyr Leu Gly Ala Val Phe Asn Leu Thr Ser Ala Asp
        35                  40                  45

His Leu Tyr Val Asn
    50
```

PEPTIDES AND METHODS FOR INDUCING CELL DEATH

This application claims the benefit of priority of U.S. Provisional application Ser. No. 61/338,747, filed Feb. 22, 2010, the entire contents of which are incorporated herein by reference.

FIELD OF THE INVENTION

The present invention relates generally to compositions and methods for inducing cell death, and more specifically to peptides and compositions having antimicrobial, anti-cancer, anti-inflammatory and/or anti-proliferative activity and methods of using the peptides and compositions as therapeutics.

BACKGROUND OF THE INVENTION

Programmed cell death pathways are known to exist in most if not all organisms on Earth, ranging from microbes to man. Proteins that effect this function, also known as apoptosis, have been identified in human, other mammals, plants, protozoa, fungi, and bacteria, among other forms of life. In humans, these proteins target the mitochondria, causing permeabilization, dissipation of the membrane potential, activation of intracellular signaling pathways, and ultimate death of the cell. Eukaryotic pathogens also contain mitochondria, and mitochondria are now widely accepted by evolutionary biologists to be decedents of specialized symbiotic bacteria in eukaryotic cells.

Given these close parallels between mitochondria and bacteria, it is contemplated that specific human, eukaryotic or prokaryotic proteins have necessarily evolved to control prokaryotic symbionts (eg. mitochondria, chloroplasts) or competitors, and directly or indirectly prompt death of microbes or infected or abnormal cells. These types of proteins exhibit similarities in structures (eg., cationic helical domains) and mechanisms of action (eg., membrane interaction or perturbation that can lead to programmed cell death). Thus, such proteins may serve as excellent templates for novel therapeutic molecules, and reveal new insights into host-pathogen co-evolution, cancer biology, and other disease prevention, pathogenesis and treatment.

SUMMARY OF INVENTION

Embodiments of the invention provide isolated peptides, protides and conjugates having novel peptide sequences which are able to induce antimicrobial, anti-cancer, anti-inflammatory, anti-proliferative or programmed cell death activity. Peptides, protides and conjugates provided by the invention comprise, consist essentially of, or consist of amino acid sequences represented by SEQ ID NOS:1-263 and 288-289. In some aspects, peptides, protides and conjugates described herein have conservative amino acid substitutions or alternative residues at specific locations within a peptide sequence. Non-limiting examples of such substitutions or alternative residues include when the amino acid residue is represented by (x) a serine, a threonine, a tyrosine, a H-bond donor residue or a H-bond acceptor residue can be substituted, or alternatively, when the amino acid residue is represented by (b) a lysine, an arginine, an asparagine, a glutamine or a basic residue can be substituted, or alternatively, when the amino acid residue is represented by (j) a cysteine or a thiol residue can be substituted, or alternatively, when the amino acid residue is represented by (o) an anthrylalanine or other non-natural amino acid can be substituted.

Embodiments of the invention also provide methods of inducing programmed cell death in a cell by exposing the cell to an isolated peptide, protide or conjugate described herein. In some aspects, the methods can be used in the diagnosis, prevention, or treatment of a disease, such as an infection, cancer, autoimmune disease, or inflammatory disease.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows the amino acid sequence of exemplary programmed cell death/holin-like proteins (Dnm-1 (SEQ ID NO:280), Bax (SEQ IN NO:281) and Bcl-2 (SEQ ID NO:282)) identified in *Homo sapiens.*

FIG. 2 shows the amino acid sequence of exemplary programmed cell death proteins (CidA (SEQ ID NO:283) and LrgA (SEQ IN NO:284)) identified in *Staphylococcus aureus.*

FIG. 3 shows the amino acid sequence of exemplary candidate proteins (Perforin 1 from *Bos taurus* (SEQ ID NO:285), Bcl-2 from *Homo sapiens* (SEQ ID NO:286), and BCL-W from *Homo sapiens* (SEQ ID NO:287)) used for the iterative primary structure analysis of the protein databases (Blastp and/or equivalent thereof) available from the National Center for Biotechnology Information utilizing the basic local alignment sequence tool (BLAST).

FIG. 4 shows an exemplary data score table sorted by alignment score using the multisequence alignment tool ClustalW (Larkin et al., *Bioinformatics* 23(21): 2947-2948 (2007)) available online from EMBL-EBI.

FIG. 5 shows exemplary multisequence alignments (SEQ ID NOS. 297-332) using the multisequence alignment tool ClustalW (Larkin et al., *Bioinformatics* 23(21): 2947-2948 (2007)) available online from EMBL-EBI.

HUMC #ATCC at pH 5.5. Positive control peptides RP1, 6W-RP1, IK and PMP-2, whereas the negative control of double-distilled water (DDH2O) are also shown. The size of the complete zone of inhibition (ZOI) is represented by a blue bar, whereas the size of the partial (ZOI) is represented by a red bar.

Figure 44:
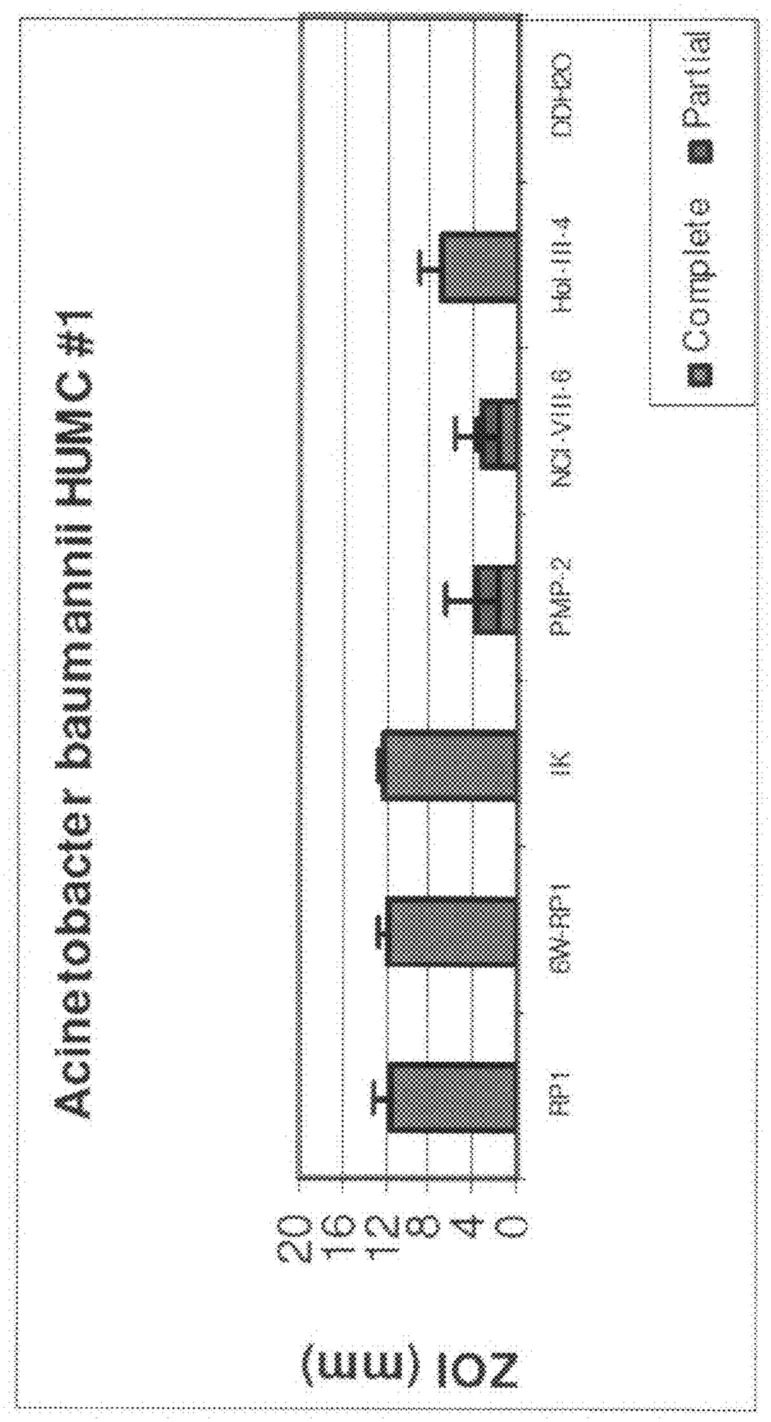

FIG. 44 shows a histogram of the antimicrobial spectra of exemplary peptides Hol-III-4 (SEQ ID NO. 268) and NCl-VIII-6 (SEQ ID NO. 152) against *Acinetobacter baumannii* HUMC #1 at pH 5.5. Positive control peptides RP1, 6W-RP1, IK and PMP-2, whereas the negative control of double-distilled water (DDH2O) are also shown. The size of the complete zone of inhibition (ZOI) is represented by a blue bar, whereas the size of the partial (ZOI) is represented by a red bar.

Figure 45:
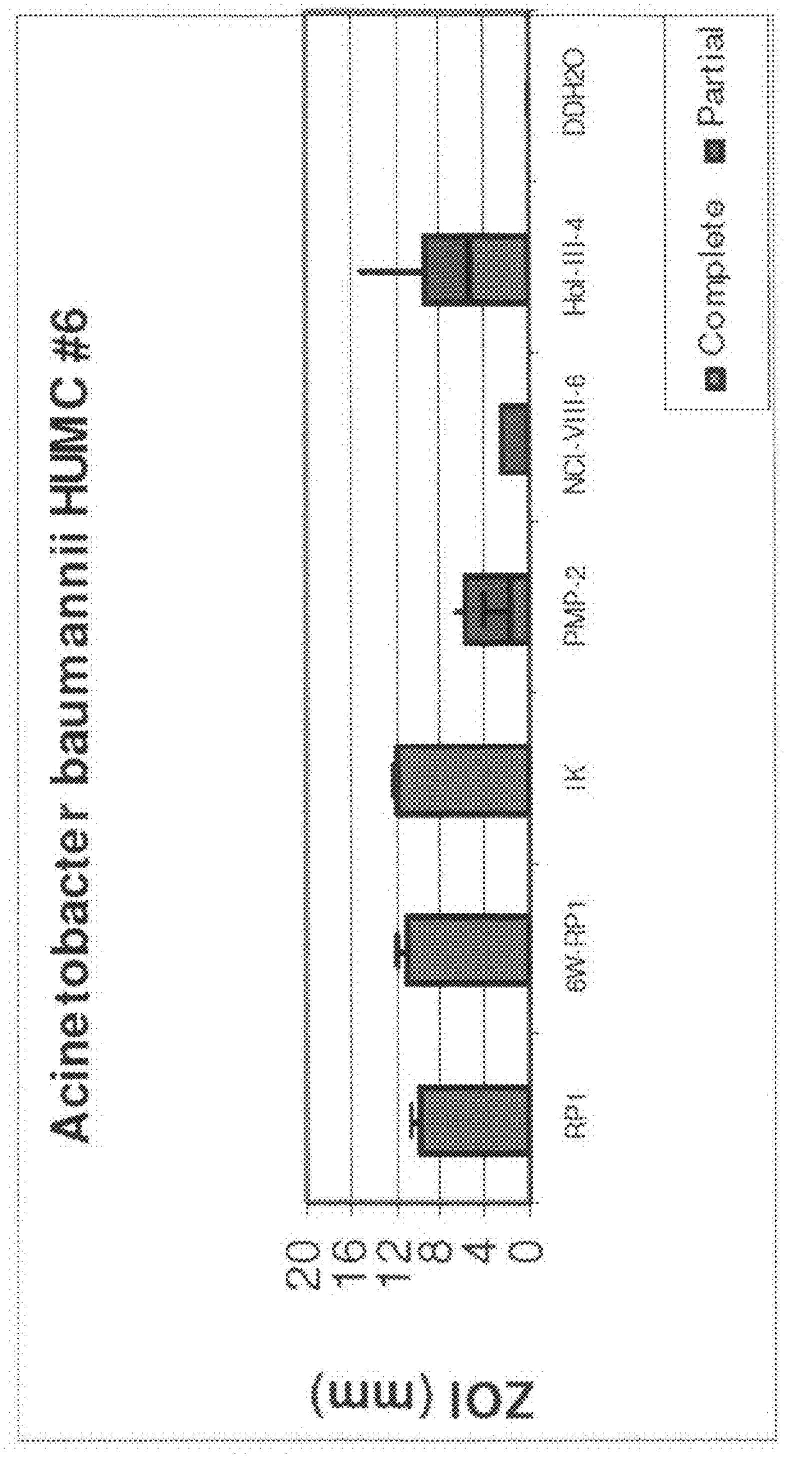

FIG. 45 shows a histogram of the antimicrobial spectra of exemplary peptides Hol-III-4 (SEQ ID NO. 268) and NCl-VIII-6 (SEQ ID NO. 152) against *Acinetobacter baumannii* HUMC #6 at pH 5.5. Positive control peptides RP1, 6W-RP1, IK and PMP-2, whereas the negative control of double-distilled water (DDH2O) are also shown. The size of the complete zone of inhibition (ZOI) is represented by a blue bar, whereas the size of the partial (ZOI) is represented by a red bar.

Figure 46:
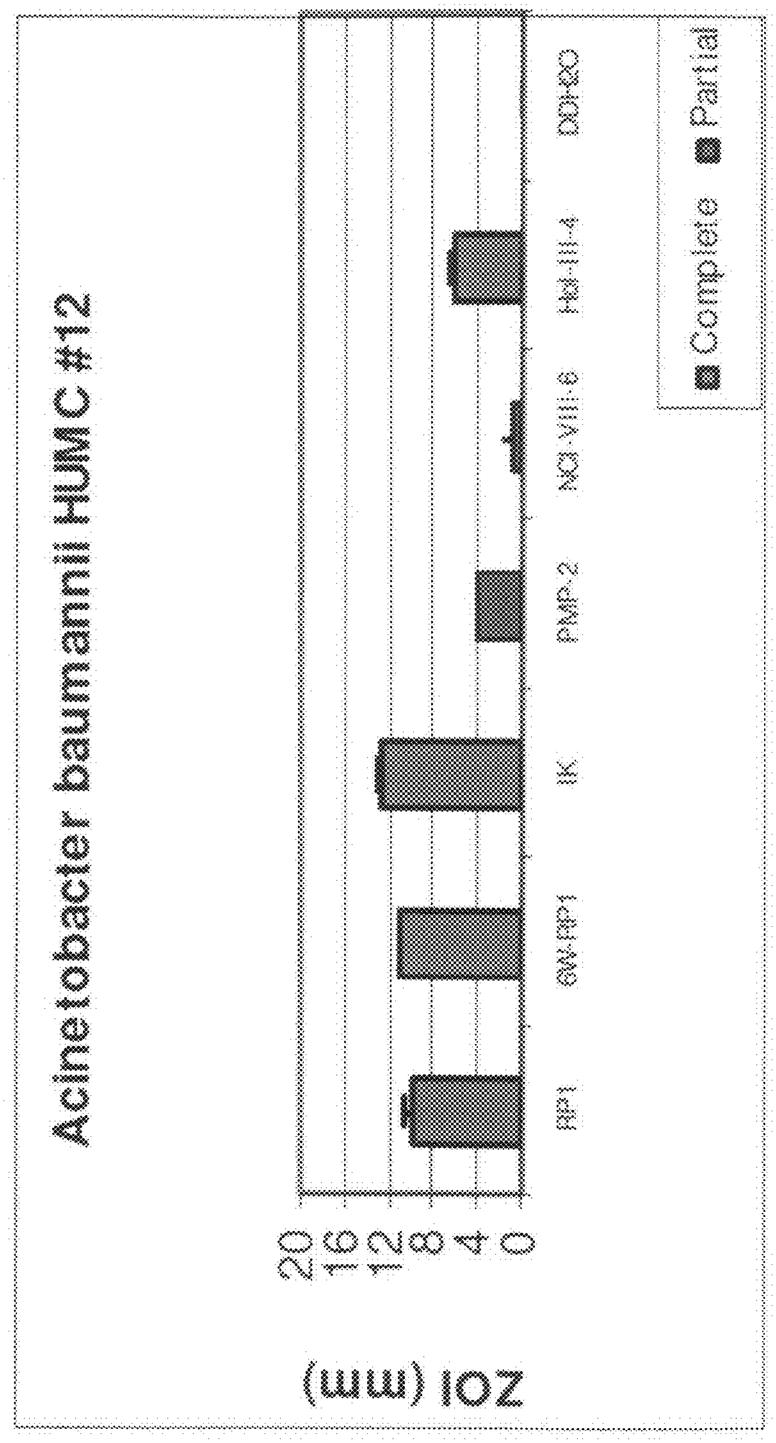

FIG. 46 shows a histogram of the antimicrobial spectra of exemplary peptides Hol-III-4 (SEQ ID NO. 268) and NCl-VIII-6 (SEQ ID NO. 152) against *Acinetobacter baumannii* HUMC #12 at pH 5.5. Positive control peptides RP1, 6W-RP1, IK and PMP-2, whereas the negative control of double-distilled water (DDH2O) are also shown. The size of the complete zone of inhibition (ZOI) is represented by a blue bar, whereas the size of the partial (ZOI) is represented by a red bar.

Figure 47:
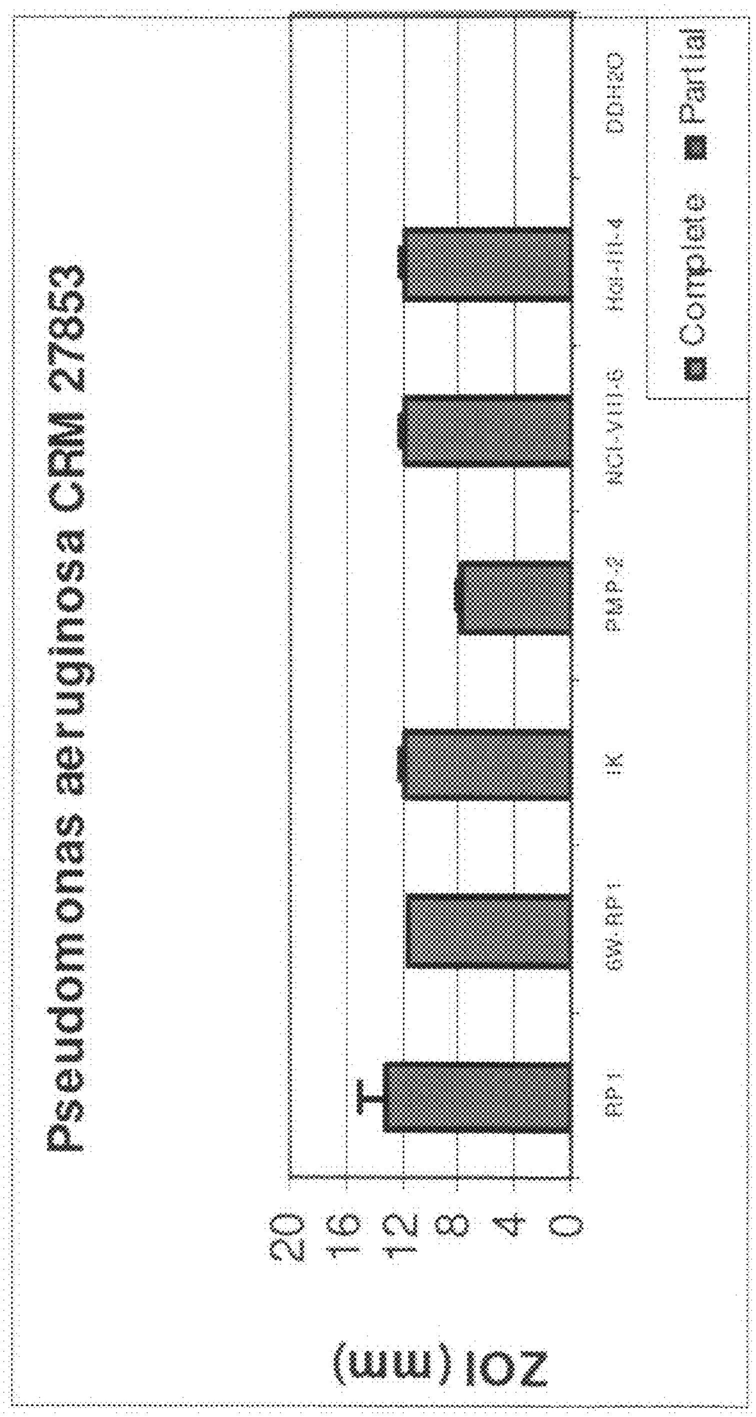

FIG. 47 shows a histogram of the antimicrobial spectra of exemplary peptides Hol-III-4 (SEQ ID NO. 268) and NCl-VIII-6 (SEQ ID NO. 152) against *Pseudomonas aeruginosa* CRM27853 at pH 7.5. Positive control peptides RP1, 6W-RP1, IK and PMP-2, whereas the negative control of double-distilled water (DDH2O) are also shown. The size of the complete zone of inhibition (ZOI) is represented by a blue bar, whereas the size of the partial (ZOI) is represented by a red bar.

Figure 48:
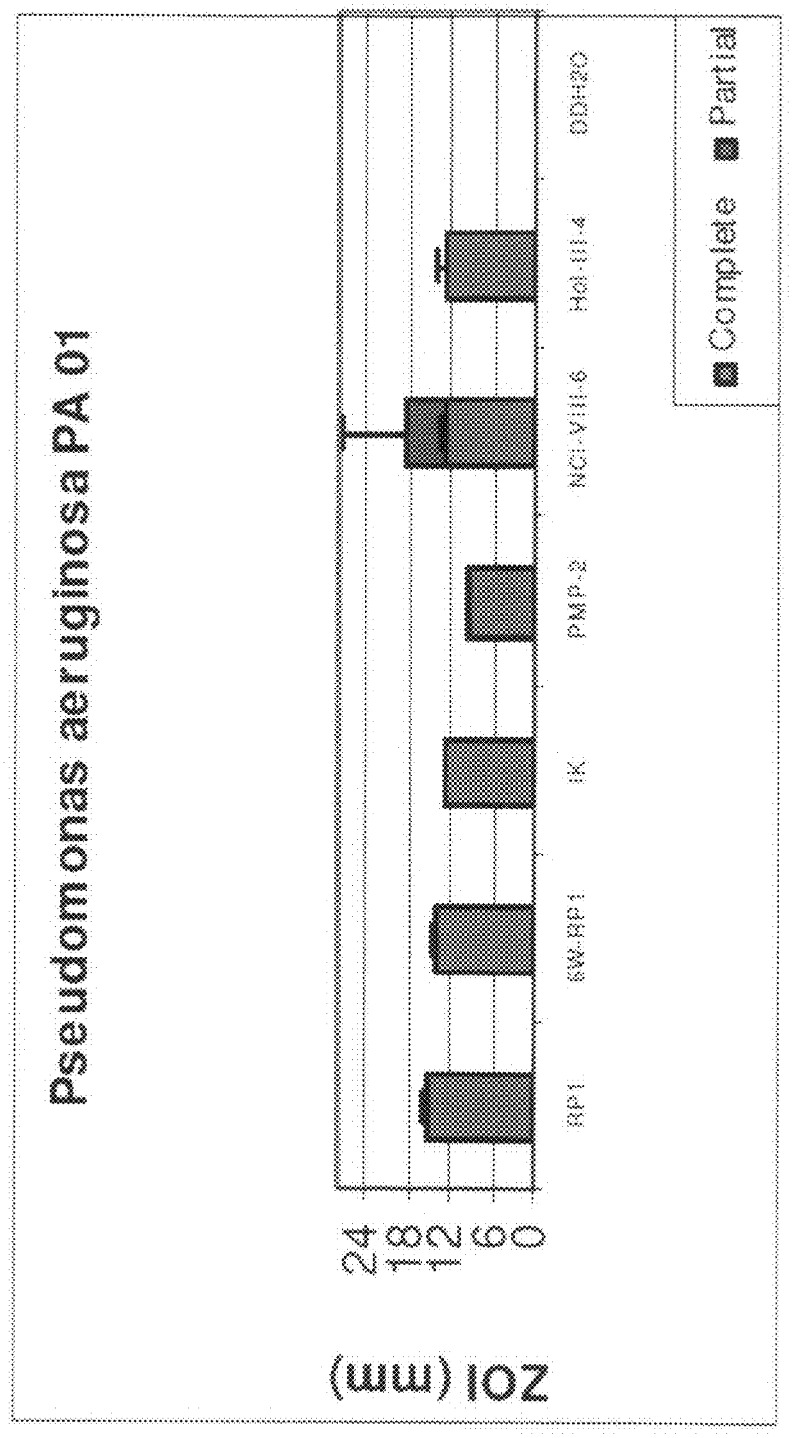

FIG. 48 shows a histogram of the antimicrobial spectra of exemplary peptides Hol-III-4 (SEQ ID NO. 268) and NCl-VIII-6 (SEQ ID NO. 152) against *Pseudomonas aeruginosa* PA 01 at pH 7.5. Positive control peptides RP1, 6W-RP1, IK and PMP-2, whereas the negative control of double-distilled water (DDH2O) are also shown. The size of the complete zone of inhibition (ZOI) is represented by a blue bar, whereas the size of the partial (ZOI) is represented by a red bar.

Figure 49:
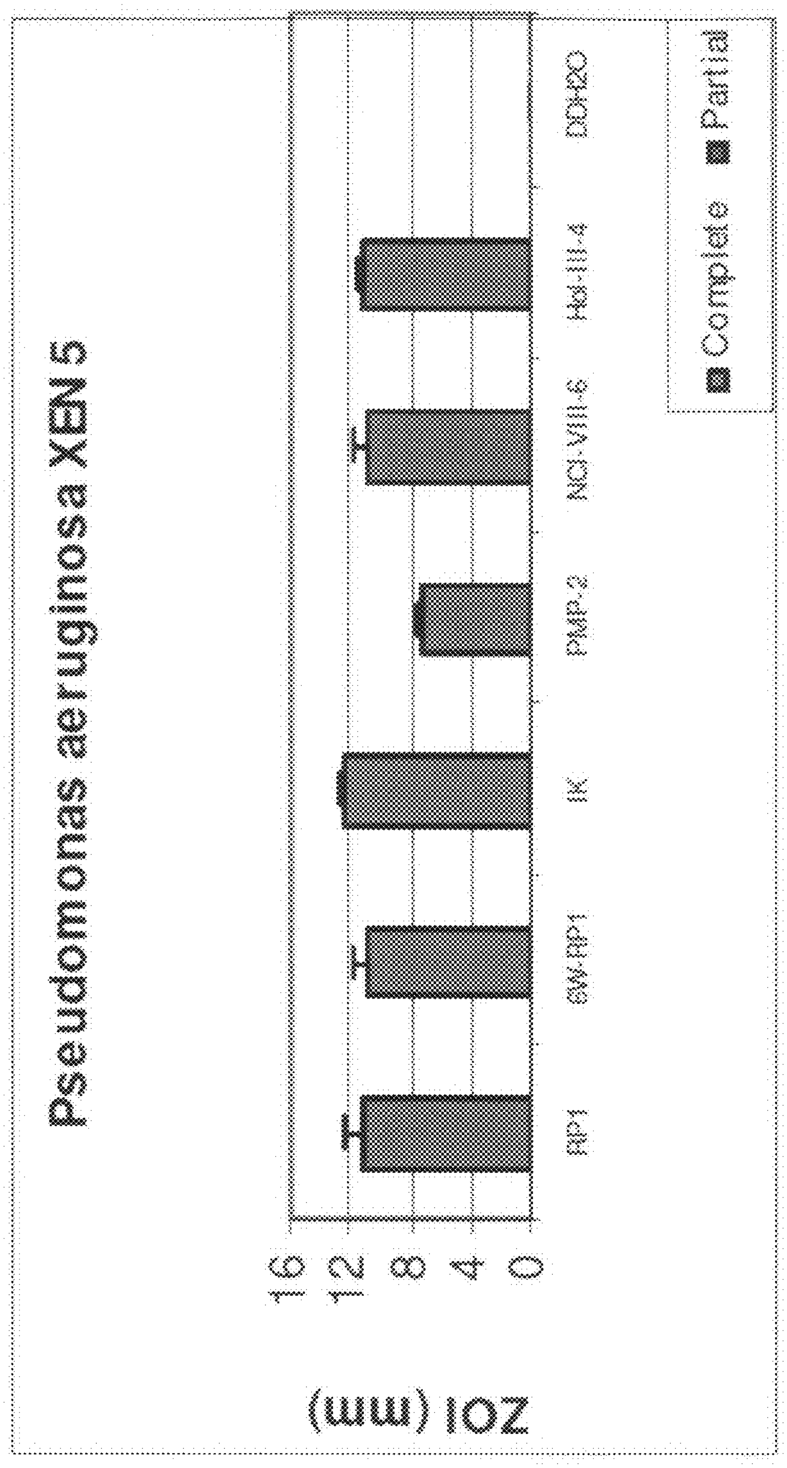

FIG. 49 shows a histogram of the antimicrobial spectra of exemplary peptides Hol-III-4 (SEQ ID NO. 268) and NCl-VIII-6 (SEQ ID NO. 152) against *Pseudomonas aeruginosa* XEN 5 at pH 7.5. Positive control peptides RP1, 6W-RP1, IK and PMP-2, whereas the negative control of double-distilled water (DDH2O) are also shown. The size of the complete zone of inhibition (ZOI) is represented by a blue bar, whereas the size of the partial (ZOI) is represented by a red bar.

Figure 50:
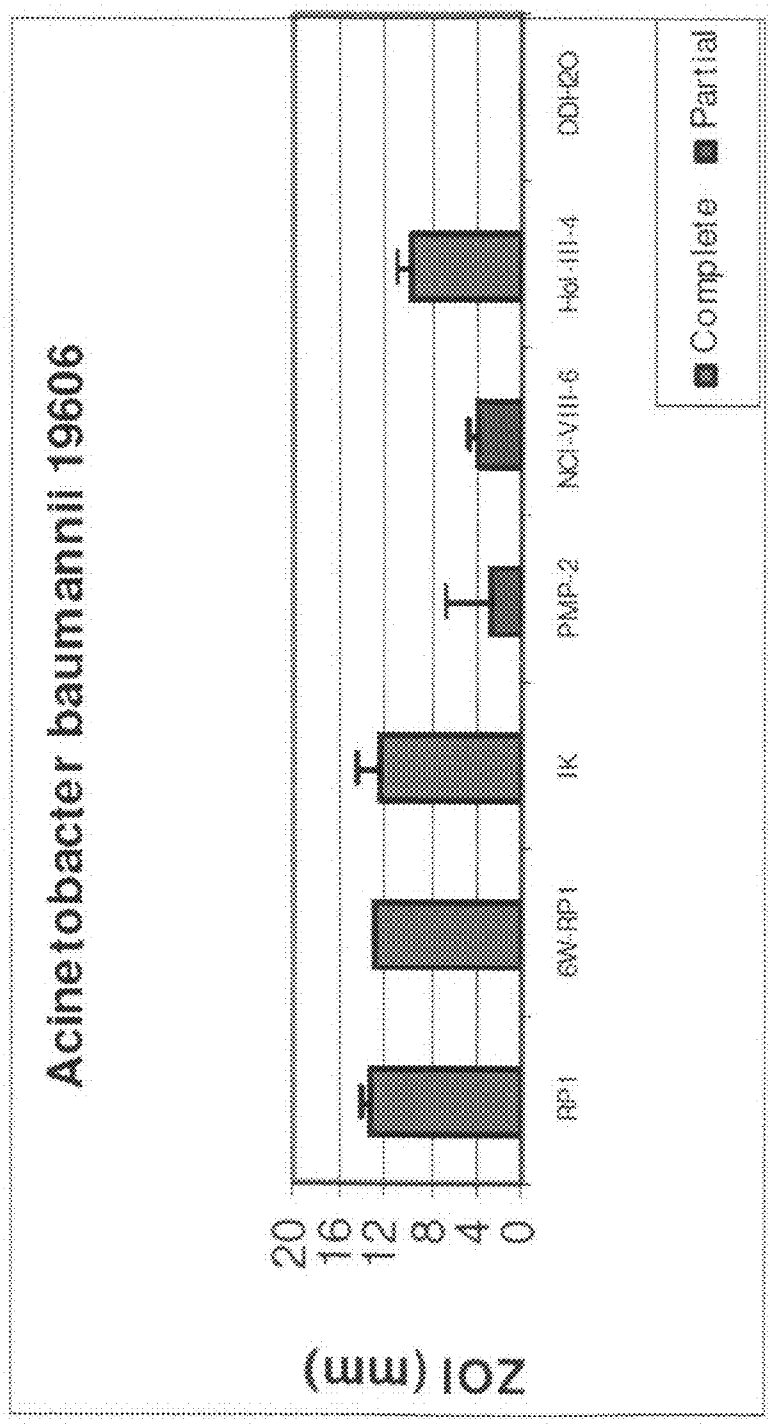

FIG. 50 shows a histogram of the antimicrobial spectra of exemplary peptides Hol-III-4 (SEQ ID NO. 268) and NCl-VIII-6 (SEQ ID NO. 152) against *Acinetobacter baumannii* 19606 at pH 7.5. Positive control peptides RP1, 6W-RP1, IK and PMP-2, whereas the negative control of double-distilled water (DDH2O) are also shown. The size of the complete zone of inhibition (ZOI) is represented by a blue bar, whereas the size of the partial (ZOI) is represented by a red bar.

Figure 51:
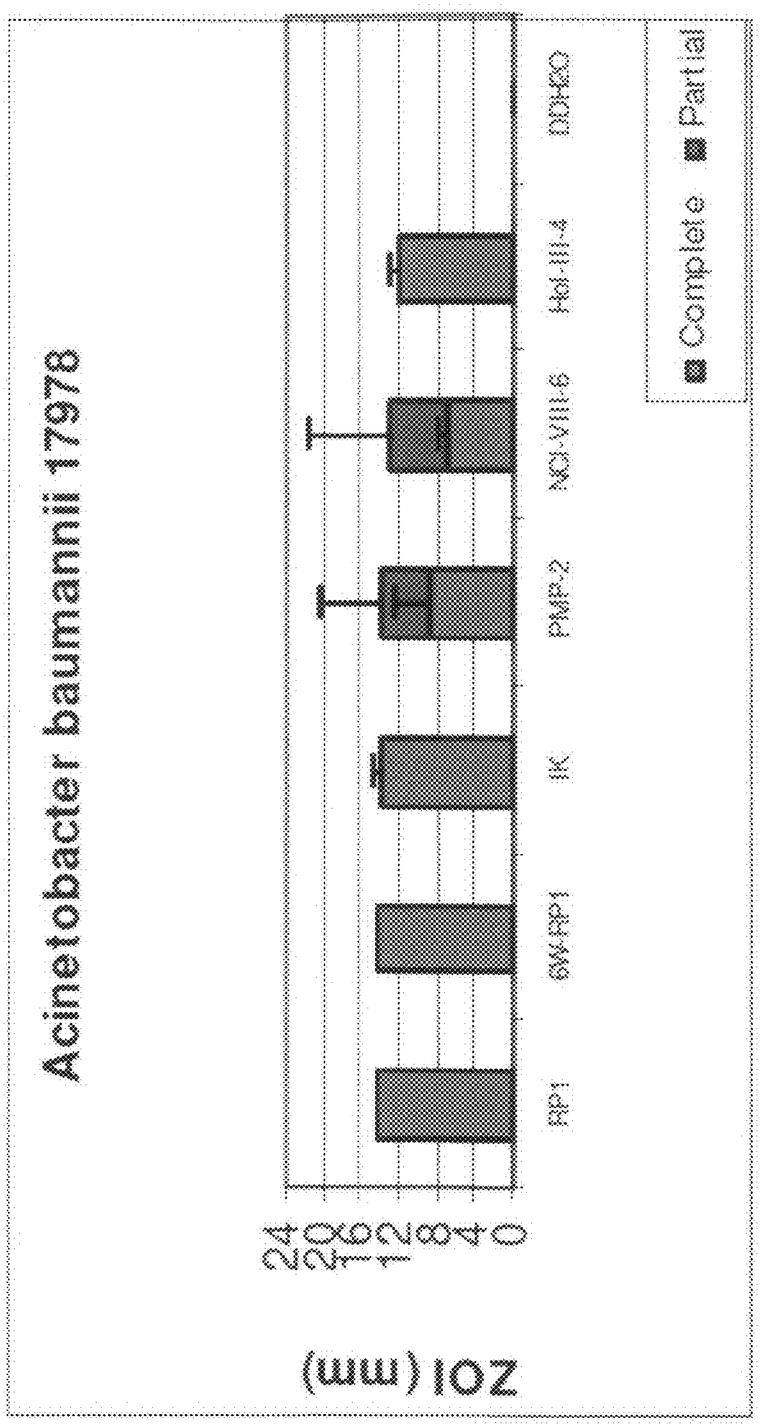

FIG. 51 shows a histogram of the antimicrobial spectra of exemplary peptides Hol-III-4 (SEQ ID NO. 268) and NCl-VIII-6 (SEQ ID NO. 152) against *Acinetobacter baumannii* 17978 at pH 7.5. Positive control peptides RP1, 6W-RP1, IK and PMP-2, whereas the negative control of double-distilled water (DDH2O) are also shown. The size of the complete zone of inhibition (ZOI) is represented by a blue bar, whereas the size of the partial (ZOI) is represented by a red bar.

Figure 52:
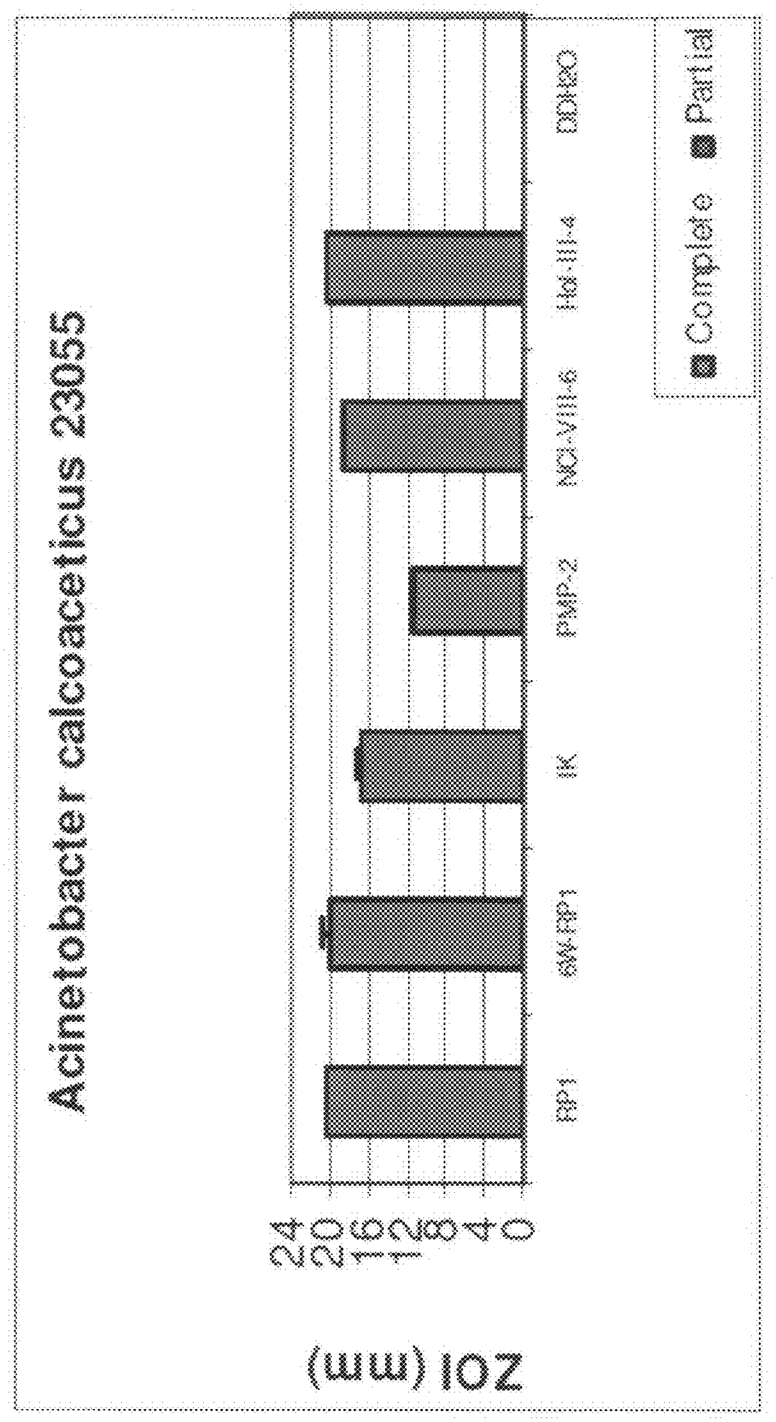

FIG. 52 shows a histogram of the antimicrobial spectra of exemplary peptides Hol-III-4 (SEQ ID NO. 268) and NCl-VIII-6 (SEQ ID NO. 152) against *Acinetobacter calcoaceticus* 23055 at pH 7.5. Positive control peptides RP1, 6W-RP1, IK and PMP-2, whereas the negative control of double-distilled water (DDH2O) are also shown. The size of the complete zone of inhibition (ZOI) is represented by a blue bar, whereas the size of the partial (ZOI) is represented by a red bar.

Figure 53:
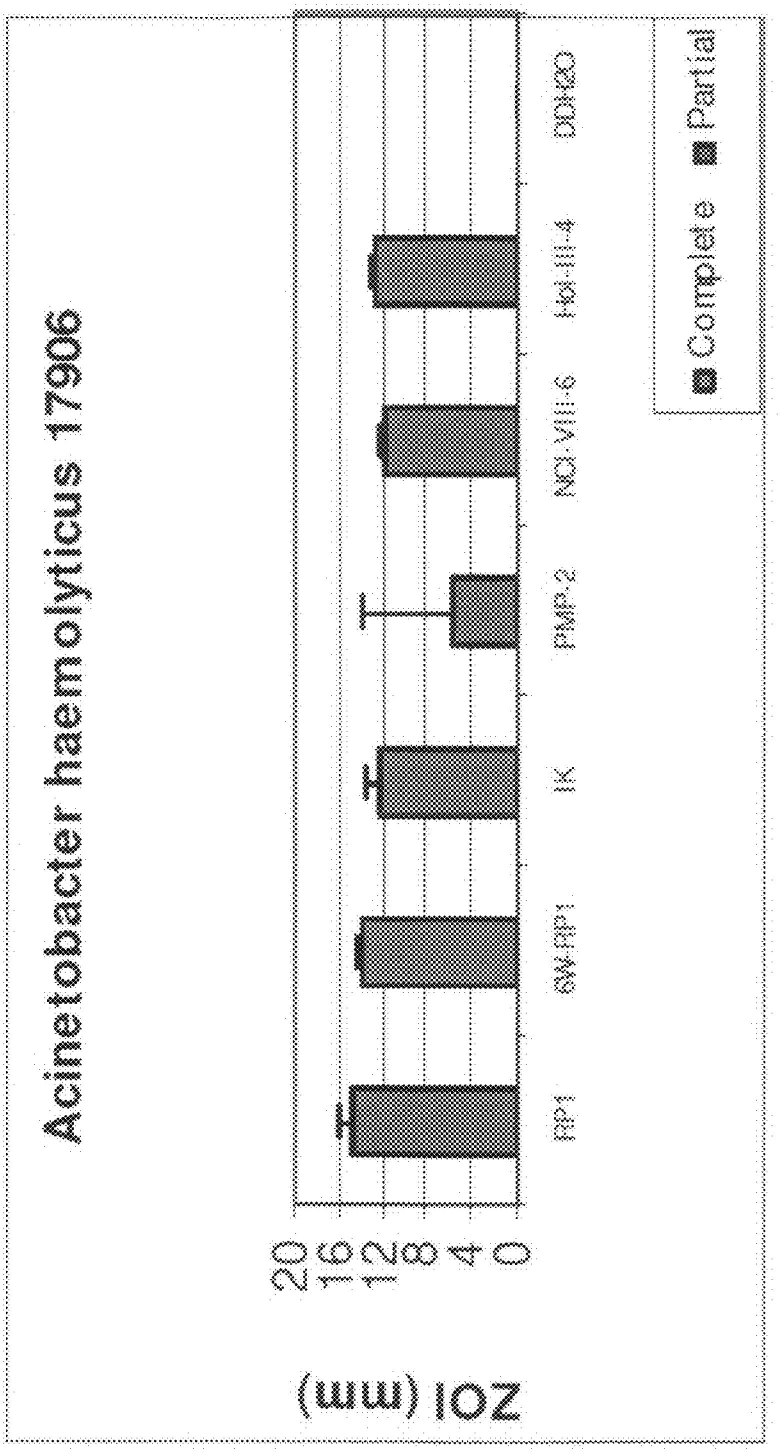

FIG. 53 shows a histogram of the antimicrobial spectra of exemplary peptides Hol-III-4 (SEQ ID NO. 268) and NCl-VIII-6 (SEQ ID NO. 152) against *Acinetobacter haemolyticus* 17906 at pH 7.5. Positive control peptides RP1, 6W-RP1, IK and PMP-2, whereas the negative control of double-distilled water (DDH2O) are also shown. The size of the complete zone of inhibition (ZOI) is represented by a blue bar, whereas the size of the partial (ZOI) is represented by a red bar.

Figure 54:
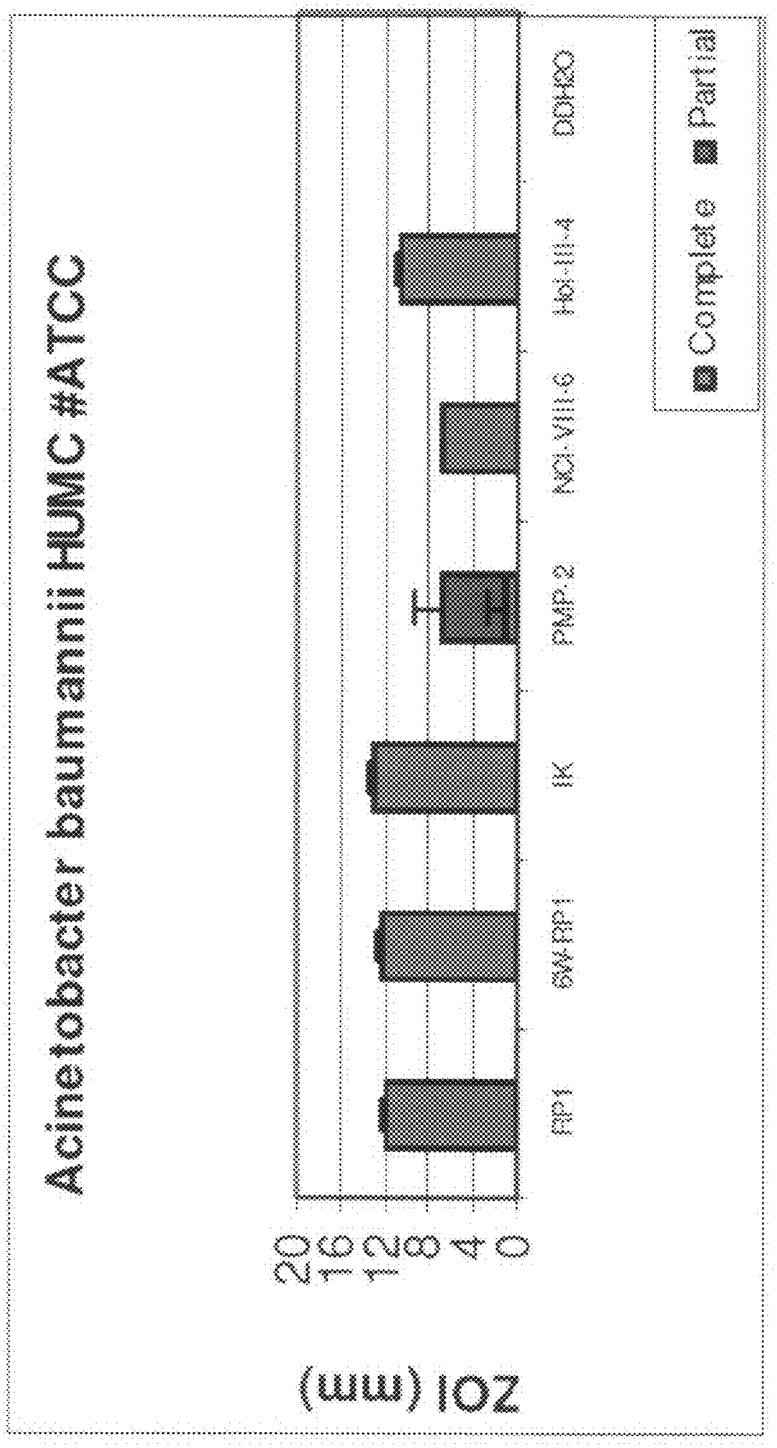

FIG. 54 shows a histogram of the antimicrobial spectra of exemplary peptides Hol-III-4 (SEQ ID NO. 268) and NCl-VIII-6 (SEQ ID NO. 152) against *Acinetobacter baumannii* HUMC #ATCC at pH 7.5. Positive control peptides RP1, 6W-RP1, IK and PMP-2, whereas the negative control of double-distilled water (DDH2O) are also shown. The size of the complete zone of inhibition (ZOI) is represented by a blue bar, whereas the size of the partial (ZOI) is represented by a red bar.

Figure 55:
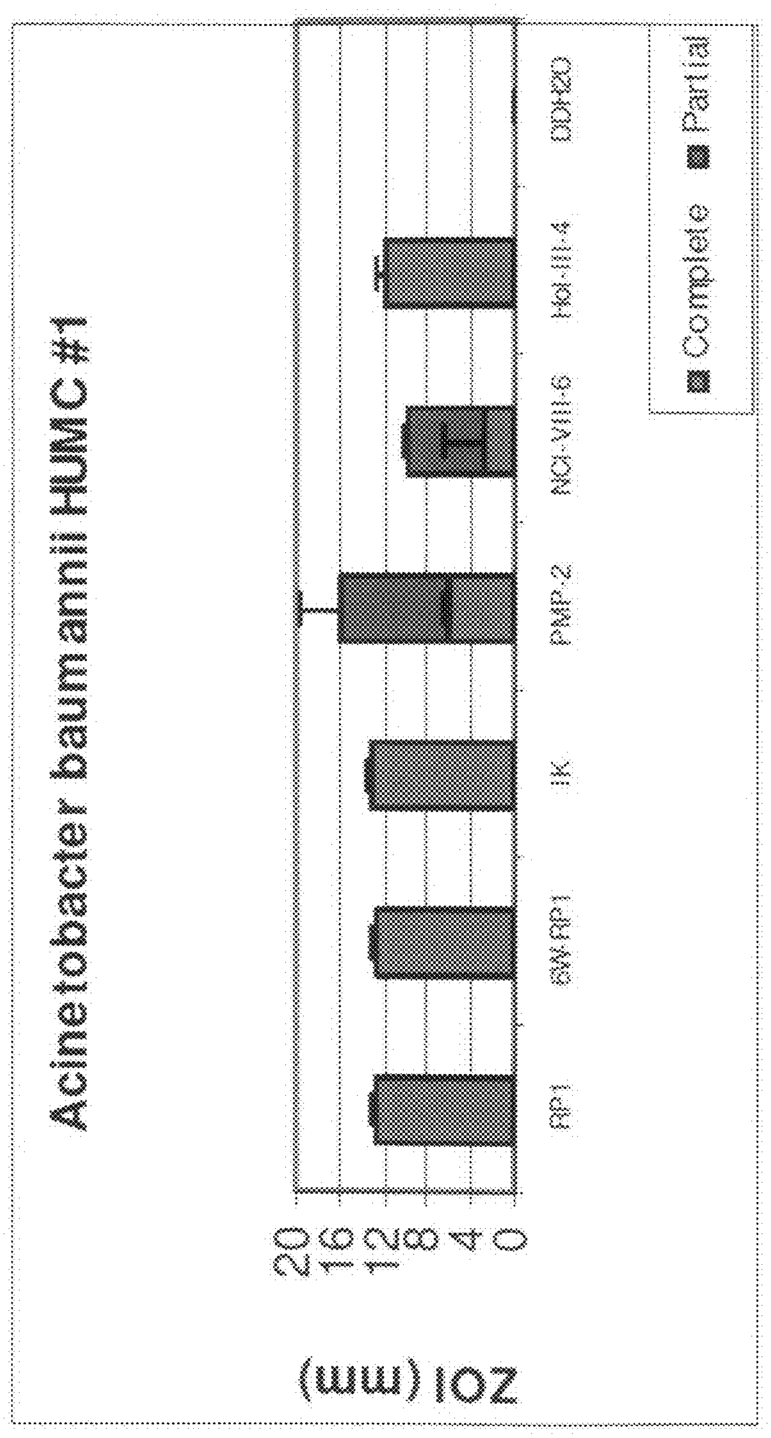

FIG. 55 shows a histogram of the antimicrobial spectra of exemplary peptides Hol-III-4 (SEQ ID NO. 268) and NCl-VIII-6 (SEQ ID NO. 152) against *Acinetobacter baumannii* HUMC #1 at pH 7.5. Positive control peptides RP1, 6W-RP1, IK and PMP-2, whereas the negative control of double-distilled water (DDH2O) are also shown. The size of the complete zone of inhibition (ZOI) is represented by a blue bar, whereas the size of the partial (ZOI) is represented by a red bar.

Figure 56:
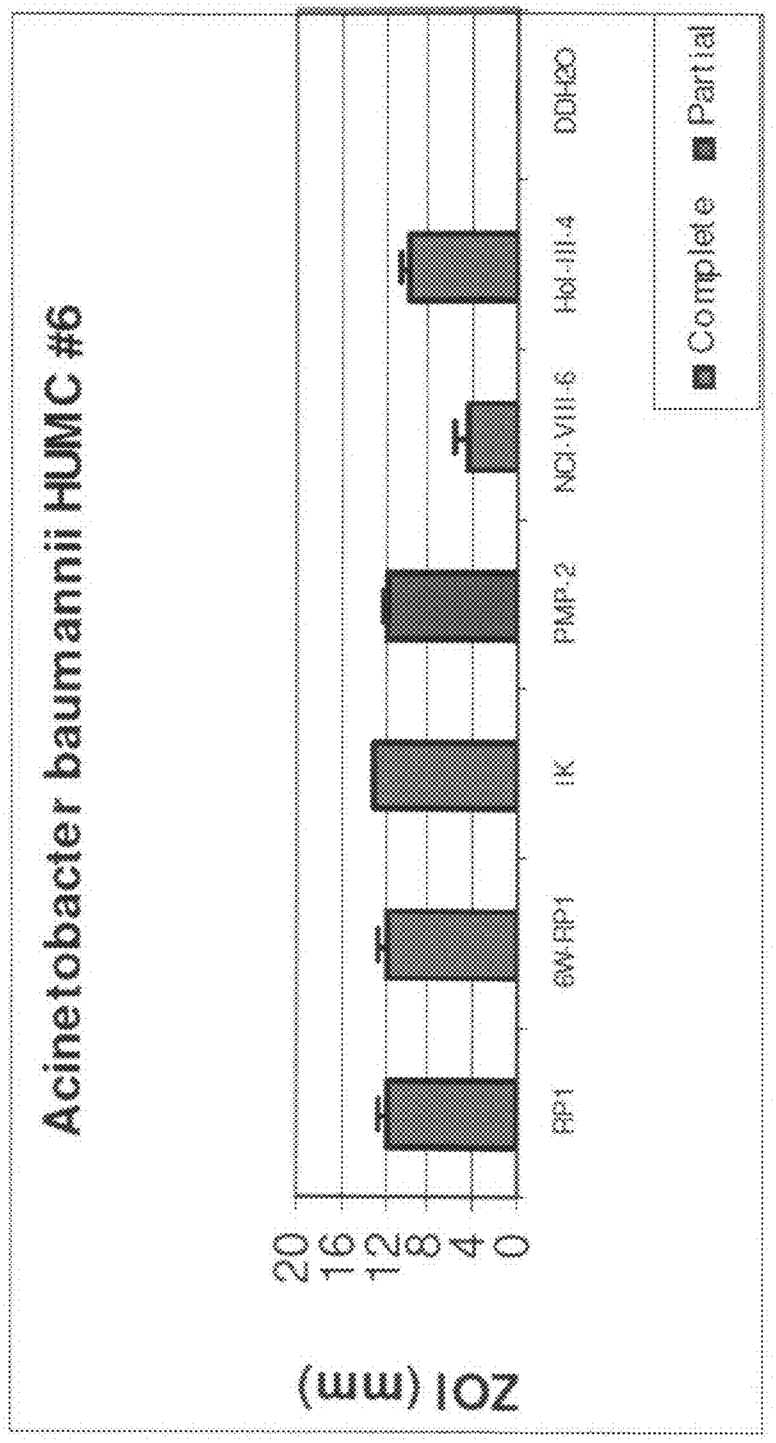

FIG. 56 shows a histogram of the antimicrobial spectra of exemplary peptides Hol-III-4 (SEQ ID NO. 268) and NCl-VIII-6 (SEQ ID NO. 152) against *Acinetobacter baumannii* HUMC #6 at pH 7.5. Positive control peptides RP1, 6W-RP1, IK and PMP-2, whereas the negative control of double-distilled water (DDH2O) are also shown. The size of the complete zone of inhibition (ZOI) is represented by a blue bar, whereas the size of the partial (ZOI) is represented by a red bar.

Figure 57:
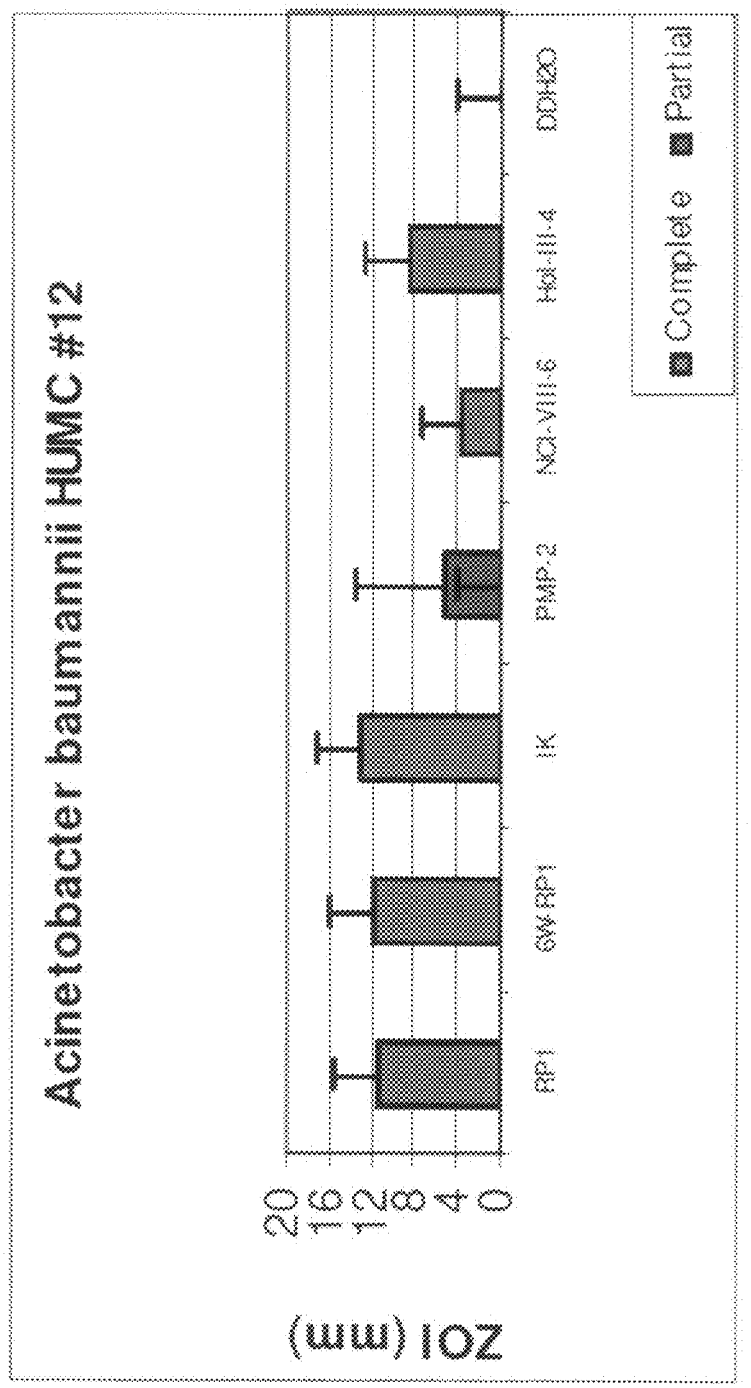

FIG. 57 shows a histogram of the antimicrobial spectra of exemplary peptides Hol-III-4 (SEQ ID NO. 268) and NCl-VIII-6 (SEQ ID NO. 152) against *Acinetobacter baumannii* HUMC #12 at pH 7.5. Positive control peptides RP1, 6W-RP1, IK and PMP-2, whereas the negative control of double-distilled water (DDH2O) are also shown. The size of the complete zone of inhibition (ZOI) is represented by a blue bar, whereas the size of the partial (ZOI) is represented by a red bar.

DETAILED DESCRIPTION OF THE INVENTION

Over the last several years, unforeseen structural, functional, and evolutionary relationships among host defenses and other proteins across all kingdoms of life have been discovered. In the course of the studies described herein, unifying themes among polypeptides based on sequence formulae, functional mechanisms, and/or 3D structures have been identified. Embodiments provided by the invention are based in part on the observations that 1) programmed cell death and apoptosis pathway proteins contain archetype sequences that confer membrane interacting/modifying domains similar to those of antimicrobial or other host defense peptides; 2) such sequences encode helical or other sequence and/or 3D structural signatures; and 3) such peptides exert antimicrobial and anti-cancer cell activities. Without being bound by theory, such peptides induce or regulate programmed cell death or related responses in target cells (e.g. microbial pathogens, cancer cells, etc.) leading to death of these cells. It is also contemplated that the mechanisms of action of peptides based on programmed cell death may activate archetypal apoptosis pathways in target cells, thus killing the target cell and circumventing resistance to existing antimicrobial, anti-cancer, or other preventive or therapeutic agents.

Embodiments of the invention provide that novel antimicrobial, anti-cancer, anti-inflammatory and/or anti-proliferative activity peptides reside in peptide sequences of programmed cell death effector proteins by virtue of the evolutionary necessity for control of microbial and cancer cell survival by increasingly complex eukaryotic systems/symbionts. Thus mitochondrial, chloroplast, and/or nuclear-encoded proteins capable of activating and/or modulating programmed cell death pathways are contemplated to be evolutionary relatives/descendents of polypeptides that originally provided a survival advantage in the face of microbial or neoplastic challenge.

The peptides, protides and conjugates described herein have the potential to create, augment, or improve several existing therapeutic, prophylactic, diagnostic, and basic research problems. For example, therapeutically, these peptides, protides and conjugates can address the problem of antibiotic-resistant infections and antineoplastic-resistant cancers. Likewise, the peptides, protides and conjugates may serve as immunotherapeutic agents to enhance or restore efficacy of endogenous host defenses. As adjunctive agents, these peptides, protides and conjugates will increase efficacy of conventional agents (such as antibiotics or anti-neoplastic agents), enhance immune functions, and activate or inactivate apoptotic mechanisms of cell regulation associated with aging or other degenerative conditions, and many other potential applications. The scope and diversity of other uses for these peptides, protides and conjugates are considerable. For example, the peptides, protides and conjugates described herein can be used as diagnostic probes in isotopic or non-isotopic forms to localize or characterize diseases or conditions containing signatures such as those characteristic of microbial, neoplastic, necrotic, apoptotic, or other tissues or cells. Additionally, extensions of the above concepts are applicable to the construction, design, delivery, and use of such peptides as research reagents.

As will be clear to those skilled in the art, the above novel concepts relating to structure-activity relationships in programmed cell death proteins enabled the design of novel antimicrobial, anti-cancer, anti-inflammatory and anti-proliferative peptides, protides and conjugates. These peptides and compositions are useful as diagnostic, prophylactic, and/or therapeutic agents that exploit programmed cell death pathways in pathogens, cancer cells, autoimmune cells, and other disease-caused cells and tissues. Specific examples of peptides, variants, congeners, and mimetics of these molecules are included herein. Embodiments of the invention provide conjugates in which one given molecule can represent or include one or more antimicrobial, anti-cancer, anti-inflammatory, immunomodulatory peptide and one or more non-peptide functional motifs or domains, or combinations of these. Embodiments of the invention also provide protides which are multifunctional and context-activated polypeptides that have two or more effectors with individually distinct biological functions and one or more corresponding activator sites that can each initiate or amplify the biological function of one or more effectors upon context-activation. Therefore, peptides, protides and conjugates exemplified herein are relevant to Antibiotide, Immodulotide, Antineotide, Apoptide, and/or Cascatide class peptides.

The novel concepts, peptide design strategies, and exemplifying peptides encompass conceptual as well as material inventions. Moreover, variations upon these fundamental themes are applicable to novel therapeutic agents and strategies in virtually any area of medicine, including, but not limited to diagnosis, prevention, and therapy of infectious diseases, cancer and cancer-like diseases, immune and autoimmune disorders, cardiology, aging, and/or other conditions or disease states. Furthermore, the novel peptides based on programmed cell death effectors described herein represent agents and strategies to treat human, animal, and agricultural diseases. Other applications include their use in diagnosis, prevention, or research of diseases, or as research tools to investigate pathogenesis, apoptosis, or related biological phenomena.

Embodiments of the invention, herein provide an isolated peptide comprising one or more amino acid sequences selected from the group consisting of SEQ ID NOS: 3, 4, 6, 8, 10, 11, 13, 17, 18, 19, 21-25, 30, 31-36, 39-47, 49-52, 54-57, 59-63, 66-75, 84-93, 102-106, 108-121, 132-175, 179-187, 191-199, 205-209, 211-223, 227-235, 238-243, 245-247, 249-251, 253-256 and 260-263, wherein the amino acid residue represented by (x) is a serine, a threonine, a tyrosine, a H-bond donor residue or a H-bond acceptor residue, wherein the amino acid residue represented by (b) is a lysine, an arginine, an asparagine, a glutamine or a basic residue, wherein the amino acid residue represented by (j) is a cysteine or a thiol residue, wherein in the amino acid residue represented by (o) is an anthrylalanine or other non-natural amino acid and wherein the peptide induces antimicrobial, anti-cancer, anti-inflammatory, anti-proliferative or programmed cell death activity.

In one aspect, the isolated peptide comprises one or more amino acid sequence, identified from the Bax protein, which are represented by amino acid sequences of SEQ ID NOS: 3, 4, 6, 8, 10, 11, 13, 264, 270 and 271. In one aspect, the isolated peptide comprises one or more amino acid sequence, identified from the Bcl-W protein, which are represented by amino acid sequences of SEQ ID NOS: 17, 18, 19, 21-25, 269 and 272. In one aspect, the isolated peptide comprises one or more amino acid sequence, identified from the Bcl-xβ protein, which are represented by amino acid sequences of SEQ ID NOS: 30, 31-36 and 273. In one aspect, the isolated peptide comprises one or more amino acid sequence, identified from the Bak protein, which are represented by amino acid sequences of SEQ ID NOS: 39-47. In one aspect, the isolated peptide comprises one or more amino acid sequence, identified from the Bcl-2 protein, which are represented by amino acid sequences of SEQ ID NOS: 49-52. In one aspect, the isolated peptide comprises one or more amino acid sequence, identified from the Bcl-2 isoform 1 protein, which are represented by amino acid sequences of SEQ ID NOS: 54-57. In one aspect, the isolated peptide comprises one or more amino acid sequence, identified from the Mfn-1 protein, which are represented by amino acid sequences of SEQ ID NOS: 59-63 and 274. In one aspect, the isolated peptide comprises one or more amino acid sequence, identified from the Mfn-2 protein, which are represented by amino acid sequences of SEQ ID NOS: 66-75. In one aspect, the isolated peptide comprises one or more amino acid sequence, identified from the Dnm-1 protein, which are represented by amino acid sequences of SEQ ID NOS: 84-93 and 275. In one aspect, the isolated peptide comprises one or more amino acid sequence, identified from the Dnm-2 protein, which are represented by amino acid sequences of SEQ ID NOS: 102-106, 108-121, 267, 276 and 277. In one aspect, the isolated peptide comprises one or more amino acid sequence, identified from the Ncl protein, which are represented by amino acid sequences of SEQ ID NOS: 132-175. In one aspect, the isolated peptide comprises one or more amino acid sequence, identified from the Csp3 protein, which are represented by amino acid sequences of SEQ ID NOS: 179-187, 266 and 278. In one aspect, the isolated peptide comprises one or more amino acid sequence, identified from the Bad protein, which are represented by amino acid sequences of SEQ ID NOS: 191-199. In one aspect, the isolated peptide comprises one or more amino acid sequence, identified from the Prf-1 protein, which are represented by amino acid sequences of SEQ ID NOS: 205-209 and 211-223. In one aspect, the isolated peptide comprises one or more amino acid sequence, identified from the Granulysin protein, which are represented by amino acid sequences of SEQ ID NOS: 227-235. In one aspect, the isolated peptide comprises one or more amino acid sequence, identified from the CidA protein, which are represented by amino acid sequences of SEQ ID NOS: 238-243, 245-247, 265 and 279. In one aspect, the isolated peptide comprises one or more amino acid sequence, identified from the LrgA protein, which are represented by amino acid sequences of SEQ ID NOS: 249-251. In one aspect, the isolated peptide comprises one or more amino acid sequence, identified from the Lambda S21 protein, which are represented by amino acid sequences of SEQ ID NOS: 253-256. In one aspect, the isolated peptide comprises one or more amino acid sequence, identified from the Holin protein, which are represented by amino acid sequences of SEQ ID NOS: 260-263 and 268.

Embodiments of the invention provide an isolated peptide consisting of an amino acid sequence selected from the group consisting of SEQ ID NOS: 1, 2, 5, 7, 9, 12, 14-16, 20, 26-29, 37, 38, 48, 53, 58, 64, 65, 72, 76-83, 94-101, 107, 114, 122-131, 170, 176-178, 188-190, 200-204, 210, 224-226, 236, 237, 244, 248, 252, 257-259 and 288-289, wherein the peptide induces antimicrobial, anti-cancer, anti-inflammatory, anti-proliferative or programmed cell death activity.

In one aspect, the isolated peptide consists of one or more amino acid sequence, identified from the Bax protein, which are represented by amino acid sequences of SEQ ID NOS: 1, 2, 5, 7, 9 and 12. In one aspect, the isolated peptide consists of one or more amino acid sequence, identified from the Bcl-W protein, which are represented by amino acid sequences of SEQ ID NOS: 14-16 and 20. In one aspect, the isolated peptide consists of one or more amino acid sequence, identified from the Bcl-xβ protein, which are represented by amino acid sequences of SEQ ID NOS: 26-29. In one aspect, the isolated peptide consists of one or more amino acid sequence, identified from the Bak protein, which are represented by amino acid sequences of SEQ ID NOS: 37 or 38. In one aspect, the isolated peptide consists of the amino acid sequence, identified from the Bcl-2 protein, which is represented by amino acid sequence of SEQ ID NO: 48. In one aspect, the isolated peptide consists of the amino acid sequence, identified from the Bcl-2 isoform 1 protein, which is represented by amino acid sequence of SEQ ID NOS: 53. In one aspect, the isolated peptide consists of one or more amino acid sequence, identified from the Mfn-1 protein, which are represented by amino acid sequences of SEQ ID NOS: 58 or 64. In one aspect, the isolated peptide consists of one or more amino acid sequence, identified from the Mfn-2 protein, which are represented by amino acid sequences of SEQ ID NOS: 65 or 72. In one aspect, the isolated peptide consists of one or more amino acid sequence, identified from the Dnm-1 protein, which are represented by amino acid sequences of SEQ ID NOS: 76-83. In one aspect, the isolated peptide consists of one or more amino acid sequence, identified from the Dnm-2 protein, which are represented by amino acid sequences of SEQ ID NOS: 94-101, 107 and 114. In one aspect, the isolated peptide consists of one or more amino acid sequence, identified from the Ncl protein, which are represented by amino acid sequences of SEQ ID NOS: 122-131 and 170. In one aspect, the isolated peptide consists of one or more amino acid sequence, identified from the Csp3 protein, which are represented by amino acid sequences of SEQ ID NOS: 176-178. In one aspect, the isolated peptide consists of one or more amino acid sequence, identified from the Bad protein, which are represented by amino acid sequences of SEQ ID NOS: 188-190. In one aspect, the isolated peptide consists of one or more amino acid sequence, identified from the Prf-1 protein, which are represented by amino acid sequences of SEQ ID NOS: 200-204 and 210. In one aspect, the isolated peptide consists of one or more amino acid sequence, identified from the Granulysin protein, which are represented by amino acid sequences of SEQ ID NOS: 224-226. In one aspect, the isolated peptide consists of one or more amino acid sequence, identified from the CidA protein, which are represented by amino acid sequences of SEQ ID NOS: 236, 237 and 244. In one aspect, the isolated peptide consists of the amino acid sequence, identified from the LrgA protein, which is represented by amino acid sequence of SEQ ID NOS: 248. In one aspect, the isolated peptide consists of the amino acid sequence, identified from the Lambda S21 protein, which is represented by amino acid sequences of SEQ ID NOS: 252. In one aspect, the isolated peptide consists of one or more amino acid sequence, identified from the Holin protein, which are represented by amino acid sequences of SEQ ID NOS: 257-259. In one aspect, the isolated peptide consists of one or more amino acid sequence, identified from human Bcl-xL protein, which is represented by the amino acid sequence SEQ ID NO: 288 or human CTL Granulysin, which is represented by the amino acid sequence SEQ ID NO: 289. In one aspect, an isolated peptide as described herein has a C-terminus comprising a carboxamide.

Embodiments of the invention are intended to be used as in ways similar to antibiotic, anti-cancer, or similar medical administration either as local (e.g. topical, oral rinse, inhaled, nebulized, etc.) or systemic (oral ingestion, intravenous, intramuscular, etc) agents. Additionally, the peptides may be used as research tools for basic molecular biology, microbiology, biochemistry or other disciplines as they relate broadly to cellular or molecular biology, infection and immunity, cell regulation and apoptosis, gene expression, signal transduction, or any other area of investigation in which a concept, approach, or specific peptide or may be used.

In certain embodiments, the invention provides novel isolated peptides having one or more continuous amino acids sequences. As used herein, a "peptide" generally has from about 3 to about 100 amino acids, whereas a polypeptide or protein has about 100 or more amino acids, up to a full length sequence translated from a gene. Additionally, as used herein a peptide can be a subsequence or a portion of a polypeptide or protein. In certain embodiments the size of at least one peptide may comprise, but is not limited to, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 amino acid residues.

As used herein, an “amino acid residue” refers to any naturally or non-naturally occurring amino acid, any amino acid derivative or any amino acid mimic known in the art. In certain embodiments, the residues of the peptide are sequential, without any non-amino acid interrupting the sequence of amino acid residues. In other embodiments, the sequence may comprise one or more non-amino acid moieties. In particular embodiments, the sequence of residues of the peptide may be interrupted by one or more non-amino acid moieties. Accordingly, the term peptide encompasses amino acid sequences comprising at least one of the common amino acids found in naturally occurring proteins, or at least one modified or unusual or non-natural amino acid, including, but not limited to, Anthrylalanine, 2 Aminoadipic acid (Aad), N Ethylasparagine (EtAsn), 3 Aminoadipic acid (Baad), Hydroxylysine (Hyl), β alanine, β Amino propionic acid (Bala), allo Hydroxylysine (AHy1), 2 Aminobutyric acid (Abu), 3 Hydroxyproline (3Hyp), 4 Aminobutyric acid (4Abu), 4 Hydroxyproline (4Hyp), 6 Aminocaproic acid (Acp), Isodesmosine (Ide), 2 Aminoheptanoic acid (Ahe), allo Isoleucine (AIle), 2 Aminoisobutyric acid (Aib), N Methylglycine (MeGly), 3 Aminoisobutyric acid (Baib), N Methylisoleucine (Melle), 2 Aminopimelic acid (Apm), 6 N Methyllysine (MeLys), 2,4 Diaminobutyric acid (Dbu), N Methylvaline (MeVal), Desmosine (Des), Norvaline (Nva), 2,2'Diaminopimelic acid (Dpm), Norleucine (Nle), 2,3 Diaminopropionic acid (Dpr), Ornithine (Orn), or N Ethylglycine (EtGly).

A peptide containing one or more mimetic structures having a similar charge and spatial or steric arrangements as the reference amino acid residues is included within the definition of the term so long as the peptide containing the mimetic portion exhibits a similar or enhanced activity as compared with the reference peptide. It is thus understood that a peptide described herein includes such mimetics as chemically modified peptides, peptide-like molecules containing non-naturally occurring amino acids, and peptoids, which are peptide-like molecules resulting from oligomeric assembly of N-substituted glycines, with similar or enhanced activity as compared with the reference protide upon which the mimetic is derived or having any other property desired by the user, for example, enhanced biostability (see, for example, Goodman and Ro, Peptidomimetics for Drug Design, in “Burger's Medicinal Chemistry and Drug Discovery” Vol. 1 (ed. M. E. Wolff; John Wiley & Sons 1995), pages 803 861), which is incorporated herein by reference in its entirety. Mimetics also include constrained-structures so as to maintain optimal spacing and charge interactions of the amino acid or of the amino acid functional groups. Those skilled in the art know or can determine what structures constitute functionally equivalent amino acid analogs and amino acid mimetics useful for preparation of a peptide described herein.

Specific examples of amino acid analogs and mimetics can be found described in, for example, Roberts and Vellaccio, The Peptides: Analysis, Synthesis, Biology, Eds. Gross and Meinhofer, Vol. 5, p. 341, Academic Press, Inc., New York, N.Y. (1983), the entire volume of which is incorporated herein by reference. Other examples include peralkylated amino acids, particularly permethylated amino acids. See, for example, Combinatorial Chemistry, Eds. Wilson and Czarnik, Ch. 11, p. 235, John Wiley & Sons Inc., New York, N.Y. (1997), which is incorporated herein by reference in its entirety. Yet other examples include amino acids whose amide portion and, therefore, the amide backbone of the resulting peptide, has been replaced, for example, by a sugar ring, steroid, benzodiazepine or carbo cycle. See, for example, Burger's Medicinal Chemistry and Drug Discovery, supra, Ch. 15, pp. 619 620, which is incorporated herein by reference in its entirety. Methods for synthesizing peptides, polypeptides, peptidomimetics and proteins are well known in the art (see, for example, U.S. Pat. No. 5,420,109; Bodanzsky, Principles of Peptide Synthesis (1st ed. & 2d rev. ed.), Springer-Verlag, New York, N.Y. (1984 & 1993), see Chapter 7; Stewart and Young, Solid Phase Peptide Synthesis, (2d ed.), Pierce Chemical Co., Rockford, Ill. (1984), each of which is incorporated-herein by reference in its entirety).

In one aspect, the peptide, protide or conjugate can comprise conservatively substituted sequences or alternative residues at specifically identified positions described herein, for example, residues identified in SEQ ID NOS: 3, 4, 6, 8, 10, 11, 13, 17, 18, 19, 21-25, 30, 31-36, 39-47, 49-52, 54-57, 59-63, 66-75, 84-93, 102-106, 108-121, 132-175, 179-187, 191-199, 205-209, 211-223, 227-235, 238-243, 245-247, 249-251, 253-256 and 260-263. In general, a conservative substitution refers to replacement of a given amino acid residue with a residue having similar physiochemical characteristics. Examples of conservative substitutions include (1) non-polar amino acids (Gly, Ala, Val, Leu, and Ile); (2) polar neutral amino acids (Cys, Met, Ser, Thr, Asn, and Gln); (3) polar acidic amino acids (Asp and Glu); (4) polar basic amino acids (Lys, Arg and His); and (5) aromatic amino acids (Phe, Trp, Tyr, and His). Other such conservative substitutions, for example, include substitutions of entire regions having similar hydrophobicity characteristics or substitution of one H-bond donor/acceptor with another H-bond donor/acceptor. An alternative residue refers to a residue that may not be traditionally considered a conservative substitution, but when substituted at the designated position does not adversely effect the functional characteristics of the peptide.

Hydrogen bonding (H-bond) is a non-covalent type of bonding between molecules or within them, intermolecularly or intramolecularly, and in the context of the peptides described herein include H-bond between amino acids. The H-bond donor is the molecule that has a hydrogen atom bonded to a highly electronegative, small atom with available valence. For example, H—O, H—N, and H—F bonds are extremely polar and as a result, the electron density is easily withdrawn from the hydrogen atom towards the electronegative atom. The partially positive hydrogen in one molecule attracts to partially negative lone pair of the electronegative atom on the other molecule, i.e. an H-bond acceptor, and thus a H-bond forms as a result of such an interaction.

A “basic” residue refer to an amino acid residue which has a second basic group, which can be, but is not limited to, an amino group (i.e. lysine), a guanidine group (i.e. arginine), or an imidazole ring (i.e. histidine).

A “thiol” residue refers to an amino acid residue which has a functional sulfur-hydrogen present in the side chain (i.e. cysteine or methionine). A thiol residue, such as cysteine, can also play an important role in the folding and stability of some peptides and proteins through the formation of disulfide bonds.

A pathological condition appropriate for treatment with a peptide, protide or conjugate described here can be a symptomatic disease or other abnormal condition or injury of a mammalian cell or tissue. Such pathological conditions include, for example, hyperproliferative and unregulated neoplastic cell growth, degenerative conditions, inflammatory diseases, autoimmune diseases and infectious diseases. Hyperplastic and cancer cells proliferate in an unregulated manner, causing destruction of tissues and organs. Specific examples of hyperplasias include benign prostatic hyperplasia and endometrial hyperplasia.

Abnormal cellular growth can also result from infectious diseases in which foreign organisms cause excessive growth. For example, human papilloma viruses can cause abnormal growth of tissues. The growth of cells infected by a pathogen is abnormal due to the alteration of the normal condition of a cell resulting from the presence of a foreign organism. Specific examples of infectious diseases include DNA and RNA viral diseases, bacterial diseases, fungal diseases, and protozoal or parasitic diseases. Similarly, the cells mediating autoimmune and inflammatory diseases are aberrantly regulated which results in, for example, the continued proliferation and activation of immune mechanisms with the destruction of tissues and organs. Accordingly, "anti-inflammatory activity" refers to a cellular response to a substance or treatment that reduces inflammation and "anti-proliferative activity" refers to a cellular response to a substance that prevents the proliferation or uncontrolled dividing of cells. Specific examples of autoimmune diseases include, for example, rheumatoid arthritis and systemic lupus erythmatosis. Specific examples of degenerative disease include osteoarthritis and Alzheimer's disease. Similarly, the terms infectious diseases, degenerative diseases, autoimmune diseases and inflammatory diseases are intended to include all classes and types of these pathological conditions. Those skilled in the art will know the various classes and types of proliferative, neoplastic, infectious, autoimmune and inflammatory diseases.

By specific mention of the above categories of pathological conditions, those skilled in the art will understand that such terms include all classes and types of these pathological conditions. For example, the term cancer is intended to include all known cancers, whether characterized as malignant, benign, soft tissue or solid tumors, or hematologic tumors relating to cells in circulation, such as Anal Cancer, Basal Cell Carcinoma, Bladder Cancer, Bone Cancer (Osteosarcoma and Malignant Fibrous Histiocytoma), Brain Tumor, Breast Cancer, Bronchial Tumors, Burkitt Lymphoma, Central Nervous System Lymphoma, Cervical Cancer, Childhood Cancers, Colon Cancer, Colorectal Cancer, Eye Cancer (Intraocular Melanoma or Retinoblastoma), Gallbladder Cancer, Gastric (Stomach) Cancer, Germ Cell Tumor, Head and Neck Cancer, Kidney (Renal Cell) Cancer, Lip and Oral Cavity Cancer, Liver Cancer, Lung Cancer (Non-Small Cell), Lung Cancer (Small Cell), Neuroblastoma, Oral Cancer (Oropharyngeal Cancer), Ovarian Epithelial Cancer, Pancreatic Cancer, Paranasal Sinus and Nasal Cavity Cancer, Parathyroid Cancer, Penile Cancer, Prostate Cancer, Rhabdomyosarcoma, Salivary Gland Cancer, Sarcoma, Skin Cancer (Nonmelanoma), Skin Cancer (Melanoma), Skin Carcinoma (Merkel Cell), Testicular Cancer, Throat Cancer, Thymoma and Thymic Carcinoma, Thyroid Cancer, Urethral Cancer and Vaginal Cancer. Accordingly, "anti-cancer activity" refers to a cellular response to a substance that kills or inhibits the growth of a cancer cell. Cancer cells typically display uncontrolled growth (division beyond the normal limits), invasion (intrusion on and destruction of adjacent tissues), and sometimes metastasis (spread to other locations in the body via lymph or blood). Peptides, protides and conjugates described herein which have anti-cancer activity can kill the cancer cell or prevent the invasion or metastasis of the cancer cell into other tissues. It is contemplated that the mechanism of action through which this activity occurs is through the programmed cell death or related responses in the cells.

"Antimicrobial activity" refers to a cellular response to a substance that kills or inhibits the growth of a microorganism, such as bacteria, fungi or protozoans. Peptides described herein which have antimicrobial activity can either kill the microorganism (microbicidal) or prevent the growth of the microorganism (microbistatic). In some aspects, the peptides, protides and conjugates described herein show antimicrobial activity again pathogenic microorganisms. A "pathogenic microorganism" refers to a microorganism that causes a disease, disorder or condition, which is commonly referred to as an infection. Pathogenic microorganisms are well known to one of skill in the art and include pathogenic bacteria such as *Acinotobacter baumannii, Acinotobacter calcoaceticus, Acinotobacter haemolyticus, Bordetella pertussis, Borrelia burgdorferi, Brucella abortus, Brucella canis, Brucella melitensis, Brucella suis, Campylobacter jejuni, Chlamydia pneumoniae, Chlamydia psittaci, Chlamydia trachomatis, Clostridium botulinum, Clostridium difficile, Clostridium perfringens, Clostridium tetani, Corynebacterium diphtheriae, Enterococcus faecalis, Enterococcus faecum, Escherichia coli, Francisella tularensis, Haemophilus influenzae, Helicobacter pylori, Legionella pneumophila, Leptospira interrogans, Listeria monocytogenes, Mycobacterium leprae, Mycobacterium tuberculosis, Mycoplasma pneumoniae, Neisseria gonorrhoeae, Neisseria meningitides, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae* and *Yersinia pestis*, pathogenic fungi such as *Cryptococcus neoformans, Aspergillus fumigatus, Aspergillus flavus, Aspergillus clavatus, Cryptococcus neoformans, Cryptococcus laurentii, Crytococcus albidus, Histoplasma capsulatum, Pneumocystis jirovecii, Stachybotrys chartarum* and several members of the *Canidida* species, such as *C. albicans, C. glabrata, C. tropicalis, C. stellatoidea, C. glabrata, C. Krusei, C. parapsilosis, C. guilliermondii, C. viswanathii* and *C. lusitaniae*. Additional examples of pathogenic microorganisms are described by Jorgensen and Pfaller in "A Clinician's Dictionary of Pathogenic Microorganisms" ASM Press (2004), which is herein incorporated by reference in its entirety.

Human infections due to antibiotic-resistant bacteria and fungi are increasing in frequency and severity. Microbial pathogens exhibiting resistance to one or more antibiotics can now commonly be found in community and nosocomial settings. Antibiotic resistant pathogens currently of the greatest concern are methicillin (multiple) resistant *Staphylococcus aureus* (MRSA), vancomycin resistant *Enterococcus faecalis* and *Enterococcus faecium* (VRE), multi-drug-resistant *Streptococcus pneumoniae* (MDRSPn) or *Streptococcus pyogenes* (MDRBRSPy), *Pseudomonas aeruginosa* (MDRA), and *Candida albicans* (MDRCA).

"Programmed cell death" or "PCD" is death of a cell in any form, mediated by an intracellular program. In contrast to other types of cell death, such as necrosis, PCD is carried out as a regulated process which generally confers advantages during an organism's life-cycle. A strategic advantage of apoptosis is that it typically does not induce broader inflammatory responses, which can be injurious and/or delay wound healing, whereas necrosis often iduces considerable inflammation. PCD is commonly categorized by two types, apoptosisin (type I cell-death) or autophagic (type II cell death).

Apoptosisin, also known as apoptosis, is a series of biochemical events leading to a characteristic cell morphology including blebbing, loss of membrane asymmetry and attachment, cell shrinkage, nuclear fragmentation, chromatin condensation and chromosomal DNA fragmentation known as laddering. Autophagic PCD is a catabolic process involving the degradation of a cell's own components and organelles through the lysosomal machinery prior to the nucleus being destroyed. Additionally, in some aspects, PCD refers to other pathways that have been described including non-apoptotic (i.e. caspase-independent) programmed cell-death, necrosis-like programmed cell death, anoikis, excitotoxicity and Wallerian degeneration.

Embodiments of the invention provide a context-activated protide having at least one activator site and two or more effectors, wherein at least one effector comprises an amino acid sequence selected from the group consisting of SEQ ID NOS: 3, 4, 6, 8, 10, 11, 13, 17, 18, 19, 21-25, 30, 31-36, 39-47, 49-52, 54-57, 59-63, 66-75, 84-93, 102-106, 108-121, 132-175, 179-187, 191-199, 205-209, 211-223, 227-235, 238-243, 245-247, 249-251, 253-256 and 260-263, wherein the amino acid residue represented by (x) is a serine, a threonine, a tyrosine, a H-bond donor residue or a H-bond acceptor residue, wherein the amino acid residue represented by (b) is a lysine, an arginine, an asparagine, a glutamine or a basic residue, wherein the amino acid residue represented by (j) is a cysteine or a thiol residue, wherein the amino acid residue represented by (o) is an anthrylalanine or other non-natural amino acid and wherein the at least one effector induces antimicrobial, anti-cancer, anti-inflammatory, anti-proliferative or programmed cell death activity. Embodiments of the invention also provide a context-activated protide comprising at least one activator site and two or more effectors, wherein at least one effector comprises an amino acid sequence selected from the group consisting of SEQ ID NOS: 1, 2, 5, 7, 9, 12, 14-16, 20, 26-29, 37, 38, 48, 53, 58, 64, 65, 72, 76-83, 94-101, 107, 114, 122-131, 170, 176-178, 188-190, 200-204, 210, 224-226, 236, 237, 244, 248, 252, 257-259 and 288-289, wherein the at least one effector induces antimicrobial, anti-cancer, anti-inflammatory, anti-proliferative or programmed cell death activity In one aspect of the invention, the protide has at least one effector comprising an amino acid sequence, identified from the Bax protein, referenced by the amino acid sequence of SEQ ID NOS: 1-13, 264, 270 and 271. In one aspect of the invention, the protide has at least one effector comprising an amino acid sequence, identified from the Bcl-W protein; referenced by the amino acid sequence of SEQ ID NOS: 14-25, 269 and 272. In one aspect of the invention, the protide has at least one effector comprising an amino acid sequence, identified from the Bcl-xβ protein, referenced by the amino acid sequence of SEQ ID NOS: 26-36 and 273. In one aspect of the invention, the protide has at least one effector comprising an amino acid sequence, identified from the Bak protein, referenced by the amino acid sequence of SEQ ID NOS: 37-47. In one aspect of the invention, the protide has at least one effector comprising an amino acid sequence, identified from the Bcl-2 protein, referenced by the amino acid sequence of SEQ ID NOS: 48-52. In one aspect of the invention, the protide has at least one effector comprising an amino acid sequence, identified from the Bcl-2 isoform 1 protein, referenced by the amino acid sequence of SEQ ID NOS: 53-57. In one aspect of the invention, the protide has at least one effector comprising an amino acid sequence, identified from the Mfn-1 protein, referenced by the amino acid sequence of SEQ ID NOS: 58-64 and 274. In one aspect of the invention, the protide has at least one effector comprising an amino acid sequence, identified from the Mfn-2 protein, referenced by the amino acid sequence of SEQ ID NOS: 65-75. In one aspect of the invention, the protide has at least one effector comprising an amino acid sequence, identified from the Dnm-1 protein, referenced by the amino acid sequence of SEQ ID NOS: 76-93 and 275. In one aspect of the invention, the protide has at least one effector comprising an amino acid sequence, identified from the Dnm-2 protein, referenced by the amino acid sequence of SEQ ID NOS: 94-121, 267, 276 and 277. In one aspect of the invention, the protide has at least one effector comprising an amino acid sequence, identified from the Ncl protein, referenced by the amino acid sequence of SEQ ID NOS: 122-175. In one aspect of the invention, the protide has at least one effector comprising an amino acid sequence, identified from the Csp3 protein, referenced by the amino acid sequence of SEQ ID NOS: 176-187, 266 and 278. In one aspect of the invention, the protide has at least one effector comprising an amino acid sequence, identified from the Bad protein, referenced by the amino acid sequence of SEQ ID NOS: 188-199. In one aspect of the invention, the protide has at least one effector comprising an amino acid sequence, identified from the Prf-1 protein, referenced by the amino acid sequence of SEQ ID NOS: 200-223. In one aspect of the invention, the protide has at least one effector comprising an amino acid sequence, identified from the Granulysin protein, referenced by the amino acid sequence of SEQ ID NOS: 224-235. In one aspect of the invention, the protide has at least one effector comprising an amino acid sequence, identified from the CidA protein, referenced by the amino acid sequence of SEQ ID NOS: 236-247, 265 and 279. In one aspect of the invention, the protide has at least one effector comprising an amino acid sequence, identified from the LrgA protein, referenced by the amino acid sequence of SEQ ID NOS: 248-251. In one aspect of the invention, the protide has at least one effector comprising an amino acid sequence, identified from the Lambda S21 protein, referenced by the amino acid sequence of SEQ ID NOS: 252-256. In one aspect of the invention, the protide has at least one effector comprising an amino acid sequence, identified from the Holin protein, referenced by the amino acid sequence of SEQ ID NOS: 257-263 and 268. In one aspect, the protide has at least one effector comprising an amino acid sequence, identified from human Bcl-xL protein, which is represented by the amino acid sequence SEQ ID NO: 288 or human CTL Granulysin, which is represented by the amino acid sequence SEQ ID NO: 289.

In one aspect, the activator site is context-activated. The invention also provides that upon context-activation, the protide inititate programmed cell death of the target cells. In some aspects, the context-activation results from a physiologal condition, such as, but not limited to acidity, alkalinity, ionic strength or osmotic strength. In some aspects, the context-activation results from association with an activator molecule. The activator molecules can modify the activator site upon association. In some aspects, modification of the activator site includes cleavage of the activator site. In some aspects, the activoator molecule is an enzyme, such as a protease, esterase or lipase. In one aspect, the activator is expressed by a pathogenic microorganism as described herein. In another aspect, the activator is present in the context of a tumor cell, such as a tumor-specific protease. An example of a tumor-specific protease is a matrix bound protein such as matrix metalloproteinase. In another aspect, the activator is present in the context of an inflammatory response, wherein activators such as thrombin, bradykinin, elastase and metalloproteinase are expressed.

The term "protide," as used herein, refers to a mosaic molecule composed of two or more peptide or non-peptide functional domains, referred to as effectors, and one or more corresponding activator sites. A protide can consist of an indefinite number of effector and activator domains that can vary in function, activation, position, continuity, or sequence. Additional examples of protide compositions and designs are described in U.S. Patent Application Publication 2006-0074016, 2006-0135416 and U.S. Pat. No. 7,067,621, which are herein incorporated by reference.

The protides described herein have two or more distinct biological functions and are designed to be activated within a defined or characteristic context. The protides described herein have at least one activator site and two or more effectors, wherein at least one of the effectors has and amino acid sequence of a peptide described herein. Protides have the advantage of designs that can be customized, engineered, chosen, or combined to allow for highly selective correspondence to or association with or unique to a specific pathological condition or etiology. The distinct biological functions can further be associated with distinct functional aims, for example, therapy, prevention, amplification and detoxification. As described herein, a multifunctional, context-activated protide can be designed to be activated in any context desired by the user, a feature which makes the protides useful to applications in many areas of medicine and biomedical research, including, for example, diagnosis, imaging, detection, speciation or other specification, prevention/prophylaxis, and therapy of a wide range of pathological conditions such as infectious diseases, neoplastic diseases, immune and autoimmune disorders, cardiovascular conditions, disorders in metabolism or physiology, diseases of inheritance or genetic abnormality, a variety of pathological conditions associated with gene expression, mitochondrial dysfunction or regulation, as well as cell death and/or cellular senescence.

As described herein, in addition to their direct antimicrobial efficacies, the peptides, protides and conjugate described herein are useful based on their ability to circumvent or minimize conventional resistance mechanisms by pathogens or tumor cells. For example, this can be the result of activation by activators that are present outside of the target cell such that the peptides, protides or conjugate need not necessarily enter the target cell to be activated and to achieve subsequent efficacy, thus minimizing the likelihood for resistance due to reduced target access or increased efflux of the peptides, protides or conjugate. Furthermore, in many conventional resistance mechanisms, resistance can be induced by the presence of the anti-infective agent itself. In particular, protides can be designed to be activated by such microbial counter-responses or virulence factors. Thus, the more of the activator that is made by the organism, the more protide activation results, yielding an expected amplification of the anti-pathogenic efficacy of the protide. Conversely, decreased production of the activators can translate in turn to decreased presence or function of these same activators such as virulence factors or mediators of pathogenesis, in essence turning off the pathogenic potential of the target cell, or reducing its ability to protect itself from otherwise normal host defenses. Similarly, protides can be beneficial by reconstituting tumor cell or microbial pathogen susceptibility to conventional therapeutic agents, to which these pathogenic cells would otherwise be resistant. Thus, the protides can either be activated from upregulation of resistance- or virulence factor expression, or can impact efficacy by effecting the downregulation of virulence factor expression by pathogenic cells or organisms.

In applications of the methods described herein, involving an established infection or a host response to infection, activators can be present or generated. An activator useful for activation of a protide of the invention can be advantageously selected based on a high concentration in the immediate proximity of the infection locus so as to allow for activation of the majority of protides in the desired context. One skilled in the art will be able to select an activator that represents the desired activation context. For applications of the invention methods in the arena of microbial infection, context-activation can be designed to specifically occur in the local context of infection so as to effect optimal relative protide effector concentrations in specific contexts of infection. In addition to context activation that maximizes efficacy, the protides and methods of the invention also minimize the potential for inadvertent host cytotoxicity in areas that do not represent the context. Therefore, in the absence of infection, the protide activators are either absent or are present at concentrations insufficient for effective protide activation, thereby minimizing inadvertent or indiscriminant acute toxicity.

In addition to specific pathogen or host molecules that can serve as activators as described above, protides can also be designed to become activated to diagnose, prevent, or treat infection in unique and/or specific biochemical or physiological contexts associated with microbial pathogens. Examples of such biochemical or environmental contexts include ionic, osmotic, pH, oxidation/reduction, or other conditions that are unique to, characteristic of, or present in the context of infection or disease processes that occur upon infection, or host responses to these events. For example, a protide can be designed to require the influence of protonation, conformation change, or other modification that occurs uniquely or disproportionately in the context of acidic pH, to activate the protide or its ensuing effectors by altering their structure-activity relationship(s) from inactive to active. As one example, genitourinary tissues, such as renal-tissues or genitourinary mucosa, can exhibit pH values that are decreased normally, or in the setting of infection. A protide designed to be activated only under such acidic conditions could be designed to either be vulnerable to activation in these conditions, or directly activated by these conditions, and thus would be predicted to be active only in such contexts. Alternatively, protides can be designed to be inactive in particular contexts or conditions, such as conditions of relatively high osmotic strength or relatively high pH, so as to minimize or prevent untoward or toxic effects such as nephro- or hepatotoxicity. By way of a further example, activation as well as leukocyte accumulation are conditions associated with infection. Moreover, a fundamental strategy of host defense phagocytes is to phagocytize the microbial pathogen, subjecting it to the harsh environment of the acidic phagolysosome. The compartment so created can become acidified to pH values of 5.5 or lower as the leukocyte responds to the pathogen. Therefore, a protide can be designed that is activated or has amplified or antimicrobial activities, for example, by pH, phagolysosomal enzymes or reactants, or a combination of these conditions, or can amplify or potentiate the antimicrobial mechanisms of leukocytes or other host cells within such settings, so as to inhibit or kill pathogens that enter such cells.

Protide activation also can include conformational, oxidation or reduction-mediated changes in disulfide array, assembly into multimers of two or more homomeric (identical) or heteromeric (non-identical) effectors, or other modifications of the protide and/or its subsequent effectors. In a particular embodiment, protide activation is triggered as a result of protide accumulation, or its resulting effector components, so as to achieve or surpass threshold concentrations required to optimize or catalyze activation or activity through multimerization or other modification in structure or function of the protide or its effectors.

It is understood, that activation can involve combinations of the protide activation strategies described above. For example, a protide can be designed that is not responsive to an activator unless both the protide and the activator are present within a context associated with or resulting from infection or other disease.

The term "context-activated," as used herein in reference to a protide of the invention, refers to the initiation, activation or amplification of a biological or other desired, for example, diagnostic or prophylactic function of one or more protide effectors in a particular temporal, spatial, pathological and/or biochemical context. Context-activation can be initiated by direct or indirect interaction between a protide activator site and a corresponding activator that is selectively associated with the particular context. As used herein, context-activation encompasses activation in a wide variety of contexts that can include, for example, local, regional, systemic, and/or temporal proximity; as well as the presence or absence of an etiological agent, pathologic condition, or characteristic components thereof.

Thus, context need not be limited to a place, time or quality, but also can be the presence or absence of an activator, for example, an enzyme elaborated by an organism such as, for example, a specific strain of bacteria. The context for activation can consequently be of any breadth desired by the user, for example, can target a class of organisms or cell types, for example, by using an activator that is ubiquitous to the targeted class, or can alternatively have a more narrow focus by using an activator that represents a more narrowly defined target, for example, a particular genus, organism, species, subspecies, strain, or cell or tissue type. The context can be associated with a pathological condition, but also can be selected to represent a non-pathological environment, for example, in prophylactic applications of the invention practiced to preserve a normal or homeostatic condition.

As used herein, the term "effector" refers to the peptide or non-peptide functional domains of a protide provide herein that have specific individual functions, which are initiated or amplified upon activation and achieve specific functions relating to the diagnosis, prevention, or treatment of a disease. As described herein, a protide has at least two effector domains with distinct, complementary and/or synergistic biological functions. An effector is inactive or exhibits relatively reduced or attenuated biological activity unless an activator, by virtue of either its presence or absence, alters or facilitates or allows the altering of its corresponding activator site and, as a result, initiates or amplifies the diagnostic, prophylactic, therapeutic, or other biological function(s) of the effector(s). Multiple effectors can be induced by the same activator site. Peptide and non-peptide effectors can be present in the same protide, which can be referred to as a hybrid protide. Similarly, a protide can consist exclusively of peptide effectors, also referred to as a peptide protide. Similarly, a protide of the invention can consist exclusively of non-peptidic effectors. The biological function(s) of an effector that corresponds to a protide described herein can be, for example, antimicrobial, immunomodulatory, pro- or anti-inflammatory, tumoricidal, pro- or anti-apoptotic, pro- and anti-angiogenic and/or hemolytic.

As described herein, a protide of the invention can be bifunctional or multifunctional, with two or more unique complementary effectors, and one or more activators as determined by specific effector and activator site domains engineered into the mosaic protide, which can be activated by specific molecules or conditions present in unique or strategic contexts of interest. Examples of such effectors can include one or more antimicrobial, anti-neoplastic, anti-inflammatory, immunomodulatory, or other peptide or non-peptide functional domains, or combinations thereof.

As used herein, the term "activator site" when used in reference to a protide of the invention, refers to a domain of the protide that, in the presence of an activator, initiates, promotes, amplifies or modulates the specific biological function of one or more effectors. As described herein, an activator site can be modified, cleaved, processed or otherwise altered in the presence of an activator. In addition, an activator site can be sensitive either to the absolute presence or absence of an activator as well as can be sensitive to a threshold concentration of an activator rather than its mere presence.

An activator site useful in the invention can include one or more sites for cleavage, modification, processing or other triggering by strategic activators, which can be, for example, proteases, esterases, lipases, or other endogenous enzymatic activators or cascades generated by or associated with a specific condition such as, for example, the presence of pathogenic microorganisms, damaged or inflamed tissues, or hematologic or solid neoplastic or pre-neoplastic cells or tumors. Such an activator site also can be selected to exploit contexts associated with biochemical or physical conditions such as requisite acidity or alkalinity, for example, acidic phagolysomes containing intracellular bacteria or fungi; or ionic or osmotic strength, for example, in a renal context, that represent a specific pathologic or non-pathologic context. Furthermore, an activator site can be selected to exploit normal rather than a pathologic context.

An activator site can be subject to proteolytic as well as non-proteolytic activation. For example, the activator site can be located within the peptide moiety, and require a protease activator. In other embodiments, the non-proteolytic activator can target a non-proteinaceous substrate component of the protide. For example, a protide of the invention can include an esterase activator and can link peptide and/or non-peptide moieties (eg. a protide consisting of peptide and conventional antibiotic effectors) by means of an ester bond. Other biochemically relevant bonds or linkages that can serve as activation sites in an invention protide can include, for example, lipase—(lipid cleaving), nuclease—(nucleic acid cleaving), and kinase or phosphatase—(phosphate addition or removal) sensitive activators that target substrates other than peptides. For example, certain microbial pathogens or tumor cells can express, or abnormally express restriction enzymes that can provide a suitable basis for design of a protide that could be activated only-within the target cell, further reducing indiscriminant host cytotoxicity.

As used herein, the term "activator" refers to a molecule or condition that, by altering the activator site, causes the liberation or onset of a specific diagnostic or biological function of effector(s). As described herein, an activator can be a normal or abnormal exogenous or endogenous cell, structure or molecule, a condition or milieu (normal or abnormal), or a combination thereof that is associated with a specific context in which activation of the protide is desired. Thus, an activator can be selected based on its presence in a temporal, spatial, or physiological context, which can be normal or abnormal, that is associated with the desired context for protide activation. An activator can consequently include physiological conditions including, for example, acidity, alkalinity, conditions of oxidation or reduction, and/or ionic and/or osmotic strength, that are associated with a particular context, and modulate protide activation. Alternatively, an activator can be a structure or molecule, for example, an enzyme, that is present in a particular spatial, temporal or pathological context. The activator molecule can modify the activator site upon association, for example, by cleavage or other modification that results in activation in the particular context, or can facilitate interaction between protide and activator(s). The activator molecule can be an enzyme including, for example, protease, esterase, lipase, nucleases or peptidase.

In one embodiment of the invention, an activator site can encompass one or more domains for cleavage, modification, processing or any other type of liberation by an activator, for example, a protease, esterase, lipase or other endogenous or exogenous enzymatic activator or cascade. The choice of one or more activator sites that correspond to specific activators depends directly on the desired context for activation. Thus, an activator can be a particular pathologic setting or condition that is chosen based on its association with a particular etiological agent or host response. In the presence of the activator, one or more effectors are liberated so as to achieve a specific function relating to, for example, the treatment, prevention, or diagnosis of a targeted disease. An activator site can thus be strategically designed to become activated in temporal and spatial proximity to activator expression, thereby allowing the activation of a protide to be targeted to a particular context and over time so as to maximize the desired therapeutic or prophylactic effect, while minimizing untoward or undesirable toxicities or other side effects.

As described herein, an activator site is selected based on its correspondence and/or association with the context in which the two or more protide effectors are to be liberated so as to initiate or potentiate their functions. Therefore, as long as an activator is associated with the context, the invention can be practiced with any context desired. Those skilled in the art will appreciate that, given the versatility of activators useful for practicing the invention as described herein, a protide can be designed based on virtually any context desired, including, for example, vascular injury, presence of a neoplasm or cancer, infection, and inflammation.

In one embodiment, the protide is an antimicrobial protide, which also can be referred to as an antimicrotide. Cleavage sites for strategic proteases can be engineered into multifunctional antimicrobial protides so as to represent the activator site of the protide. Upon activation of the protease in the localized or generalized context of tissue injury or infection, as selected by the user, the inactive protide is cleaved, liberating independent and active molecules to effect their respective biological functions. Prior to and beyond the setting of activation of the strategic protease representing the activator, the mosaic protide construct is relatively inactive both with respect to antimicrobial function and host cell toxicity. A mosaic protide construct can consist of an indefinite number (1 through n) of effector and activator domains that can vary in function, activation, position, continuity, or sequence. Effectors corresponding to one or more protides activated by the same or distinct activators also can function synergistically, and/or can recombine in a manner facilitating their complementary functions. As an example, in the context of vascular injury, a protide activator can be selected that specifically represents this particular context, for example, a clotting cascade protease such as thrombin, or a complement fixing protease such as a C3 convertase, for example, C4B2A or C3bBb. Similarly, as another example, a protide activator can be selected that represents a broader constellation of symptoms or conditions, such as sepsis, in which corresponding activators can include serine proteases associated with systemic inflammation, sepsis, or injury, such as activated protein C.

A further embodiment of the invention encompasses antineoplastic protides, which also are referred to as antineotides. Many tumor cells produce or overexpress characteristic activators, such as matrix metalloproteinases (MMP) or other enzymes that are not expressed by, or at levels much higher than normal cells. Consequently, the activator can be a tumor-specific protease, for example, a matrix metalloproteinase or thymidylate synthase (TS), which is overexpressed in the majority of cancers. A tumor-specific protease also can be associated with a more narrow neoplastic context, such as a serine protease that is specifically expressed in prostate cells, for example, PSA, human kallikrein-2 (hK2), human kallikrein-11 (hK11) and TMPRSS2.

Embodiment of the invention provide a conjugate having one or more amino acid sequence selected from the group consisting of SEQ ID NOS: 3, 4, 6, 8, 10, 11, 13, 17, 18, 19, 21-25, 30, 31-36, 39-47, 49-52, 54-57, 59-63, 66-75, 84-93, 102-106, 108-121, 132-175, 179-187, 191-199, 205-209, 211-223, 227-235, 238-243, 245-247, 249-251, 253-256 and 260-263 and a moiety, wherein the amino acid residue represented by (x) is a serine, a threonine, a tyrosine, a H-bond donor residue or a H-bond acceptor residue, wherein the amino acid residue represented by (b) is a lysine, an arginine, an asparagine, a glutamine or a basic residue, wherein the amino acid residue represented by (j) is a cysteine or a thiol residue, wherein in the amino acid residue represented by (o) is an anthrylalanine or other non-natural amino acid and wherein the conjugate induces antimicrobial, anti-cancer, anti-inflammatory, anti-proliferative or programmed cell death activity. Embodiments of the invention also provide a conjugate having one or more amino acid sequence selected from the group consisting of SEQ ID NOS: 1, 2, 5, 7, 9, 12, 14-16, 20, 26-29, 37, 38, 48, 53, 58, 64, 65, 72, 76-83, 94-101, 107, 114, 122-131, 170, 176-178, 188-190, 200-204, 210, 224-226, 236, 237, 244, 248, 252, 257-259 and 288-289 and a moiety, wherein said conjugate induces antimicrobial, anti-cancer, anti-inflammatory, anti-proliferative or programmed cell death activity.

In one aspect of the invention, the conjugate has at least one or more amino acid sequence, identified from the Bax protein, referenced by the amino acid sequence of SEQ ID NOS: 1-13, 264, 270 and 271. In one aspect of the invention, the conjugate has at least one or more amino acid sequence, identified from the Bcl-W protein, referenced by the amino acid sequence of SEQ ID NOS: 14-25, 269 and 272. In one aspect of the invention, the conjugate has at least one or more amino acid sequence, identified from the Bcl-x13 protein, referenced by the amino acid sequence of SEQ ID NOS: 26-36 and 273. In one aspect of the invention, the conjugate has at least one or more amino acid sequence, identified from the Bak protein, referenced by the amino acid sequence of SEQ ID NOS: 37-47. In one aspect of the invention, the conjugate has at least one or more amino acid sequence, identified from the Bcl-2 protein, referenced by the amino acid sequence of SEQ ID NOS: 48-52. In one aspect of the invention, the conjugate has at least one or more amino acid sequence, identified from the Bcl-2 isoform 1 protein, referenced by the amino acid sequence of SEQ ID NOS: 53-57. In one aspect of the invention, the conjugate has at least one or more amino acid sequence, identified from the Mfn-1 protein, referenced by the amino acid sequence of SEQ ID NOS: 58-64 and 274. In one aspect of the invention, the conjugate has at least one or more amino acid sequence, identified from the Mfn-2 protein, referenced by the amino acid sequence of SEQ ID NOS: 65-75. In one aspect of the invention, the conjugate has at least one or more amino acid sequence, identified from the Dnm-1 protein, referenced by the amino acid sequence of SEQ ID NOS: 76-93 and 275. In one aspect of the invention, the conjugate has at least one or more amino acid sequence, identified from the Dnm-2 protein, referenced by the amino acid sequence of SEQ ID NOS: 94-121, 267, 276 and 277. In one aspect of the invention, the conjugate has at least one or more amino acid sequence, identified from the Ncl protein, referenced by the amino acid sequence of SEQ ID NOS: 122-175. In one aspect of the invention, the conjugate has at least one or more amino acid sequence, identified from the Csp3 protein, referenced by the amino acid sequence of SEQ ID NOS: 176-187, 266 and 278. In one aspect of the invention, the conjugate has at least one or more amino acid sequence, identified from the Bad protein, referenced by the amino acid sequence of SEQ ID NOS: 188-199. In one aspect of the invention, the conjugate has at least one or more amino acid sequence, identified from the Prf-1 protein, referenced by the amino acid sequence of SEQ ID NOS: 200-223. In one aspect of the invention, the conjugate has at least one or more amino acid sequence, identified from the Granulysin protein, referenced by the amino acid sequence of SEQ ID NOS: 224-235. In one aspect of the invention, the conjugate has at least one or more amino acid sequence, identified from the CidA protein, referenced by the amino acid sequence of SEQ ID NOS: 236-247, 265 and 279. In one aspect of the invention, the conjugate has at least one or more amino acid sequence, identified from the LrgA protein, referenced by the amino acid sequence of SEQ ID NOS: 248-251. In one aspect of the invention, the conjugate has at least one or more amino acid sequence, identified from the Lambda S21 protein, referenced by the amino acid sequence of SEQ ID NOS: 252-256. In one aspect of the invention, the conjugate has at least one or more amino acid sequence, identified from the Holin protein, referenced by the amino acid sequence of SEQ ID NOS: 257-263 and 268. In one aspect, the conjugate has at least one or more amino acid sequence, identified from human Bcl-xL protein, which is represented by the amino acid sequence SEQ ID NO: 288 or human CTL Granulysin, which is represented by the amino acid sequence SEQ ID NO: 289.

In one aspect, the moiety comprises a therapeutic agent, a targeting peptide or a label. In one aspect, therapeutic agent is a cytotoxic agent, such as an antibiotic or a chemotherapeutic agent. In one aspect, the targeting peptide selectively homes a conjugate described herein to a microorganism, a tumor tissue, tumor cell or tumor vasculature. In one aspect, the targeting peptide selectively homes the conjugate to an immune regulatory cell or an immune effector cell. In one aspect, the conjugate described herein has a targeting peptide, such as, but not limited to, an antibody or a fragment thereof. In another aspect, the moiety of the conjugate described herein is a label, such as a radioisotope or a dye.

As used herein, the term "conjugate" refers to a peptide having an amino acid sequence as described herein linked to a moiety. A "moiety" is used broadly to mean a physical, chemical, or biological material that is linked to a peptide for the purpose of targeting the peptide to a select organ, tissue or cell type or providing an additional functional group to the peptide. In particular, a moiety is a biologically useful moiety such as therapeutic moiety, a diagnostic moiety or a drug delivery vehicle. Thus, a moiety can be a therapeutic agent, for example, a cancer chemotherapeutic agent. Cancer chemotherapeutic agents are well known to one of skill in the art and include, without limitation, alkylating agents such as cyclophosphamide, mechlorethamine, chlorambucil and melphalan, anthracyclines such as daunorubicin, doxorubicin, epirubicin, idarubicin, mitoxantrone and valrubicin, cytoskeletal disruptors such as paclitaxel and docetaxel, epothilones such as epothilones A through F, inhibitors of topoisomerase II such as etoposide, teniposide and tafluposide, nucleotide analogs and precursor analogs such as azacitidine, azathioprine, capecitabine, cytarabine, doxifluridine, fluorouracil, gemcitabine, mercaptopurine, methotrexate, and tioguanine, peptide antibiotics, such as bleomycin, platinum-based agents such as carboplatin, cisplatin and oxaliplatin, retinoids such as tretinoin, and vinca alkaloids or their derivatives such as vinblastine, vincristine, vindesine and vinorelbine. Such a moiety when linked to a peptide, provides a conjugate useful for treating a cancer in a subject. In addition, a moiety can be a drug delivery vehicle such as a chambered microdevice, a cell, a liposome or a virus, which can contain an agent such as a drug or a nucleic acid.

A moiety also can be a targeting peptide or nucleic acid, to which a peptide as described herein is grafted for the purpose of directing the peptide to a selected organ, tissue, tumor or cell (Smith et al., *J. Biol. Chem.* 269:32788-32795 (1994); Goldman et al., *Cancer Res.* 15:1447-1451 (1997) and U.S. Pat. No. 6,576,239, each of which is incorporated herein by reference). For example, a targeting peptide or nucleic acid can be expressed as a fusion protein with a desired peptide such that the peptide or nucleic acid targets the grafted peptide to a selected tumor tissue, tumor cell or tumor vasculature. Such a desired peptide, which is grafted to the tumor homing peptide, can be a polypeptide involved in initiating a programmed cell death pathway as described herein or inducing any other cellular response resulting in anti-cancer activity. Additionally, targeting peptides, which can be grafted to a peptide as described herein having antimicrobial activity, include peptides that selectively home to a microorganism. For example, peptide sequences have been identified that selectively bind to surface molecules of fugal pathogens such as invasive *Aspergillus* species as described in U.S. Patent Application 2005-0187161. Still further, the invention provides a conjugate wherein the targeting peptide selectively homes the desired peptide to a cell involved in the immune response, including immune regulatory cells such as lymphocytes or immune effector cells such as macrophages or granulocytes. Conjugates provided herein include these and other exemplary peptide or nucleic acid sequences grafted to a peptide described herein, tumor tissue, tumor cell, tumor vasculature, immune regulatory cell or immune effector cell.

A "targeting peptide" is a peptide comprising a contiguous sequence of amino acids, which is characterized by selective localization to an organ, tissue, or cell type. Selective localization may be determined, for example, by methods disclosed below, wherein the putative targeting peptide sequence is incorporated into a protein that is displayed on the outer surface of a phage. Administration to a subject of a library of such phage that have been genetically engineered to express a multitude of such targeting peptides of different amino acid sequence is followed by collection of one or more organs, tissues, or cell types from the subject and identification of phage found in that organ, tissue, or cell type. A phage expressing a targeting peptide sequence is considered to be selectively localized to a tissue or organ if it exhibits greater binding in that tissue or organ compared to a control tissue or organ. Preferably, selective localization of a targeting peptide should result in a two-fold or higher enrichment of the phage in the target organ, tissue, or cell type, compared to a control organ, tissue, or cell type. Selective localization resulting in at least a three-fold, four-fold, five-fold, six-fold, seven-fold, eight-fold, nine-fold, ten-fold or higher enrichment in the target organ compared to a control organ, tissue or cell type is more preferred. Alternatively, a phage expressing a targeting peptide sequence that exhibits selective localization preferably shows an increased enrichment in the target organ compared to a control organ when phage recovered from the target organ are reinjected into a second host for another round of screening. Further enrichment may be exhibited following a third round of screening. Another alternative means to determine selective localization is that phage expressing the putative target peptide preferably exhibit a two-fold, more preferably a three-fold or higher enrichment in the target organ or tissue compared to control phage that express a non-specific peptide or that have not been genetically engineered to express any putative target peptides. Another means to determine selective localization is that localization to the target organ or tissue of phage expressing the target peptide is at least partially blocked by the co-administration of a synthetic peptide containing the target peptide sequence. “Targeting peptide” and “homing peptide” are used synonymously herein.

A targeting peptide is useful, for example, for targeting a desired peptide to the selected tumor as discussed above. In addition, a targeting peptide in conjunction with a detectable label can be used to identify the delivery of a desired peptide to a sample. As used herein, the term “sample” is used in its broadest sense to mean a cell, tissue, organ or portion thereof, including a tumor, that is isolated from the body. A sample can be, for example, a histologic section or a specimen obtained by biopsy or cells that are placed in or adapted to tissue culture.

The term “antibody” is well-known in the art and refers to a protein functionally defined as a binding protein and structurally defined as comprising an amino acid sequence that is recognized by one of skill in the art as having variable and constant regions. A typical antibody structural unit is known to comprise a tetramer. Each tetramer is composed of two identical pairs of polypeptide chains, each pair having one “light” and one “heavy” chain. The N-terminal portion of each chain defines the variable region of about 100 to about 110 amino acids, which are primarily responsible for antigen recognition and binding. The terms variable heavy chain ($V_H$) and variable light chain ($V_L$) regions refer to these light and heavy chains, respectively. The variable region includes the segments of Framework 1 (FR1), CDR1, Framework 2 (FR2), CDR2, Framework 3, CDR3 and Framework 4 (FR4). Antibodies are typically divided into five major classes, IgM, IgG, IgA, IgD, and IgE, based on their constant region structure and immune function. The constant region is identical in all antibodies of the same isotype, but differs in antibodies of different isotypes. Heavy chains γ, α and δ have a constant region composed of three tandem (in a line) Ig domains, and a hinge region for added flexibility; heavy chains μ and ϵ have a constant region composed of four immunoglobulin domains. Antibody classes can also be divided into subclasses, for example, there are four IgG subclasses IgG1, IgG2, IgG3 and IgG4. The structural characteristics that distinguish these subclasses from each other are known to those of skill in the art and can include the size of the hinge region and the number and position of the interchain disulfide bonds between the heavy chains. The constant region also determines the mechanism used to destroy the bound antigen. A light chain has two successive regions: one constant region, which are designated as κ and λ, and one variable region.

As used herein, the term “functional fragment” when used in reference to the antibodies described herein is intended to refer to a portion of the antibody including heavy or light chain polypeptides which still retains some or all or the binding activity of the antibody. Such functional fragments can include, for example, antibody functional fragments such as Fab, $F(ab)_2$ Fv, and single chain Fv (scFv). Other functional fragments can include, for example, heavy or light chain polypeptides, variable region polypeptides or CDR polypeptides or portions thereof so long as such functional fragments retain binding activity, specificity, inhibitory and activation activity. The term is also intended to include polypeptides encompassing, for example, modified forms of naturally occurring amino acids such as D-stereoisomers, non-naturally occurring amino acids, amino acid analogues and mimetics so long as such polypeptides retain functional activity as defined above.

A moiety can be a detectable label such a radiolabel or can be a cytotoxic agent, including a toxin such as ricin or a drug such as a chemotherapeutic agent or can be a physical, chemical or biological material such as a liposome, microcapsule, micropump or other chambered microdevice, which can be used, for example, as a drug delivery system. Generally, such microdevices, should be nontoxic and, if desired, biodegradable. Various moieties, including microcapsules, which can contain an agent, and methods for linking a moiety, including a chambered microdevice, to a molecule of the invention are well known in the art and commercially available (see, for example, “Remington’s Pharmaceutical Sciences” 18th ed. (Mack Publishing Co. 1990), chapters 89-91; Harlow and Lane, Antibodies: A laboratory manual (Cold Spring Harbor Laboratory Press 1988), each of which is incorporated herein by reference; see, also, Hermanson, Bioconjugate Techniques (Academic Press 1996)).

A “label” refers a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into a HIPK1 nucleic acids, proteins and antibodies at any position. For example, the label should be capable of producing, either directly or indirectly, a detectable signal. The detectable moiety may be a radioisotope, such as $^{3}H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the label may be employed, including those methods described by Hunter et al., *Nature,* 144:945 (1962); David et al., *Biochemistry,* 13:1014 (1974); Pain et al., *J. Immunol. Meth.,* 40:219 (1981); and Nygren, *J. Histochem. and Cytochem.,* 30:407 (1982).

Peptides, protides and conjugates, which are identified herein, can be synthesized in required quantities using routine methods of solid state peptide synthesis or can be purchased from commercial sources (for example, Anaspec; San Jose Calif.) and a desired moiety can be linked to the peptide. Several methods useful for linking a moiety to a peptide are known in the art, depending on the particular chemical characteristics of the molecule. For example, methods of linking haptens to carrier proteins as used routinely in the field of applied immunology (see, for example, Harlow and Lane, supra, 1988; Hermanson, supra, 1996).

A moiety such as a therapeutic or diagnostic agent can be conjugated to a peptide using, for example, carbodiimide conjugation (Bauminger and Wilchek, *Meth. Enzymol.* 70:151-159 (1980), which is incorporated herein by reference). Carbodiimides comprise a group of compounds that have the general formula R—N═C═N—R', where R and R' can be aliphatic or aromatic, and are used for synthesis of peptide bonds. The preparative procedure is simple, relatively fast, and is carried out under mild conditions. Carbodiimide compounds attack carboxylic groups to change them into reactive sites for free amino groups. Carbodiimide conjugation has been used to conjugate a variety of compounds to carriers for the production of antibodies.

The water soluble carbodiimide, 1-ethyl-3-(3-dimethylaminopropyl)carbodiimide (EDC) is particularly useful for conjugating a moiety to a peptide and was used to conjugate doxorubicin to tumor homing peptides (U.S. Patent Application Publication 2004-0131623). The conjugation of doxorubicin and a tumor homing peptide requires the presence of an amino group, which is provided by doxorubicin, and a carboxyl group, which is provided by the peptide.

In addition to using carbodlimides for the direct formation of peptide bonds, EDC also can be used to prepare active esters such as N-hydroxysuccinimide (NHS) ester. The NHS ester, which binds only to amino groups, then can be used to induce the formation of an amide bond with the single amino group of a moiety. The use of EDC and NHS in combination is commonly used for conjugation in order to increase yield of conjugate formation (Bauminger and Wilchek, supra, 1980).

Other methods for conjugating a moiety to a peptide can also be used. For example, sodium periodate oxidation followed by reductive alkylation of appropriate reactants can be used, as can glutaraldehyde crosslinking. However, it is recognized that, regardless of which method of producing a conjugate of the invention is selected, a determination may be needed to confirm that the peptide described herein maintains its antimicrobial, anti-cancer, anti-inflammatory, anti-proliferative or programmed cell death activity and that the moiety maintains its relevant function. Methods for determining the activity of the conjugates are well know to one of skill in the art.

An agar radial diffusion assay has been used as described herein to determine antimicrobial activities of proteins against microbial pathogens in vitro. One million CFU will be mixed into 10 ml (i.e., $1\times10^5$ CFU/ml) of melted 1% agarose (in 10 mM $NaHPO_4$ and cooled to 42° C.) containing minimal nutrient and adjusted to either pH 5.5 or pH 7.2. The agar is solidified in culture dishes, and sample wells are formed. Peptides at various concentrations are dissolved in 10 μl of 0.01% acetic acid buffer (pH 5.5 or 7.2), loaded into individual wells, and incubated at 37° C. for three hours. The plate is then overlayed with 1% agarose containing nutrients and incubated (37° C., for at least 24 hours). Peptides purified by RP-HPLC lacking antimicrobial activity are tested in parallel as controls. Zones of inhibition are measured to quantify antimicrobial activity. This assay will not distinguish between microbicidal and microbiostatic actions, but is highly sensitive to peptides with one or both functions.

Minimum inhibitory (MIC) and microbiocidal concentration (MMC) assays can also be performed, and may include a microvolume assay which is used to quantitatively screen peptides for antimicrobial activities. In this assay, suspensions of bacteria or fungi in appropriate media are placed in 100-200 μl final volumes in microtiter plates. Poly-L-lysine coated or otherwise positively charged plates are used for these assays, since cationic peptides may bind to anionic surfaces. Purified peptides are then serially diluted, descending from 100 μg/ml. Organisms are inoculated into wells to a concentration of $1\times10^5$ CFU/ml, and plates incubated (37° C., for at least 24 hours). Well turbidities are then assessed visually and by spectrophotometry to quantify growth inhibition versus wells containing no peptide. MMCs are then determined by quantitative culture of MIC wells exhibiting no visible growth.

Microbicidal kinetics of purified peptides are assessed by resuspending the peptides in 0.01% acetic acid buffer (pH 5.5 or 7.2), and organisms are resuspended to a concentration of $1\times10^5$ CFU/ml in 50-250 μl of sterile buffer containing peptide concentrations from 0 to 40 μg/ml. Controls contain buffer alone or non-antimicrobial proteins and organism as above. Mixtures are incubated at 37° C. for up to 48 hours, after which aliquots are quantitatively cultured and incubated for 24 to 48 hours. Killing is expressed as decrease in logarithm$_{10}$ surviving CFU/ml. The limit of sensitivity in microbicidal assays is considered to be a 1 log reduction in viable cells.

Flow cytometry can also be used to examine kinetics and mechanisms of the action of the peptides on bacterial membrane integrity and energetics. Peptides which differ in activity or specificity for their ability to depolarize and/or permeabilize microbial membranes can also be compared by analysis of membrane depolarization, and permeabilization. $DiOC_5$ is a charged lipophilic dye which partitions into the cytoplasm, and is dependent on intact transmembrane potential (ΔΨ) for intracellular retention. Organisms prepared as above are labeled in darkness for 30 minutes at about 20° C. in PBS containing 0.05 μM $DiOC_5$ Organisms are resuspended to a concentration of $5\times10^8$ CFU/ml in $K^+$ MEM containing an individual peptide, and incubated at 37° C. For flow cytometry, organisms are washed, sonicated, counted, and resuspended in $K^+$ MEM buffer. Reductions in mean $DiOC_5$ fluorescence relative to controls are interpreted to represent loss of $DiOC_5$, indicating membrane depolarization. Positive control cells exposed to valinomycin, as well as control cells not exposed to any peptides, are analyzed for $DiOC_5$ fluorescence in parallel.

Propidium iodide is excluded from cells with normal membrane integrity, but enters cells permealized to molecules ≧2 nm in diameter, and can be stimulated to emit fluorescence at >620 nm. Organisms prepared as above are resuspended to a concentration of $5\times10^8$ CFU/ml in $K^+$ MEM containing a selected peptide, and incubated for pre-selected times (ranging from zero up to about 120 minutes) at 37° C. Cells are washed in fresh $K^+$ MEM, sonicated, counted, and resuspended in $K^+$ MEM buffer containing 20 μM propidium iodide. Control cells exposed to ethanol (positive control for permeabilization) are assessed for propidium iodide uptake in parallel. Increases in mean propidium iodide fluorescence relative to control cells are interpreted to indicate increases in permeability.

Erythrocyte permeabilizing and hemolytic activities of peptides exhibiting potent microbicidal activity are also studied as indicators of potential in vivo toxicity. Four-percent (vol/vol) of washed human erythrocytes (in PBS alone, or in PBS plus 10% heat-inactivated PNHS are incubated with selected peptides ranging in concentration up to 100 times greater than geometric mean MICs. After 24 hours of incubation at 37° C., erythrocyte permeabilization and hemolysis are determined spectrophotometrically. Permeabilization and hemolysis will be compared to buffers alone, and with a triton X-100 control (100% hemolysis).

Endothelial cell injury due to peptides can also be measured using a standard $^{51}Cr$ release assay, described in Filler et al., *J Infect Dis.*, 164:928-935 (1991); Filler, et al., *Infect Immun.* 62:1064-1069 (1994); Filler et al., *Infect Immun.* 63:976-983 (1995). Briefly, endothelial cells in 96 well tissue culture plates are incubated with $Na^51$ $CrO_4$ overnight. The following day, the unincorporated isotope tracer is removed by rinsing, and peptides in 0.01% acetic acid buffer are added to the endothelial cells. Control wells are exposed to buffer alone. After a predetermined incubation period, the medium is aspirated and the amount of $^{51}Cr$ released into the medium is measured by scintillation. This approach facilitates toxicity screening of multiple peptides simultaneously, and minimizes the amount of peptide necessary for assessment.

Each antimicrobial and toxicity assay described above is performed independently a minimum of two times, and means±standard error is calculated for each peptide under varying exposure conditions (concentration or pH) as compared with control samples. Statistical analyses of microbicidal data are performed using Student t test or Kruskall-Wallis rank sum analysis for non-parametric data, and corrected for multiple comparisons as appropriate.

The yield of moiety/peptide conjugate formed is determined using routine methods. For example, HPLC or capillary electrophoresis or other qualitative or quantitative method can be used (see, for example, Liu et al., *J. Chromatogr.* 735:357-366 (1996); Rose et al., *J. Chromatogr.* 425: 419-412 (1988), each of which is incorporated herein by reference). In particular, the skilled artisan will recognize that the choice of a method for determining yield of a conjugation reaction depends, in part, on the physical and chemical characteristics of the specific moiety and peptide. Following conjugation, the reaction products can be desalted to remove any free peptide and free drug.

Embodiments of the invention provide a method of inducing programmed cell death in a cell, including contacting the cell with an isolated peptide, protide or conjugate described herein. In one aspect, the cell is a microorganism, or in some aspects a pathogenic microorganism. In some aspects, the pathogenic microorganism is *Staphylococcus aureus, Escherichia coli, Salmonella typhimurium, Pseudomonas aeruginosa, Bacillus subtilis, Acinotobacter baumannii, Acinotobacter calcoaceticus, Acinotobacter haemolyticus, Pseudomonas aeruginosa, Candida albicans*, or any of the pathogenic microorganisms described herein. In another aspect, the cell is a tumor cell, including both a malignant and non-malignant tumor cell, or in a preferred aspect a malignant cell. In yet another aspect, the cell is an immune regulatory cell or an immune effector cell.

A peptide, protide or conjugate of the invention useful for practicing the methods of the invention can be formulated and administered by those skilled in the art in a manner and in an amount appropriate for the pathological condition to be treated, for example, an infection, neoplastic disorder, inflammation; the rate or amount of inflammation; the weight, gender, age and health of the individual; the biochemical nature, bioactivity, bioavailability and side effects of the particular compound; and in a manner compatible with concurrent treatment regimens. An appropriate amount and formulation for decreasing the severity of a pathological condition in humans can be extrapolated from credible animal models known in the art of the particular disorder. It is understood, that the dosage of a therapeutic substance has to be adjusted based on the binding affinity of the substance, such that a lower dose of a substance exhibiting significantly higher binding affinity can be administered compared to the dosage necessary for a substance with lower binding affinity. For a peptide, protide or conjugate described herein several factors can be taken into account when determining the proper dosage. For example, for a protide, the nature of the protide effectors and their bioactivity upon activation, the anticipated concentration of activator and the responsiveness of the activator site to presence of the activator, may be taken into account.

The total amount of peptide, protide or conjugate can be administered as a single dose or by infusion over a relatively short period of time, or can be administered in multiple doses administered over a more prolonged period of time. Such considerations will depend on a variety of case-specific factors such as, for example, whether the disease category is characterized by acute episodes or gradual or chronic deterioration. For an individual affected with an acute infection or inflammatory response, for example, as associated with a bacterial infection, the substance can be administered as a single dose or by infusion of several large doses in a relatively short period of time. For an individual affected with chronic deterioration, for example, as associated with a neuroinflammatory disorder, the substance can be administered in a slow-release matrice, which can be implanted for systemic delivery or at the site of the target tissue, which means an area proximal to the desired context. Contemplated matrices useful for controlled release of therapeutic compounds are well known in the art, and include materials such as DepoFoam™, biopolymers, micropumps, and the like.

The peptides, protides and conjugates administered in the methods of the invention can be administered to the individual by any number of routes known in the art including, for example, systemically, such as intravenously or intraarterially. A therapeutic peptide, protide or conjugate can be provided in the form of isolated and substantially purified polypetides in pharmaceutically acceptable formulations using formulation methods known to those of ordinary skill in the art. These formulations can be administered by standard routes, including for example, topical, transdermal, intraperitoneal, intracranial, intracerebroventricular, intracerebral, intravaginal, intrauterine, oral, rectal or parenteral such as intravenous, intraspinal, intrathecal, subcutaneous or intramuscular routes. Intrathecal administration of a therapeutic peptide, protide or conjugate into the intradural or subarachnoid space can be an appropriate route for decreasing the severity of a neuroinflammatory condition. Intravenous administration of a terhapeutic substance containing a peptide, protide or conjugate also is a preferred route for practicing the invention. In addition, a therapeutic substance administered in the methods of the invention can be incorporated into biodegradable polymers allowing for sustained release of the substance useful for prophylactic and reconstitutive applications described above. Biodegradable polymers and their use are described, for example, in Brem et al., *J. Neurosurg.* 74:441 446 (1991), which is incorporated herein by reference.

The methods for treating a particular pathological condition additionally can be practiced in conjunction with other therapies. For example, for treating cancer, the methods of the invention can be practiced prior to, during, or subsequent to conventional cancer treatments such as surgery, chemotherapy, including administration of cytokines and growth factors, radiation or other methods known in the art. Similarly, for treating pathological conditions which include infectious disease, the methods of the invention can be practiced prior to, during, or subsequent to conventional treatments, such as antibiotic administration, against infectious agents or other methods known in the art. Treatment of pathological conditions of autoimmune disorders also can be accomplished by combining the methods of the invention for inducing an immune response with conventional treatments for the particular autoimmune diseases. Conventional treatments include, for example, chemotherapy, steroid therapy, insulin and other growth factor and cytokine therapy, passive immunity and inhibitors of T cell receptor binding. The peptides, protides and conjugates of the invention can be administered in conjunction with these or other methods known in the art and at various times prior, during or subsequent to initiation of conventional treatments. For a description of treatments for pathological conditions characterized by aberrant cell growth see, for example, The Merck Manual, Sixteenth Ed, (Berkow, R., Editor) Rahway, N.J., 1992.

As described above, administration of a peptide, protide or conjugate can be, for example, simultaneous with or delivered in alternative administrations with the conventional therapy, including multiple administrations. Simultaneous administration can be, for example, together in the same formulation or in different formulations delivered at about the same time or immediately in sequence. Alternating administrations can be, for example, delivering a peptide, protide or conjugate formulation and a conventional therapeutic treatment in temporally separate administrations. Temporally separate administrations of a peptide, protide or conjugate and conventional therapy can use different modes of delivery and routes.

A therapeutic peptide, protide or conjugate containing substance administered in the methods of the invention also can be administered as a solution or suspension together with a pharmaceutically acceptable medium. Such a pharmaceutically acceptable medium can include, for example, sterile aqueous solvents such as sodium phosphate buffer, phosphate buffered saline, normal saline or Ringer's solution or other physiologically buffered saline, or other solvent or vehicle such as a glycol, glycerol, an oil such as olive oil or an injectable organic ester. A pharmaceutically acceptable medium can additionally contain physiologically acceptable compounds that act, for example, stabilize the neutralizing agent, increase its solubility, or increase its absorption. Such physiologically acceptable compounds include, for example, carbohydrates such as glucose, sucrose or dextrans; antioxidants such as ascorbic acid or glutathione; receptor mediated permeabilizers, which can be used to increase permeability of the blood-brain barrier; chelating agents such as EDTA, which disrupts microbial membranes; divalent metal ions such as calcium or magnesium; low molecular weight proteins; lipids or liposomes; or other stabilizers or excipients. Those skilled in the art understand that the choice of a pharmaceutically acceptable carrier depends on the route of administration of the compound containing the protides and on its particular physical and chemical characteristics.

Formulations suitable for parenteral administration include aqueous and non-aqueous sterile injection solutions such as the pharmaceutically acceptable mediums described above. The solutions can additionally contain, for example, buffers, bacteriostats and solutes which render the formulation isotonic with the blood of the intended recipient. Other formulations include, for example, aqueous and non-aqueous sterile suspensions which can include suspending agents and thickening agents. The formulations can be presented in unit-dose or multi-dose containers, for example, sealed ampules and vials, and can be stored in a lyophilized condition requiring, for example, the addition of the sterile liquid carrier, immediately prior to use. Extemporaneous injection solutions and suspensions can be prepared from sterile powders, granules and tablets of the kind previously described.

For applications that require the peptide, protide, or conjugate containing compounds to cross the blood-brain barrier, formulations that increase the lipophilicity of the compound are particularly desirable. For example, the neutralizing agent can be incorporated into liposomes (Gregoriadis, Liposome Technology, Vols. I to III, 2nd ed. (CRC Press, Boca Raton Fla. (1993)). Liposomes, which consist of phospholipids or other lipids, are nontoxic, physiologically acceptable and metabolizable carriers that are relatively simple to make and administer.

A therapeutic peptide, protide or conjugate containing substance administered in the methods of the invention can also be prepared as nanoparticles. Adsorbing peptide compounds onto the surface of nanoparticles has proven effective in delivering peptide drugs to the brain (see Kreuter et al., *Brain Research* 674:171 174 (1995)). Exemplary nanoparticles are colloidal polymer particles of poly-butylcyanoacrylate with a therapeutic protide-containing substance to be administered in the methods of the invention adsorbed onto the surface and then coated with polysorbate 80.

Image-guided ultrasound delivery of a therapeutic peptide, protide or conjugate containing substance administered in the methods of the invention through the blood-brain barrier to selected locations in the brain can be utilized as described in U.S. Pat. No. 5,752,515. Briefly, to deliver a therapeutic substance past the blood-brain barrier a selected location in the brain is targeted and ultrasound used to induce a change detectable by imaging in the central nervous system (CNS) tissues and/or fluids at that location. At least a portion of the brain in the vicinity of the selected location is imaged, for example, via magnetic resonance imaging (MRI), to confirm the location of the change. An therapeutic substance administered in the methods of the invention into the patient's bloodstream can be delivered to the confirmed location by applying ultrasound to effect opening of the blood-brain barrier at that location and, thereby, to induce uptake of the substance.

In addition, polypeptides called receptor mediated permeabilizers (RMP) can be used to increase the permeability of the blood-brain barrier to molecules such as therapeutic, prophylactic or diagnostic substances as described in U.S. Pat. Nos. 5,268,164; 5,506,206; and 5,686,416. These receptor mediated permeabilizers can be intravenously co-administered to a host with molecules whose desired destination is the cerebrospinal fluid compartment of the brain, for example, in the treatment of a neuroinflammatory condition. The permeabilizer polypeptides or conformational analogues thereof allow therapeutic substances to penetrate the blood-brain barrier and arrive at their target destination which can be selected based on its proximity to the desired activation context. Such polypeptides can be designed as part of strategic invention protides.

In current treatment regimes for most diseases, more than one compound is often administered to an individual for management of the same or different aspects of the disease. Similarly, in the methods of the invention for treating neoplastic condition, microbial infection, a condition associated with decreased cell death or inflammatory condition, a therapeutic peptide, protide or conjugate containing substance can advantageously be formulated with a second therapeutic compound such as an anti-inflammatory compound, antimicrobail compound, chemotherapeutic compound, immunosuppressive compound or any other compound that manages the same or different aspects of the particular disease. As an example, for treatment of an infectious disease a therapeutic substance can advantageously be formulated with a second therapeutic compound such as an antibiotic. Contemplated methods of treating a pathological condition by administering to a subject a therapeutically effective amount of a peptide, protide or conjugate therefore include administering a therapeutic substance useful in the methods of the invention alone, in combination with, or in sequence with, such other compounds. Alternatively, combination therapies can consist of fusion proteins, where a therapeutic substance useful for treating a particular pathological condition is linked to a heterologous protein, such as an invention protide.

It is understood that modifications which do not substantially affect the activity of the various embodiments of this invention are also provided within the definition of the invention provided herein. Accordingly, the following examples are intended to illustrate but not limit the present invention.

Example I

Antimicrobial, Anti-Cancer, and Other Therapeutic Applications of Peptides Designed from Programmed Cell Death Effector Proteins Candidate proteins representing a variety of nuclear- or mitochondrial-encoded programmed cell death effector and/or modulatory molecules from eukaryotic sources were identified for comparison. When candidate proteins were compared, similarities in sequences and helical domains that have amphipathic and cationic characteristics were identified. Analogues were also identified where possible from prokaryotic sources.

Template proteins were initially chosen based on the following: 1) mammalian or other eukaryotic cell nuclear-encoded peptides with structure-activity relationships to antimicrobial peptide sequences that afford interaction/control/inhibition of mitochondria or chloroplast symbionts, or host cell apoptosis (examples include Bax, Bcl-W, dynamin, mitofusin, nucleolin, and other programmed cell death effector proteins); and 2) structural and/or functional homologues of such proteins in prokaryotes (examples include CidA/B, LrgA/B, and other holin-like or programmed cell death effector proteins). The identification of candidate peptide sequences was achieved through an iterative process, which included a search of protein databases for additional candidate proteins, multiseqeunce alignments of the identified candidates, followed by an integration and analysis of candidate sequences.

Upon identification of an initial group of template proteins having the above-identified characteristics, additional candidate proteins were identified using primary sequence similarity searches of protein databases using the basic local alignment search tool (BLAST) available from the National Center for Biotechnology Information. The searches utilized the amino acid sequences of candidate template proteins having the desired characteristics as query sequences. FIG. 3 shows exemplary amino acid sequence used as the query sequences.

Once all additional candidate template proteins were identified, a compiled set of query sequences were submitted for analysis to the modeling server ClustalW (Larkin et al., *Bioinformatics* 23(21): 2947-2948 (2007)) available online from EMBL-EBI. Utilizing the modeling server, multisequence alignments were performed to identify regions of sequence homology within the candidate sequences or with known host defense or antimicrobial peptide sequences. For example, candidate proteins were ranked based on their alignment score (FIG. 4) and/or analyzed for conserved residues through multisequence alignments (FIG. 5). Additionally, phylogenetic and cladogenetic analyses were conducted between the candidate proteins, followed by multiseqeunce alignments of identified putative helical domains (FIGS. 6-14).

The results from the above processes were integrated to analyze and prioritize candidate sequences. The criteria for their prioritization included: 1) conservation of sequence homology or motif(s); 2) homology to known antimicrobial or anti-cancer peptides; 3) similarity to known or recognized antimicrobial peptide structure-activity relationships (SAR; including presence, periodicity, and distribution of cationic, hydrophobic, and aromatic residues); and 4) visual inspection. Candidate sequences that were identified included mitochondria-targeting proteins, such as Bcl-2, Bcl-W, Bax, and Mitofusin; NK/Tcyto cell effectors, such as Granulysin, Granzyme H, Perforin-1 and Azurocidin (CAP37); apoptosis/cell signaling proteins, such as Fas ligand, Caspase 7 and Dynamin 1; and other related proteins, such as Serpin B9 (CytoPro3), Fractalkine (CX3CL1), CXCL3 and Atrophin 1.

Following the above interactive primary structure analysis, a secondary (2°) structure analysis was conducted. This analysis included visualization, qualitative, and/or quantitative analyses of candidate sequences identified above. This analysis, including 3D visualization of target sequences, conformation 3D homology, qualitative 3D analysis of target sequences, quantitative 3D analysis of target sequences and comparative 3D refinement of target sequences.

3D visualization of target sequences was achieved using Cn3D software available through PubMed. Exemplary 3D visualization of identified candidate peptides within the native total protein are shown in FIG. 15-21. These results identified specific sequences as novel targets for further analysis/design. The conformational 3D homology of target sequences to known antimicrobial or anti-cancer template polypeptides was assessed using the threading and 3D homology fold recognition server Protein Homology/analogy Recognition Engine (PHYRE) "Protein structure prediction on the web: a case study using the Phyre server" (Kelley and Sternberg *Nature Protocols* 4:363-371 (2009). Statistical e values were used to guide prioritization of molecules for further analysis.

Priority target sequences identified above were visualized for qualitative analysis of distribution of 3D physicochemical attributes using the public domain UCSF software package Chimera. Next, priority target sequences were quantitatively evaluated for structural homology and/or structure-activity relationships to known antimicrobial and/or anti-cancer peptides/proteins using a combinatorial extension method of Shindyalov and Bourne, *Protein Engineering* 11:739-747 (1998). The results from these analyses provided quantitative alignment of compositional elements, including charged and hydrophobic residues (FIGS. 22-29). The results included root mean square deviation (RMSD) scores as quantitative data that allowed further prioritization of target sequences. The priority target sequences emanating from the process described above were then used as novel templates for 3D analyses using VAST and/or 3Dpssm software to identify homologous sequences and discover other novel target sequences.

As a final step, a computation simulation of the antimicrobial activity of the selected sequences was conducted. Selected target sequences emerging from the above process were subjected to a computational assessment tool which integrates multiple physical and biochemical attributes of polypeptide sequences to generate a predicted minimal inhibitory concentration (MIC) based on the inverse of the target sequence calculated hydrophobic moment (1/MH; see U.S. Pat. No. 6,743,769).

Based on the above process, specific peptide sequences were identified, which have the desired primary and secondary structure within the candidate proteins (Tables 1-20). These identified peptides are predicted to have antimicrobial and anti-cancer activity. Exemplifying predictive accuracy, candidate peptides have been synthesized and antimicrobial efficacy has been demonstrated in vitro against a panel of Gram-positive and Gram-negative bacteria and fungi (see Example II). Furthermore, specific amino acid substitutions were identified for several peptide sequences (Tables 1-19). The identified peptide residues were prioritized/ranked utilizing to above process (Table 21).

TABLE 1

| Engineered peptides based on Bax protein (pro-apoptotic protein/human/nuclear-encoded). | |
|---|---|
| SEQ ID NO: | Amino Acid Sequence |
| Native Sequence Domains | |
| 1. | $^{104}$nfnwgrvvalfyfasklvlkalctkv$^{129}$ |
| 2. | $^{168}$twqtvtifvagvltasltiwkk$^{190}$ |
| Synthetic Peptides | |
| 1. | $H_2N$-nfnwgrvvalfyfasklvlkalctkv-COOH |
| 1. | $H_2N$-nfnwgrvvalfyfasklvlkalctkv-$CONH_2$ |
| 3. | $H_2N$-nfnwgrvvalfyfasklvlkalxtkv-COOH |
| 3. | $H_2N$-nfnwgrvvalfyfasklvlkalxtkv-$CONH_2$ |
| 4. | $H_2N$-nfnwgrvvalfyfasklvlkalbtjv-COOH |
| 4. | $H_2N$-nfnwgrvvalfyfasklvlkalbtjv-$CONH_2$ |
| 5. | $H_2N$-wgrvvalfyfasklvlkalctkv-COOH |
| 5. | $H_2N$-wgrvvalfyfasklvlkalctkv-$CONH_2$ |
| 6. | $H_2N$-wgrvvalfyfasklvlkalxtkv-COOH |
| 6. | $H_2N$-wgrvvalfyfasklvlkalxtkv-$CONH_2$ |
| 7. | $H_2N$-rvvalfyfasklylkalctkv-COOH |
| 7. | $H_2N$-rvvalfyfasklvlkalctkv-$CONH_2$ |
| 8. | $H_2N$-rvvalfyfasklvlkalxtkv-COOH |
| 8. | $H_2N$-rvvalfyfasklvlkalxtkv-$CONH_2$ |
| 9. | $H_2N$-alfyfasklvlkalctkv-COOH |
| 9. | $H_2N$-alfyfasklvlkalctkv-$CONH_2$ |
| 10. | $H_2N$-alfyfasklvlkalxtkv-COOH |
| 10. | $H_2N$-alfyfasklvlkalxtkv-$CONH_2$ |
| 2. | $H_2N$-twqtytifvagvltasltiwkk-COOH |
| 2. | $H_2N$-twqtvtifvagvltasltiwkk-$CONH_2$ |
| 11. | $H_2N$-twqtvtifvabvltasltiwkk-COOH |
| 11. | $H_2N$-twqtvtifvabvltasltiwkk-$CONH_2$ |
| 12. | $H_2N$-tvtifvagvltasltiwkk-COOH |
| 12. | $H_2N$-tvtifvagvltasltiwkk-$CONH_2$ |
| 13. | $H_2N$-tvtifvabvltasltiwkk-COOH |
| 13. | $H_2N$-tvtifvabvltasltiwkk-$CONH_2$ |

Underlined residues indicate substitutions;
x = s, t, y, other natural/non-natural H-bond donor/acceptor residue;
b = k, r, n, q, other natural/non-natural basic residue;
j = cysteine or other natural/non-natural thiol residue.

TABLE 2

| Engineered peptides based on Bcl-W protein (pro-apoptotic protein/human/ nuclear-encoded). | |
|---|---|
| SEQ ID NO: | Amino Acid Sequence |
| Native Sequence Domains | |
| 14. | $^{10}$tralvadfvgyklrqkgyv$^{28}$ |
| 15. | $^{55}$trfrrtfsdlaaqlhvt$^{71}$ |
| 16. | $^{159}$arrlregnwasvrtvltgavalgalvtvgaffask$^{193}$ |
| Synthetic Peptides | |
| 14. | $H_2N$-tralvadfvgyklrqkgyv-COOH |
| 14. | $H_2N$-tralvadfvgyklrqkgyv-$CONH_2$ |
| 17. | $H_2N$-tralvabfvgyklrqkgyv-COOH |
| 17. | $H_2N$-tralvabfvgyklrqkgyv-$CONH_2$ |
| 15. | $H_2N$-trfrrtfsdlaaqlhvt-COOH |
| 15. | $H_2N$-trfrrtfsdlaaqlhvt-$CONH_2$ |
| 18. | $H_2N$-trfrbtfsdlaaqlhvt-COOH |
| 18. | $H_2N$-trfrbtfsdlaaqlhvt-$CONH_2$ |
| 19. | $H_2N$-trfrrtfsblaaqlhvt-COOH |
| 19. | $H_2N$-trfrrtfsblaaqlhvt-$CONH_2$ |
| 20. | $H_2N$-rrlregnwasvrtvltgavalgalvtvgaffask-COOH |
| 20. | $H_2N$-rrlregnwasvrtvltgavalgalvtvgaffask-$CONH_2$ |
| 21. | $H_2N$-rrlrbgnwasvrtvltgavalgalvtvgaffask-COOH |
| 21. | $H_2N$-rrlrbgnwasvrtvltgavalgalvtvgaffask-$CONH_2$ |
| 22. | $H_2N$-rrlregnwasvrtvltbavalgalvtvgaffask-COOH |
| 22. | $H_2N$-rrlregnwasvrtvltbavalgalvtvgaffask-$CONH_2$ |
| 23. | $H_2N$-rrlregnwasvrtvltgavalbalvtvgaffask-COOH |
| 23. | $H_2N$-rrlregnwasvrtyltgavalbalvtvgaffask-$CONH_2$ |
| 24. | $H_2N$-rrlregnwasvrtvltgavalgalvtvbaffask-COOH |
| 24. | $H_2N$-rrlregnwasvrtvltgavalgalvtvbaffask-$CONH_2$ |
| 25. | $H_2N$-rrlrbgnwasvrtvltbavalbalvtvbaffask-COOH |
| 25. | $H_2N$-rrlrbgnwasvrtvltbavalbalvtvbaffask-$CONH_2$ |

Underlined residues indicate substitutions;
b = k, r, n, q, other natural/non-natural basic residue.

TABLE 3

| Engineered peptides based on Bcl-xβ protein (apoptotic protein/human/nuclear-encoded). | |
|---|---|
| SEQ ID NO: | Amino Acid Sequence |
| Native Sequence Domains | |
| 26. | $^{12}$flsyklsqkgyswsqfs$^{28}$ |
| 27. | $^{99}$lryrrafsdltsqlhitpgtayqf$^{122}$ |

TABLE 3-continued

Engineered peptides based on Bcl-xβ protein (apoptotic protein/human/nuclear-encoded).

| SEQ ID NO: | Amino Acid Sequence |
|---|---|
| 28. | $^{187}$gwvrtkplvcpfslasgqrs$^{196}$ |
| 29. | $^{203}$gqrsptalllylfllcwvivg$^{223}$ |
| | Synthetic Peptides |
| 26. | $H_2N$-flsyklsqkgyswsqfs-COOH |
| 26. | $H_2N$-flsyklsqkgyswsqfs-$CONH_2$ |
| 27. | $H_2N$-lryrrafsdltsqlhitpgtayqsf-COOH |
| 27. | $H_2N$-lryrrafsdltsqlhitpgtayqsf-$CONH_2$ |
| 30. | $H_2N$-lryrrafsbltsqlhitpgtayqsf-COOH |
| 30. | $H_2N$-lryrrafsbltsqlhitpgtayqsf-$CONH_2$ |
| 28. | $H_2N$-gwvrtkplvcpfslasgqrs-COOH |
| 28. | $H_2N$-gwvrtkplvcpfslasgqrs-$CONH_2$ |
| 31. | $H_2N$-gwvrtkplvxpfslasgqrs-COOH |
| 31. | $H_2N$-gwvrtkplvxpfslasgqrs-$CONH_2$ |
| 32. | $H_2N$-gwvrtkplvxpfslasbqrs-COOH |
| 32. | $H_2N$-gwvrtkplvxpfslasbqrs-$CONH_2$ |
| 29. | $H_2N$-gqrsptalllylfllcwvivg-COOH |
| 29. | $H_2N$-gqrsptalllylfllcwvivg-$CONH_2$ |
| 33. | $H_2N$-gqrsptalxlylfllcwvivg-COOH |
| 33. | $H_2N$-gqrsptalxlylfllcwvivg-$CONH_2$ |
| 34. | $H_2N$-gqrsptalllylfllxwvivg-COOH |
| 34. | $H_2N$-gqrsptalllylfllxwvivg-$CONH_2$ |
| 35. | $H_2N$-gqrsptalllylfllcwvivb-COOH |
| 35. | $H_2N$-gqrsptalllylfllcwvivb-$CONH_2$ |
| 36. | $H_2N$-gqrsptalxlylfllxwvivb-COOH |
| 36. | $H_2N$-gqrsptalxlylfllxwvivb-$CONH_2$ |

Underlined residues indicate substitutions;
b = k, r, n, q, other natural/non-natural basic residue
x = s, t, y, other natural/non-natural H-bond donor/acceptor residue.

TABLE 4

Engineered peptides based on Bak protein (apoptotic protein/human/nuclear-encoded).

| SEQ ID NO: | Amino Acid Sequence |
|---|---|
| | Native Sequence Domains |
| 37. | $^{127}$rvvallgfgyrlalhvyq$^{144}$ |
| 38. | $^{187}$ilnylvvlgvvllgqfvvrrffks$^{211}$ |
| | Synthetic Peptides |
| 37. | $H_2N$-rvvallgfgyrlalhvyq-COOH |
| 37. | $H_2N$-rvvallgfgyrlalhvyq-$CONH_2$ |

TABLE 4 -continued

Engineered peptides based on Bak protein (apoptotic protein/human/nuclear-encoded).

| SEQ ID NO: | Amino Acid Sequence |
|---|---|
| 39. | $H_2N$-rvvallbfgyrlalhvyq-COOH |
| 39 | $H_2N$-rvvallbfgyrlalhvyq-$CONH_2$ |
| 40. | $H_2N$-rvvallgfbyrlalhvyq-COOH |
| 40. | $H_2N$-rvvallgfbyrlalhvyq-$CONH_2$ |
| 41. | $H_2N$-rvvallbfbyrlalhvyq-COOH |
| 41. | $H_2N$-rvvallbfbyrlalhvyq-$CONH_2$ |
| 42. | $H_2N$-rvvalygfgyrlalhvyq-COOH |
| 42. | $H_2N$-rvvalygfgyrlalhvyq-$CONH_2$ |
| 43. | $H_2N$-rvvalwgfgyrlalhvyq-COOH |
| 43. | $H_2N$-rvvalwgfgyrlalhvyq-$CONH_2$ |
| 44. | $H_2N$-rvvalybfbyrlalhvyq-COOH |
| 44. | $H_2N$-rvvalybfbyrlalhvyq-$CONH_2$ |
| 45. | $H_2N$-rvvalwbfbyrlalhvyq-COOH |
| 45. | $H_2N$-rvvalwbfbyrlalhvyq-$CONH_2$ |
| 38. | $H_2N$-ilnvlvvlgvvllgqfvvrrffks-COOH |
| 38. | $H_2N$-ilnvlvvlgvvllgqfvvrrffks-$CONH_2$ |
| 46. | $H_2N$-ilnvlvxlgvvllgqfvvrrffks-COOH |
| 46. | $H_2N$-ilnvlvxlgvvllgqfvvrrffks-$CONH_2$ |
| 47. | $H_2N$-ilnvlvblvlgqfvrfks-COOH |
| 47. | $H_2N$-ilnvlvblvlgqfvrfks-$CONH_2$ |

Underlined residues indicate substitutions;
b = k, r, n, q, other natural/non-natural basic residue;
x = s, t, y, other natural/non-natural H-bond donor/acceptor residue.

TABLE 5

Engineered peptides based on Bcl-2 protein (apoptotic regulator/human).

| SEQ ID NO: | Amino Acid Sequence |
|---|---|
| | Native Sequence Domain |
| 48. | $^{11}$nreivmkyihyklsqrgy$^{28}$ |
| | Synthetic Peptides |
| 48. | $H_2N$-nreivmkyihyklsqrgy-COOH |
| 48. | $H_2N$-nreivmkyihyklsqrgy-$CONH_2$ |
| 49. | $H_2N$-nrbivmkyihyklsqrgy-COOH |
| 49. | $H_2N$-nrbivmkyihyklsqrgy-$CONH_2$ |
| 50. | $H_2N$-nreivxkyihyklsqrgy-COOH |
| 50. | $H_2N$-nreivxkyihyklsqrgy-$CONH_2$ |
| 51. | $H_2N$-nreivmkyibyklsqrgy-COOH |
| 51. | $H_2N$-nreivmkyibyklsqrgy-$CONH_2$ |

TABLE 5-continued

| Engineered peptides based on Bcl-2 protein (apoptotic regulator/human). | |
|---|---|
| SEQ ID NO: | Amino Acid Sequence |
| 52. | $H_2N$-nrbivxkyibyklsqrgy-COOH |
| 52. | $H_2N$-nrbivxkyibyklsqrgy-$CONH_2$ |

Underlined residues indicate substitutions;
b = k, r, n, q, other natural/non-natural basic residue;
x = s, t, y, other natural/non-natural H-bond donor residue.

TABLE 6

| Engineered peptides based on Bcl-2 isoform 1 protein (apoptotic regulator/human). | |
|---|---|
| SEQ ID NO: | Amino Acid Sequence |
| Native Sequence Domain | |
| 53. | $^{54}$lalrqagddfsrryrg$^{69}$ |
| Synthetic Peptides | |
| 53. | $H_2N$-lalrqagddfsrryrg-COOH |

TABLE 6-continued

| Engineered peptides based on Bcl-2 isoform 1 protein (apoptotic regulator/human). | |
|---|---|
| SEQ ID NO: | Amino Acid Sequence |
| 53. | $H_2N$-lalrqagddfsrryrg-$CONH_2$ |
| 54. | $H_2N$-lalrqagbdfsrryrg-COOH |
| 54. | $H_2N$-lalrqagbdfsrryrg-$CONH_2$ |
| 55. | $H_2N$-lalrqagdbfsrryrg-COOH |
| 55. | $H_2N$-lalrqagdbfsrryrg-$CONH_2$ |
| 56. | $H_2N$-lalrqagbxfsrryrg-COOH |
| 56. | $H_2N$-lalrqagbxfsrryrg-$CONH_2$ |
| 57. | $H_2N$-lalrqaobxfsrryrg-COOH |
| 57. | $H_2N$-lalrqaobxfsrryrg-$CONH_2$ |

Underlined residues indicate substitutions;
b = k, r, n, q, other natural/non-natural basic residue;
x = s, t, y, other natural/non-natural H-bond donor/acceptor residue;
o = anthrylalanine or other non-natural amino acid.

TABLE 7

| Engineered peptides based on Mfn-1 protein (mitofusin-1; human mitochondrial regulator). | |
|---|---|
| SEQ ID NO: | Amino Acid Sequence |
| Native Sequence Domain | |
| 58. | $^{699}$keidqlekiqnnskllrnkavqlenelenftkqfl$^{734}$ |
| Synthetic Peptides | |
| 58. | $H_2N$-keidqlekiqnnskllrnkavqlenelenftkqfl-COOH |
| 58. | $H_2N$-keidqlekiqnnskllrnkavqlenelenftkqfl-$CONH_2$ |
| 59. | $H_2N$-keibqlekiqnnskllrnkavqlenelenftkqfl-COOH |
| 59 | $H_2N$-keibqlekiqnnskllrnkavqlenelenftkqfl-$CONH_2$ |
| 60. | $H_2N$-keibqlbkiqnnskllrnkavqlbnelenftkqfl-COOH |
| 60. | $H_2N$-keibqlbkiqnnskllrnkavqlbnelenftkqfl-$CONH_2$ |
| 61. | $H_2N$-keibqlbkiqnnskllrnkavqlbnelenftkqfl-COOH |
| 61. | $H_2N$-keibqlbkiqnnskllrnkavqlbnelenftkqfl-$CONH_2$ |
| 62. | $H_2N$-keibqlbkiqnnskllrnkavqlbnblenftkqfl-COOH |
| 62. | $H_2N$-keibqlbkiqnnskllrnkavqlbnblenftkqfl-$CONH_2$ |
| 63. | $H_2N$-keibqlbkiqnnskllrnkavqlbnblbnftkqfl-COOH |
| 63. | $H_2N$-keibqlbkiqnnskllinkavqlbnblbnftkqfl-$CONH_2$ |
| 64. | $H_2N$-kiqnnskllrnkavql-COOH |
| 64. | $H_2N$-kiqnnskllrnkavql-$CONH_2$ |

Underlined residues indicate substitutions;
b = k, r, n, q, other natural/non-natural basic residue.

TABLE 8

| SEQ ID NO: | Amino Acid Sequence |
|---|---|
| Engineered peptides based on Mfn-2 protein (mitofusin-1; human mitochondrial regulator). | |
| Native Sequence Domain | |
| 65. | $^{718}$nkkievldslqskakllrnkagwldselnmfthqylqpsr$^{757}$ |
| Synthetic Peptides | |
| 65. | $H_2N$-nkkievldslqskakllrnkagwldselnmfthqylqpsr-CCOH |
| 65. | $H_2N$-nkkievldslqskakllrnkagwldselnmfthqylqpsr-$COOH_2$ |
| 66. | $H_2N$-nkkibvldslqskakllrnkagwldselnmfthqylqpsr-COOH |
| 66. | $H_2N$-nkkibvldslqskakllrnkagwldselnmfthqylqpsr-$CONH_2$ |
| 67. | $H_2N$-nkkievlbslqskakllrnkagwldselnmfthqylqpsr-COOH |
| 67. | $H_2N$-nkkievlbslqskakllrnkagwldselnmfthqylqpsr-$CONH_2$ |
| 68. | $H_2N$-nkkievldslqskakllrnkagwlbselnmfthqylqpsr-COOH |
| 68. | $H_2N$-nkkievldslqskakllrnkagwlbselnmfthqylqpsr-$CONH_2$ |
| 69. | $H_2N$-nkkievldslqskakllrnkagwldsblnmfthqylqpsr-COOH |
| 69. | $H_2N$-nkkievldslqskakllrnkagwldsblnmfthqylqpsr-$CONH_2$ |
| 70. | $H_2N$-nkkievldslqskakllrnkagwldselnxfthqylqpsr-COOH |
| 70. | $H_2N$-nkkievldslqskakllrnkagwldselnxfthqylqpsr-$CONH_2$ |
| 71. | $H_2N$-nkkibvlbslqskakllrnkagwlbsblnxfthqylqpsr-COOH |
| 71. | $H_2N$-nkkibvlbslqskakllrnkagwlbsblnxfthqylqpsr-$CONH_2$ |
| 72. | $H_2N$-kkievldslqskakllrnkagwl-COOH |
| 72. | $H_2N$-kkievldslqskakllrnkagwl-$CONH_2$ |
| 73. | $H_2N$-kkibvldslqskakllrnkagwl-COOH |
| 73. | $H_2N$-kkibvldslqskakllrnkagwl-$CONH_2$ |
| 74. | $H_2N$-kkievlbslqskakllrnkagwl-COOH |
| 74. | $H_2N$-kkievlbslqskakllrnkagwl-$CONH_2$ |
| 75. | $H_2N$-kkibvlbslqskakllrnkagwl-COOH |
| 75. | $H_2N$-kkibvlbslqskakllrnkagwl-$CONH_2$ |

Underlined residues indicate substitutions;
b = k, r, n, q, other natural/non-natural basic residue;
x = s, t, y, other natural/non-natural H-bond donor/acceptor residue.

TABLE 9

| SEQ ID NO: | Amino Acid Sequence |
|---|---|
| Engineered peptides based on Dnm-1 protein (dynamin-1; human mitochondrial regulator). | |
| Native Sequence Domains | |
| 76. | $^{223}$kllplrrgyigvvnrsqk$^{240}$ |
| 77. | $^{256}$rkfflshpsyrhla$^{269}$ |
| 78. | $^{294}$glrnklqsqllsiek$^{309}$ |
| 79. | $^{323}$arktkallqmvqqfavdf$^{340}$ |
| 80. | $^{411}$atvkkqvqklk$^{501}$ |
| 81. | $^{519}$virkgwltinnigimkggsk$^{539}$ |
| 82. | $^{569}$nlklrdvekgfmsskhifalfnteqrnvyk$^{598}$ |
| 83. | $^{617}$kasflragvypervgdk$^{633}$ |
| Synthetic Peptides | |
| 76. | $H_2N$-kllplrrgyigvvnrsqk-COOH |
| 76. | $H_2N$-kllplrrgyigvvnrsqk-$CONH_2$ |
| 77. | $H_2N$-rkfflshpsyrhla-COOH |
| 77. | $H_2N$-rkfflshpsyrhla-$CONH_2$ |
| 78. | $H_2N$-glrnklqsqllsiek-COOH |
| 78. | $H_2N$-glrnklqsqllsiek-$CONH_2$ |
| 84. | $H_2N$-glrnklqsqllsibk-COOH |
| 84. | $H_2N$-glrnklqsqllsibk-$CONH_2$ |
| 79. | $H_2N$-arktkallqmvqqfavdf-COOH |
| 79. | $H_2N$-arktkallqmvqqfavdf-$CONH_2$ |
| 85. | $H_2N$-arktkallqmvqqfavbf-COOH |
| 85. | $H_2N$-arktkallqmvqqfavbf-$CONH_2$ |
| 80. | $H_2N$-atvkkqvqklk-COOH |
| 80. | $H_2N$-atvkkqvqklk-$CONH_2$ |
| 81. | $H_2N$-virkgwltinnigimkggsk-COOH |
| 81. | $H_2N$-virkgwltinnigimkggsk-$CONH_2$ |
| 82. | $H_2N$-nlklrdvekgfmsskhifalfnteqrnvyk-COOH |
| 82. | $H_2N$-nlklrdvekgfmsskhifalfnteqrnvyk-$CONH_2$ |
| 86. | $H_2N$-nlklrbvekgfmsskhifalfnteqrnvyk-COOH |
| 86. | $H_2N$-nlklrbvekgfmsskhifalfnteqrnvyk-$CONH_2$ |
| 87. | $H_2N$-nlklrdvbkgfmsskhifalfnteqrnvyk-COOH |
| 87. | $H_2N$-nlklrdvbkgfmsskhifalfnteqrnvyk-$CONH_2$ |
| 88. | $H_2N$-nlklrdvekgfmsskhifalfntbqrnvyk-COOH |
| 88. | $H_2N$-nlklrdvekgfmsskhifalfntbqrnvyk-$CONH_2$ |
| 89. | $H_2N$-nlklrbvbkgfmsskhifalfnteqrnvyk-COOH |
| 89. | $H_2N$-nlklrbvbkgfmsskhifalfnteqrnvyk-$CONH_2$ |
| 90. | $H_2N$-nlklrbvbkgfmsskhifalfntbqrnvyk-COOH |

TABLE 9-continued

Engineered peptides based on Dnm-1 protein (dynamin-1; human mitochondrial regulator).

| SEQ ID NO: | Amino Acid Sequence |
|---|---|
| 90. | $H_2N$-nlklrbvbkgfmsskhifalfntbqrnvyk-$CONH_2$ |
| 83. | $H_2N$-kasflragvypervgdk-COOH |
| 83. | $H_2N$-kasflragvypervgdk-$CONH_2$ |
| 91. | $H_2N$-kasflragvypbrvgdk-COOH |
| 91. | $H_2N$-kasflragvypbrvgdk-$CONH_2$ |
| 92. | $H_2N$-kasflragvypervgbk-COOH |
| 92. | $H_2N$-kasflragvypervgbk-$CONH_2$ |
| 93. | $H_2N$-kasflragvypbrvgbk-COOH |
| 93. | $H_2N$-kasflragvypbrvgbk-$CONH_2$ |

Underlined residues indicate substitutions;
b = k, r, n, q, other natural/non-natural basic residue.

TABLE 10

Engineered peptides based on Dnm-2 protein (dynamin-2; human mitochondrial regulator).

| SEQ ID NO: | Amino Acid Sequence |
|---|---|
| | **Native Sequence Domains** |
| 94. | $^{187}$klakevdpqglrtigvitkl$^{206}$ |
| 95. | $^{295}$alrsklqsqllslek$^{309}$ |
| 96. | $^{323}$trktkallqmvqqfgv$^{338}$ |
| 97. | $^{420}$aivkkqvvklk$^{421}$ |
| 98. | $^{499}$aqqrstqlnkkraipnqg$^{516}$ |
| 99. | $^{559}$kekkymlpldnlkirdvekgfmsnkhvfaifnteqrnvyk$^{598}$ |
| 100. | $^{569}$nlkirdvekgfmsnkhvfaifnteqrnvyk$^{598}$ |
| 101. | $^{615}$swkasflragvypekdqa$^{632}$ |
| | **Synthetic Peptides** |
| 94. | $H_2N$-klakevdpqglrtigvitkl-COOH |
| 94. | $H_2N$-klakevdpqglrtigvitkl-$CONH_2$ |
| 102. | $H_2N$-klakbvdpqglrtigvitkl-COOH |
| 102. | $H_2N$-klakbvdpqglrtigvitkl-$CONH_2$ |
| 103. | $H_2N$-klakevbpqglrtigvitkl-COOH |
| 103. | $H_2N$-klakevbpqglrtigvitkl-$CONH_2$ |
| 104. | $H_2N$-klakbvbpqglrtigvitkl-COOH |
| 104. | $H_2N$-klakbvbpqglrtigvitkl-$CONH_2$ |
| 95. | $H_2N$-alrsklqsqllslek-COOH |
| 95. | $H_2N$-alrsklqsqllslek-$CONH_2$ |
| 105. | $H_2N$-alrsklqsqllslbk-COOH |

TABLE 10-continued

Engineered peptides based on Dnm-2 protein (dynamin-2; human mitochondrial regulator).

| SEQ ID NO: | Amino Acid Sequence |
|---|---|
| 105 | $H_2N$-alrsklqsqllslbk-$CONH_2$ |
| 96. | $H_2N$-trktkallqmvqqfgv-COOH |
| 96. | $H_2N$-trktkallqmvqqfgv-$CONH_2$ |
| 97. | $H_2N$-aivkkqvvklk-COOH |
| 97. | $H_2N$-aivkkqvvklk-$CONH_2$ |
| 106. | $H_2N$-oivkkqvvklk-COOH |
| 106. | $H_2N$-oivkkqvvklk-$CONH_2$ |
| 98. | $H_2N$-aqqrstqlnkkraipnqg-COOH |
| 98. | $H_2N$-aqqrstqlnkkraipnqg-$CONH_2$ |
| 99. | $H_2N$-kekkymlpldnlkirdvekgfmsnkhvfaifnteqrnvyk-COOH |
| 99. | H2N-kekkymlpldnlkirdvekgfmsnkhvfaifnteqrnvyk-$CONH_2$ |
| 107. | $H_2N$-kekkymlpldnlkir-COOH |
| 107. | $H_2N$-kekkymlpldnlkir-$CONH_2$ |
| 108. | $H_2N$-kxkkymlpldnlkir-COOH |
| 108. | $H_2N$-kxkkymlpldnlkir-$CONH_2$ |
| 109. | $H_2N$-kekkyxlpldnlkir-COOH |
| 109. | $H_2N$-kekkyxlpldnlkir-$CONH_2$ |
| 110. | $H_2N$-kekkymlplbnlkir-COOH |
| 110. | $H_2N$-kekkymlplbnlkir-$CONH_2$ |
| 111. | $H_2N$-kekkymlplxnlkir-COOH |
| 111. | $H_2N$-kekkymlplxnlkir-$CONH_2$ |
| 112. | $H_2N$-kxkkymlplbnlkir-COOH |
| 112. | $H_2N$-kxkkymlplbnlkir-$CONH_2$ |
| 113. | $H_2N$-kxkkyxlplbnlkir-COOH |
| 113. | $H_2N$-kxkkyxlplbnlkir-$CONH_2$ |
| 114. | $H_2N$-kgfmsnkhvfaifnteqrnvyk-COOH |
| 114. | $H_2N$-kgfmsnkhvfaifnteqrnvyk-$CONH_2$ |
| 115. | $H_2N$-kxkkymlpldnlkirdvekgfmsnkhvfaifnteqrnvyk-COOH |
| 115. | $H_2N$-kxkkymlpldnlkirdvekgfmsnkhvfaifnteqrnvyk-$CONH_2$ |
| 116. | $H_2N$-kekkyxlpldnlkirdvekgfmsnkhvfaifnteqrnvyk-COOH |
| 116. | $H_2N$-kekkyxlpldnlkirdvekgfmsnkhvfaifnteqrnvyk-$CONH_2$ |
| 117. | $H_2N$-kekkymlpldnlkirdvekgfxsnkhvfaifnteqrnvyk-COOH |
| 117. | $H_2N$-kekkymlpldnlkirdvekgfxsnkhvfaifnteqrnvyk-$CONH_2$ |

TABLE 10-continued

| Engineered peptides based on Dnm-2 protein (dynamin-2; human mitochondrial regulator). | |
|---|---|
| SEQ ID NO: | Amino Acid Sequence |
| 100. | $H_2N$-nlkirdvekgfmsnkhvfaifnteqrnvyk-COOH |
| 100. | $H_2N$-nlkirdvekgfmsnkhvfaifnteqrnvyk-$CONH_2$ |
| 118. | $H_2N$-nlkirbvekgfmsnkhvfaifnteqrnvyk-COOH |
| 118. | $H_2N$-nlkirbvekgfmsnkhvfaifnteqrnvyk-$CONH_2$ |
| 119. | $H_2N$-nlkirdvbkgfmsnkhvfaifnteqrnvyk-COOH |
| 119. | $H_2N$-nlkirdvbkgfmsnkhvfaifnteqrnvyk-$CONH_2$ |
| 120. | $H_2N$-nlkirbvbkgfmsnkhvfaifntbqrnvyk-COOH |
| 120. | $H_2N$-nlkirbvbkgfmsnkhvfaifntbqrnvyk-$CONH_2$ |
| 101. | $H_2N$-swkasflragvypekdqa-COOH |
| 101. | $H_2N$-swkasflragyypekdqa-$CONH_2$ |
| 121. | $H_2N$-swkasflragyypbkdqa-COOH |
| 121. | $H_2N$-swkasflragvypbkdqa-$CONH_2$ |

Underlined residues indicate substitutions;
b = k, r, n, q, other natural/non-natural basic residue;
o = anthrylalanine or other non-natural amino acid;
x = s, t, y, other natural/non-natural H-bond donor/acceptor residue.

TABLE 11

| Engineered peptides based on Ncl protein (nucleolin; human mitochondrial regulator). | |
|---|---|
| SEQ ID NO: | Amino Acid Sequence |
| Native Sequence Domains | |
| 122. | $^{50}$qkkgkkaaatsakkvvvs$^{67}$ |
| 123. | $^{69}$tkkvavatpakkaavt$^{84}$ |
| 124. | $^{124}$kkgaaipakgakngknakk$^{142}$ |
| 125. | $^{216}$akgkkaakvvpvkaknva$^{233}$ |
| 126. | $^{273}$vkeapgkrklcemakqkaa$^{290}$ |
| 127. | $^{362}$kaleltglkvfgneiklek$^{380}$ |
| 128. | $^{382}$kgkdskkerdartllaknlpykvtq$^{406}$ |
| 129. | $^{419}$irlvskdgkskgiayi$^{434}$ |
| 130. | $^{467}$kgqnqdyrggknstwsgesktlvlsnlsysat$^{498}$ |
| 131. | $^{508}$katfikvpqnqngkskgyafi$^{528}$ |
| Synthetic Peptides | |
| 122. | $H_2N$-qkkgkkaaatsakkvvvs-COOH |
| 122. | $H_2N$-qkkgkkaaatsakkvvvs-$CONH_2$ |
| 132. | $H_2N$-qkkgkkaxatsakkvyvs-COOH |
| 132. | $H_2N$-qkkgkkaxatsakkvyvs-$CONH_2$ |
| 133. | $H_2N$-qkkgkkaaatsakkvyvs-COOH |

TABLE 11-continued

| Engineered peptides based on Ncl protein (nucleolin; human mitochondrial regulator). | |
|---|---|
| SEQ ID NO: | Amino Acid Sequence |
| 133. | $H_2N$-qkkgkkaaatsakkvyvs-$CONH_2$ |
| 134. | $H_2N$-qkkgkkaaatsakkvwvs-COOH |
| 134. | $H_2N$-qkkgkkaaatsakkvwvs-$CONH_2$ |
| 135. | $H_2N$-qkkgkkaxatsakkvyvs-COOH |
| 135. | $H_2N$-qkkgkkaxatsakkvyvs-$CONH_2$ |
| 136. | $H_2N$-qkkgkkaxatsakkvwvs-COOH |
| 136. | $H_2N$-qkkgkkaxatsakkvwvs-$CONH_2$ |
| 123. | $H_2N$-tkkvavatpakkaavt-COOH |
| 123. | $H_2N$-tkkvavatpakkaavt-$CONH_2$ |
| 124. | $H_2N$-kkgaaipakgakngknakk-COOH |
| 124. | $H_2N$-kkgaaipakgakngknakk-$CONH_2$ |
| 137. | $H_2N$-kkgaxipakgakngknakk-COOH |
| 137. | $H_2N$-kkgaxipakgakngknakk-$CONH_2$ |
| 125. | $H_2N$-akgkkaakvvpvkaknva-COOH |
| 125. | $H_2N$-akgkkaakvvpvkaknva-$CONH_2$ |
| 138. | $H_2N$-akgkkaakvvxvkaknva-COOH |
| 138. | $H_2N$-akgkkaakvvxvkaknva-$CONH_2$ |
| 126. | $H_2N$-vkeapgkrkkemakqkaa-COOH |
| 126. | $H_2N$-vkeapgkrkkemakqkaa-$CONH_2$ |
| 139. | $H_2N$-vkbapgkrkkemakqkaa-COOH |
| 139 | $H_2N$-vkbapgkrkkemakqkaa-$CONH_2$ |
| 140. | $H_2N$-vkeapgkrkkbmakqkaa-COOH |
| 140. | $H_2N$-vkeapgkrkkbmakqkaa-$CONH_2$ |
| 141. | $H_2N$-vkeapgkrkkexakqkaa-COOH |
| 141. | $H_2N$-vkeapgkrkkexakqkaa-$CONH_2$ |
| 142. | $H_2N$-vkbapgkrkkbxakqkaa-COOH |
| 142. | $H_2N$-vkbapgkrkkbxakqkaa-$CONH_2$ |
| 127. | $H_2N$-kaleltglkvfgneiklek-COOH |
| 127. | $H_2N$-kaleltglkvfgneiklek-$CONH_2$ |
| 143. | $H_2N$-kalbltglkvfgneiklek-COOH |
| 143. | $H_2N$-kalbltglkvfgneiklek-$CONH_2$ |
| 144. | $H_2N$-kaleltglkvfgnbiklek-COOH |
| 144. | $H_2N$-kaleltglkvfgnbiklek-$CONH_2$ |
| 145. | $H_2N$-kaleltglkvfgneiklbk-COOH |
| 145. | $H_2N$-kaleltglkvfgneiklbk-$CONH_2$ |
| 146. | $H_2N$-kalbltglkvfgnbiklbk-COOH |
| 146. | $H_2N$-kalbltglkvfgnbiklbk-$CONH_2$ |

TABLE 11-continued

Engineered peptides based on Ncl protein (nucleolin; human mitochondrial regulator).

| SEQ ID NO: | Amino Acid Sequence |
|---|---|
| 128. | $H_2N$-kgkdskkerdartllaknlpykytq-COOH |
| 128. | $H_2N$-kgkdskkerdartllaknlpykvtq-$CONH_2$ |
| 147. | $H_2N$-kgkxskkerdartllaknlpykytq-COOH |
| 147. | $H_2N$-kgkxskkerdartllaknlpykvtq-$CONH_2$ |
| 148. | $H_2N$-kgkdskkxrdartllaknlpykvtq-COOH |
| 148. | $H_2N$-kgkdskkxrdartllaknlpykvtq-$CONH_2$ |
| 149. | $H_2N$-kgkdskkerbartllaknlpykvtq-COOH |
| 149. | $H_2N$-kgkdskkerbartllaknlpykvtq-$CONH_2$ |
| 150. | H2N-kgkxskkbrbartllaknlpykvtq-COOH |
| 150. | H2N-kgkxskkbrbartllaknlpykvtq-$CONH_2$ |
| 129. | $H_2N$-irlvskdgkskgiayi-COOH |
| 129. | $H_2N$-irlvskdgkskgiayi-$CONH_2$ |
| 151. | $H_2N$-irlvskfgkskgiayi-COOH |
| 151. | $H_2N$-irlvskfgkskgiayi-$CONH_2$ |
| 152. | $H_2N$-irlvskygkskgiayi-COOH |
| 152. | $H_2N$-irlvskygkskgiayi-$CONH_2$ |
| 153. | $H_2N$-irlvskwgkskgiayi-COOH |
| 153 | $H_2N$-irlvskwgkskgiayi-$CONH_2$ |
| 154. | $H_2N$-irlvsklwgkskgiayi-COOH |
| 154 | $H_2N$-irlvsklwgkskgiayi-$CONH_2$ |
| 155. | $H_2N$-irlvskdgkskg-COOH |
| 155. | $H_2N$-irlvskdgkskg-$CONH_2$ |
| 156. | $H_2N$-irlvskfgkskgi-COOH |
| 156. | $H_2N$-irlvskfgkskg-$CONH_2$ |
| 157. | $H_2N$-irlvskygkskg-COOH |
| 157. | $H_2N$-irlvskygkskg-$CONH_2$ |
| 158. | $H_2N$-irlvskwgkskg-COOH |
| 158. | $H_2N$-irlvskwgkskg-$CONH_2$ |
| 159. | $H_2N$-irlvsklwgkskg-COOH |
| 159. | $H_2N$-irlvsklwgkskgi-$CONH_2$ |
| 130. | $H_2N$-kgqnqdyrggknstwsgesktlvlsnlsysat-COOH |
| 130. | $H_2N$-kgqnqdyrggknstwsgesktlvlsnlsysat-$CONH_2$ |
| 160. | $H_2N$-kgqnqbyrggknstwsgesktlvlsnlsysat-COOH |
| 160. | $H_2N$-kgqnqbyrggknstwsgesktlvlsnlsysat-$CONH_2$ |
| 161. | $H_2N$-kgqnqdyrggknstwsgbsktlvlsnlsysat-COOH |
| 161. | $H_2N$-kgqnqdyrggknstwsgbsktlvlsnlsysat-$CONH_2$ |
| 162. | $H_2N$-kgqnqbyrggknstwsgbsktlvlsnlsysat-COOH |
| 162 | $H_2N$-kgqnqbyrggknstwsgbsktlvlsnlsysat-$CONH_2$ |
| 163. | $H_2N$-kgbnqdyrlgknstwsgbsktlvlsnlsysat-COOH |
| 163. | $H_2N$-kgbnqdyrlgknstwsgbskttvlsnlsysat-$CONH_2$ |
| 164. | $H_2N$-kgbnqdyrlgknstwsgbskt-COOH |
| 164. | $H_2N$-kgbnqdyrlgknstwsgbskt-$CONH_2$ |
| 131. | $H_2N$-katfikvpqnqngkskgyafi-COOH |
| 131. | $H_2N$-katfikvpqnqngkskgyafi-$CONH_2$ |
| 165. | $H_2N$-katfikvpqnqnxkskgyafi-COOH |
| 165. | $H_2N$-katfikvpqnqnxkskgyafi-$CONH_2$ |
| 166. | $H_2N$-katfikvpqnqnlkskgyafi-COOH |
| 166. | $H_2N$-katfikvpqnqnlkskgyafi-$CONH_2$ |
| 167. | $H_2N$-katfikvpqnqnykskgyafi-COOH |
| 167. | $H_2N$-katfikvpqnqnykskgyafi-$CONH_2$ |
| 168. | $H_2N$-katfikvpqnqnfkskgyafi-COOH |
| 168. | $H_2N$-katfikvpqnqnfkskgyafi-$CONH_2$ |
| 169. | $H_2N$-katfikvpqnqnwkskgyafi-COOH |
| 169. | $H_2N$-katfikvpqnqnwkskgyafi-$CONH_2$ |
| 170. | $H_2N$-katfikvpqnqngkskgy-COOH |
| 170. | $H_2N$-katfikvpqnqngkskgy-$CONH_2$ |
| 171. | $H_2N$-katfikvpqnqnxkskgy-COOH |
| 171. | $H_2N$-katfikvpqnqnxkskgy-$CONH_2$ |
| 172. | $H_2N$-katfikvpqnqnlkskgy-COOH |
| 172. | $H_2N$-katfikvpqnqnlkskgy-$CONH_2$ |
| 173. | $H_2N$-katfikvpqnqnykskgy-COOH |
| 173. | $H_2N$-katfikvpqnqnykskgy-$CONH_2$ |
| 174. | $H_2N$-katfikvpqnqnfkskgy-COOH |
| 174. | $H_2N$-katfikvpqnqnfkskgy-$CONH_2$ |
| 175. | $H_2N$-katfikvpqnqnwkskgy-COOH |
| 175. | $H_2N$-katfikvpqnqnwkskgy-$CONH_2$ |

Underlined residues indicate substitutions;
b = k, r, n, q, other natural/non-natural basic residue;
x = s, t, y, other natural/non-natural H-bond donor/acceptor residue.

TABLE 12

Engineered peptides based on Csp3 protein (caspase 3; apoptosis effector/nuclear encoded).

| SEQ ID NO: | Amino Acid Sequence |
|---|---|
| | Native Sequence Domains |
| 176. | $^{10}$sksiknlepkiihgs$^{24}$ |
| 177. | $^{136}$lkkitnffrgdrcrsltgkpklfiiqacrgt$^{166}$ |
| 178. | $^{215}$fiqslcamlkqyadklefmhiltrvnrkvat$^{245}$ |
| 176. | $H_2N$-sksiknlepkiihgs-COOH |
| 176. | $H_2N$-sksiknlepkiihgs-$CONH_2$ |
| 179. | $H_2N$-sksiknlbpkiihgs-COOH |
| 179. | $H_2N$-sksiknlbpkiihgs-$CONH_2$ |
| 180. | $H_2N$-sksiknlepkiiygs-COOH |
| 180. | $H_2N$-sksiknlepkiiygs-$CONH_2$ |
| 181. | $H_2N$-sksiknlepkiiybs-COOH |
| 181. | $H_2N$-sksiknlepkilybs-$CONH_2$ |
| 182. | $H_2N$-sksiknlbpkiiybs-COOH |
| 182. | $H_2N$-sksiknlbpkiiybs-$CONH_2$ |
| 177. | $H_2N$-lkkitnffrgdrcrsltgkpklfiiqacrgt-COOH |
| 177. | $H_2N$-lkkitnffrgdrcrsltgkpklfiiqacrgt-$CONH_2$ |
| 183. | $H_2N$-lkkitnffrgbrcrsltgkpklfiiqacrgt-COOH |
| 183. | $H_2N$-lkkitnffrgbrcrsltgkpklfiiqacrgt-$CONH_2$ |
| 184. | $H_2N$-lkkitnffrgdrxrsltgkpklfiiqacrgt-COOH |
| 184. | $H_2N$-lkkitnffrgdrxrsltgkpklfiiqacrgt-$CONH_2$ |
| 185. | $H_2N$-lkkitnffrgdrcrsltgkpklfiiqaxrgt-COOH |
| 185. | $H_2N$-lkkitnffrgdrcrsltgkpklfiiqaxrgt-$CONH_2$ |
| 186. | $H_2N$-lkkitnfrgbrxrsltgkpklfiiqaxrgt-COOH |
| 186. | $H_2N$-lkkitnfrgbrxrsltgkpklfiiqaxrgt-$CONH_2$ |
| 187. | $H_2N$-lkkitnfrgbrxrsltgk-COOH |
| 187. | $H_2N$-lkkitnfrgbrxrsltgk-$CONH_2$ |

Underlined residues indicate substitutions;
b = k, r, n, q, other natural/non-natural basic residue;
x = s, t, y, other natural/non-natural H-bond donor/acceptor residue.

TABLE 13

Engineered peptides based on Bad protein (apoptotic protein/human/nuclear-encoded).

| SEQ ID NO: | Amino Acid Sequence |
|---|---|
| | Native Sequence Domains |
| 188. | $^{93}$frgrsrsappnlwaaqrygrelrr$^{116}$ |
| 189. | $^{115}$rrmsdefvdsfkkglprpksagtatq$^{140}$ |
| 190. | $^{121}$fvdsfkkglprpksagtatq$^{140}$ |

TABLE 13-continued

Engineered peptides based on Bad protein (apoptotic protein/human/nuclear-encoded).

| SEQ ID NO: | Amino Acid Sequence |
|---|---|
| | Synthetic Peptides |
| 188. | $H_2N$-frgrsrsappnlwaaqrygrelrr-COOH |
| 188. | $H_2N$-frgrsrsappnlwaaqrygrelrr-$CONH_2$ |
| 191. | $H_2N$-frgrsrsappnlwaaqrygrblrr-COOH |
| 191. | $H_2N$-frgrsrsappnlwaaqrygrblrr-$CONH_2$ |
| 189. | $H_2N$-rrmsdefvdsfkkglprpksagtatq-COOH |
| 189. | $H_2N$-rrmsdefvdsfkkglprpksagtatq-$CONH_2$ |
| 192. | $H_2N$-rrmsbefvdsfkkglprpksagtatq-COOH |
| 192. | $H_2N$-rrmsbefvdsfkkglprpksagtatq-$CONH_2$ |
| 193. | $H_2N$-rrmsdbfvdsfkkglprpksagtatq-COOH |
| 193. | $H_2N$-rrmsdbfvdsfkkglprpksagtatq-$CONH_2$ |
| 194. | $H_2N$-rrmsdefvbsfkkglprpksagtatq-COOH |
| 194. | $H_2N$-rrmsdefvbsfkkglprpksagtatq-$CONH_2$ |
| 195. | $H_2N$-rrmsbbfvbsfkkglprpksagtatq-COOH |
| 195. | $H_2N$-rrmsbbfvbsfkkglprpksagtatq-$CONH_2$ |
| 196. | $H_2N$-rrxsbbfvbsfkkglprpksagtatq-COOH |
| 196. | $H_2N$-rrxsbbfvbsfkkglprpksagtatq-$CONH_2$ |
| 190. | $H_2N$-fvdsfkkglprpksagtatq-COOH |
| 190. | $H_2N$-fvdsfkkglprpksagtatq-$CONH_2$ |
| 197. | $H_2N$-fvbsfkkglprpksagtatq-COOH |
| 197. | $H_2N$-fvbsfkkglprpksagtatq-$CONH_2$ |
| 198. | $H_2N$-fvbsfkkglxrpksag-COOH |
| 198. | $H_2N$-fvbsfkkglxrpksag-$CONH_2$ |
| 199. | $H_2N$-fvbsfkkglyrpksag-COOH |
| 199. | $H_2N$-fvbsfkkglyrpksag-$CONH_2$ |

Underlined residues indicate substitutions;
b = k, r, n, q, other natural/non-natural basic residue;
x = s, t, y, other natural/non-natural H-bond donor/acceptor residue.

TABLE 14

Engineered peptides based on Prf-1 protein (perforin-1/apoptotic/human/nuclear-encoded).

| SEQ ID NO: | Amino Acid Sequence |
|---|---|
| | Native Sequence Domains |
| 200. | $^{32}$krshkfvpgawlag$^{45}$ |
| 201. | $^{49}$vtslrrsgsfpvdtqrflr$^{68}$ |
| 202. | $^{123}$rsirndwkvgldvtpk$^{138}$ |
| 203. | $^{356}$rrealrralsqyltdrarwr$^{375}$ |

TABLE 14-continued

Engineered peptides based on Prf-1 protein (perforin-1/apoptotic/human/nuclear-encoded).

| SEQ ID NO: | Amino Acid Sequence |
|---|---|
| 204. | $^{520}$nlnhghlkfryhar$^{534}$ |
| | Synthetic Peptides |
| 200. | $H_2N$-krshkfvpgawlag-COOH |
| 200. | $H_2N$-krshkfvpgawlag-$CONH_2$ |
| 205. | $H_2N$-krshkfvxgawlag-COOH |
| 205. | $H_2N$-krshkfvxgawlag-$CONH_2$ |
| 201. | $H_2N$-vtslrrsgsfpvdtqrflr-COOH |
| 201. | $H_2N$-vtslrrsgsfpvdtqrflr-$CONH_2$ |
| 206. | $H_2N$-vtslrrsgsfxvdtqrflr-COOH |
| 206. | $H_2N$-vtslrrsgsfxvdtqrflr-$CONH_2$ |
| 207. | $H_2N$-vtslrrsgsfpvbtqrflr-COOH |
| 207. | $H_2N$-vtslrrsgsfpvbtqrflr-$CONH_2$ |
| 208. | $H_2N$-vtslrrsgsfxvbtqrflr-COOH |
| 208. | $H_2N$-vtslrrsgsfxvbdtqrflr-$CONH_2$ |
| 202. | $H_2N$-rsirndwkvgldvtpk-COOH |
| 202. | $H_2N$-rsirndwkvgldvtpk-$CONH_2$ |
| 209. | $H_2N$-rsirnbwkvgldvtpk-COOH |
| 209. | $H_2N$-rsirnbwkvgldvtpk-$CONH_2$ |
| 210. | $H_2N$-rsirndwkvgldvt-COOH |
| 210. | $H_2N$-rsirndwkvgldvt-$CONH_2$ |
| 211. | $H_2N$-rsirnbwkvgldvt-COOH |
| 211. | $H_2N$-rsirnbwkvgldvt-$CONH_2$ |
| 203. | $H_2N$-rrealrralsqyltdrarwr-COOH |
| 203. | $H_2N$-rrealrralsqyltdrarwr-$CONH_2$ |
| 212. | $H_2N$-rrbalrralsqyltdrarwr-COOH |
| 212. | $H_2N$-rrbalrralsqyltdrarwr-$CONH_2$ |
| 213. | $H_2N$-rrealrralsqyltbrarwr-COOH |
| 213. | $H_2N$-rrealrralsqyltbrarwr-$CONH_2$ |
| 214. | $H_2N$-rrbalrralsqyltbrarwr-COOH |
| 214. | $H_2N$-rrbalrralsqyltbrarwr-$CONH_2$ |
| 215. | $H_2N$-rxbalrralsqyltbrarwr-COOH |
| 215. | $H_2N$-rxbalrralsqyltbrarwr-$CONH_2$ |
| 204 | $H_2N$-nlnhghlkfryhar-COOH |
| 204. | $H_2N$-nlnhghlkfryhar-$CONH_2$ |
| 216. | $H_2N$-nlnbghlkfryhar-COOH |
| 216. | $H_2N$-nlnbghlkfryhar-$CONH_2$ |
| 217. | $H_2N$-nlnbgblkfryhar-COOH |
| 217. | $H_2N$-nlnbgblkfryhar-$CONH_2$ |
| 218. | $H_2N$-nlnbgblkfrybar-COOH |
| 218. | $H_2N$-nlnbgblkfrybar-$CONH_2$ |
| 219. | $H_2N$-nlnxghlkfryhar-COOH |
| 219. | $H_2N$-nlnxghlkfryhar-$CONH_2$ |
| 220. | $H_2N$-nlnbgxlkfryhar-COOH |
| 220. | $H_2N$-nlnbgxlkfryhar-$CONH_2$ |
| 221. | $H_2N$-nlnbgblkfryxar-COOH |
| 221. | $H_2N$-nlnbgblkfryxar-$CONH_2$ |
| 222. | $H_2N$-olnbgblkfrybar-COOH |
| 222. | $H_2N$-olnbgblkfrybar-$CONH_2$ |
| 223. | $H_2N$-olnbgblkfryxar-COOH |
| 223. | $H_2N$-olnbgblkfryxar-$CONH_2$ |

Underlined residues indicate substitutions;
b = k, r, n, q, other natural/non-natural basic residue;
x = s, t, y, other natural/non-natural H-bond donor/acceptor residue;
o = anthrylalanine or other non-natural amino acid.

TABLE 15

Engineered peptides based on Granulysin protein (granulysin-1/apoptotic/human/nuclear-encoded).

| SEQ ID NO: | Amino Acid Sequence |
|---|---|
| | Native Sequence Domains |
| 224. | $^{62}$lgrdyrtcltivqklkk$^{78}$ |
| 225. | $^{82}$kptqrsvsnaatrvcrtgrsrwr$^{104}$ |
| 226. | $^{101}$srwrrryqsrvtqglvag$^{125}$ |
| | Synthetic Peptides |
| 224. | $H_2N$-lgrdyrtcltivqklkk-COOH |
| 224. | $H_2N$-lgrdyrtcltivqklkk-$CONH_2$ |
| 227. | $H_2N$-lgrbyrtcltivqklkk-COOH |
| 227. | $H_2N$-lgrbyrtcltivqklkk-CONH2 |
| 228. | $H_2N$-lgrdyrtxltivqklkk-COOH |
| 228. | $H_2N$-lgrdyrtxltivqklkk-$CONH_2$ |
| 229. | $H_2N$-lgrbyrtxltivqklkk-COOH |
| 229. | $H_2N$-lgrbyrtxltivqklkk-$CONH_2$ |
| 225. | $H_2N$-kptqrsysnaatrvcrtgrsrwr-COOH |
| 225. | $H_2N$-kptqrsysnaatrvcrtgrsrwr-$CONH_2$ |
| 230. | $H_2N$-kptqrsvsnaatrvxrtgrsrwr-COOH |
| 230. | $H_2N$-kptqrsvsnaatrvxrtgrsrwr-$CONH_2$ |

TABLE 15-continued

Engineered peptides based on Granulysin protein (granulysin-1/apoptotic/human/nuclear-encoded).

| SEQ ID NO: | Amino Acid Sequence |
|---|---|
| 231. | H₂N-kptqrsvsnaatrv<u>x</u>rtg-COOH |
| 231. | H₂N-kptqrsvsnaatrv<u>x</u>rtg-CONH₂ |
| 232. | H₂N-kptqrsvsn<u>y</u>atrv<u>x</u>rtg-COOH |
| 232. | H₂N-kptqrsvsn<u>y</u>atrv<u>x</u>rtg-CONH₂ |
| 233. | H₂N-kptqrsvsn<u>f</u>atrv<u>x</u>rtg-COOH |
| 233. | H₂N-kptqrsvsn<u>f</u>atrv<u>x</u>rtg-CONH₂ |
| 226. | H₂N-srwrrryqsrvtqglvag-COOH |
| 226. | H₂N-srwrrryqsrvtqglvag-CONH₂ |
| 234. | H₂N-srwrryqsrvtq<u>y</u>lvag-COOH |
| 234. | H₂N-srwrryqsrvtq<u>y</u>lvag-CONH₂ |
| 235. | H₂N-<u>o</u>rwrryqsrvtq<u>y</u>lvag-COOH |
| 235. | H₂N-<u>o</u>rwrryqsrvtq<u>y</u>lvag-CONH₂ |

Underlined residues indicate substitutions;
b = k, r, n, q, other natural/non-natural basic residue;
x = s, t, y, other natural/non-natural H-bond donor/acceptor residue;
o = anthrylalanine or other non-natural amino acid.

TABLE 16

Engineered peptides based on CidA protein (pro-programmed cell death protein/*S. aureus*).

| SEQ ID NO: | Amino Acid Sequence |
|---|---|
| | Native Sequence Domains |
| 236. | ²⁸qkifhlplagsivglflfylllqfkiv⁵⁴ |
| 237. | ⁸⁸eitlnyilffaviiigtcivalssgyiaekmsvkhkqrkgi¹²⁷ |
| | Synthetic Peptides |
| 236. | H₂N-qkifhlplagsivglflfylllqfkiv-COOH |
| 236. | H₂N-qkifhlplagsivglflfylllqfkiv-CONH₂ |
| 238. | H₂N-qkifhlpla<u>b</u>sivglflfylllqfkiv-COOH |
| 238. | H₂N-qkifhlpla<u>b</u>sivglflfylllqfkiv-CONH₂ |
| 239. | H₂N-qkifhlplagsivglflfyl<u>g</u>lqfkiv-COOH |
| 239. | H₂N-qkifhlplagsivglflfyl<u>g</u>lqfkiv-CONH₂ |
| 240. | H₂N-qkifhlpla<u>b</u>sivglflfyl<u>g</u>lqfkiv-COOH |
| 240. | H₂N-qkifhlpla<u>b</u>sivglflfyl<u>g</u>lqfkiv-CONH₂ |
| 241. | H₂N-la<u>b</u>sivglflfyl<u>g</u>lqfkiv-COOH |
| 241. | H₂N-la<u>b</u>sivglflfyl<u>g</u>lqfkiv-CONH₂ |
| 242. | H₂N-la<u>b</u>siv<u>b</u>lflfyl<u>g</u>lqfkiv-COOH |
| 242. | H₂N-la<u>b</u>siv<u>b</u>lflfyl<u>g</u>lqfkiv-CONH₂ |

TABLE 16-continued

Engineered peptides based on CidA protein (pro-programmed cell death protein/*S. aureus*).

| SEQ ID NO: | Amino Acid Sequence |
|---|---|
| 237. | H₂N-eitlnyilffaviiigtcivalssgyiaekmsvkhkqrkgi-COOH |
| 237. | H₂N-eitlnyilffaviiigtcivalssgyiaekmsvkhkqrkgi-CONH₂ |
| 243. | H₂N-eitlnyilffaviiigt<u>x</u>ivalssgyiaek<u>x</u>svkhkqrkgi-COOH |
| 243. | H₂N-eitlnyilffaviiigt<u>x</u>ivalssgyiaek<u>x</u>svkhkqrkgi-CONH₂ |
| 244. | H₂N-ae<u>l</u>msvkhkqrkgi-COOH |
| 244. | H₂N-aekmsvkhkqrkgi-CONH₂ |
| 245. | H₂N-a<u>b</u>kmsvkhkqrkgi-COOH |
| 245. | H₂N-a<u>b</u>kmsvkhkgrkgi-CONH₂ |
| 246. | H₂N-a<u>l</u>kmsvkhkqrkgi-COOH |
| 246. | H₂N-a<u>l</u>kmsvkhkqrkgi-CONH₂ |
| 247. | H₂N-a<u>l</u>k<u>x</u>svkhkqrkgi-COOH |
| 247. | H₂N-a<u>l</u>k<u>x</u>svkhkqrkgi-CONH₂ |

Underlined residues indicate substitutions;
b = k, r, n, q, other natural/non-natural basic residue;
x = s, t, y, other natural/non-natural H-bond donor/acceptor residue.

TABLE 17

Engineered peptides based on LrgA protein (anti-programmed cell death protein/*S. aureus*).

| SEQ ID NO: | Amino Acid Sequence |
|---|---|
| | Native Sequence Domains |
| 248. | ¹²³kvtsrskgdkvtkkiki¹³⁹ |
| | Synthetic Peptides |
| 248. | H₂N-kvtsrskgdkvtkkiki-COOH |
| 248. | H₂N-kvtsrskgdkvtkkiki-CONH₂ |
| 249. | H₂N-kvtsrskgdkvtk<u>w</u>iki-COOH |
| 249. | H₂N-kvtsrskgdkvtk<u>w</u>iki-CONH₂ |
| 250. | H₂N-kvtsrskgdkvtk<u>z</u>iki-COOH |
| 250. | H₂N-kvtsrskgdkvtk<u>z</u>iki-CONH₂ |
| 251. | H₂N-kvtsrskgdkvtk<u>x</u>iki-COOH |
| 251. | H₂N-kvtsrskgdkvtk<u>x</u>iki-CONH₂ |

Underlined residues indicate substitutions;
z = d, e, other anionic residue;
x = s, t, y, other natural/non-natural H-bond donor/acceptor residue.

TABLE 18

Engineered peptides based on Lambda S21 protein (lytic regulator protein/λ21 phage).

| SEQ ID NO: | Amino Acid Sequence |
|---|---|
| | Native Sequence Domains |
| 252. | $^{44}$slvlgfltyltnlyfkiredrrkaarge$^{71}$ |
| | Synthetic Peptides |
| 252. | $H_2N$-slvlgfltyltnlyfkiredrrkaarge-COOH |
| 252. | $H_2N$-slvlgfltyltnlyfkiredrrkaarge-$CONH_2$ |
| 253. | $H_2N$-Slvlgfltyltnlyfkirbdrrkaarge-COOH |
| 253. | $H_2N$-slvlgfltyltnlyfkirbdrrkaarge-$CONH_2$ |
| 254. | $H_2N$-slvlgfltyltnlyfkirebrrkaarge-COOH |
| 254. | $H_2N$-slvlgfltyltnlyfkirebrrkaarge-$CONH_2$ |
| 255. | $H_2N$-slvlgfltyltnlyfkirxxrrkaarge-COOH |
| 255. | $H_2N$-slvlgfltyltnlyfkirxxrrkaarge-$CONH_2$ |
| 256. | $H_2N$-lyfkirxxrrkaarg-COOH |
| 256. | $H_2N$-lyfkirxxrrkaarg-$CONH_2$ |

Underlined residues indicate substitutions;
b = k, r, n, q, other natural/non-natural basic residue;
x = s, t, y, other natural/non-natural H-bond donor/acceptor residue.

TABLE 19

Engineered peptides based on Holin protein (lytic regulatory protein/Enterobacteria λ phage).

| SEQ ID NO: | Amino Acid Sequence |
|---|---|
| | Native Sequence Domains |
| 257. | $^{27}$aylrgrynggaftktvi$^{44}$ |
| 258. | $^{84}$sigslikrfaakkagvedgrnq$^{105}$ |
| 259. | $^{84}$sigslikrfaakkagv$^{100}$ |
| | Synthetic Peptides |
| 257. | $H_2N$-aylrgrynggaftktvi-COOH |

TABLE 19-continued

Engineered peptides based on Holin protein (lytic regulatory protein/Enterobacteria λ phage).

| SEQ ID NO: | Amino Acid Sequence |
|---|---|
| 257. | $H_2N$-aylrgrynggaftktvi-$CONH_2$ |
| 260. | $H_2N$-oylrgrynggaftktvi-COOH |
| 260. | $H_2N$-oylrgrynggaftktvi-$CONH_2$ |
| 258. | $H_2N$-sigslikrfaakkagvedgrnq-COOH |
| 258. | $H_2N$-sigslikrfaakkagvedgrnq-$CONH_2$ |
| 261. | $H_2N$-sigslikrfaakkagvbdgrnq-COOH |
| 261. | $H_2N$-sigslikrfaakkagvbdgrnq-$CONH_2$ |
| 262. | $H_2N$-sigslikrfaakkagvebgrnq-COOH |
| 262. | $H_2N$-sigslikrfaakkagvebgrnq-$CONH_2$ |
| 259 | $H_2N$-sigslikrfaakkagv-COOH |
| 259. | $H_2N$-sigslikrfaakkagv-$CONH_2$ |
| 263. | $H_2N$-sigslikrfaxkkagv-COOH |
| 263. | $H_2N$-sigslikrfaxkkagv-$CONH_2$ |

Underlined residues indicate substitutions;
o = anthrylalanine or other non-natural amino acid;
b = k, r, n, q, other natural/non-natural basic residue;
x = s, t, y, other natural/non-natural H-bond donor/acceptor residue.

TABLE 20

Additional engineered peptides based on programmed cell death effector proteins.

| Native Protein | SEQ ID NO: | Amino Acid Sequence |
|---|---|---|
| Human Bcl-xL | 288 | $H_2N$-SQSNRELVVDFLSYKLSQK-COOH |
| Human Bcl-xL | 288 | $H_2N$-SQSNRELVVDFLSYKLSQK-$CONH_2$ |
| Human CTL Granulysin | 289 | $H_2N$-QKLKKMVDKPTQRSVSN-COOH |
| Human CTL Granulysin | 289 | $H_2N$-QKLKKMVDKPTQRSVSN-$CONH_2$ |

TABLE 21

Novel Therapeutic Peptide Designs Based on Programmed Cell Death Effector Domains.

| ID Name | Sequence | SEQ ID NO: | Length | Priority |
|---|---|---|---|---|
| BaxP-I-18 | $H_2N$-alfyfasklvlkalytkv-$CONH_2$ | 264. | 18 | 1 |
| CidA-II-12 | $H_2N$-alkysvkhkqrkgi-$CONH_2$ | 265. | 14 | 2 |
| Ncl-VIII-6 | $H_2N$-irlvskygkskgiayi-$CONH_2$ | 152. | 16 | 3 |
| Csp3-II-12 | $H_2N$-lkkitnfrgkryrsltgk-$CONH_2$ | 266. | 18 | 4 |
| Dnm2-II-4 | $H_2N$-alrsklqsqllslrk-$CONH_2$ | 267. | 15 | 5 |
| Dnm1-IV-2 | $H_2N$-atvkkqvqklk-$CONH_2$ | 80. | 11 | 6 |
| BclXb-I-2 | $H_2N$-flsyklsqkgyswsqfs-$CONH_2$ | 26. | 17 | 7 |

TABLE 21-continued

Novel Therapeutic Peptide Designs Based on Programmed Cell Death Effector Domains.

| ID Name | Sequence | SEQ ID NO: | Length | Priority |
|---|---|---|---|---|
| Hol-III-4 | $H_2N$-sigslikrfaykkagv-$CONH_2$ | 268. | 16 | 8 |
| Mfn1-II-2 | $H_2N$-kiqnnskllrnkavql-$CONH_2$ | 64. | 16 | 9 |
| BclWP-I-4 | $H_2N$-tralvakfvgyklrqkgyv-$CONH_2$ | 269. | 19 | 10 |
| LrgA-I-4 | $H_2N$-kvtsrskgdkvtkwiki-$CONH_2$ | 249. | 17 | 11 |
| BaxP-I-1 | $H_2N$-nfnwgrvvalfyfasklvlkalytkv-$CONH_2$ | 270. | 26 | |
| BaxP-II-8 | $H_2N$-tvtifvakvltasltiwkk-$CONH_2$ | 271. | 19 | |
| BclWP-II-6 | $H_2N$-trfrrtfsklaaqlhvt-$CONH_2$ | 272. | 17 | |
| BclXb-IV-10 | $H_2N$-gqrsptalslylfllywvivk-$CONH_2$ | 273. | 21 | |
| Mfn1-II-20 | $H_2N$-kkievlkslqskakllrnkagwl-$CONH_2$ | 274. | 23 | |
| Dnm1-III-4 | $H_2N$-glrnklqsqllsikk-$CONH_2$ | 275. | 15 | |
| Dnm2-I-4 | $H_2N$-klakkvdpqglrtigvitkl-$CONH_2$ | 276. | 21 | |
| Dnm2-VI-16 | $H_2N$-kskkytlplknlkir-$CONH_2$ | 277. | 15 | |
| Csp3-I-10 | $H_2N$-sksiknlkpkiiyks-$CONH_2$ | 278. | 15 | |
| CidA-I-12 | $H_2N$-laksivrlflfylglqfkiv-$CONH_2$ | 279. | 20 | |

Example II

In Vitro Antimicrobial Assay

The following assay is designed to measure the relative antimicrobial activity of peptides by determining zones of growth inhibition.

The top eleven prioritized target sequences identified in Example I (see Table 21) were synthesized by solid-phase chain extension synthesis using conventional techniques. Each synthetic peptide was purified by RP-HPLC, and authenticated for purity and correct sequence by mass spectroscopy. Stock concentrations of the synthetic peptides were prepared at 1 mg/mL in 0.01% acetic acid and adjusted to pH 7.2. Synthetic peptides were assessed for antimicrobial efficacy, spectra, and conditional optima (pH 5.5 or 7.5) using the following modified radial diffusion assay, as detailed in Yount and Yeaman, *PNAS* 1010:7363-7368 (2004).

Media Preparation

Molecular grade agarose (1.0%) in 10 mM $NaH_2PO_4H_2O$ was prepared, pH adjusted to 7.5 or 5.5, and autoclaved for 15 minutes at 121° C., then held in a waterbath set at 48° C. until used. Mueller Hinton II overlay agarose was prepared by adding molecular grade agarose to Mueller Hinton II Broth at a final concentration of 1.0%, pH adjusted to 7.5 or 5.5, autoclaved for 10 minutes at 121° C., and then held at 48° C. until used.

Inoculum Preparation

Trypticase Soy Broth (TSB) (10 mL) we inoculated with an overnight growth of the test organism and incubated three to six hours until the organism reached log phase. The cells were collected by centrifugation, washed in PBS, then 0.01% acetic acid adjusted to pH 7.2. The pellet was resuspended in TSB and standardized to a 0.5 McFarland turbidity standard. A 10 µl aliquot of the inoculum is added to 10 mL of the pH-adjusted 1.0% molecular grade agarose cooled to 48° C. resulting in a final inoculum concentration of $5\times10^5$ CFU/mL. The suspension is poured into a 15×100 mm Petri dish and allowed to solidify.

After solidification had occurred, five 4 mm diameter wells were bored into the agarose. The central well was used as the acetic acid control while 10 µl of peptide stock solution was added to each of the other wells resulting in a final concentration of 10 µg peptide/well. The plates were incubated upright for three hours at 37° C., then overlaid with 10 mL of Mueller Hinton II agarose. After the overlay solidified, the plates were inverted and incubated overnight at 37° C.

Activity Determination

The synthetic peptides identified in Table 22 were assayed for antimicrobial activity against known pathogenic microorganisms. These pathogenic microorganisms included five species of bacteria (*Staphylococcus aureus, Escherichia coli, Salmonella typhimurium, Pseudomonas aeruginosa* and *Bacillus subtilis*) and one species of fungi (*Candida albicans*) (see Table 23). Zones of growth inhibition were measured and were grouped as complete and/or partial growth zones for the assayed microorganism. Zones were considered complete clearance when there was no visible growth (i.e. completely clear or free of growth). Zones were considered partial clearance when growth was impeded or partially cleared (i.e. reduction in microbial density as compared to adjacent confluent growth). The larger the zone size, the greater the antimicrobial activity of the test peptide. The lack of a zone is an indication of no antimicrobial activity of the test peptide against the target organism under the conditions tested.

TABLE 22

| Peptide key for antimicrobial assay (FIGS. 30-35). | | | | |
|---|---|---|---|---|
| Template | Identifier* | Design Sequence | SEQ ID NO: | Length |
| Holin protein | Hol-III-4 | $H_2N$-sigslikrfaykkagv-$CONH_2$ | 268. | 16 |
| Dynamin-2 | Dnm2-II-4 | $H_2N$-alrsklqsqllslrk-$CONH_2$ | 267. | 15 |
| BclW protein | BclWP-I-4 | $H_2N$-tralvakfvgyklrqkgyv-$CONH_2$ | 269. | 19 |
| Caspase-3 | Csp3-II-12 | $H_2N$-lkkitnfrgkryrsltgk-$CONH_2$ | 266 | 18 |
| LrgA protein | LrgA-I-4 | $H_2N$-kvtsrskgdkvtkwiki-$CONH_2$ | 249. | 17 |
| Dynamin-1 | Dnm1-IV-2 | $H_2N$-atvkkqvqklk-$CONH_2$ | 80. | 11 |
| BclXb protein | BclXb-I-2 | $H_2N$-flsyklsqkgyswsqfs-$CONH_2$ | 26. | 17 |
| Nucleolin | Ncl-VIII-6 | $H_2N$-irlvskygkskgiayi-$CONH_2$ | 152. | 16 |
| Mitofusin-1 | Mfn1-II-2 | $H_2N$-kiqnnskllrnkavql-$CONH_2$ | 64. | 16 |
| Bax protein | BaxP-I-18 | $H_2N$-alfyfasklvlkalytkv-$CONH_2$ | 264. | 18 |
| CidA protein | CidA-II-12 | $H_2N$-alkysvkhkqrkgi-$CONH_2$ | 265. | 14 |

*Note:
identifier formula = [Template] - [Model Domain] - [Design No.]

TABLE 23

| Microorganism key for antimicrobial assay (FIGS. 30-35). | | |
|---|---|---|
| Genus/Species | Identifier | Strain |
| Bacteria | | |
| *Staphylococcus aureus* | SAISP479C | ISP479C |
| *Escherichia coli* | ECML-35 | ML-35 |
| *Salmonella typhimurium* | ST14028 | 14028 |
| *Pseudomonas aeruginosa* | PA01 | 01 |
| *Bacillus subtilis* | BS6633 | ATCC 6633 |
| Fungi | | |
| *Candida albicans* | CA36082S | 36082S |

Results

Figure 6:
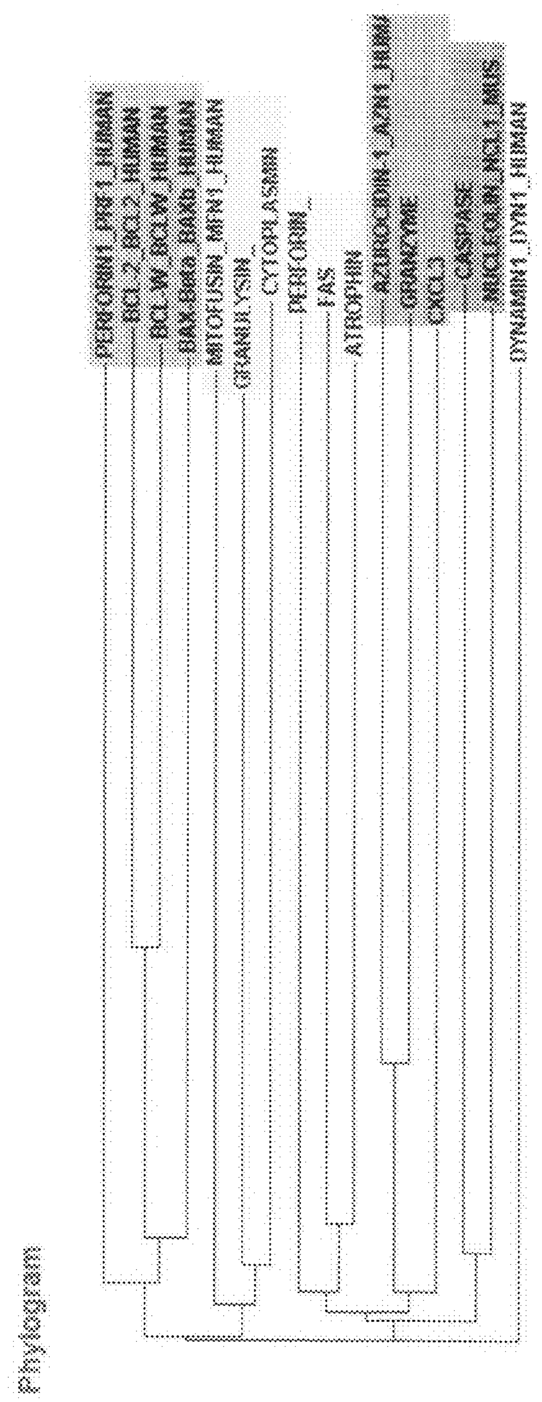
FIG. 6 shows a phylogram of candidate programmed cell death effector peptides using the multisequence alignment tool ClustalW (Larkin et al., *Bioinformatics* 23(21): 2947-2948 (2007)) available online from EMBL-EBI.
Figure 7:
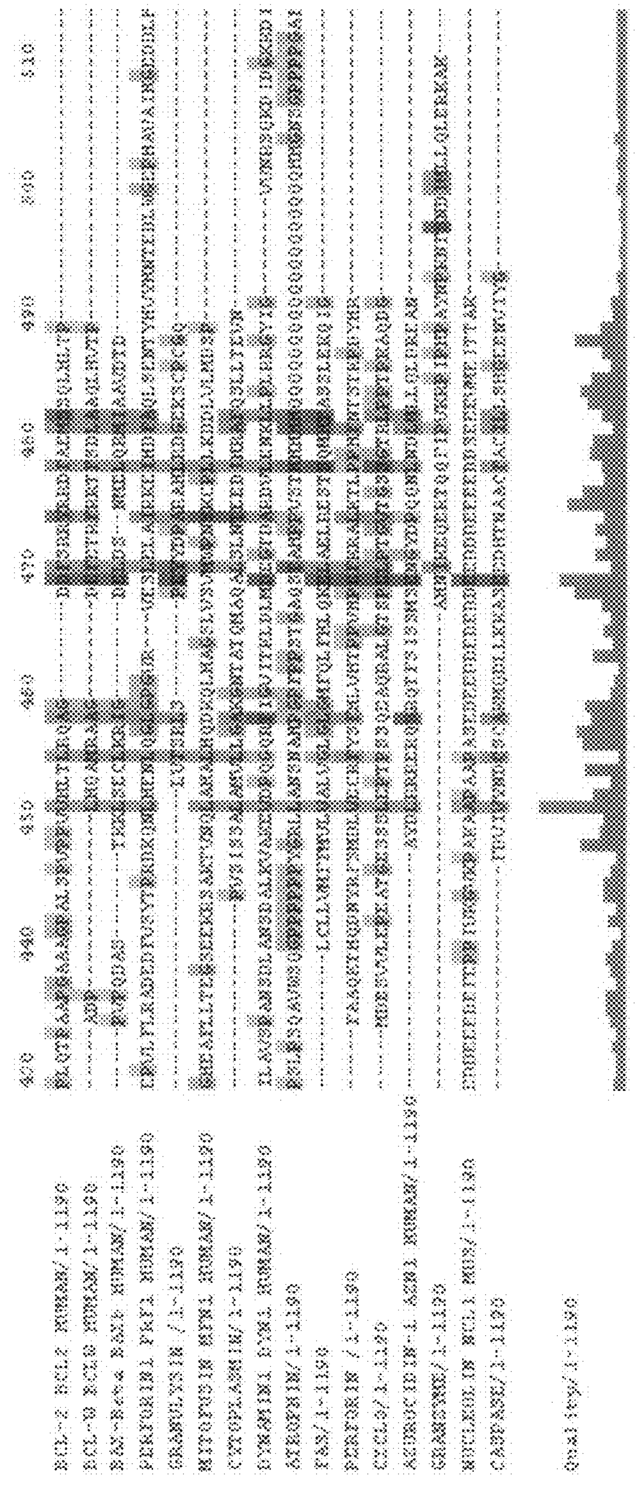
FIG. 7 shows a similarity alignment of helical region 1 (amino acids—~450-490) between candidate peptides (SEQ ID NOS. 333-348) identified in the phylogram of FIG. 6 using the multisequence alignment tool ClustalW (Larkin et al., *Bioinformatics* 23(21): 2947-2948 (2007)) available online from EMBL-EBI.
Figure 8:
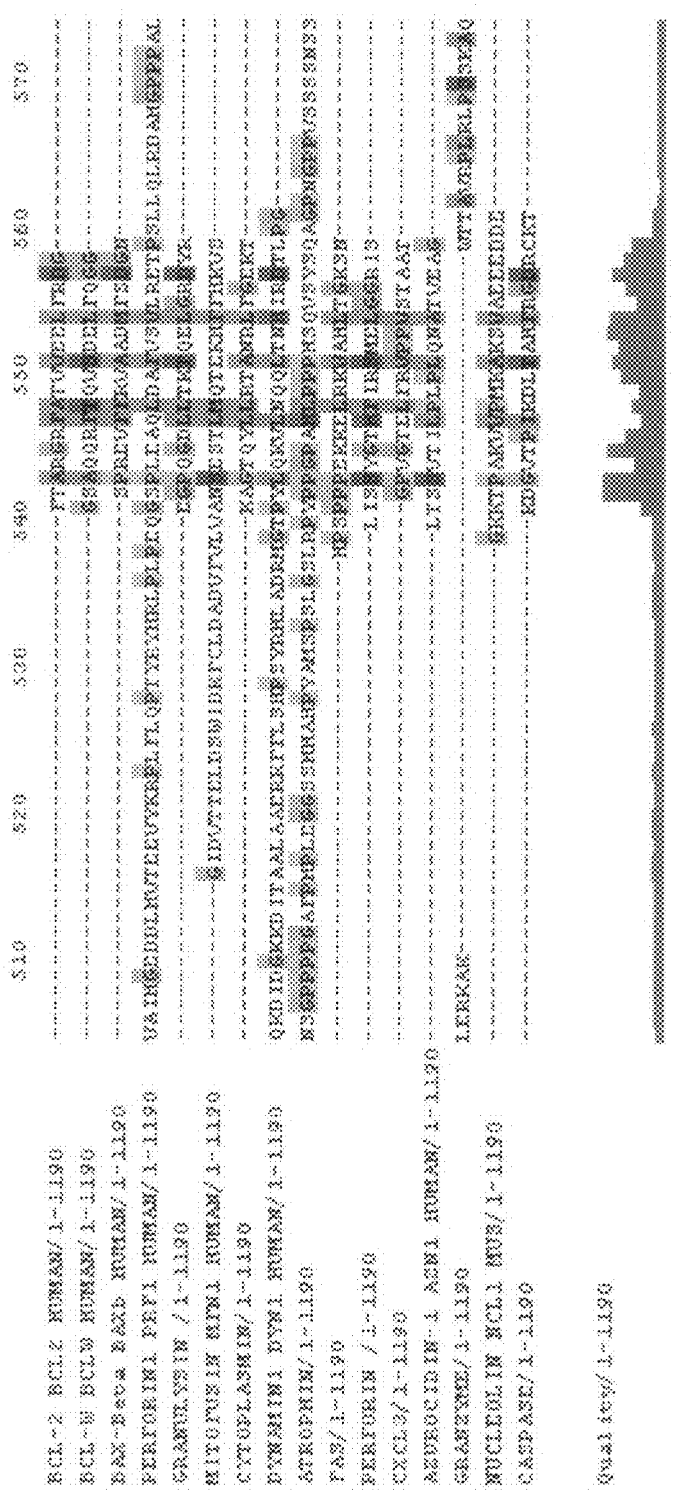
FIG. 8 shows a similarity alignment of helical region 2 (amino acids—~540-560) between candidate peptides (SEQ ID NOS. 349-364) identified in the phylogram of FIG. 6 using the multisequence alignment tool ClustalW (Larkin et al., *Bioinformatics* 23(21): 2947-2948 (2007)) available online from EMBL-EBI.
Figure 9:
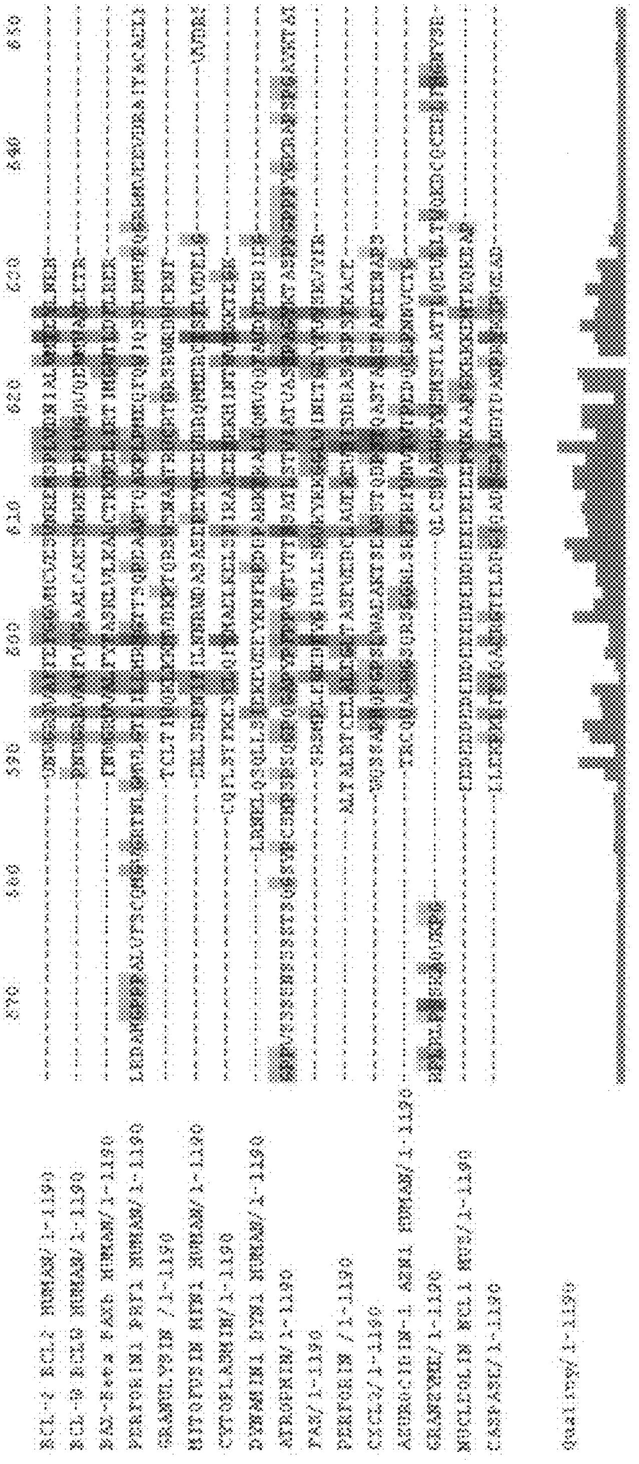
FIG. 9 shows a similarity alignment of helical region 3 (amino acids—~590-620) between candidate peptides (SEQ ID NOS. 365-380) identified in the phylogram of FIG. 6 using the multisequence alignment tool ClustalW (Larkin et al., *Bioinformatics* 23(21): 2947-2948 (2007)) available online from EMBL-EBI.
Figure 10:
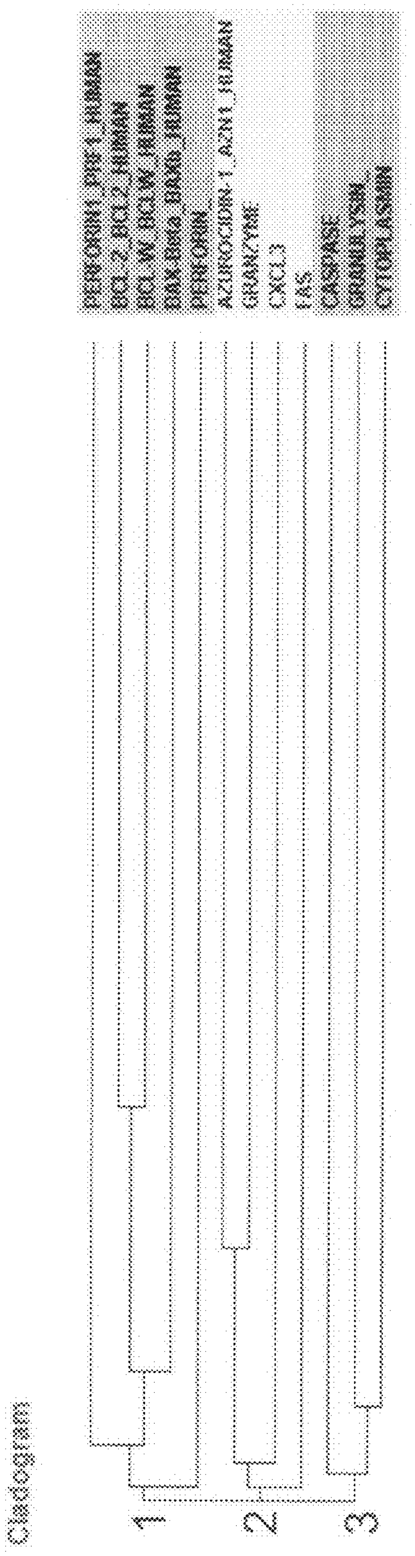
FIG. 10 shows a cladogram of candidate programmed cell death effector molecule subset 1 using the multisequence alignment tool ClustalW (Larkin et al., *Bioinformatics* 23(21): 2947-2948 (2007)) available online from EMBL-EBI.
Figure 11:
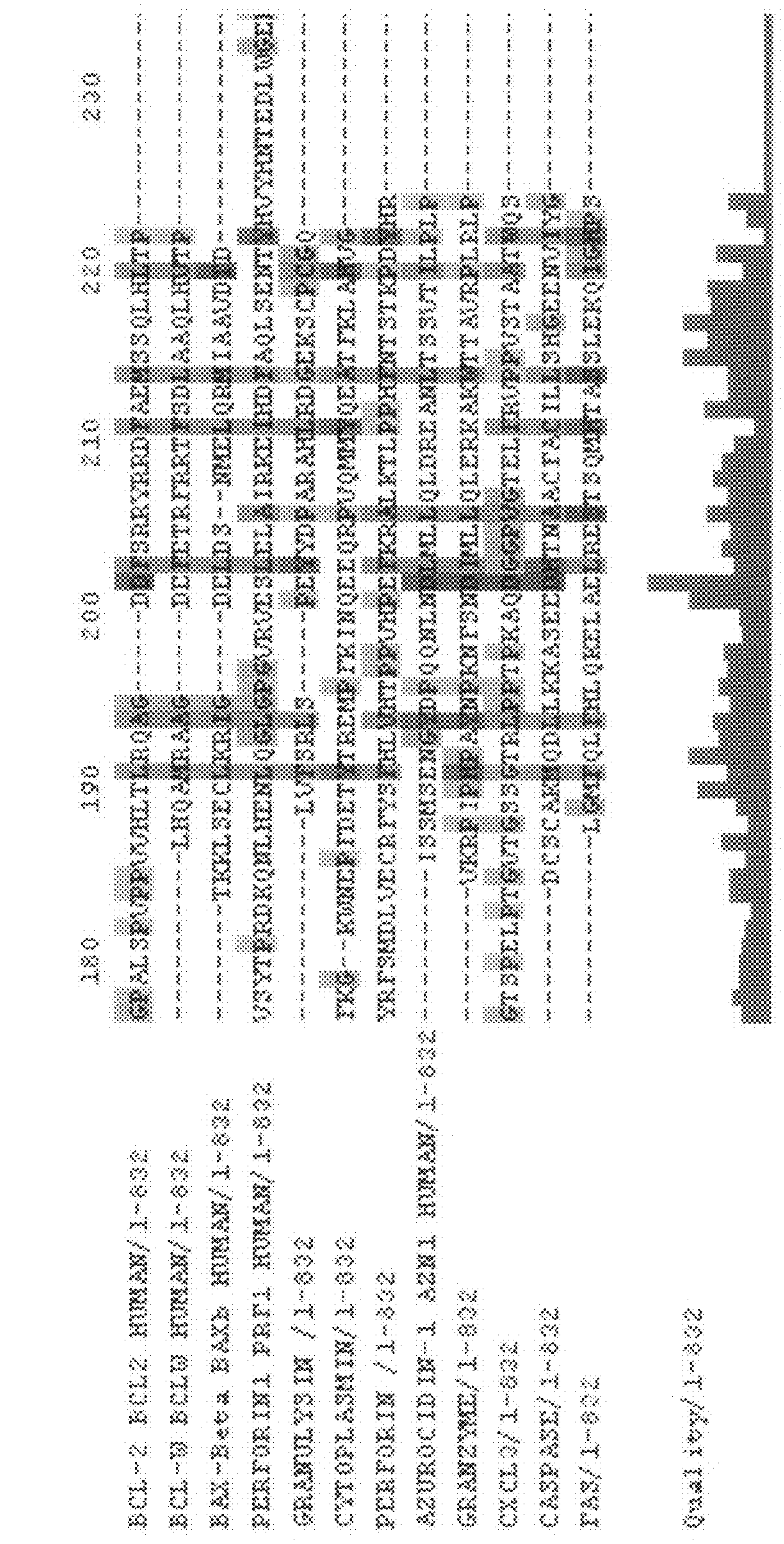
FIG. 11 shows a similarity alignment of helical region 1/subset 1 (amino acids—~180-225) between candidate programmed cell death effector molecules (SEQ ID NOS. 381-392) identified in the cladogram of FIG. 10 using the multi-sequence alignment tool ClustalW (Larkin et al., *Bioinformatics* 23(21): 2947-2948 (2007)) available online from EMBL-EBI.
Figure 12:
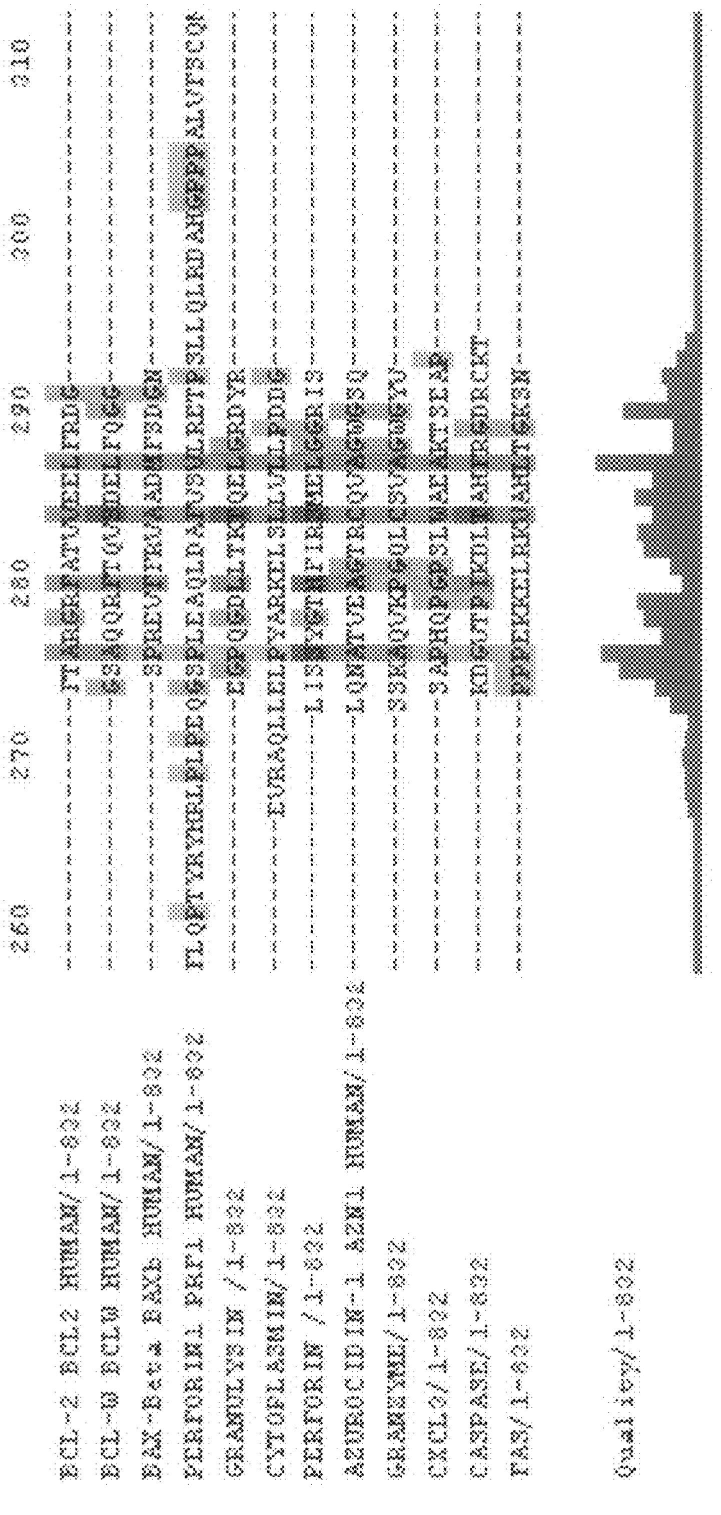
FIG. 12 shows a similarity alignment of helical region 2/subset 1 (amino acids—~270-290) between candidate programmed cell death effector molecules (SEQ ID NOS. 393-404) identified in the cladogram of FIG. 10 using the multi-sequence alignment tool ClustalW (Larkin et al., *Bioinformatics* 23(21): 2947-2948 (2007)) available online from EMBL-EBI.
Figure 13:
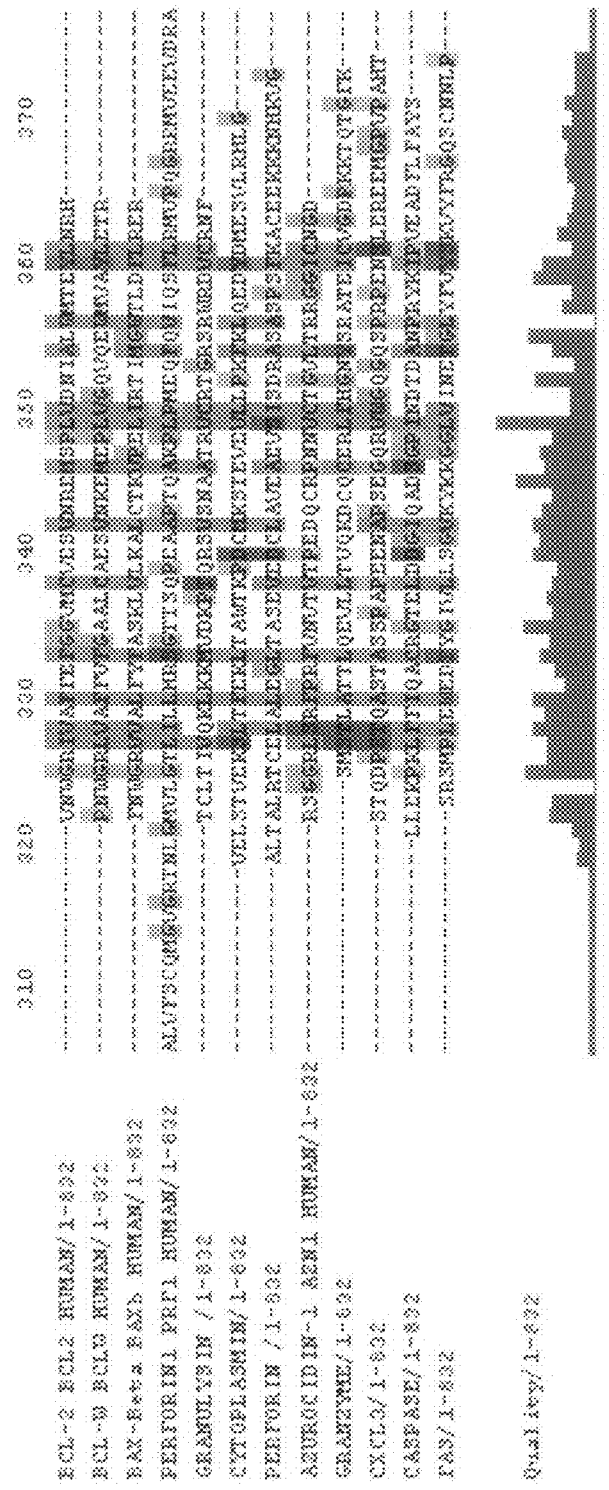
FIG. 13 shows a similarity alignment of helical region 3/subset 1 (amino acids—~320-360) between candidate programmed cell death effector molecules (SEQ ID NOS. 405-416) identified in the cladogram of FIG. 10 using the multi-sequence alignment tool ClustalW (Larkin et al., *Bioinformatics* 23(21): 2947-2948 (2007)) available online from EMBL-EBI.
Figure 14:
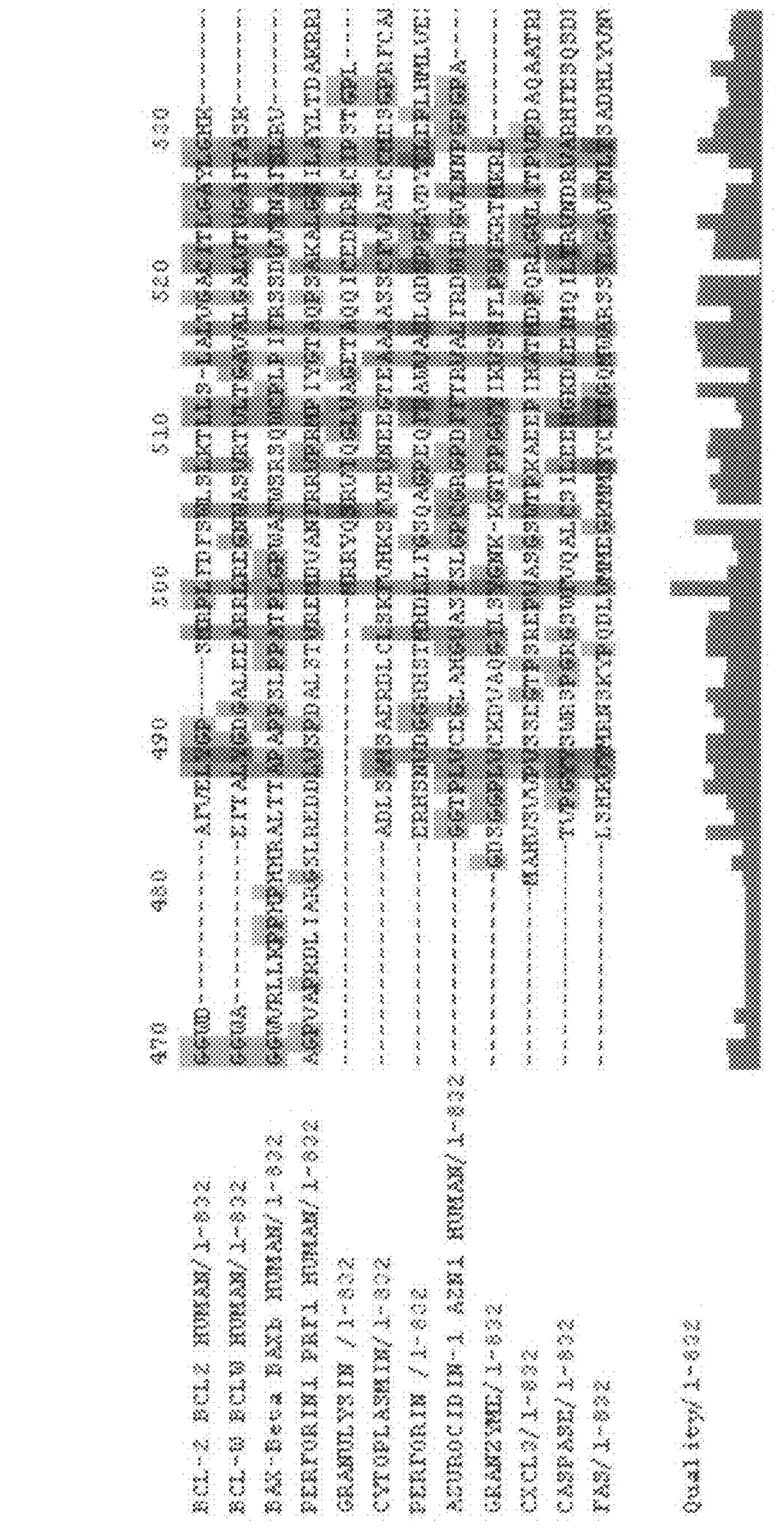
FIG. 14 shows a similarity alignment of helical region 4/subset 1 (amino acids—~490-530) between candidate programmed cell death effector molecules (SEQ ID NOS. 417-428) identified in the cladogram of FIG. 10 using the multi-sequence alignment tool ClustalW (Larkin et al., *Bioinformatics* 23(21): 2947-2948 (2007)) available online from EMBL-EBI.
Figure 15:
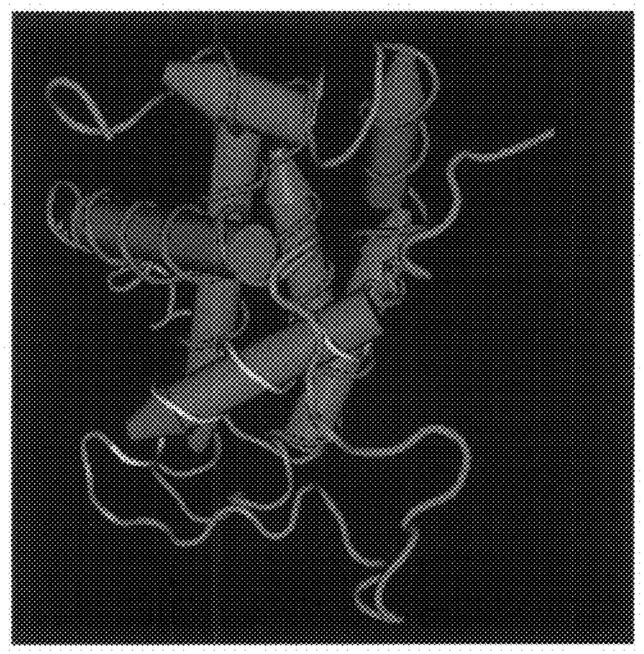
FIG. 15 shows a secondary structure diagram of human Bcl-2, isoform 1 or 2. Cylinders represent alpha helices. The colors are green for alpha helices, orange for beta strands, and blue for coils. The arrows on the helix cylinders point in the N-terminal to C-terminal direction. The amino acid sequence NREIVMKYIHYKLS (residues 1-14 of SEQ ID NO:48) of a peptide predicted to have antimicrobial activity is shown in yellow within (SEQ ID NO: 290).
Figure 16:
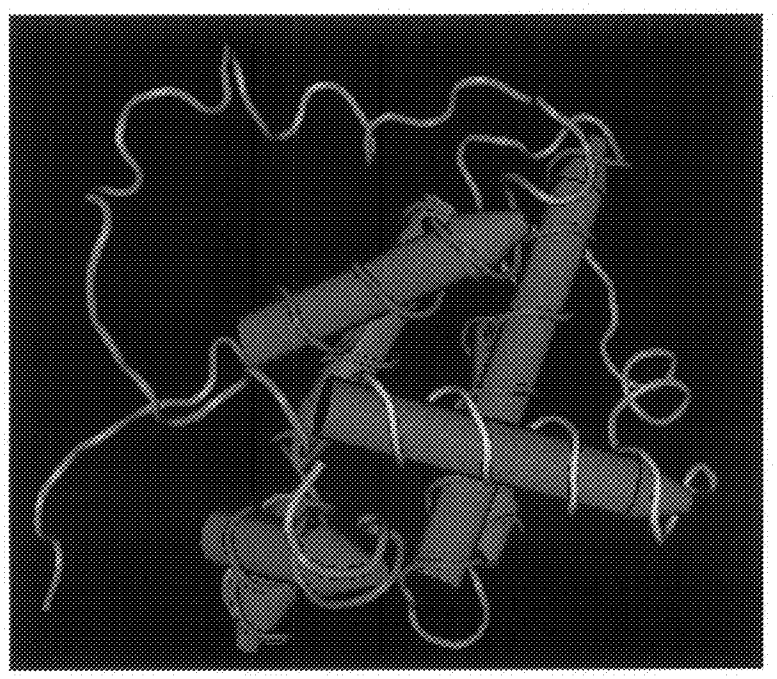
FIG. 16 shows a secondary structure diagram of human Bcl-2, isoform 1 or 2. Cylinders represent alpha helices. The colors are green for alpha helices, orange for beta strands, and blue for coils. The arrows on the helix cylinders point in the N-terminal to C-terminal direction. The amino acid sequence HLALRQAGDDFSRRYR having a peptide predicted to have antimicrobial activity (SEQ ID NO:53) is shown in yellow within (SEQ ID NO: 291).
Figure 17:
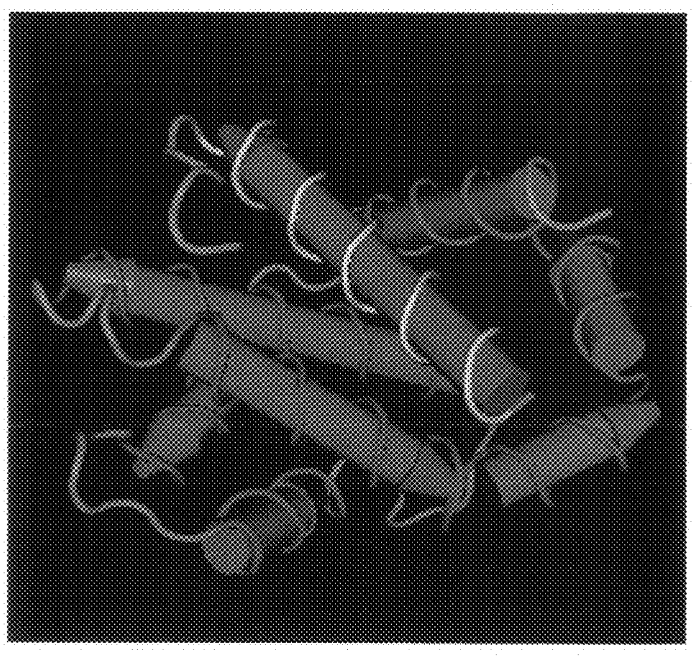
FIG. 17 shows a secondary structure diagram of human Bcl-xL. Cylinders represent alpha helices. The colors are green for alpha helices, orange for beta strands, and blue for coils. The arrows on the helix cylinders point in the N-terminal to C-terminal direction. The amino acid sequence SQSNRELVVDFLSYKLSQK (SEQ ID NO:288) of a peptide predicted to have antimicrobial activity is shown in yellow within (SEQ ID NO: 292). The amino acid sequence SQSNRELVVDFLSYKLSQK (SEQ ID NO:288) has also been identified as being conserved in multiple PCD-effector templates, including human Bcl-xL and Bcl-xβ, murine Bcl-xγ, and various related proteins.
Figure 18:
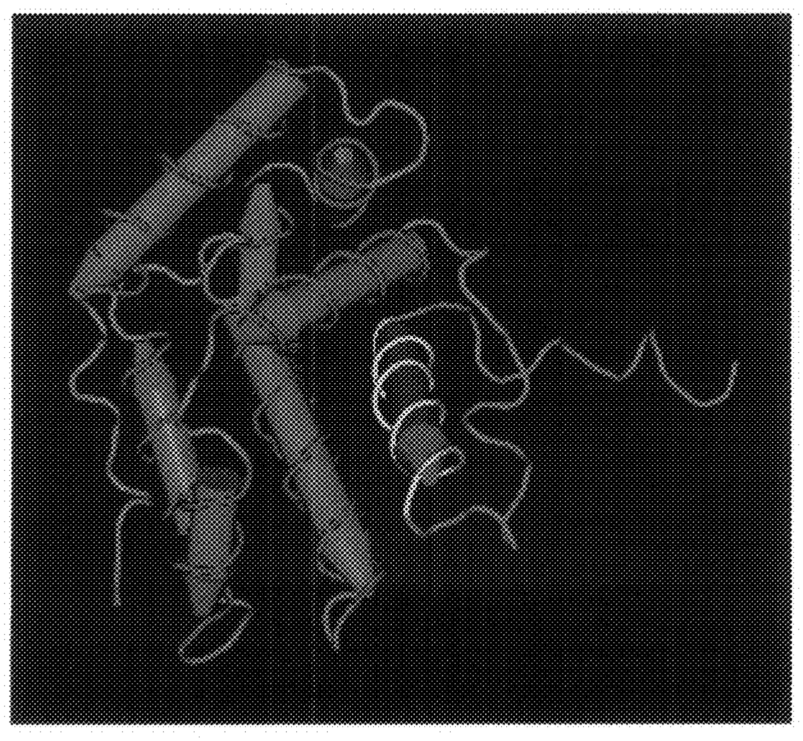
FIG. 18 shows a secondary structure diagram of human Bcl-W. Cylinders represent alpha helices. The colors are green for alpha helices, orange for beta strands, and blue for coils. The arrows on the helix cylinders point in the N-terminal to C-terminal direction. The amino acid sequence TRALVADFVGYKLRQK (residues 1-16 of SEQ ID NO:14) of a peptide predicted to have antimicrobial activity is shown in yellow within (SEQ ID NO: 293).
Figure 19:
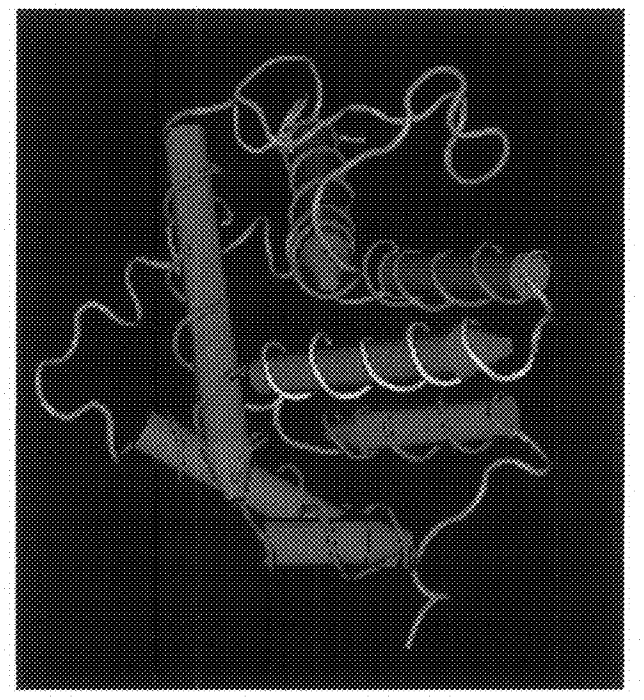
FIG. 19 shows a secondary structure diagram of human Bax. Cylinders represent alpha helices. The colors are green for alpha helices, orange for beta strands, and blue for coils. The arrows on the helix cylinders point in the N-terminal to C-terminal direction. The amino acid sequence RVVALFYFASKLVLKALCTK (residues 1-20 of SEQ ID NO:7) of a peptide predicted to have antimicrobial activity is shown in yellow within (SEQ ID NO: 294).
Figure 20:
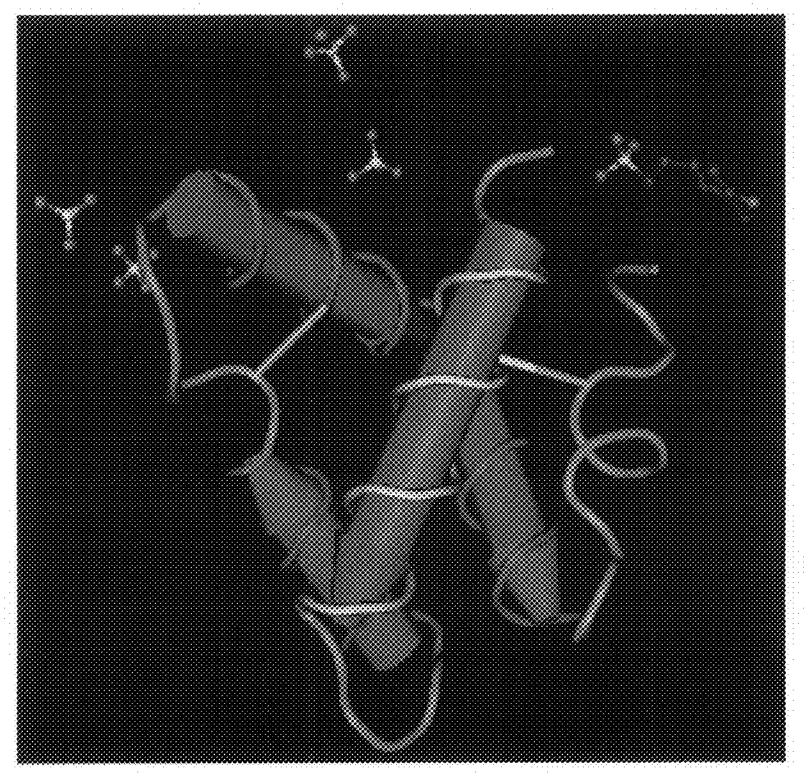
FIG. 20 shows a secondary structure diagram of human CTL Granulysin. Cylinders represent alpha helices. The colors are green for alpha helices, orange for beta strands, and blue for coils. The arrows on the helix cylinders point in the N-terminal to C-terminal direction. The amino acid sequence RDYRTCLTIVQKLKKM having a peptide predicted of have antimicrobial activity (residues 3-17 of SEQ ID NO:224) is shown in yellow within (SEQ ID NO: 295).
Figure 21:
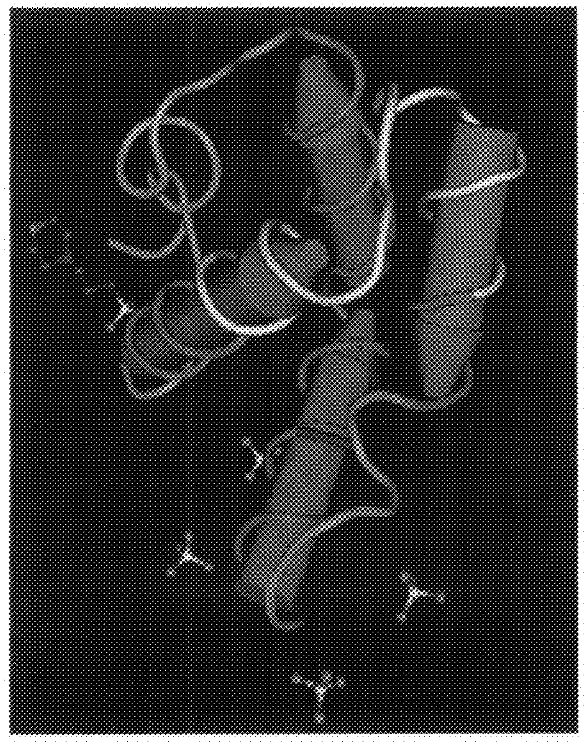
FIG. 21 shows secondary structure diagram of human CTL Granulysin. Cylinders represent alpha helices. The colors are green for alpha helices, orange for beta strands, and blue for coils. The arrows on the helix cylinders point in the N-terminal to C-terminal direction. The amino acid sequence QKLKKIVIVDKPTQRSVSN (SEQ ID NO:289) of a peptide predicted to have antimicrobial activity is shown in yellow within (SEQ ID NO: 296).
Figure 22:
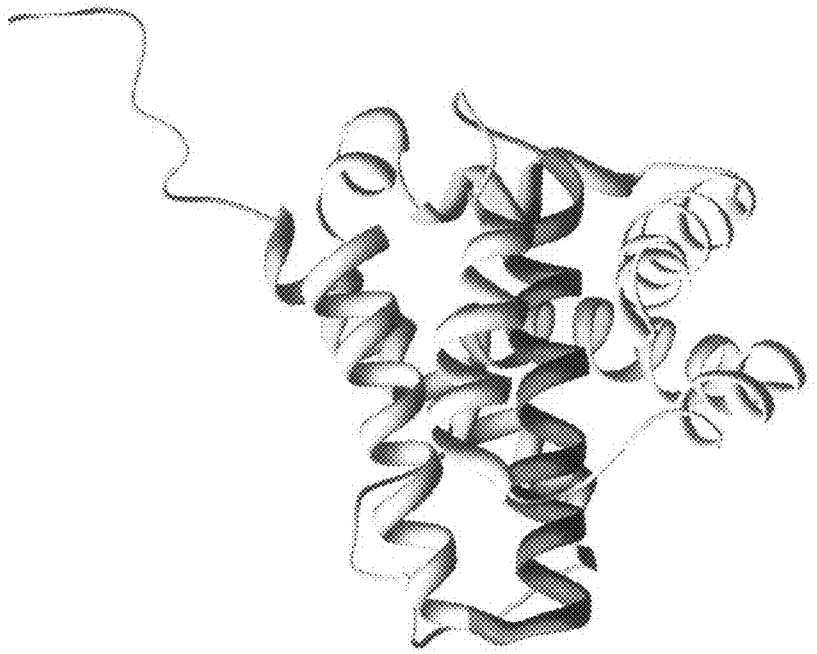
FIG. 22 shows a secondary structure ribbon diagram of human Bax (1F16) protein. Helix-1, residues 104-129 are represented in red.
Figure 23:
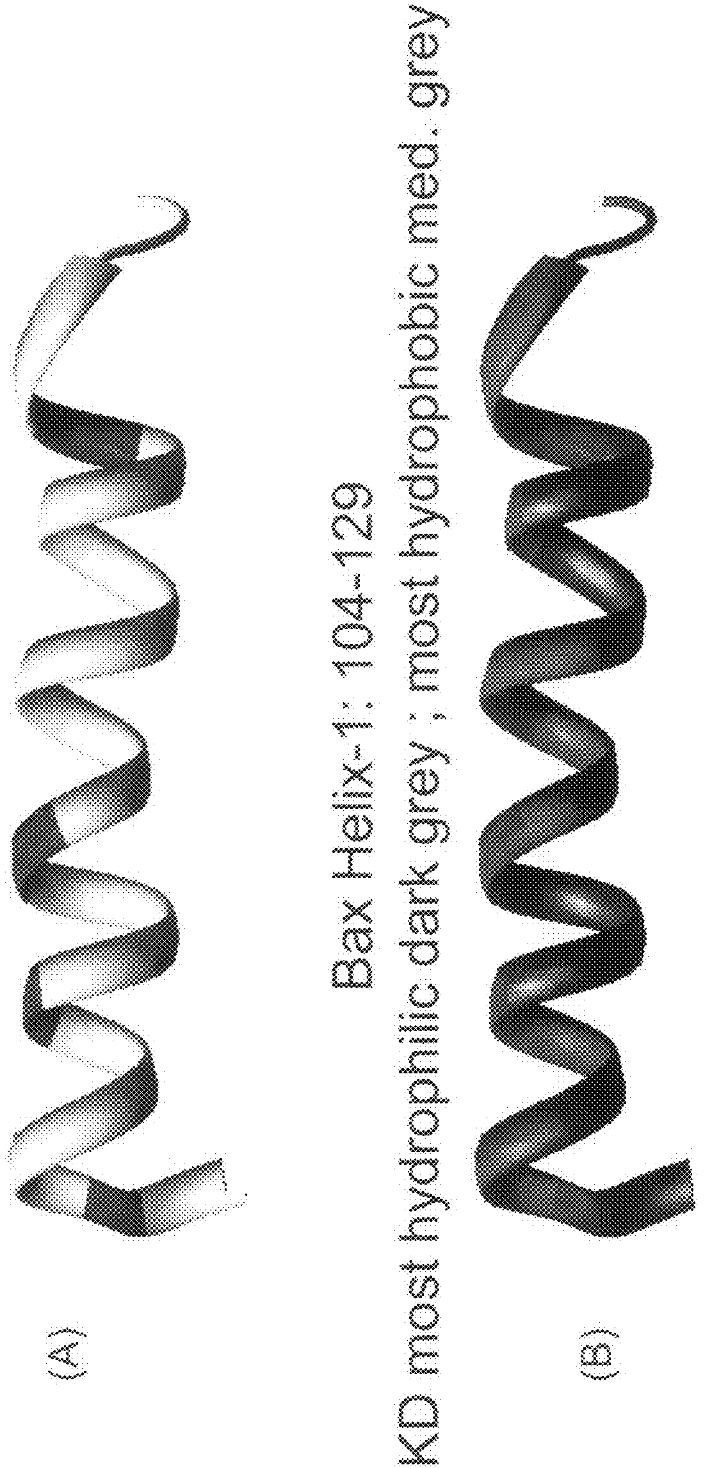
FIG. 23 shows a secondary structure ribbon diagram of human Bax Helix-1, residues 104-129. Structure A shows the location of positive residues in blue. Structure B shows the most hydrophilic residues in blue and the most hydrophobic in brown.
Figure 24:
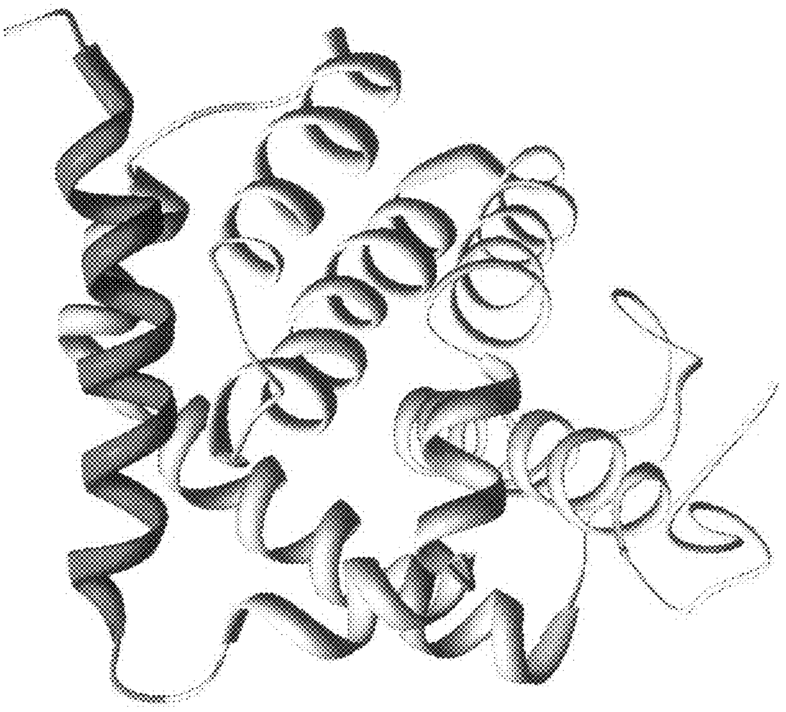
FIG. 24 shows a secondary structure ribbon diagram of human Bax (1F16) protein. Helix-2, residues 168-190 are represented in red.
Figure 25:
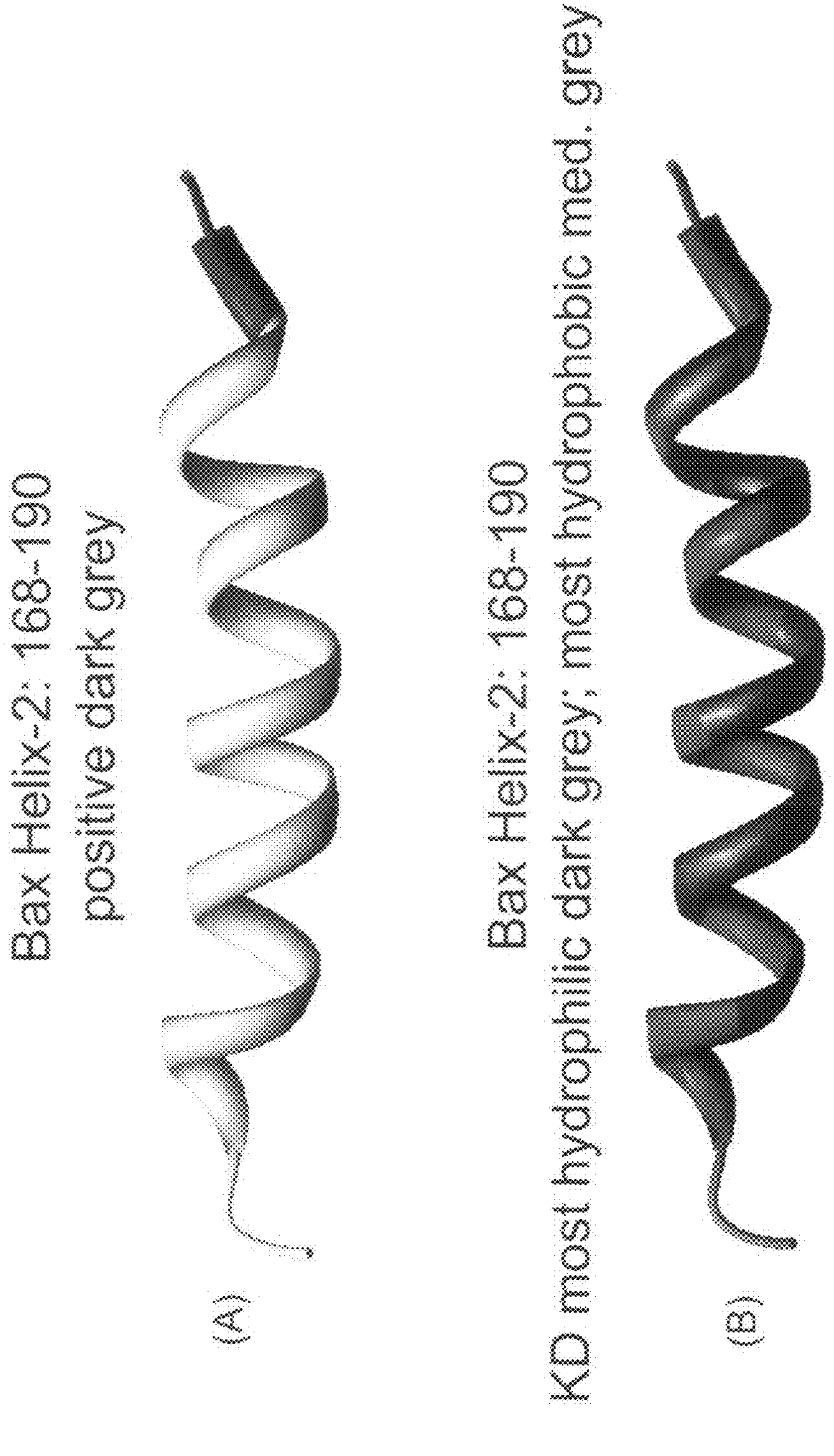
FIG. 25 shows a secondary structure ribbon diagram of human Bax Helix-2, residues 168-190. Structure A shows the location of positive residues in blue. Structure B shows the most hydrophilic residues as represented in blue and the most hydrophobic residues as represented in brown.
Figure 26:
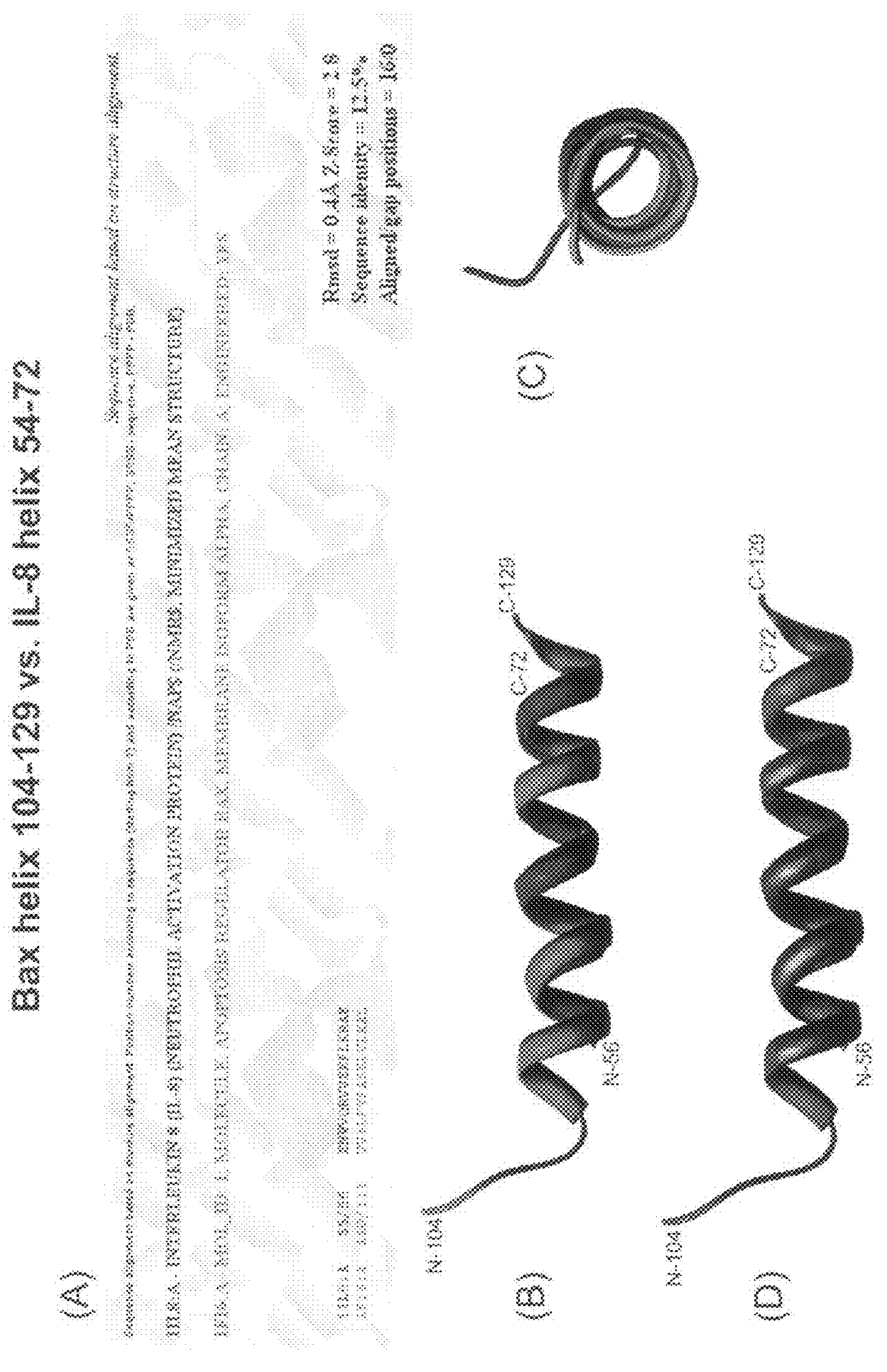
FIG. 26, panels A-D, show three dimensional alignments between human Bax Helix-1, residues 104-129 vs. IL-8 helix, residues 55-72. For the alignment analyses, comparative sequences of X and Y length are entered, and the computation prioritizes which span of those length are most comparable. Panel A shows a sequence alignment based on the following structural alignment. Panel B shows a horizontal view of a ribbon diagram alignment between Bax, residues 104-129 (Red) and IL-8, residues 56-72 (Blue), whereas panel C shows an axial view of the same alignment. Panel D shows the same ribbon alignment as panel B, wherein the most hydrophilic residues are represented in blue and the most hydrophobic residues are represented in brown. Also included in the figure are the root mean square deviation (RMSD) score and other results from the alignment.
Figure 27:
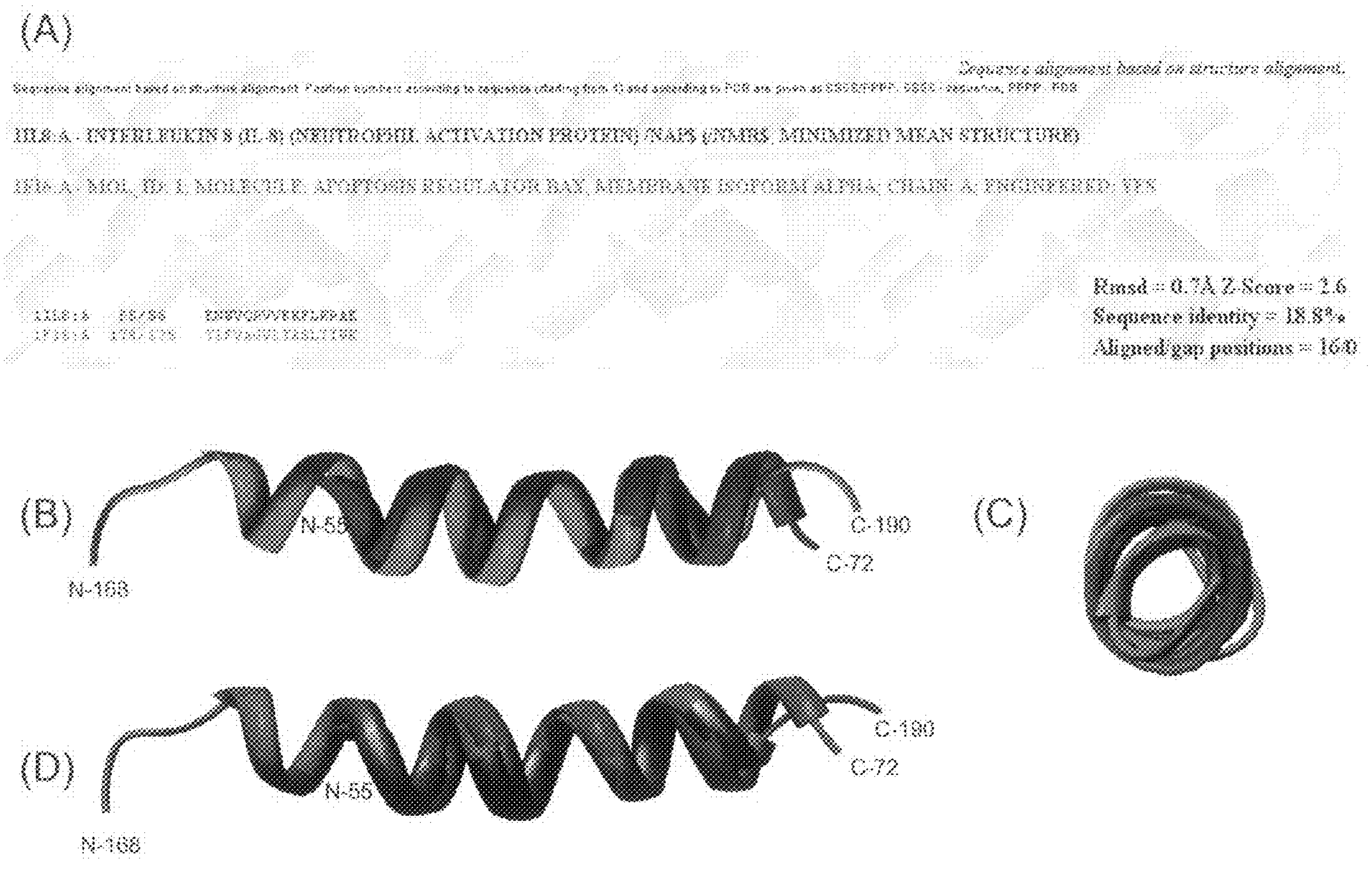
FIG. 27, panels A-D, show three dimensional alignments between human Bax helix, residues 168-190 vs. IL-8 helix, residues 55-72. For the alignment analyses, comparative sequences of X and Y length are entered, and the computation prioritizes which span of those length are most comparable. Panel A shows a sequence alignment based on the following structural alignment. Panel B shows a horizontal view of a ribbon diagram alignment between Bax, residues 168-190 (Red) and IL-8, residues 55-72 (Blue), whereas panel C shows an axial view of the same alignment. Panel D shows the same ribbon alignment as panel B, wherein the most hydrophilic residues are represented in blue and the most hydrophobic residues are represented in brown. Also included in the figure are the root mean square deviation (RMSD) score and other results from the alignment.
Figure 28:
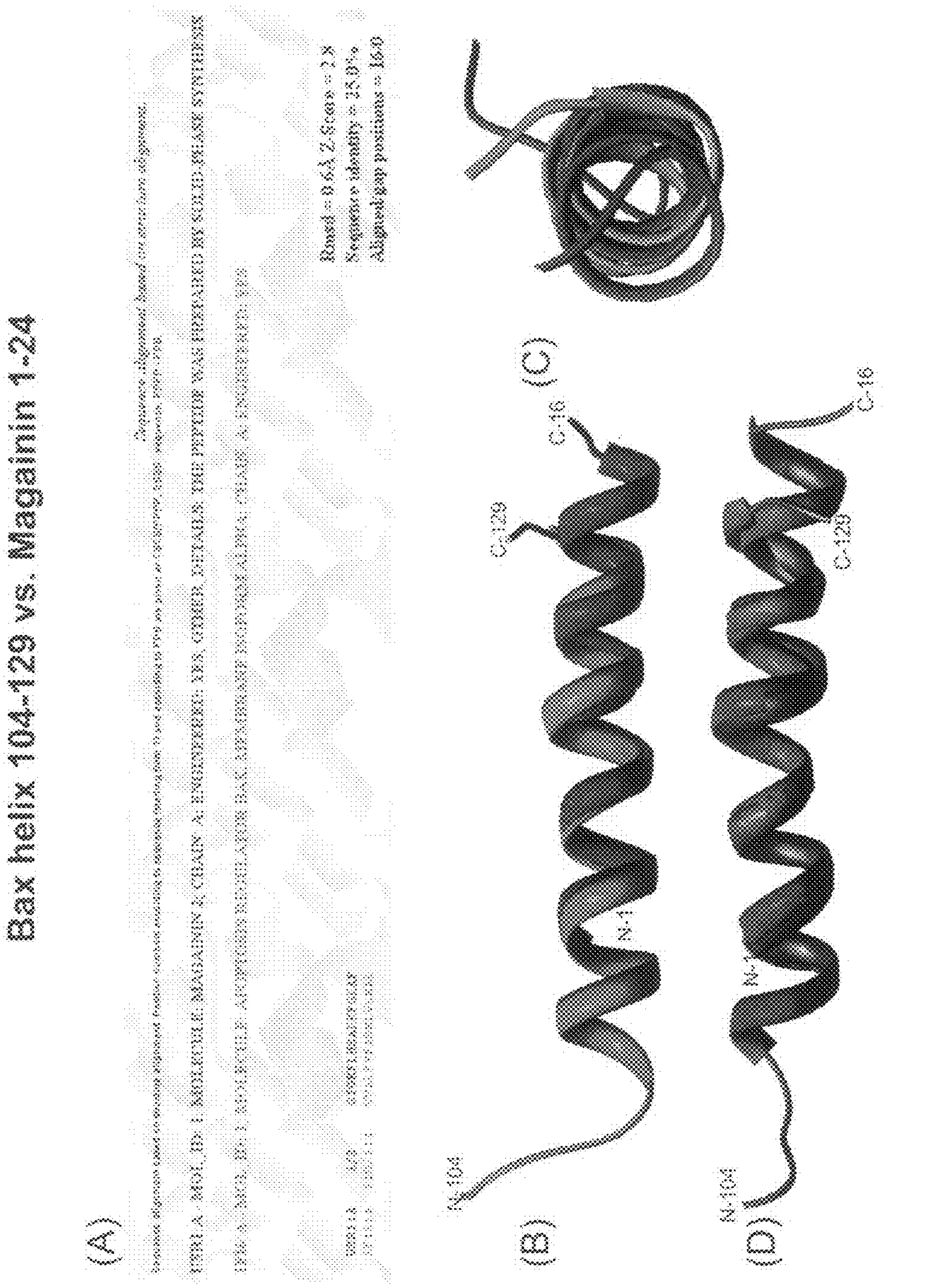
FIG. 28, panels A-D, show three dimensional alignments between human Bax helix, residues 104-129 vs. magainin residues 1-16. For the alignment analyses, comparative sequences of X and Y length are entered, and the computation prioritizes which span of those length are most comparable. Panel A shows a sequence alignment based on the following structural alignment. Panel B shows a horizontal view of a ribbon diagram alignment between Bax, residues 104-129 (Red) and magainin, residues 1-16 (Blue), whereas panel C shows an axial view of the same alignment. Panel D shows the same ribbon alignment as panel B, wherein the most hydrophilic residues are represented in blue and the most hydrophobic residues are represented in brown. Also included in the figure are the root mean square deviation (RMSD) score and other results from the alignment.
Figure 29:
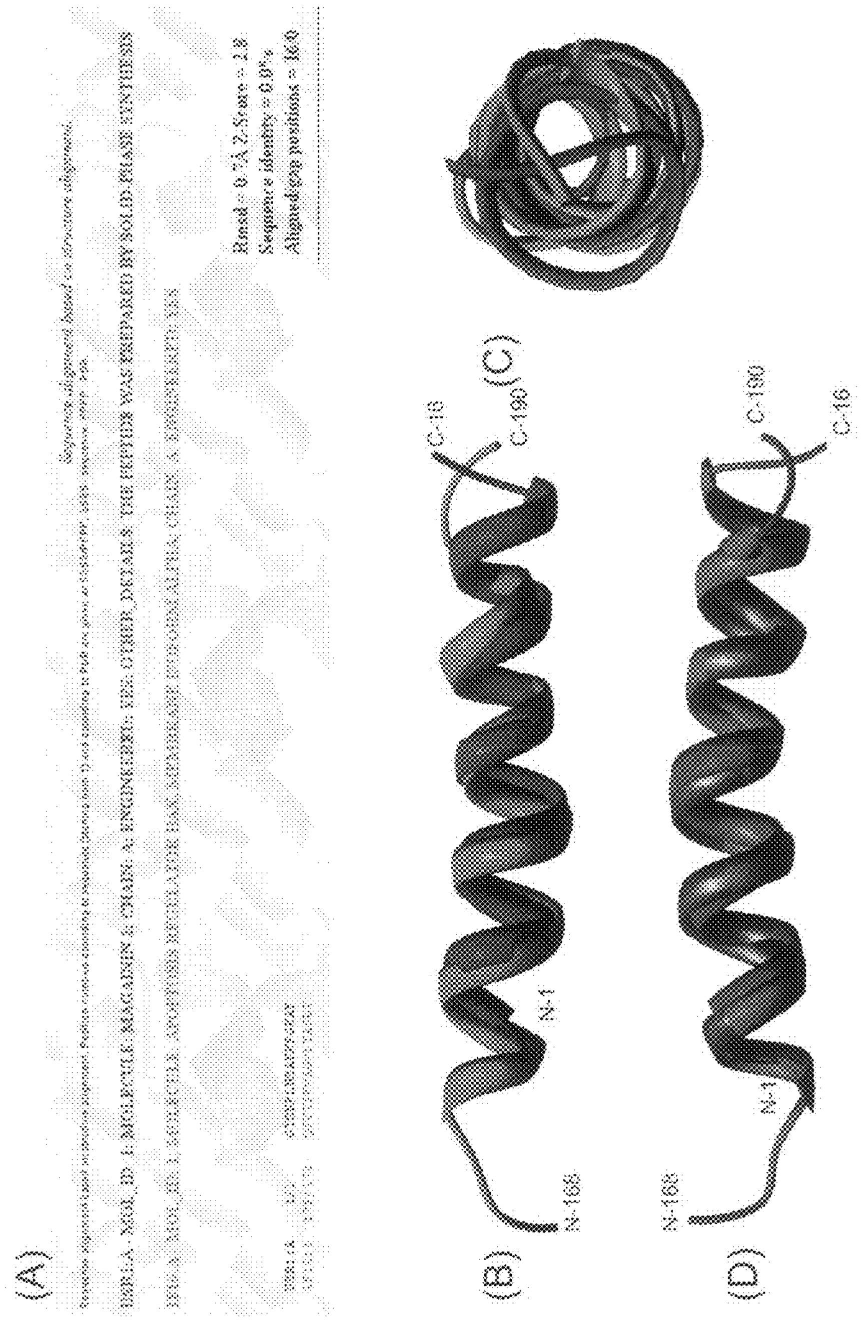
FIG. 29, panels A-D, show three dimensional alignments between human Bax helix, residues 168-190 vs. magainin residues 1-16. For the alignment analyses, comparative sequences of X and Y length are entered, and the computation prioritizes which span of those length are most comparable. Panel A shows a sequence alignment based on the following structural alignment. Panel B shows a horizontal view of a ribbon diagram alignment between Bax, residues 168-190 (Red) and magainin, residues 1-16 (Blue), whereas panel C shows an axial view of the same alignment. Panel D shows the same ribbon alignment as panel B, wherein the most hydrophilic residues are represented in blue and the most hydrophobic residues are represented in brown. Also included in the figure are the root mean square deviation (RMSD) score and other results from the alignment.
Figure 30:
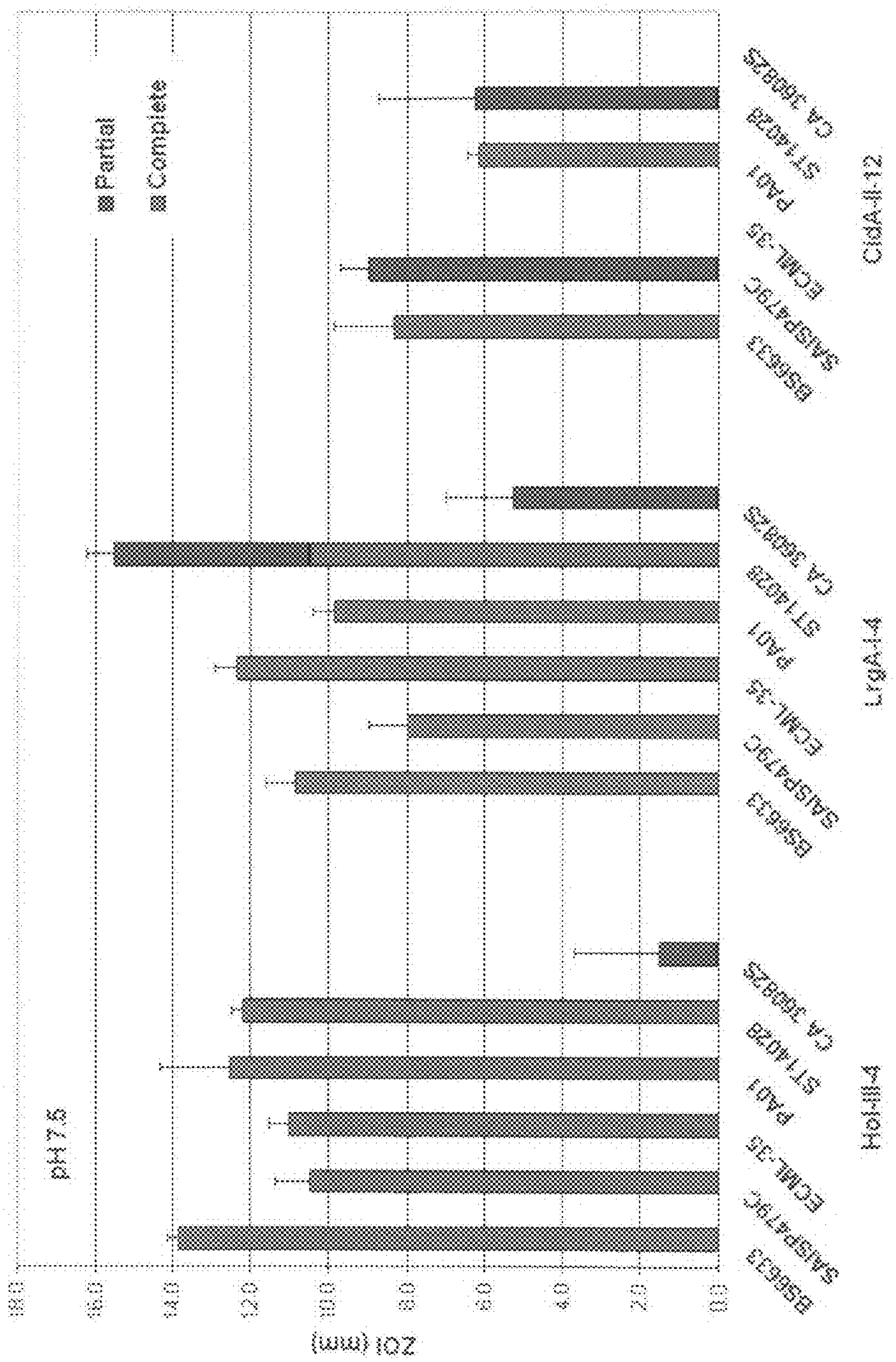
FIG. 30 shows a histogram of the antimicrobial spectra of exemplary peptides Hol-III-4, LrgA-I-4 and CidA-II-12 against pathogenic bacteria and fungi at pH 7.5. The size of the complete zone of inhibition (ZOI) is represented by a blue bar, whereas the size of the partial (ZOI) is represented by a red bar. See Tables 22 and 23 for peptide and microorganism designations.
Figure 31:
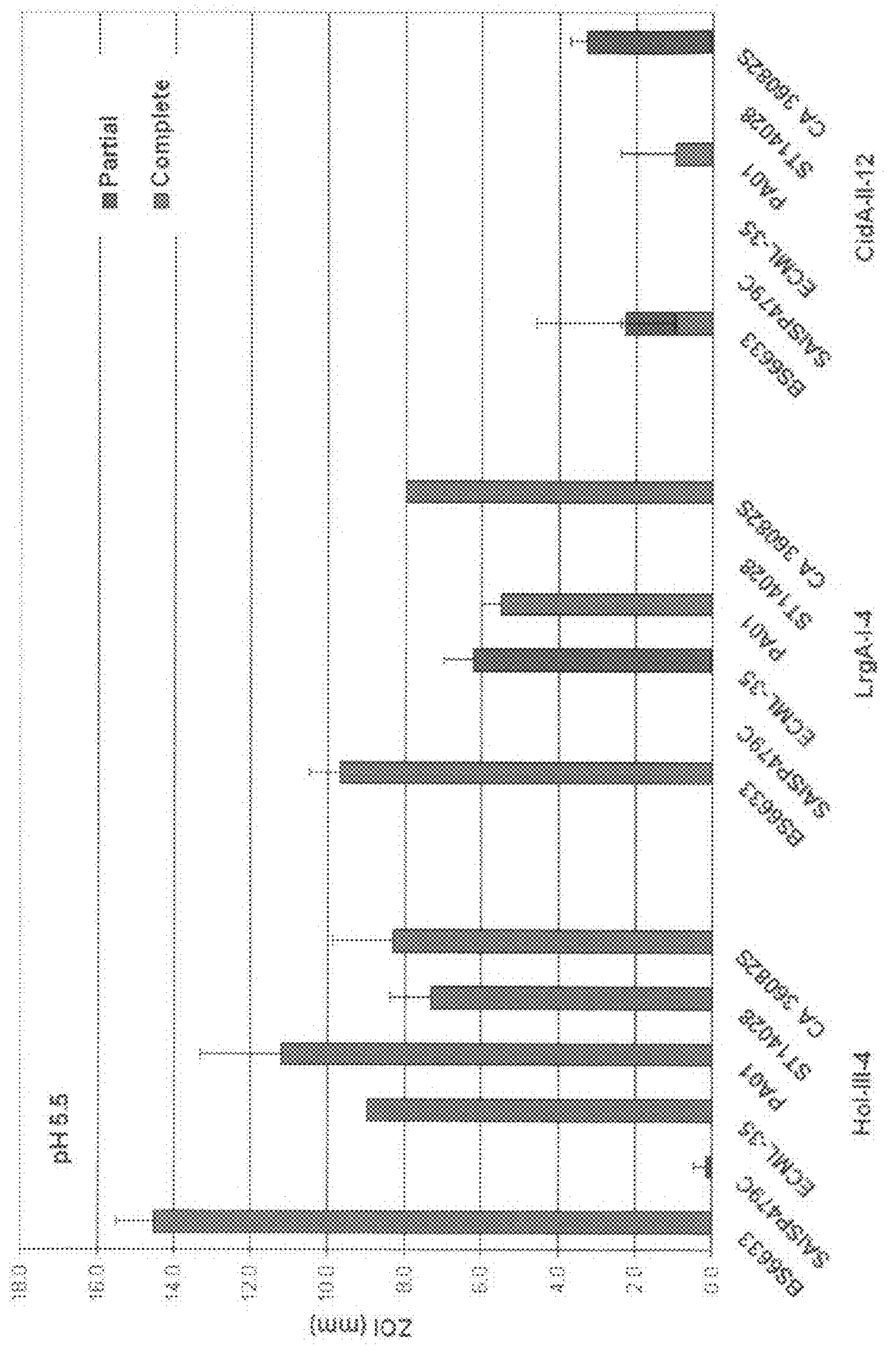
FIG. 31 shows a histogram of the antimicrobial spectra of exemplary peptides Hol-III-4, LrgA-I-4 and CidA-II-12 against pathogenic bacteria and fungi at pH 5.5. The size of the complete zone of inhibition (ZOI) is represented by a blue bar, whereas the size of the partial (ZOI) is represented by a red bar. See Tables 22 and 23 for peptide and microorganism designations.
Figure 32:
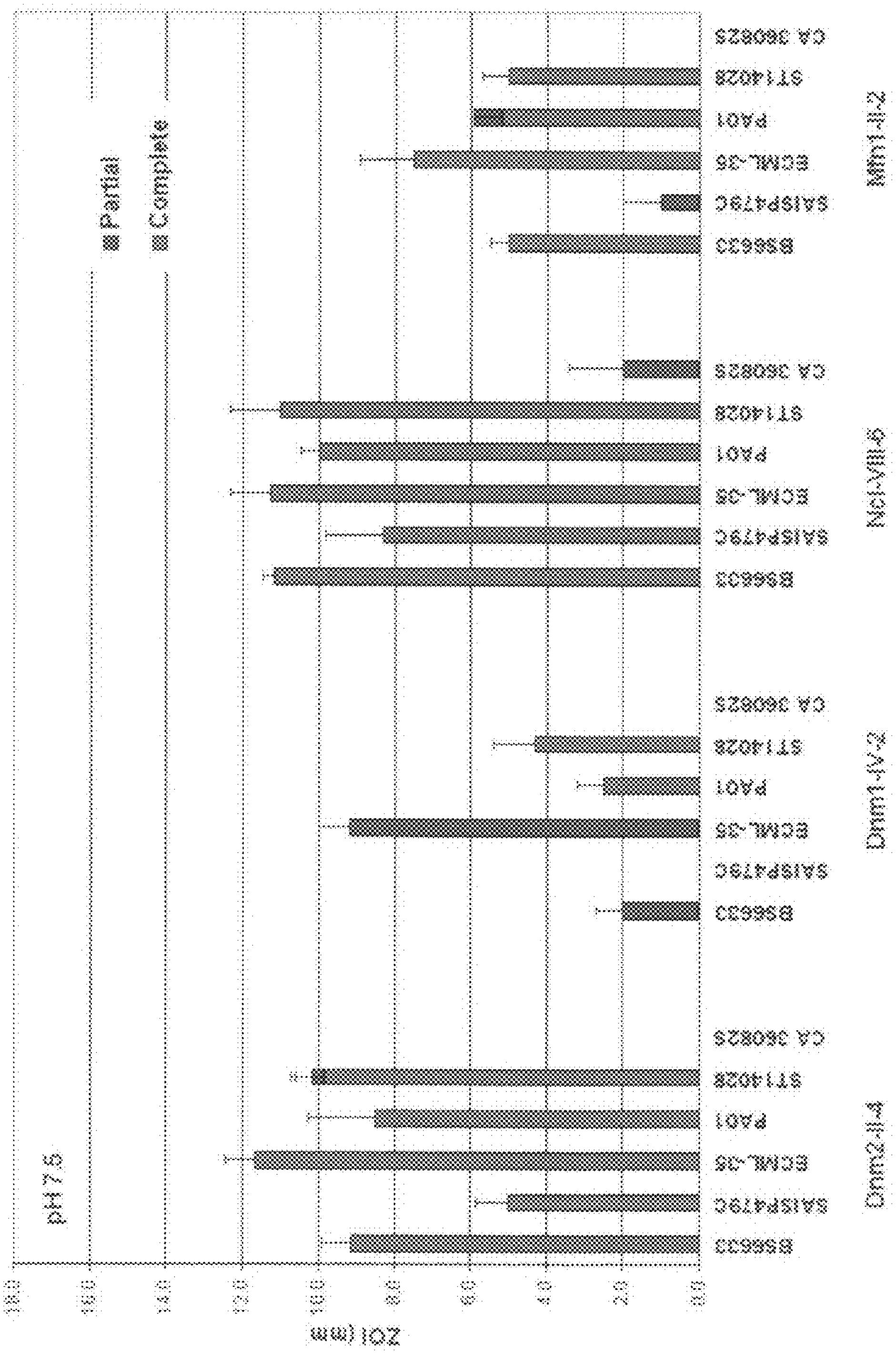
FIG. 32 shows a histogram of the antimicrobial spectra of exemplary peptides Dnm2-II-4, Dnm1-IV-2, Ncl-VIII-6 and Mfn1-II-2 against pathogenic bacteria and fungi at pH 7.5. The size of the complete zone of inhibition (ZOI) is represented by a blue bar, whereas the size of the partial (ZOI) is represented by a red bar. See Tables 22 and 23 for peptide and microorganism designations.
Figure 33:
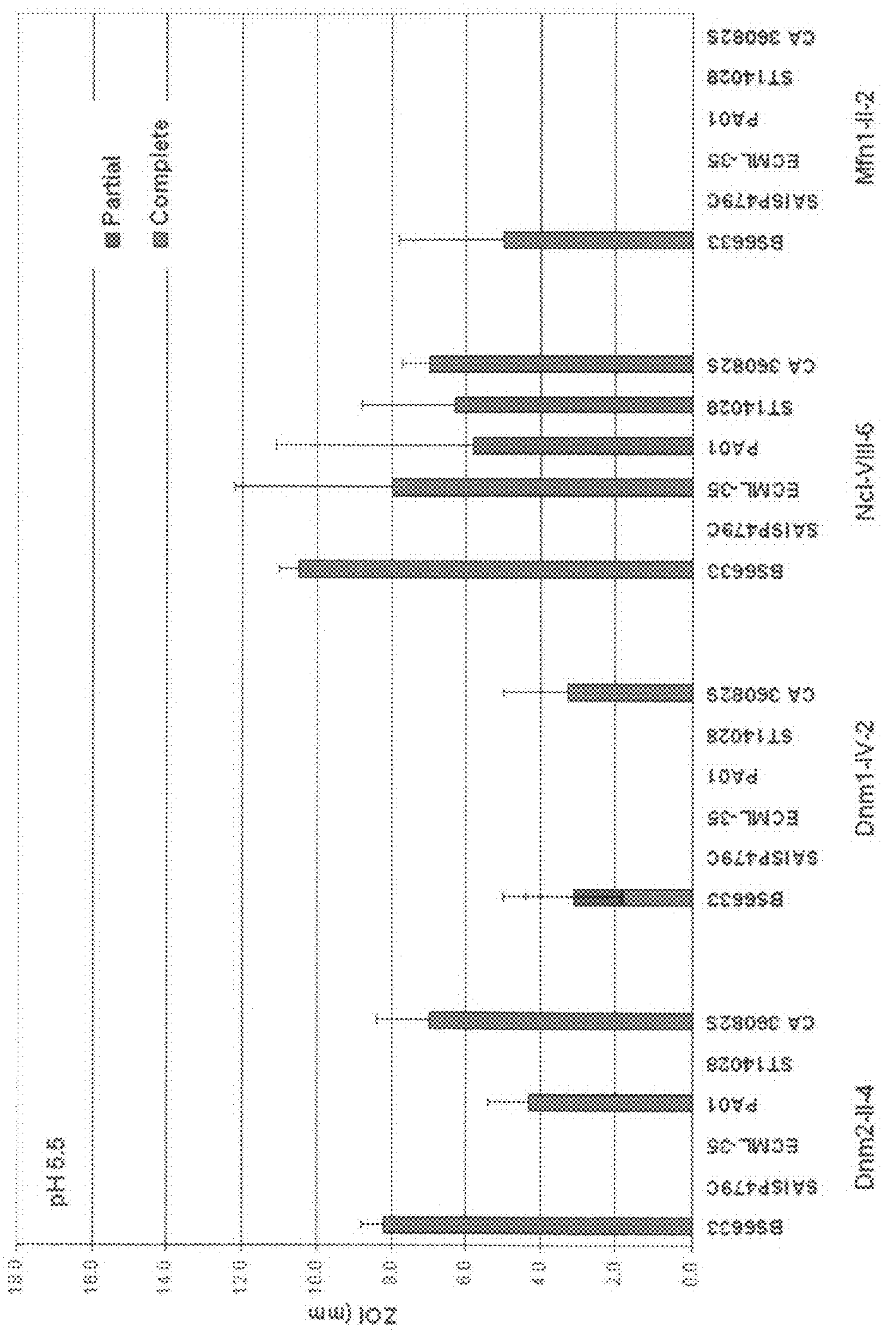
FIG. 33 shows a histogram of the antimicrobial spectra of exemplary peptides Dnm2-II-4, Dnm1-IV-2, Ncl-VIII-6 and Mfn1-II-2 against pathogenic bacteria and fungi at pH 5.5. The size of the complete zone of inhibition (ZOI) is represented by a blue bar, whereas the size of the partial (ZOI) is represented by a red bar. See Tables 22 and 23 for peptide and microorganism designations.
Figure 34:
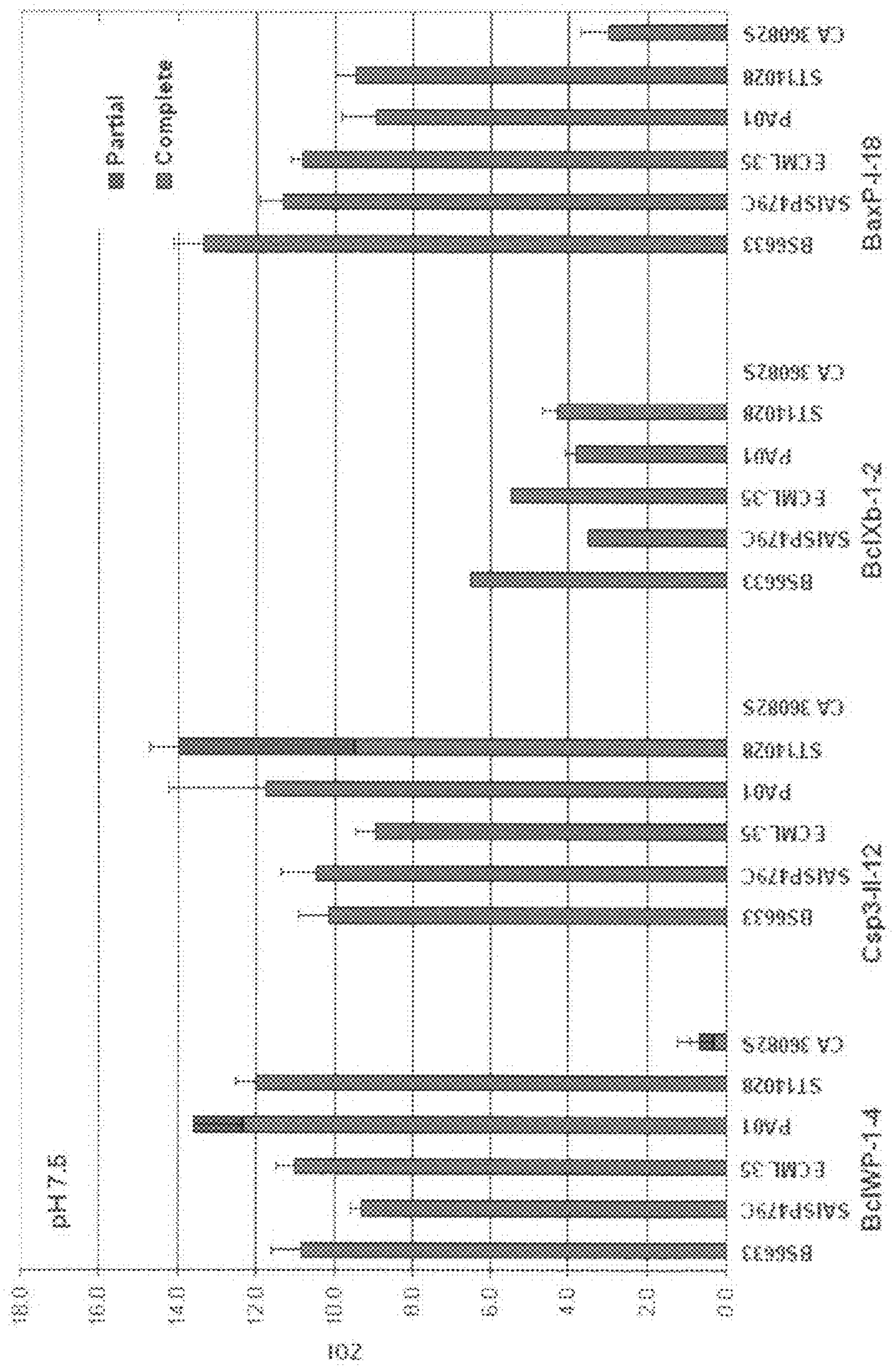
FIG. 34 shows a histogram of the antimicrobial spectra of exemplary peptides BclWP-I-4, Csp3-II-12, BclXb-I-2 and BaxP-I-18 against pathogenic bacteria and fungi at pH 7.5. The size of the complete zone of inhibition (ZOI) is represented by a blue bar, whereas the size of the partial (ZOI) is represented by a red bar. See Tables 22 and 23 for peptide and microorganism designations.
Figure 35:
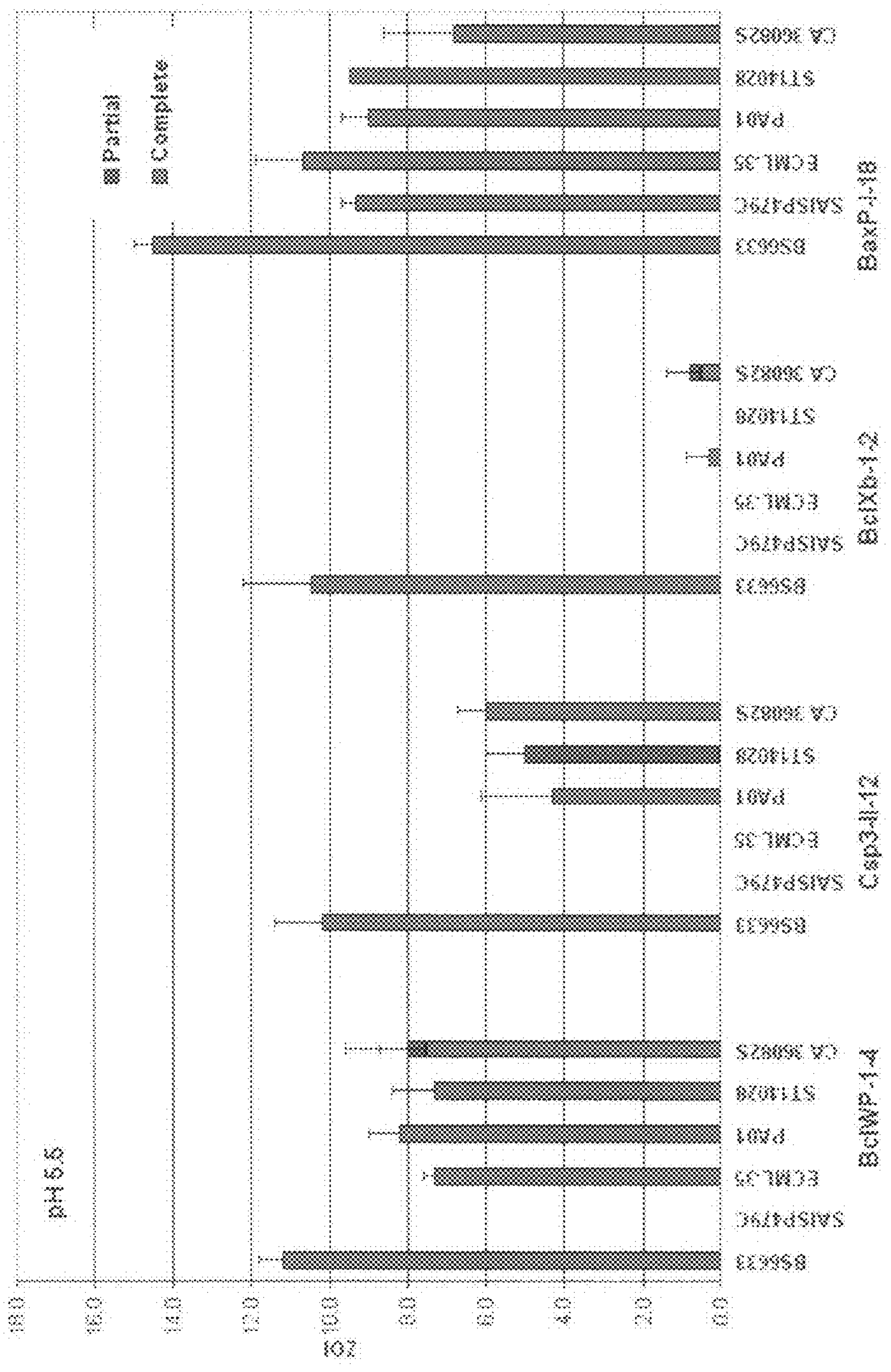
FIG. 35 shows a histogram of the antimicrobial spectra of exemplary peptides BclWP-I-4, Csp3-II-12, BclXb-I-2 and BaxP-I-18 against pathogenic bacteria and fungi at pH 5.5. The size of the complete zone of inhibition (ZOI) is represented by a blue bar, whereas the size of the partial (ZOI) is represented by a red bar. See Tables 22 and 23 for peptide and microorganism designations.
Figure 36:
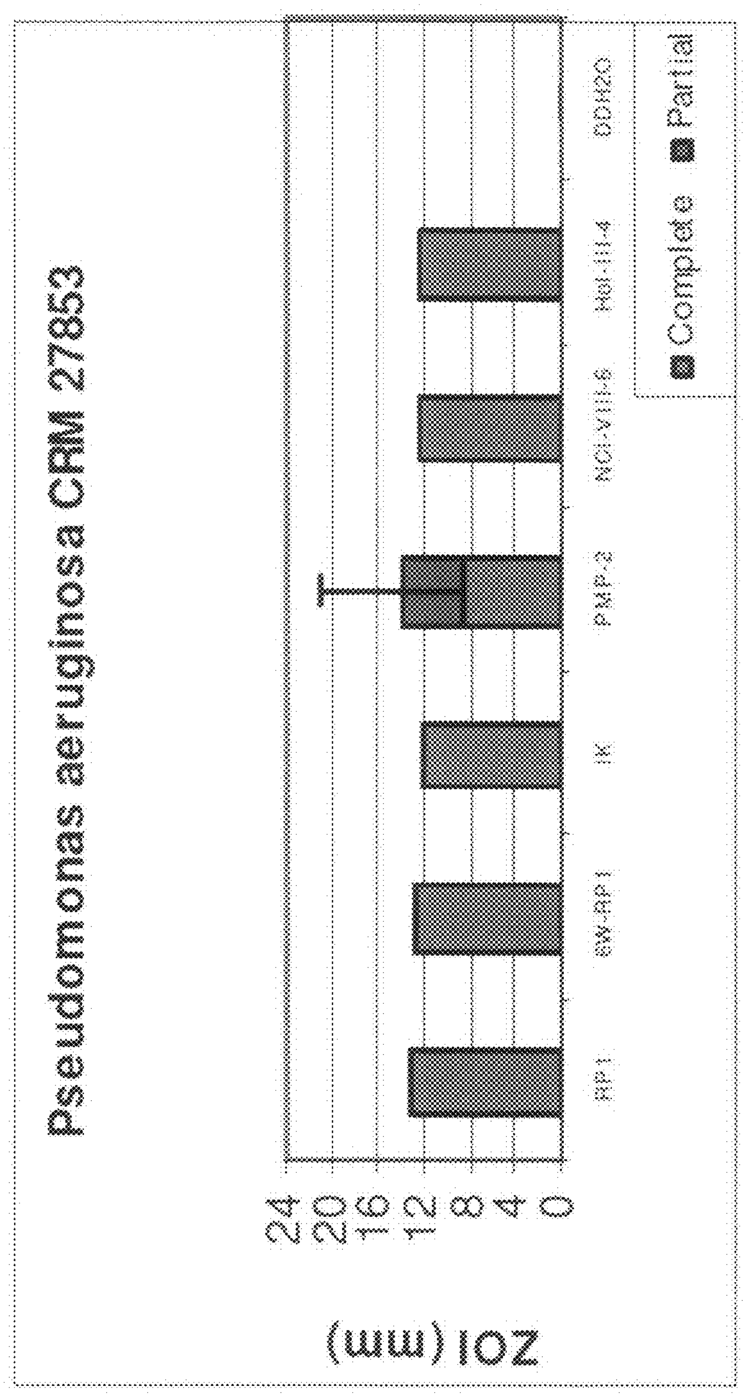
FIG. 36 shows a histogram of the antimicrobial spectra of exemplary peptides Hol-III-4 (SEQ ID NO. 268) and NCl-VIII-6 (SEQ ID NO. 152) against *Pseudomonas aeruginosa* CRM27853 at pH 5.5. Positive control peptides RP1, 6W-RP1, IK and PMP-2, whereas the negative control of double-distilled water (DDH2O) are also shown. The size of the complete zone of inhibition (ZOI) is represented by a blue bar, whereas the size of the partial (ZOI) is represented by a red bar.
Figure 37:
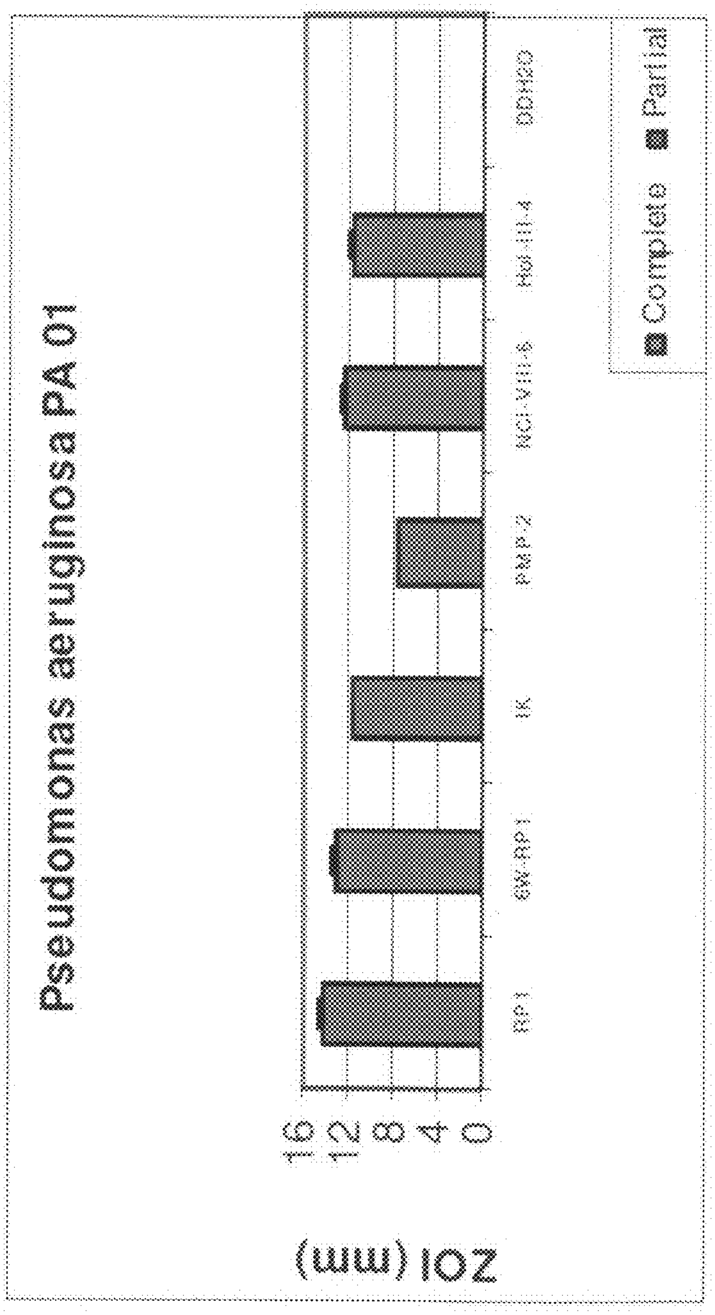
FIG. 37 shows a histogram of the antimicrobial spectra of exemplary peptides Hol-III-4 (SEQ ID NO. 268) and NCl-VIII-6 (SEQ ID NO. 152) against *Pseudomonas aeruginosa* PA 01 at pH 5.5. Positive control peptides RP1, 6W-RP1, IK and PMP-2, whereas the negative control of double-distilled water (DDH2O) are also shown. The size of the complete zone of inhibition (ZOI) is represented by a blue bar, whereas the size of the partial (ZOI) is represented by a red bar.
Figure 38:
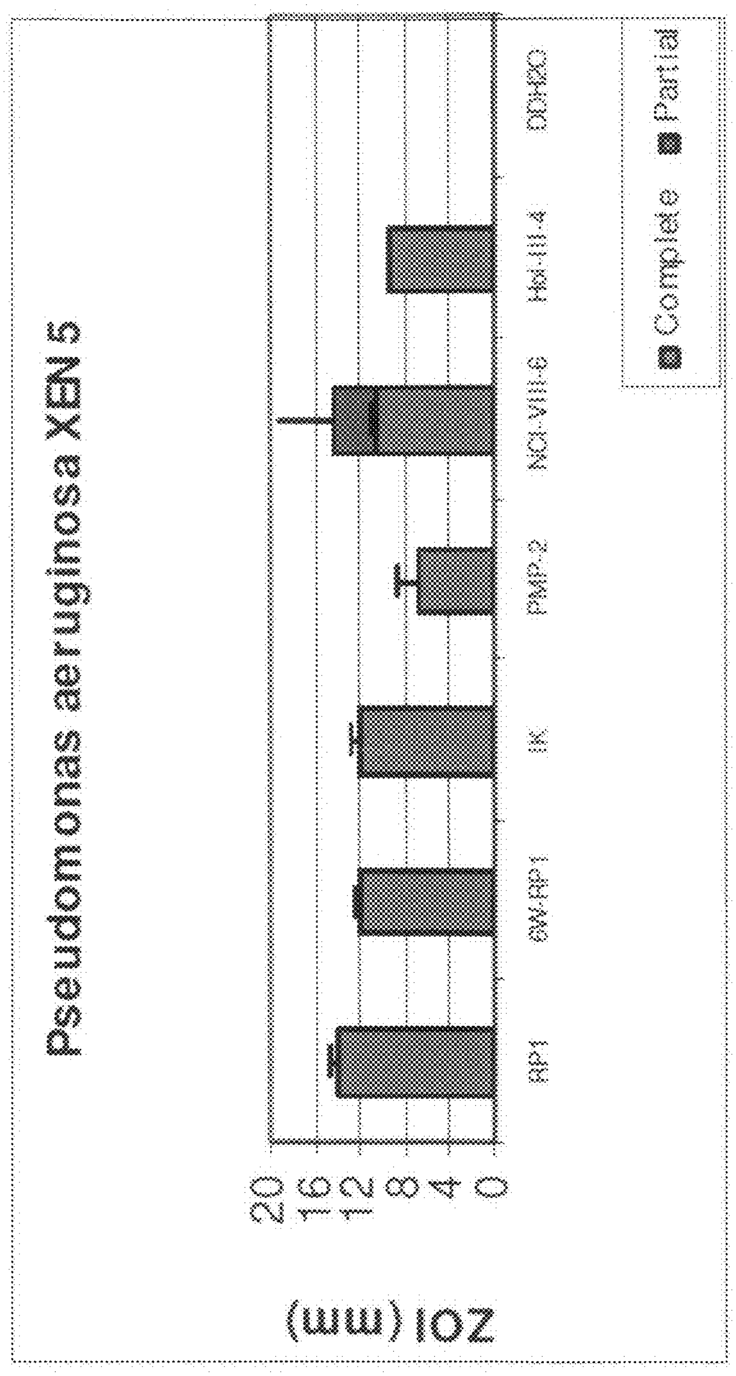
FIG. 38 shows a histogram of the antimicrobial spectra of exemplary peptides Hol-III-4 (SEQ ID NO. 268) and NCl-VIII-6 (SEQ ID NO. 152) against *Pseudomonas aeruginosa* XEN 5 at pH 5.5. Positive control peptides RP1, 6W-RP1, IK and PMP-2, whereas the negative control of double-distilled water (DDH2O) are also shown. The size of the complete zone of inhibition (ZOI) is represented by a blue bar, whereas the size of the partial (ZOI) is represented by a red bar.
Figure 39:
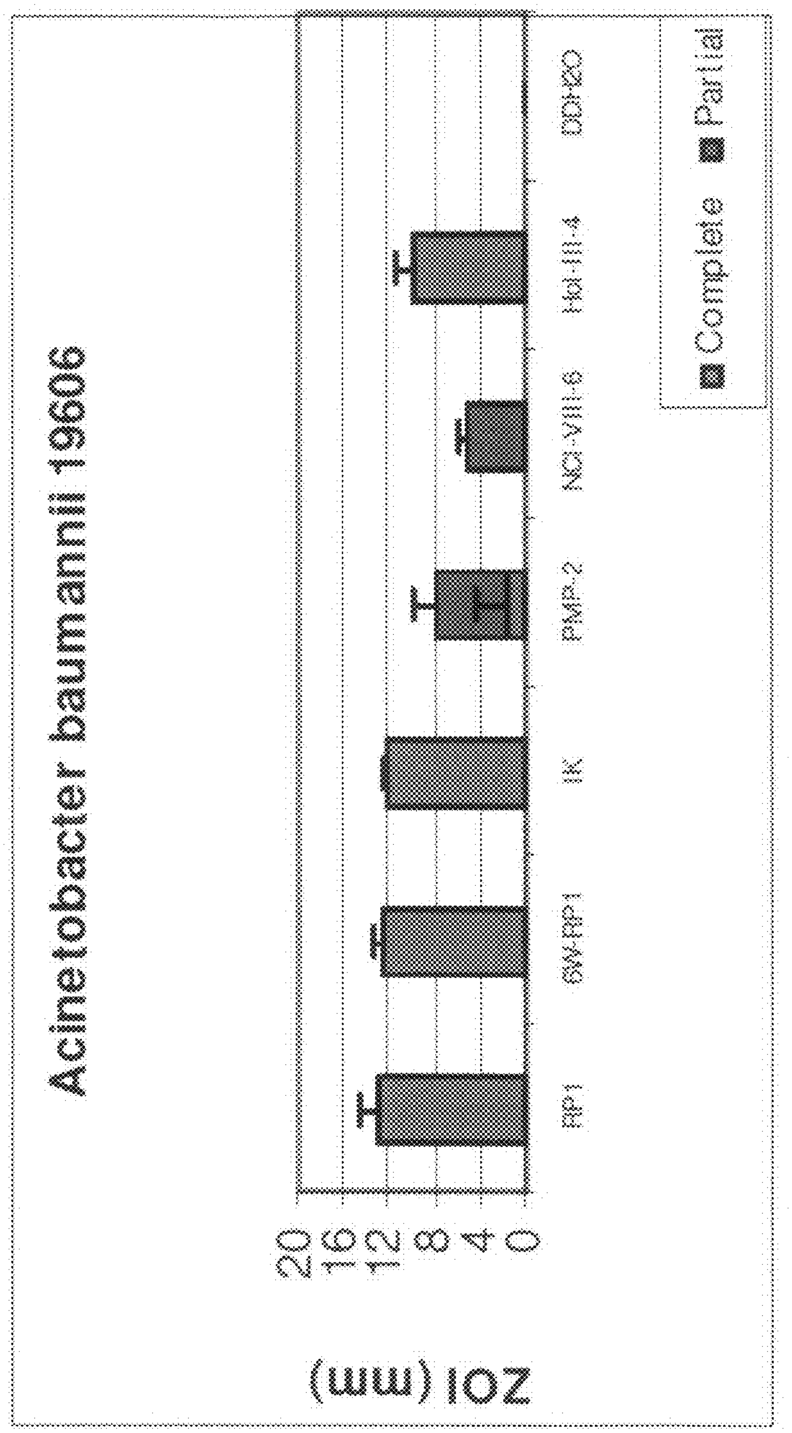
FIG. 39 shows a histogram of the antimicrobial spectra of exemplary peptides Hol-III-4 (SEQ ID NO. 268) and NCl-VIII-6 (SEQ ID NO. 152) against *Acinetobacter baumannii* 19606 at pH 5.5. Positive control peptides RP1, 6W-RP1, IK and PMP-2, whereas the negative control of double-distilled water (DDH2O) are also shown. The size of the complete zone of inhibition (ZOI) is represented by a blue bar, whereas the size of the partial (ZOI) is represented by a red bar.
Figure 40:
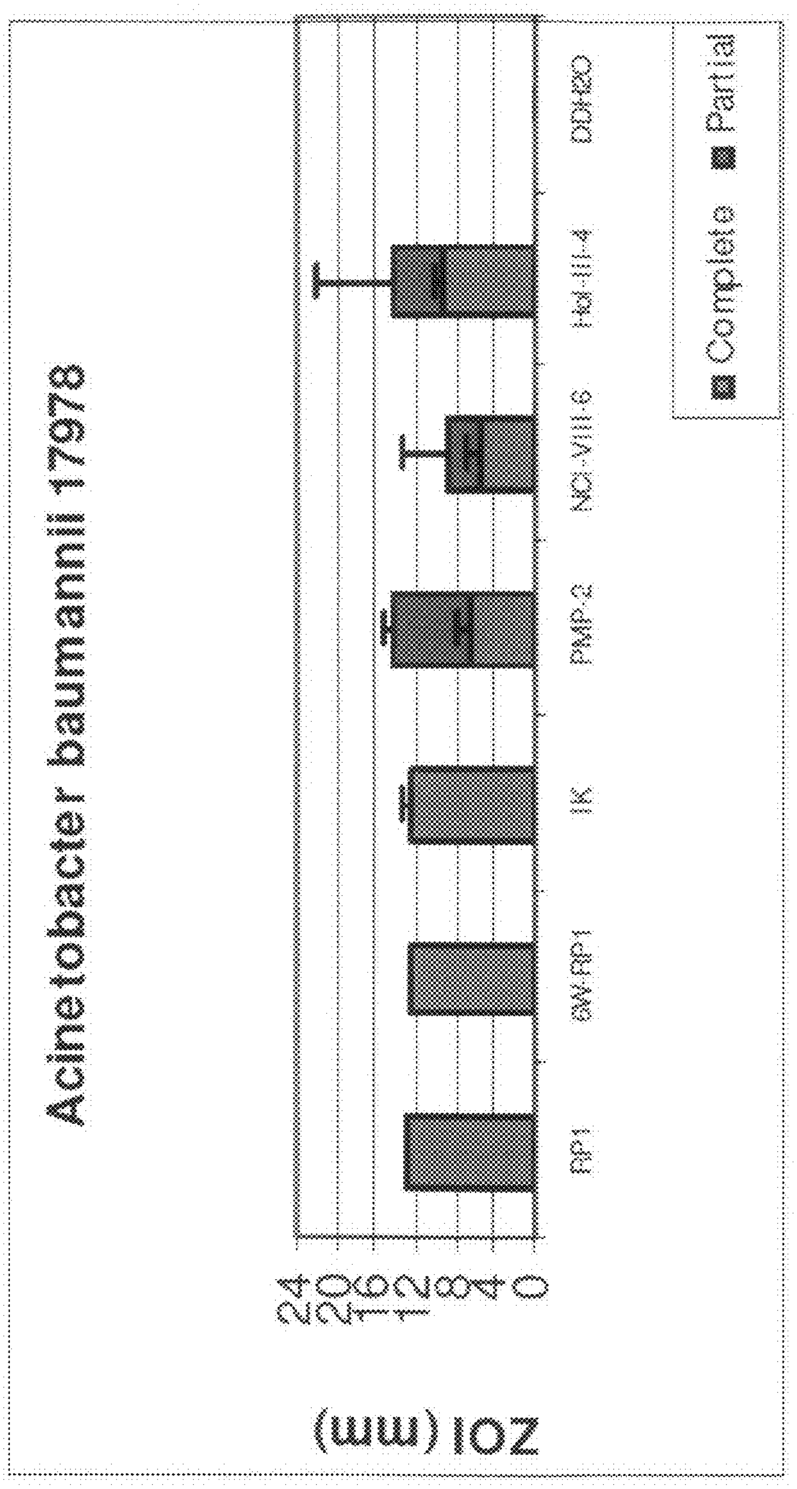
FIG. 40 shows a histogram of the antimicrobial spectra of exemplary peptides Hol-III-4 (SEQ ID NO. 268) and NCl-VIII-6 (SEQ ID NO. 152) against *Acinetobacter baumannii* 17978 at pH 5.5. Positive control peptides RP1, 6W-RP1, IK and PMP-2, whereas the negative control of double-distilled water (DDH2O) are also shown. The size of the complete zone of inhibition (ZOI) is represented by a blue bar, whereas the size of the partial (ZOI) is represented by a red bar.
Figure 41:
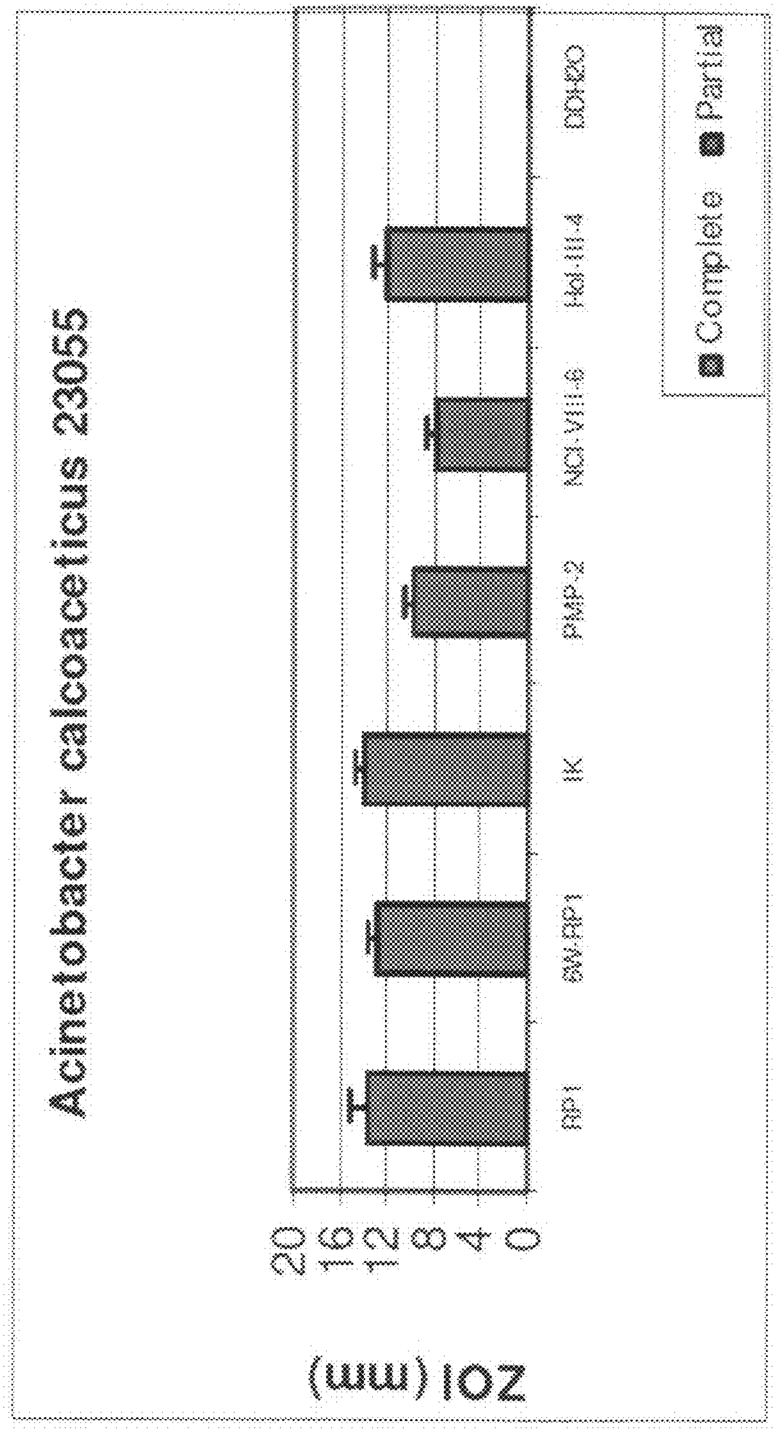
FIG. 41 shows a histogram of the antimicrobial spectra of exemplary peptides Hol-III-4 (SEQ ID NO. 268) and NCl-VIII-6 (SEQ ID NO. 152) against *Acinetobacter calcoaceticus* 23055 at pH 5.5. Positive control peptides RP1, 6W-RP1, IK and PMP-2, whereas the negative control of double-distilled water (DDH2O) are also shown. The size of the complete zone of inhibition (ZOI) is represented by a blue bar, whereas the size of the partial (ZOI) is represented by a red bar.
Figure 42:
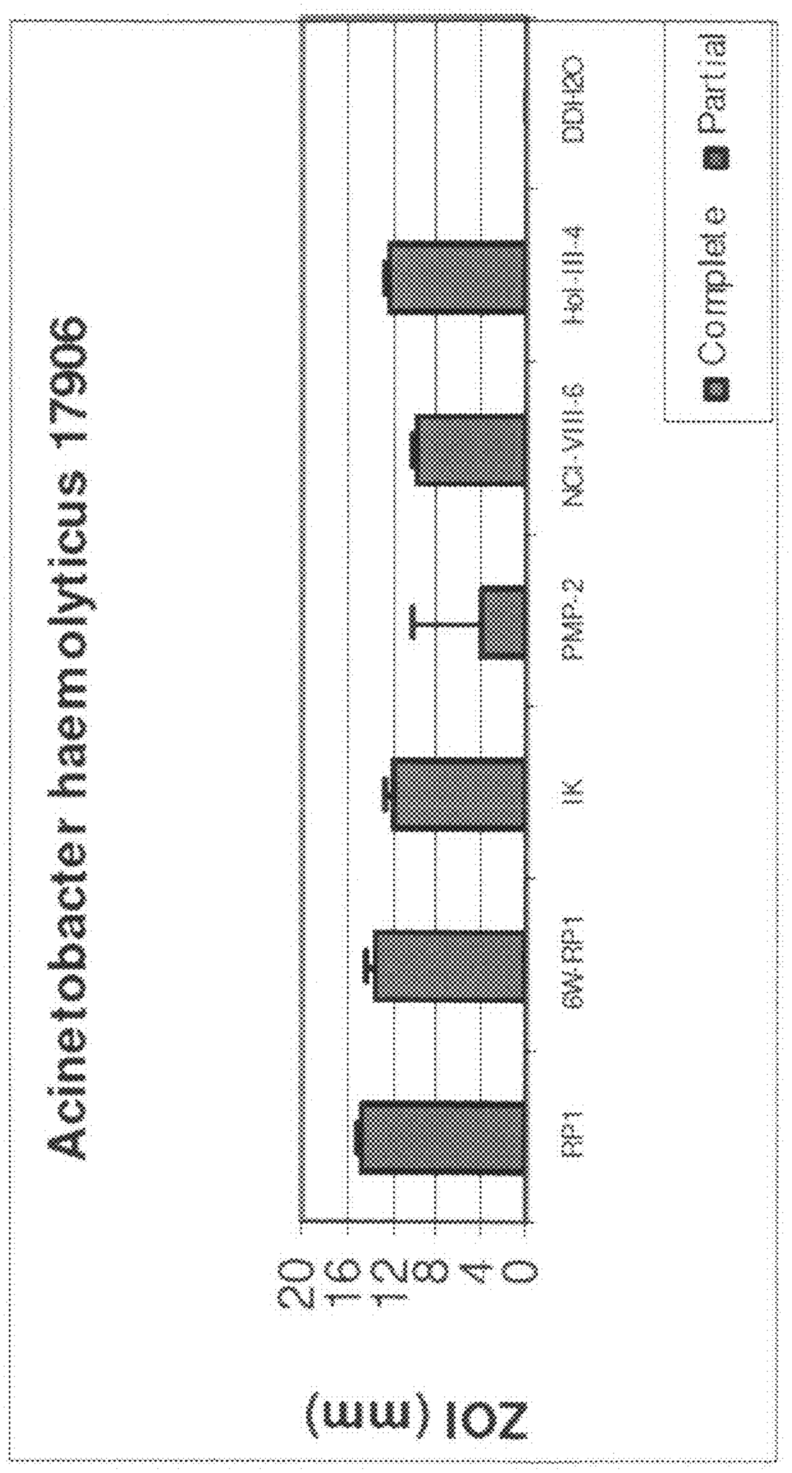
FIG. 42 shows a histogram of the antimicrobial spectra of exemplary peptides Hol-III-4 (SEQ ID NO. 268) and NCl-VIII-6 (SEQ ID NO. 152) against *Acinetobacter haemolyticus* 17906 at pH 5.5. Positive control peptides RP1, 6W-RP1, IK and PMP-2, whereas the negative control of double-distilled water (DDH2O) are also shown. The size of the complete zone of inhibition (ZOI) is represented by a blue bar, whereas the size of the partial (ZOI) is represented by a red bar.
Figure 43:
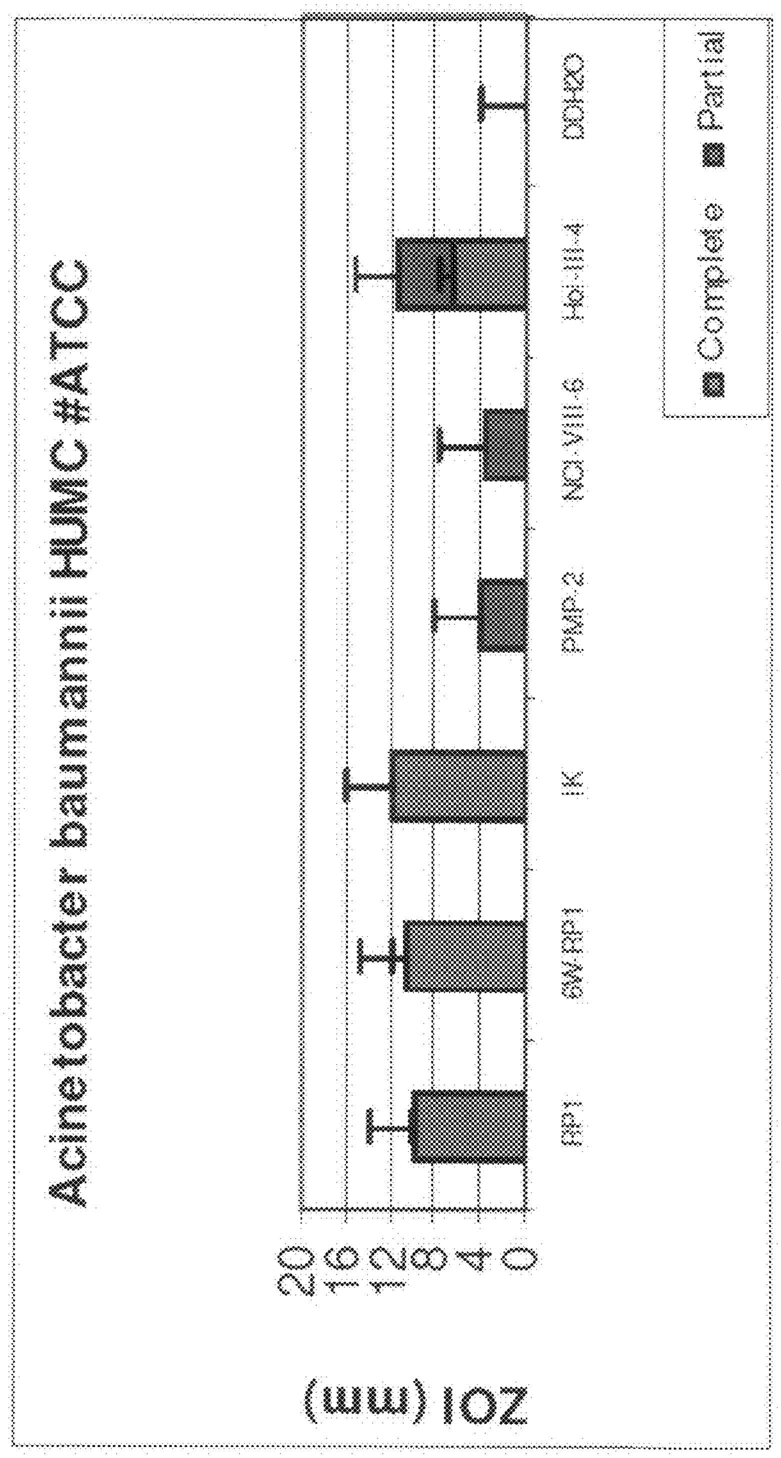
FIG. 43 shows a histogram of the antimicrobial spectra of exemplary peptides Hol-III-4 (SEQ ID NO. 268) and NCl-VIII-6 (SEQ ID NO. 152) against *Acinetobacter baumannii*

85% (46/54) of all peptide and microorganism combinations tested at neutral pH showed antimicrobial activity (FIGS. 30, 32 and 34). The majority of peptides also maintained antimicrobial activity under acidic conditions, i.e. pH 5.5 (FIGS. 31, 33 and 35), albeit at a reduced level. The acidic pH reduced the antimicrobial activity of all peptides when tested against *Staphylococcus aureus*. Additionally, 64% (7/11), 73% (8/11) and 73% (8/11) of the peptides showed lesser antimicrobial activity when tested against *Escherichia coli, Pseudomonas aeruginosa* and *Salmonella typhimurium*, respectively (FIGS. 31, 33 and 35) at pH 5.5 versus pH 7.5. However, the acidic conditions did not appear to affect the activity of peptides Hol-III-4 (SEQ ID NO:268), Ncl-VIII-6 (SEQ ID NO:152) or BaxP-I-18 (SEQ ID NO:264) against *Bacillus subtilis, Escherichia coli, Salmonella typhimurium*, and *Pseudomonas aeruginosa*. Alternatively, the antimicrobial activity was increased for 82% (9/11) of the peptides when tested against the fungal pathogen *Candida albicans* under acidic conditions. Notably, all peptides assayed showed significant and consistently high antimicrobial activity against *Bacillus subtilis* regardless of the acidity of the agarose media (FIGS. 30-35, lane designation BS6633).

The above results show that the designed peptides exerted consistent in vitro efficacy against *Bacillus*. These results supports the concept that these molecules exploit a targetable evolutionary relationship between prokaryotic organisms and eukaryotic mitochondria. Evidence underscoring the bacterium-to-mitochondrial evolution is consistent with this concept (see Herrmann, *TRENDS Micro* 11(2):74-79 (2003)). For example, proteins that are believed to mediate ion-permeability transition in mitochondria are likely to have evolved from membrane targeting motifs such as helical pre-sequences present in ancestral Gram-positive organisms such as *Bacillus*, or other prokaryotes (see von Heijne, *EMBO Journal* 5:1335-1342 (1986)). Such molecules can target mitochondria, are often comprised of 20-60 amino acids, have the potential to form amphipathic α-helices that segregate hydrophobic and hydrophilic facets, and have one facet that is positively charged. The peptides described herein are highly consistent with such molecules. Therefore, the peptides described herein which have antimicrobial activity will also have anti-cancer, anti-inflammatory, anti-rheumatologic and other efficacy by virtue of their likelihood to target mitochondria and induce or cause dysfunctions in programmed cell death circuits.

Example III

Antimicrobial Activity Against *Pseudomonas aeruginos* and *Acinetobacter* spp. Strains Further to the methods disclosed in Example II, utilizing the same antimicrobial assay above, the antimicrobial activity of peptides (SEQ ID NO: 268) and Ncl-VIII-6 (SEQ ID NO: 152 was determined by identifying zones of growth inhibition.

Hol-III-4 and Ncl-VIII-6 peptides were assayted for antimicrobial activity against a panel of drug-resistant Gram-negative bacterial pathogens, specifically *Pseudomonas aeruginosa*, and various *Acinetobacter* spp. strains. The efficacies of these peptides were tested in the context of pH 5.5 (FIGS. 36-46) and pH 7.5 (FIGS. 47-57) conditions, and compared with other peptides known to have antimicrobial activity (e.g. RP-1, 6W-RP-1 (a 6-Trp variant of RP-1), IK, and PMP-2), in the radial diffusion assay. The RP-1 peptide is well known in the art to have antimicrobial activity, as illustrated in Yeaman et al., *Antimicrobial Agents and Chemotherapy,* 46(12):3883-3891 (2002). The 6W-RP-1 peptide is a 6-Trp variant of RP-1, which also has antimicrobial activity, as illustrated in Kilelee et al, *Antimicrobial Agents and Chemotherapy* 54(10):4476-4479 (2010). PMP is the C-terminal helix of the consensus molecule cPMP, as shown in Table 1 (bottom row; N-AALYKKKIIKKLLES-C; as shown in Yeaman et al., *Bichimica et Biophysica Acta,* 1768:609-619 (2007). The IK peptide is designed to have a nearly maximal polar angle (maximum angle is approximately 180°). The results of the antimicrobial assay show that both Hol-III-4 and Ncl-VIII-6 consistently showed significant antimicrobial activity against all *Pseudomonas aeruginosa*, and all *Acinetobacter* spp. strains tested. Additionally, the antimicrobial activity of both Hol-III-4 and Ncl-VIII-6 against the various *Acinetobacter baumannii* isolates tested appeared to be pH dependent (see FIGS. 39, 40, 43-46 vs. FIGS. 50, 51, 54-57)

These results expand on and further substantiate the results shown in Example II regarding the antimicrobial efficacy of the peptides disclosed here. Additionally, the current data supports the conclusion that the PCD peptides may have a unique mechanism of action, but achieve generally equivalent efficacy as RP-1-like peptides against most organisms tested. The is evident by the following observations. The RP-1 and related antimicrobial peptides appear to target microbial cells enriched with electronegative constituents (e.g. phosphatidylglycerol, cardiolipin, etc.), and/or those having electronegative transmembrane potential. These features, in addition to conformational plasticity, inhibition of intracellular functions (e.g. macromolecular synthesis) and possibly superstructural assembly, are believed to participate in the preferential microbial targeting and antimicrobial effects of such peptides. By comparison, the current peptides are designed from programmed cell death effector or modulating proteins. Without being bound by theory, one hypothesis is that such peptides induce microbial and other target cell death by inducing or dysregulating programmed cell death. Thus, it is possible that these peptides function via a mechanism that is not identical to the RP-1-like peptides. In balance, it is also possible that PCD peptides evolved (e.g. diverged) from antimicrobial peptide sequences, based on the view that mitochondria are modern day "bacteria"; this is one hypothesis we posed in the patent. If so, then the mechanisms may be conserved among antimicrobial helices, even if the helices come from proteins believed to have vastly divergent functions (e.g. helices from PMPs, PCD proteins, chemokines, etc).

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. An isolated peptide comprising one or more amino acid sequence selected from the group consisting of:

NFNWGRVVALFYFASKLVLKALXTKV (SEQ ID NO: 3), wherein the X amino acid residue at position 23 of SEQ ID NO: 3 is a threonine, a tyrosine, a non-natural H-bond donor residue or a non-natural H-bond acceptor residue;

NFNWGRVVALFYFASKLVLKALXTXV (SEQ ID NO: 4), wherein the X amino acid residue at position 23 of SEQ ID NO: 4 is a lysine, an arginine, an asparagine, a glutamine or a basic residue, and wherein the X amino acid residue at position residue 25 of SEQ ID NO: 4 is a cysteine or a thiol residue;

WGRVVALFYFASKLVLKALXTKV (SEQ ID NO: 6), wherein the X amino acid residue at position 20 of SEQ ID NO: 6 is a threonine, a tyrosine, a non-natural H-bond donor residue or a non-natural H-bond acceptor residue;

RVVALFYFASKLVLKALXTKV (SEQ ID NO: 8), wherein the X amino acid residue at position 18 of SEQ ID NO: 8 is a threonine, a tyrosine, a non-natural H-bond donor residue or a non-natural H-bond acceptor residue;

ALFYFASKLVLKALXTKV (SEQ ID NO: 10), wherein the X amino acid residue at position 15 of SEQ ID NO: 10 is a threonine, a tyrosine, a non-natural H-bond donor residue or a non-natural H-bond acceptor residue;

TWQTVTIFVAXVLTASLTIWKK (SEQ ID NO: 11), wherein the X amino acid residue at position 11 of SEQ ID NO: 11 is a lysine, an arginine, an asparagine, a glutamine or a basic residue; and TVTIFVAXVLTASLTIWKK (SEQ ID NO: 13), wherein the X amino acid residue at position 8 of SEQ ID NO: 13 is a lysine, an arginine, an asparagine, a glutamine or a basic residue, and wherein said peptide induces antimicrobial, anti-cancer, anti-inflammatory, anti-proliferative or programmed cell death activity.

2. The isolated peptide of claim 1, wherein said peptide comprises the amino acid sequence NFNWGRVVALFY-FASKLVLKALXTKV (SEQ ID NO: 3), wherein the X amino acid residue at position 23 of SEQ ID NO: 3 is a threonine, a tyrosine, a non-natural H-bond donor residue or a non-natural H-bond acceptor residue.

3. An isolated peptide consisting of the amino acid sequence selected from the group consisting of SEQ ID NOS: 1, 5, 7, 9 and 12, wherein said peptide induces antimicrobial, anti-cancer, anti-inflammatory, anti-proliferative or programmed cell death activity.

4. The isolated peptide of claim 2, wherein said peptide consists of the amino acid sequence of NFNWGRVVALFY-FASKLVLKALYTKV (SEQ ID NO: 270).

5. The isolated peptide of claim 1, wherein said peptide comprises the amino acid sequence of NFNWGRVVALFY-FASKLVLKALXTXV (SEQ ID NO: 4), wherein the X amino acid residue at position 23 of SEQ ID NO: 4 is a lysine, an arginine, an asparagine, a glutamine or a basic residue, and wherein the X amino acid residue at position 25 of SEQ ID NO: 4 is a cysteine or a thiol residue.

6. The isolated peptide of claim 1, wherein said peptide comprises the amino acid sequence of WGRVVALFY-FASKLVLKALXTKV (SEQ ID NO: 6), wherein the X amino acid residue at position 20 of SEQ ID NO: 6 is a threonine, a tyrosine, a non-natural H-bond donor residue or a non-natural H-bond acceptor residue.

7. The isolated peptide of claim 1, wherein said peptide comprises the amino acid sequence of RVVALFYFASKLV-LKALXTKV (SEQ ID NO: 8), wherein the X amino acid residue at position 18 of SEQ ID NO: 8 is a threonine, a tyrosine, a non-natural H-bond donor residue or a non-natural H-bond acceptor residue.

8. The isolated peptide of claim 1, wherein said peptide comprises the amino acid sequence of ALFYFASKLVLKA-LXTKV (SEQ ID NO: 10), wherein the X amino acid residue at position 15 of SEQ ID NO: 10 is a threonine, a tyrosine, a non-natural H-bond donor residue or a non-natural H-bond acceptor residue.

9. The isolated peptide of claim 8, wherein said peptide consists of the amino acid sequence of ALFYFASKLVLKA-LYTKV (SEQ ID NO: 264).

10. The isolated peptide of claim 1, wherein said peptide comprises the amino acid sequence of TWQTVTIFVAXVL-TASLTIWKK (SEQ ID NO: 11), wherein the X amino acid residue at position 11 of SEQ ID NO: 11 is a lysine, an arginine, an asparagine, a glutamine or a basic residue.

11. The isolated peptide of claim 1, wherein said peptide comprises the amino acid sequence of TVTIFVAXVL-TASLTIWKK (SEQ ID NO: 13), wherein the X amino acid residue at position 8 of SEQ ID NO: 13 is a lysine, an arginine, an asparagine, a glutamine or a basic residue.

12. The isolated peptide of claim 11, wherein said peptide consists of the amino acid sequence of TVTIFVAKVL-TASLTIWKK (SEQ ID NO: 271).

13. The isolated peptide of claim 3, wherein said peptide consists of the amino acid sequence of SEQ ID NO: 1.

14. The isolated peptide of claim 3, wherein said peptide consists of the amino acid sequence of SEQ ID NO: 5.

15. The isolated peptide of claim 3, wherein said peptide consists of the amino acid sequence of SEQ ID NO: 7.

16. The isolated peptide of claim 3, wherein said peptide consists of the amino acid sequence of SEQ ID NO: 9.

17. The isolated peptide of claim 3, wherein said peptide consists of the amino acid sequence of SEQ ID NO: 12.

18. An isolated peptide consisting of the amino acid sequence selected from the group consisting of:

NFNWGRVVALFYFASKLVLKALXTKV (SEQ ID NO: 3), wherein the X amino acid residue at position 23 of SEQ ID NO: 3 is a serine;

WGRVVALFYFASKLVLKALXTKV (SEQ ID NO: 6), wherein the X amino acid residue at position 20 of SEQ ID NO: 6 is a serine;

RVVALFYFASKLVLKALXTKV (SEQ ID NO: 8), wherein the X amino acid residue at position 18 of SEQ ID NO: 8 is a serine; and ALFYFASKLVLKALXTKV (SEQ ID NO: 10), wherein the X amino acid residue at position 15 of SEQ ID NO: 10 is a serine, and wherein said peptide induces antimicrobial, anti-cancer, anti-inflammatory, anti-proliferative or programmed cell death activity.

19. The isolated peptide of claim 18, wherein the peptide consists of the amino acid sequence of NFNWGRVVALFY-FASKLVLKALXTKV (SEQ ID NO: 3), wherein the X amino acid residue at position 23 of SEQ ID NO: 3 is a serine.

20. The isolated peptide of claim 18, wherein the peptide consists of the amino acid sequence of WGRVVALFY-FASKLVLKALXTKV (SEQ ID NO: 6), wherein the X amino acid residue at position 20 of SEQ ID NO: 6 is a serine.

21. The isolated peptide of claim 18, wherein the peptide consists of the amino acid sequence of RVVALFYFASKLV-LKALXTKV (SEQ ID NO: 8), wherein the X amino acid residue at position 18 of SEQ ID NO: 8 is a serine.

22. The isolated peptide of claim 18, wherein the peptide consists of the amino acid sequence of ALFYFASKLVLKA-LXTKV (SEQ ID NO: 10), wherein the X amino acid residue at position 15 of SEQ ID NO: 10 is a serine.

23. A method of inducing programmed cell death in a cell, comprising contacting said cell with the isolated peptide of any one of claims 1, 2, 3 and 4-22.

* * * * *